US008758764B2

(12) United States Patent
Masignani et al.

(10) Patent No.: US 8,758,764 B2
(45) Date of Patent: Jun. 24, 2014

(54) PROTEINS AND NUCLEIC ACIDS FROM MENINGITIS/SEPSIS-ASSOCIATED *ESCHERICHIA COLI*

(75) Inventors: Vega Masignani, Siena (IT); Danilo Gomes Moriel, Monteriggioni (IT); Francesco Berlanda Scorza, Trento (IT); Nathalie Norais, Siena (IT); Maria Rita Fontana, Siena (IT); Mariagrazia Pizza, Siena (IT); Laura Serino, Monticiano (IT); Herve Tettelin, Gaithersburg, MD (US)

(73) Assignees: Novartis Vaccines and Diagnostics Srl, Siena (IT); J. Craig Venter Institute, Rockville, MD (US)

( * ) Notice: Subject to any disclaimer, the term of this patent is extended or adjusted under 35 U.S.C. 154(b) by 16 days.

(21) Appl. No.: 11/884,812

(22) PCT Filed: Feb. 17, 2006

(86) PCT No.: PCT/US2006/005913
§ 371 (c)(1),
(2), (4) Date: Mar. 26, 2008

(87) PCT Pub. No.: WO2006/089264
PCT Pub. Date: Aug. 24, 2006

(65) Prior Publication Data
US 2008/0193470 A1    Aug. 14, 2008

Related U.S. Application Data

(60) Provisional application No. 60/712,720, filed on Aug. 29, 2005, provisional application No. 60/654,632, filed on Feb. 18, 2005.

(51) Int. Cl.
*A61K 39/108*     (2006.01)
*C07K 14/245*     (2006.01)

(52) U.S. Cl.
USPC ............... 424/185.1; 424/257.1; 530/300; 530/350

(58) Field of Classification Search
CPC combination set(s) only.
See application file for complete search history.

(56) References Cited

U.S. PATENT DOCUMENTS

| 2003/0165870 A1 | 9/2003 | Blattner et al. |
| 2004/0123343 A1 | 6/2004 | La Rosa et al. |

FOREIGN PATENT DOCUMENTS

| EP | 1342784 A1 | 9/2003 |
| WO | WO-9822575 | 5/1998 |
| WO | WO-01/66572 A2 | 9/2001 |
| WO | WO-0216439 | 2/2002 |
| WO | WO-02/059320 | 8/2002 |
| WO | WO-02/077183 | 10/2002 |
| WO | WO-2004/005535 A2 | 1/2004 |
| WO | WO-2005/076010 | 8/2005 |

OTHER PUBLICATIONS

Houghten et al. (New Approaches to Immunization, Vaccines86, Cold Spring Harbor Laboratory, p. 21-25, 1986.*
McGuinness et al. (Lancet 337: 514-517, Mar. 1991.*
McGuinness et al. (Mol. Microbiol. 7:505-514, Feb. 1993).*
Accession No. Q46837 2002 ( or Q2M9M2 or Q46838 or Q6BF5) or Science 277:1453-1474(1997).*
EMBL accession No. AJ617685 (Created on May 11, 2004), "*Escherichia coli* pathogenicity island V, strain 536."
UniProt accession No. Q46837 (Integrated on Apr. 16, 2002). "Putative lipprotein acfD homolog."
Hughes et al. (Aug. 19, 1994). "Sequence analysis of the *Vibrio cholerae* acfD gene reveals the presence of an overlapping reading frame, orfZ, which encodes a protein that shares sequence similarity to the FliA and FliC products of *Salmonella*,", Gene 146(1): 79-82.
European Search Report mailed Dec. 23, 2008, for EP patent application No. 06748228.1, filed Feb. 17, 2006.
European Examination Report mailed Dec. 29, 2008, for EP patent application No. 06748228.1, filed Feb. 17, 2006.
International Search Report mailed Feb. 15, 2007, for International patent application No. PCT/US2006/005913, field Feb. 17, 2006.
Bernadac et al. (1998) "*Escherichia coli* tol-pal mutants form outer membrane vesicles," Journal of Bacteriology, 180(18): 4872-4878.
Wu (2002) "The relationship between outer membrane vesicles and pathogenicity" Foreign Medicine (Microbiology Section) 4:13-15.
EBI accession No. Q8FKK3, Mar. 1, 2003 (version 56, dated May 1, 2013).
EBI accession No. Q8X6G3, Mar. 1, 2002 (version 71, dated May 1, 2013).
Dean-Nystrom et al. (2002). "Vaccination of pregnant dams with intimin(O157) protects suckling piglets from *Escherichia coli* O157:H7 infection," Infect Immun. 70(5):2414-8.
Judge et al. (2004). "Plant cell-based intimin vaccine given orally to mice primed with intimin reduces time of *Escherichia coli* O157:H7 shedding in feces," Infect Immun. 72(1):168-75.
Perna et al. (2001). "Genome sequence of enterohaemorrhagic *Escherichia coli* O157:H7." Nature. 409(6819):529-33.
Welch et al. (2002). "Extensive mosaic structure revealed by the complete genome sequence of uropathogenic *Escherichia coli.*" Proc Natl Acad Sci USA. 99(26):17020-4.
Bonacorsi, S. et al. (Apr. 2000). "Identification of Regions of the *Escherichia coli* Chromosome Specific for Neonatal Meningitis-associated Strains," *Infection and Immunity* 68(4):2096-2101.
Database EMBL-EBI Accession No. AY395687, last updated Jan. 27, 2008, located at <http://www.ebi.ac.uk/cgi-bin/dbfetch?db=embl&id=AY395687&style=raw>, last visited on Jun. 19, 2008, 18 pages.

(Continued)

*Primary Examiner* — Padma V Baskar
(74) *Attorney, Agent, or Firm* — Morrison & Foerster LLP

(57) ABSTRACT

Disclosed herein are various open reading frames from a strain of *E. coli* responsible for neonatal meningitis (MNEC), and a subset of these that is of particular interest for preparing compositions for immunising against MNEC infections.

16 Claims, 4 Drawing Sheets

(56) References Cited

OTHER PUBLICATIONS

Gonzalez, M. et al. (May 1, 2001). "Adaptation of Signature-tagged Mutagenesis to *Escherichia coli* K1 and the Infant-rat Model of Invasive Disease," *FEMS Microbiology Letters* 198(2):125-128.

Henry, T. et al. (Jul. 2004). "Improved Methods for Producing Outer Membrane Vesicles in Gram-negative Bacteria," *Research in Microbiology* 155(6):437-446.

International Search Report mailed on Feb. 15, 2007, for PCT Patent Application No. PCT/US2006/005913 filed on Feb. 17, 2006, 6 pages.

Janke, B. et al. (May 15, 2001). "A Subtractive Hybridisation Analysis of Genomic Differences between the Uropathogenic *E. coli* Strain 536 and the *E. coli* K-12 Strain MG1655," *FEMS Microbiology Letters* 199(1):61-66.

Rode, C. et al. (Jan. 1999). "Type-specific Contributions to Chromosome Size Differences in *Escherichia coli*," *Infection and Immunity* 67(1):230-236.

Zhang, L. et al. (Apr. 2000). "Molecular Epidemiologic Approaches to Urinary Tract Infection Gene Discovery in Uropathogenic *Escherichi coli*," *Infection and Immunity* 68(4):2009-2015.

\* cited by examiner

— ◇ — IHE3034
— □ — DH5
▫ ○ ▫ FISIOL.

▫ ◇ ▫ OMV IHE
▫ □ ▫ OMV DH5
▫ ○ ▫ FISIOL.

PROTEINS AND NUCLEIC ACIDS FROM MENINGITIS/SEPSIS-ASSOCIATED *ESCHERICHIA COLI*

RELATED APPLICATIONS

This application claims the benefit of U.S. Provisional Application No. 60/654,632, filed Feb. 18, 2005 and U.S. Provisional Application No. 60/712,720, filed Aug. 29, 2005. The teachings of both these applications are incorporated herein in their entirety by reference.

TECHNICAL FIELD

This invention is in the field of *Escherichia coli* biology, and in particular relates to immunogens for use in immunising against extraintestinal pathogenic *E. coli* (ExPEC) strains.

BACKGROUND ART

Few microorganisms are as versatile as *E. coli*. As well as being an important member of the normal intestinal microflora of mammals, it has been widely exploited as a host in recombinant DNA technology. In addition, however, *E. coli* can also be a deadly pathogen.

*E. coli* strains have traditionally been classified as either commensal or pathogenic, and pathogenic strains are then sub-classified as intestinal or extraintestinal strains. Classification may also be based on the 'K' antigens. The best-studied 'K' antigen is 'K1', which is considered to be the major determinant of virulence among those strains of *E. coli* that cause neonatal meningitis. The K1 antigen is a homopolymer of $\alpha$-2,8-linked sialic acid, like the capsular saccharide of serogroup B meningococcus.

More recent taxonomic techniques such as multilocus enzyme electrophoresis (MLEE) classify *E. coli* into five phylogenetic groups (A, B1, B2, D & E), and these groupings do not match the traditional ones. For instance, MLEE group B1 includes both commensal and pathogenic strains, and group D includes both intestinal and extraintestinal strains.

The extraintestinal pathogenic strains (or 'ExPEC' strains [1]) of *E. coli* fall into MLEE groups B2 and D, and include both uropathogenic (UPEC) strains and meningitis/sepsis-associated (MNEC) strains. UPEC strains cause urinary tract infections (UTIs), and are a common cause of cystitis. They also cause pyelonephritis (and its complications such as sepsis) and catheter-associated infections. MNEC strains cause neonatal meningitis (0.1 cases per 1000 live births) with case fatality rates ranging from 25 to 40%, and are also responsible for around ⅙ of sepsis cases.

Most previous ExPEC vaccines have been based on cell lysates or on cellular structures. SOLCOUROVAC™ includes ten different heat-killed bacteria including six ExPEC strains, and a successful phase II clinical trial was reported in reference 2. URO-VAXOM™ is an oral tablet vaccine containing lyophilised bacterial lysates of 18 selected *E. coli* strains [3]. Baxter Vaccines developed a UTI vaccine based on pili from 6 to 10 different strains, but this product has been abandoned. MedImmune developed a product called MEDI 516 based on the FimH adhesin complex [4], but phase II clinical trials shows inadequate efficacy. Moreover, there was a risk with this vaccine that it would also affect non-pathogenic FimH$^{+ve}$ strains in the normal intestinal flora, and it was expected that it would be effective against UPEC strains only, because of its bladder-specific adherence mechanism, leaving other ExPEC strains uncontrolled.

There is thus a need for improved ExPEC vaccines, including a need to move away from crude cell lysates and towards better-defined molecules, and a need to identify further antigens that are suitable for inclusion in vaccines, particularly antigens that are prevalent among clinical ExpEC strains without also being found in commensal strains. Within the ExPEC group, there is a particular need to identify antigens suitable for immunising against MNEC strains.

One way of addressing these needs was reported in reference 5, where the inventors looked for genes present in genomes of MLEE types B2 and D but absent from MLEE types A and B1. Further comparative approaches, based on subtractive hybridisation, have been reported in references 6 & 7. Virulence genes in ExPEC strains have also been identified in reference 8. Reference 9 discloses an analysis of four pathogenicity islands in UPEC *E. coli* strain 536.

Reference 10 used the genome sequence of UPEC (O6:K2:H1) strain CFT073 [11,12] to identify sequences not present in non-pathogenic *E. coli* strains. Reference 13 discloses a comparison of the genome sequence of *E. coli* human pyelonephritis isolate 536 (O6:K15:H31), an UPEC, with sequence data for strains CFT073 (UPEC), EDL933 (enterohemorrhagic) and MG1655 (non-pathogenic laboratory strain). Genome sequences of pathogenic strains are available in the databases under accession numbers AE005174, BA000007 and NC-004431. A sequence from a non-pathogenic strain is available under accession number U00096.

It is an object of the invention to provide further antigens for use in immunisation against pathogenic *E. coli* strains, particularly against ExPEC strains, and more particularly against MNEC strains.

SUMMARY OF THE INVENTION

The inventors have identified various open reading frames from a strain of *E. coli* responsible for neonatal meningitis (MNEC), and have identified a subset of these that is of particular interest for preparing compositions for immunising against MNEC infections.

In one aspect, the present invention relates to a polypeptide comprising: (a) an amino acid sequence selected from the group consisting of SEQ ID NOs 706, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, 890, 892, 894, 896, 898, 900, 902, 904, 906, 908, 910, 912, 914, 916, 918, 920, 922, 924, 926, 928, 930, 932, 934, 936, 938, 940, 942, 944, 946, 948, 950, 952, 954, 956, 958, 960, 962, 964, 966, 968, 970, 972, 974, 976, 978, 980, 982, 984, 986, 988, 990, 992, 994, 996, 998, 1000, 1002, 1004, 1006, 1008, 1010, 1012, 1014, 1016, 1018, 1020, 1022, 1024, 1026, 1028, 1030, 1032, 1034, 1036, 1038, 1040, 1042, 1044, 1046, 1048, 1050, 1052, 1054, 1056, 1058, 1060, 1062, 1064, 1066, 1068, 1070, 1072, 1074, 1076, 1078, 1080, 1082, 1084, 1086, 1088, 1090, 1092, 1094, 1096, 1098, 1100, 1102, 1104, 1106, 1108, 1110, 1112, 1114, 1116, 1118, 1120, 1122, 1124, 1126, 1128, 1130, 1132, 1134, 1136, 1138, 1140, 1142, 1144, 1146, 1148, 1150, 1152, 1154, 1156, 1158, 1160, 1162, 1164, 1166, 1168, 1170, 1172, 1174, 1176, 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, 1300, 1302, 1304, 1306, 1308, 1310, 1312, 1314, 1316, 1318, 1320, 1322, 1324, 1326, 1328, 1330, 1332, 1334, 1336, 1338, 1340, 1342, 1344, 1346, 1348, 1350, 1352, 1354, 1356, 1358, 1360, 1362, 1364, 1366, 1368, 1370, 1372, 1374, 1376, 1378, 1380, 1382, 1384, 1386, 1388, 1390, 1392, 1394, 1396, 1398, 1400, 1402, 1404, 1406, 1408, 1410, 1412, 1414, 1416, 1418, 1420, 1422, 1424, 1426, 1428, 1430, 1432, 1434, 1436, 1438, 1440, 1442, 1444, 1446, 1448, 1450, 1452, 1454, 1456, 1458, 1460, 1462, 1464, 1466, 1468, 1470, 1472, 1474, 1476, 1478, 1480, 1482, 1484, 1486, 1488, 1490, 1492, 1494, 1496, 1498, 1500, 1502, 1504, 1506, 1508, 1510, 1512, 1514, 1516, 1518, 1520, 1522, 1524, 1526, 1528, 1530, 1532, 1534, 1536, 1538, 1540, 1542, 1544, 1546, 1548, 1550, 1552, 1554, 1556, 1558, 1560, 1562, 1564, 1566, 1568, 1570, 1572, 1574, 1576, 1578, 1580, 1582, 1584, 1586, 1588, 1590, 1592, 1594, 1596, 1598, 1600, 1602, 1604, 1606, 1608, 1610, 1612, 1614, 1616, 1618, 1620, 1622, 1624, 1626, 1628, 1630, 1632, 1634, 1636, 1638, 1640, 1642, 1644, 1646, 1648, 1650, 1652, 1654, 1656, 1658, 1660, 1662, 1664, 1666, 1668, 1670, 1672, 1674, 1676, 1678, 1680, 1682, 1684, 1686, 1688, 1690, 1692, 1694, 1696, 1698, 1700, 1702, 1704, 1706, 1708, 1710, 1712, 1714, 1716, 1718, 1720, 1722, 1724, 1726, 1728, 1730, 1732, 1734, 1736, 1738, 1740, 1742, 1744, 1746, 1748, 1750, 1752, 1754, 1756, 1758, 1760, 1762, 1764, 1766, 1768, 1770, 1772, 1774, 1776, 1778, 1780, 1782, 1784, 1786, 1788, 1790, 1792, 1794, 1796, 1798, 1800, 1802, 1804, 1806, 1808, 1810, 1812, 1814, 1816, 1818, 1820, 1822, 1824, 1826, 1828, 1830, 1832, 1834, 1836, 1838, 1840, 1842, 1844, 1846, 1848, 1850, 1852, 1854, 1856, 1858, 1860, 1862, 1864, 1866, 1868, 1870, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2030, 2032, 2034, 2036, 2038, 2040, 2042, 2044, 2046, 2048, 2050, 2052, 2054, 2056, 2058, 2060, 2062, 2064, 2066, 2068, 2070, 2072, 2074, 2076, 2078, 2080, 2082, 2084, 2086, 2088, 2090, 2092, 2094, 2096, 2098, 2100, 2102, 2104, 2106, 2108, 2110, 2112, 2114, 2116, 2118, 2120, 2122, 2124, 2126, 2128, 2130, 2132, 2134, 2136, 2138, 2140, 2142, 2144, 2146, 2148, 2150, 2152, 2154, 2156, 2158, 2160, 2162, 2164, 2166, 2168, 2170, 2172, 2174, 2176, 2178, 2180, 2182, 2184, 2186, 2188, 2190, 2192, 2194, 2196, 2198, 2200, 2202, 2204, 2206, 2208, 2210, 2212, 2214, 2216, 2218, 2220, 2222, 2224, 2226, 2228, 2230, 2232, 2234, 2236, 2238, 2240, 2242, 2244, 2246, 2248, 2250, 2252, 2254, 2256, 2258, 2260, 2262, 2264, 2266, 2268, 2270, 2272, 2274, 2276, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2324, 2326, 2328, 2330, 2332, 2334, 2336, 2338, 2340, 2342, 2344, 2346, 2348, 2350, 2352, 2354, 2356, 2358, 2360, 2362, 2364, 2366, 2368, 2370, 2372, 2374, 2376, 2378, 2380, 2382, 2384, 2386, 2388, 2390, 2392, 2394, 2396, 2398, 2400, 2402, 2404, 2406, 2408, 2410, 2412, 2414, 2416, 2418, 2420, 2422, 2424, 2426, 2428, 2430, 2432, 2434, 2436, 2438, 2440, 2442, 2444, 2446, 2448, 2450, 2452, 2454, 2456, 2458, 2460, 2462, 2464, 2466, 2468, 2470, 2472, 2474, 2476, 2478, 2480, 2482, 2484, 2486, 2488, 2490, 2492, 2494, 2496, 2498, 2500, 2502, 2504, 2506, 2508, 2510, 2512, 2514, 2516, 2518, 2520, 2522, 2524, 2526, 2528, 2530, 2532, 2534, 2536, 2538, 2540, 2542, 2544, 2546, 2548, 2550, 2552, 2554, 2556, 2558, 2560, 2562, 2564, 2566, 2568, 2570, 2572, 2574, 2576, 2578, 2580, 2582, 2584, 2586, 2588, 2590, 2592, 2594, 2596, 2598, 2600, 2602, 2604, 2606, 2608, 2610, 2612, 2614, 2616, 2618, 2620, 2622, 2624, 2626, 2628, 2630, 2632, 2634, 2636, 2638, 2640, 2642, 2644, 2646, 2648, 2650, 2652, 2654, 2656, 2658, 2660, 2662, 2664, 2666, 2668, 2670, 2672, 2674, 2676, 2678, 2680, 2682, 2684, 2686, 2688, 2690, 2692, 2694, 2696, 2698, 2700, 2702, 2704, 2706, 2708, 2710, 2712, 2714, 2716, 2718, 2720, 2722, 2724, 2726, 2728, 2730, 2732, 2734, 2736, 2738, 2740, 2742, 2744, 2746, 2748, 2750, 2752, 2754, 2756, 2758, 2760, 2762, 2764, 2766, 2768, 2770, 2772, 2774, 2776, 2778, 2780, 2782, 2784, 2786, 2788, 2790, 2792, 2794, 2796, 2798, 2800, 2802, 2804, 2806, 2808, 2810, 2812, 2814, 2816, 2818, 2820, 2822, 2824, 2826, 2828, 2830, 2832, 2834, 2836, 2838, 2840, 2842, 2844, 2846, 2848, 2850, 2852, 2854, 2856, 2858, 2860, 2862, 2864, 2866, 2868, 2870, 2872, 2874, 2876, 2878, 2880, 2882, 2884, 2886, 2888, 2890, 2892, 2894, 2896, 2898, 2900, 2902, 2904, 2906, 2908, 2910, 2912, 2914, 2916, 2918, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964, 2966, 2968, 2970, 2972, 2974, 2976, 2978, 2980, 2982, 2984, 2986, 2988, 2990, 2992, 2994, 2996, 2998, 3000, 3002, 3004, 3006, 3008, 3010, 3012, 3014, 3016, 3018, 3020, 3022, 3024, 3026, 3028, 3030, 3032, 3034, 3036, 3038, 3040, 3042, 3044, 3046, 3048, 3050, 3052, 3054, 3056, 3058, 3060, 3062, 3064, 3066, 3068, 3070, 3072, 3074, 3076, 3078, 3080, 3082, 3084, 3086, 3088, 3090, 3092, 3094, 3096, 3098, 3100, 3102, 3104, 3106, 3108, 3110, 3112, 3114, 3116, 3118, 3120, 3122, 3124, 3126, 3128, 3130, 3132, 3134, 3136, 3138, 3140, 3142, 3144, 3146, 3148, 3150, 3152, 3154, 3156, 3158, 3160, 3162, 3164, 3166, 3168, 3170, 3172, 3174, 3176, 3178, 3180, 3182, 3184, 3186, 3188, 3190, 3192, 3194, 3196, 3198, 3200, 3202, 3204, 3206, 3208, 3210, 3212, 3214, 3216, 3218, 3220, 3222, 3224, 3226, 3228, 3230, 3232, 3234, 3236, 3238, 3240, 3242, 3244, 3246, 3248, 3250, 3252, 3254, 3256, 3258, 3260, 3262, 3264, 3266, 3268, 3270, 3272, 3274, 3276, 3278, 3280, 3282, 3284, 3286, 3288, 3290, 3292, 3294, 3296, 3298, 3300, 3302, 3304, 3306, 3308, 3310, 3312, 3314, 3316, 3318, 3320, 3322, 3324, 3326, 3328, 3330, 3332, 3334, 3336, 3338, 3340, 3342, 3344, 3346, 3348, 3350, 3352, 3354, 3356, 3358, 3360, 3362, 3364, 3366, 3368, 3370, 3372, 3374, 3376, 3378, 3380, 3382, 3384, 3386, 3388, 3390, 3392, 3394, 3396, 3398, 3400, 3402,
3404, 3406, 3408, 3410, 3412, 3414, 3416, 3418, 3420, 3422,
3424, 3426, 3428, 3430, 3432, 3434, 3436, 3438, 3440, 3442,
3444, 3446, 3448, 3450, 3452, 3454, 3456, 3458, 3460, 3462,
3464, 3466, 3468, 3470, 3472, 3474, 3476, 3478, 3480, 3482,
3484, 3486, 3488, 3490, 3492, 3494, 3496, 3498, 3500, 3502,
3504, 3506, 3508, 3510, 3512, 3514, 3516, 3518, 3520, 3522,
3524, 3526, 3528, 3530, 3532, 3534, 3536, 3538, 3540, 3542,
3544, 3546, 3548, 3550, 3552, 3554, 3556, 3558, 3560, 3562,
3564, 3566, 3568, 3570, 3572, 3574, 3576, 3578, 3580, 3582,
3584, 3586, 3588, 3590, 3592, 3594, 3596, 3598, 3600, 3602,
3604, 3606, 3608, 3610, 3612, 3614, 3616, 3618, 3620, 3622,
3624, 3626, 3628, 3630, 3632, 3634, 3636, 3638, 3640, 3642,
3644, 3646, 3648, 3650, 3652, 3654, 3656, 3658, 3660, 3662,
3664, 3666, 3668, 3670, 3672, 3674, 3676, 3678, 3680, 3682,
3684, 3686, 3688, 3690, 3692, 3694, 3696, 3698, 3700, 3702,
3704, 3706, 3708, 3710, 3712, 3714, 3716, 3718, 3720, 3722,
3724, 3726, 3728, 3730, 3732, 3734, 3736, 3738, 3740, 3742,
3744, 3746, 3748, 3750, 3752, 3754, 3756, 3758, 3760, 3762,
3764, 3766, 3768, 3770, 3772, 3774, 3776, 3778, 3780, 3782,
3784, 3786, 3788, 3790, 3792, 3794, 3796, 3798, 3800, 3802,
3804, 3806, 3808, 3810, 3812, 3814, 3816, 3818, 3820, 3822,
3824, 3826, 3828, 3830, 3832, 3834, 3836, 3838, 3840, 3842,
3844, 3846, 3848, 3850, 3852, 3854, 3856, 3858, 3860, 3862,
3864, 3866, 3868, 3870, 3872, 3874, 3876, 3878, 3880, 3882,
3884, 3886, 3888, 3890, 3892, 3894, 3896, 3898, 3900, 3902,
3904, 3906, 3908, 3910, 3912, 3914, 3916, 3918, 3920, 3922,
3924, 3926, 3928, 3930, 3932, 3934, 3936, 3938, 3940, 3942,
3944, 3946, 3948, 3950, 3952, 3954, 3956, 3958, 3960, 3962,
3964, 3966, 3968, 3970, 3972, 3974, 3976, 3978, 3980, 3982,
3984, 3986, 3988, 3990, 3992, 3994, 3996, 3998, 4000, 4002,
4004, 4006, 4008, 4010, 4012, 4014, 4016, 4018, 4020, 4022,
4024, 4026, 4028, 4030, 4032, 4034, 4036, 4038, 4040, 4042,
4044, 4046, 4048, 4050, 4052, 4054, 4056, 4058, 4060, 4062,
4064, 4066, 4068, 4070, 4072, 4074, 4076, 4078, 4080, 4082,
4084, 4086, 4088, 4090, 4092, 4094, 4096, 4098, 4100, 4102,
4104, 4106, 4108, 4110, 4112, 4114, 4116, 4118, 4120, 4122,
4124, 4126, 4128, 4130, 4132, 4134, 4136, 4138, 4140, 4142,
4144, 4146, 4148, 4150, 4152, 4154, 4156, 4158, 4160, 4162,
4164, 4166, 4168, 4170, 4172, 4174, 4176, 4178, 4180, 4182,
4184, 4186, 4188, 4190, 4192, 4194, 4196, 4198, 4200, 4202,
4204, 4206, 4208, 4210, 4212, 4214, 4216, 4218, 4220, 4222,
4224, 4226, 4228, 4230, 4232, 4234, 4236, 4238, 4240, 4242,
4244, 4246, 4248, 4250, 4252, 4254, 4256, 4258, 4260, 4262,
4264, 4266, 4268, 4270, 4272, 4274, 4276, 4278, 4280, 4282,
4284, 4286, 4288, 4290, 4292, 4294, 4296, 4298, 4300, 4302,
4304, 4306, 4308, 4310, 4312, 4314, 4316, 4318, 4320, 4322,
4324, 4326, 4328, 4330, 4332, 4334, 4336, 4338, 4340, 4342,
4344, 4346, 4348, 4350, 4352, 4354, 4356, 4358, 4360, 4362,
4364, 4366, 4368, 4370, 4372, 4374, 4376, 4378, 4380, 4382,
4384, 4386, 4388, 4390, 4392, 4394, 4396, 4398, 4400, 4402,
4404, 4406, 4408, 4410, 4412, 4414, 4416, 4418, 4420, 4422,
4424, 4426, 4428, 4430, 4432, 4434, 4436, 4438, 4440, 4442,
4444, 4446, 4448, 4450, 4452, 4454, 4456, 4458, 4460, 4462,
4464, 4466, 4468, 4470, 4472, 4474, 4476, 4478, 4480, 4482,
4484, 4486, 4488, 4490, 4492, 4494, 4496, 4498, 4500, 4502,
4504, 4506, 4508, 4510, 4512, 4514, 4516, 4518, 4520, 4522,
4524, 4526, 4528, 4530, 4532, 4534, 4536, 4538, 4540, 4542,
4544, 4546, 4548, 4550, 4552, 4554, 4556, 4558, 4560, 4562,
4564, 4566, 4568, 4570, 4572, 4574, 4576, 4578, 4580, 4582,
4584, 4586, 4588, 4590, 4592, 4594, 4596, 4598, 4600, 4602,
4604, 4606, 4608, 4610, 4612, 4614, 4616, 4618, 4620, 4622,
4624, 4626, 4628, 4630, 4632, 4634, 4636, 4638, 4640, 4642,
4644, 4646, 4648, 4650, 4652, 4654, 4656, 4658, 4660, 4662,
4664, 4666, 4668, 4670, 4672, 4674, 4676, 4678, 4680, 4682,
4684, 4686, 4688, 4690, 4692, 4694, 4696, 4698, 4700, 4702,
4704, 4706, 4708, 4710, 4712, 4714, 4716, 4718, 4720, 4722,
4724, 4726, 4728, 4730, 4732, 4734, 4736, 4738, 4740, 4742,
4744, 4746, 4748, 4750, 4752, 4754, 4756, 4758, 4760, 4762,
4764, 4766, 4768, 4770, 4772, 4774, 4776, 4778, 4780, 4782,
4784, 4786, 4788, 4790, 4792, 4794, 4796, 4798, 4800, 4802,
4804, 4806, 4808, 4810, 4812, 4814, 4816, 4818, 4820, 4822,
4824, 4826, 4828, 4830, 4832, 4834, 4836, 4838, 4840, 4842,
4844, 4846, 4848, 4850, 4852, 4854, 4856, 4858, 4860, 4862,
4864, 4866, 4868, 4870, 4872, 4874, 4876, 4878, 4880, 4882,
4884, 4886, 4888, 4890, 4892, 4894, 4896, 4898, 4900, 4902,
4904, 4906, 4908, 4910, 4912, 4914, 4916, 4918, 4920, 4922,
4924, 4926, 4928, 4930, 4932, 4934, 4936, 4938, 4940, 4942,
4944, 4946, 4948, 4950, 4952, 4954, 4956, 4958, 4960, 4962,
4964, 4966, 4968, 4970, 4972, 4974, 4976, 4978, 4980, 4982,
4984, 4986, 4988, 4990, 4992, 4994, 4996, 4998, 5000, 5002,
5004, 5006, 5008, 5010, 5012, 5014, 5016, 5018, 5020, 5022,
5024, 5026, 5028, 5030, 5032, 5034, 5036, 5038, 5040, 5042,
5044, 5046, 5048, 5050, 5052, 5054, 5056, 5058, 5060, 5062,
5064, 5066, 5068, 5070, 5072, 5074, 5076, 5078, 5080, 5082,
5084, 5086, 5088, 5090, 5092, 5094, 5096, 5098, 5100, 5102,
5104, 5106, 5108, 5110, 5112, 5114, 5116, 5118, 5120, 5122,
5124, 5126, 5128, 5130, 5132, 5134, 5136, 5138, 5140, 5142,
5144, 5146, 5148, 5150, 5152, 5154, 5156, 5158, 5160, 5162,
5164, 5166, 5168, 5170, 5172, 5174, 5176, 5178, 5180, 5182,
5184, 5186, 5188, 5190, 5192, 5194, 5196, 5198, 5200, 5202,
5204, 5206, 5208, 5210, 5212, 5214, 5216, 5218, 5220, 5222,
5224, 5226, 5228, 5230, 5232, 5234, 5236, 5238, 5240, 5242,
5244, 5246, 5248, 5250, 5252, 5254, 5256, 5258, 5260, 5262,
5264, 5266, 5268, 5270, 5272, 5274, 5276, 5278, 5280, 5282,
5284, 5286, 5288, 5290, 5292, 5294, 5296, 5298, 5300, 5302,
5304, 5306, 5308, 5310, 5312, 5314, 5316, 5318, 5320, 5322,
5324, 5326, 5328, 5330, 5332, 5334, 5336, 5338, 5340, 5342,
5344, 5346, 5348, 5350, 5352, 5354, 5356, 5358, 5360, 5362,
5364, 5366, 5368, 5370, 5372, 5374, 5376, 5378, 5380, 5382,
5384, 5386, 5388, 5390, 5392, 5394, 5396, 5398, 5400, 5402,
5404, 5406, 5408, 5410, 5412, 5414, 5416, 5418, 5420, 5422,
5424, 5426, 5428, 5430, 5432, 5434, 5436, 5438, 5440, 5442,
5444, 5446, 5448, 5450, 5452, 5454, 5456, 5458, 5460, 5462,
5464, 5466, 5468, 5470, 5472, 5474, 5476, 5478, 5480, 5482,
5484, 5486, 5488, 5490, 5492, 5494, 5496, 5498, 5500, 5502,
5504, 5506, 5508, 5510, 5512, 5514, 5516, 5518, 5520, 5522,
5524, 5526, 5528, 5530, 5532, 5534, 5536, 5538, 5540, 5542,
5544, 5546, 5548, 5550, 5552, 5554, 5556, 5558, 5560, 5562,
5564, 5566, 5568, 5570, 5572, 5574, 5576, 5578, 5580, 5582,
5584, 5586, 5588, 5590, 5592, 5594, 5596, 5598, 5600, 5602,
5604, 5606, 5608, 5610, 5612, 5614, 5616, 5618, 5620, 5622,
5624, 5626, 5628, 5630, 5632, 5634, 5636, 5638, 5640, 5642,
5644, 5646, 5648, 5650, 5652, 5654, 5656, 5658, 5660, 5662,
5664, 5666, 5668, 5670, 5672, 5674, 5676, 5678, 5680, 5682,
5684, 5686, 5688, 5690, 5692, 5694, 5696, 5698, 5700, 5702,
5704, 5706, 5708, 5710, 5712, 5714, 5716, 5718, 5720, 5722,
5724, 5726, 5728, 5730, 5732, 5734, 5736, 5738, 5740, 5742,
5744, 5746, 5748, 5750, 5752, 5754, 5756, 5758, 5760, 5762,
5764, 5766, 5768, 5770, 5772, 5774, 5776, 5778, 5780, 5782,
5784, 5786, 5788, 5790, 5792, 5794, 5796, 5798, 5800, 5802,
5804, 5806, 5808, 5810, 5812, 5814, 5816, 5818, 5820, 5822,
5824, 5826, 5828, 5830, 5832, 5834, 5836, 5838, 5840, 5842,
5844, 5846, 5848, 5850, 5852, 5854, 5856, 5858, 5860, 5862,
5864, 5866, 5868, 5870, 5872, 5874, 5876, 5878, 5880, 5882,
5884, 5886, 5888, 5890, 5892, 5894, 5896, 5898, 5900, 5902,
5904, 5906, 5908, 5910, 5912, 5914, 5916, 5918, 5920, 5922,
5924, 5926, 5928, 5930, 5932, 5934, 5936, 5938, 5940, 5942,
5944, 5946, 5948, 5950, 5952, 5954, 5956, 5958, 5960, 5962,
5964, 5966, 5968, 5970, 5972, 5974, 5976, 5978, 5980, 5982,
5984, 5986, 5988, 5990, 5992, 5994, 5996, 5998, 6000, 6002,
6004, 6006, 6008, 6010, 6012, 6014, 6016, 6018, 6020, 6022,
6024, 6026, 6028, 6030, 6032, 6034, 6036, 6038, 6040, 6042,
6044, 6046, 6048, 6050, 6052, 6054, 6056, 6058, 6060, 6062, 6064, 6066, 6068, 6070, 6072, 6074, 6076, 6078, 6080, 6082,
6084, 6086, 6088, 6090, 6092, 6094, 6096, 6098, 6100, 6102,
6104, 6106, 6108, 6110, 6112, 6114, 6116, 6118, 6120, 6122,
6124, 6126, 6128, 6130, 6132, 6134, 6136, 6138, 6140, 6142,
6144, 6146, 6148, 6150, 6152, 6154, 6156, 6158, 6160, 6162,
6164, 6166, 6168, 6170, 6172, 6174, 6176, 6178, 6180, 6182,
6184, 6186, 6188, 6190, 6192, 6194, 6196, 6198, 6200, 6202,
6204, 6206, 6208, 6210, 6212, 6214, 6216, 6218, 6220, 6222,
6224, 6226, 6228, 6230, 6232, 6234, 6236, 6238, 6240, 6242,
6244, 6246, 6248, 6250, 6252, 6254, 6256, 6258, 6260, 6262,
6264, 6266, 6268, 6270, 6272, 6274, 6276, 6278, 6280, 6282,
6284, 6286, 6288, 6290, 6292, 6294, 6296, 6298, 6300, 6302,
6304, 6306, 6308, 6310, 6312, 6314, 6316, 6318, 6320, 6322,
6324, 6326, 6328, 6330, 6332, 6334, 6336, 6338, 6340, 6342,
6344, 6346, 6348, 6350, 6352, 6354, 6356, 6358, 6360, 6362,
6364, 6366, 6368, 6370, 6372, 6374, 6376, 6378, 6380, 6382,
6384, 6386, 6388, 6390, 6392, 6394, 6396, 6398, 6400, 6402,
6404, 6406, 6408, 6410, 6412, 6414, 6416, 6418, 6420, 6422,
6424, 6426, 6428, 6430, 6432, 6434, 6436, 6438, 6440, 6442,
6444, 6446, 6448, 6450, 6452, 6454, 6456, 6458, 6460, 6462,
6464, 6466, 6468, 6470, 6472, 6474, 6476, 6478, 6480, 6482,
6484, 6486, 6488, 6490, 6492, 6494, 6496, 6498, 6500, 6502,
6504, 6506, 6508, 6510, 6512, 6514, 6516, 6518, 6520, 6522,
6524, 6526, 6528, 6530, 6532, 6534, 6536, 6538, 6540, 6542,
6544, 6546, 6548, 6550, 6552, 6554, 6556, 6558, 6560, 6562,
6564, 6566, 6568, 6570, 6572, 6574, 6576, 6578, 6580, 6582,
6584, 6586, 6588, 6590, 6592, 6594, 6596, 6598, 6600, 6602,
6604, 6606, 6608, 6610, 6612, 6614, 6616, 6618, 6620, 6622,
6624, 6626, 6628, 6630, 6632, 6634, 6636, 6638, 6640, 6642,
6644, 6646, 6648, 6650, 6652, 6654, 6656, 6658, 6660, 6662,
6664, 6666, 6668, 6670, 6672, 6674, 6676, 6678, 6680, 6682,
6684, 6686, 6688, 6690, 6692, 6694, 6696, 6698, 6700, 6702,
6704, 6706, 6708, 6710, 6712, 6714, 6716, 6718, 6720, 6722,
6724, 6726, 6728, 6730, 6732, 6734, 6736, 6738, 6740, 6742,
6744, 6746, 6748, 6750, 6752, 6754, 6756, 6758, 6760, 6762,
6764, 6766, 6768, 6770, 6772, 6774, 6776, 6778, 6780, 6782,
6784, 6786, 6788, 6790, 6792, 6794, 6796, 6798, 6800, 6802,
6804, 6806, 6808, 6810, 6812, 6814, 6816, 6818, 6820, 6822,
6824, 6826, 6828, 6830, 6832, 6834, 6836, 6838, 6840, 6842,
6844, 6846, 6848, 6850, 6852, 6854, 6856, 6858, 6860, 6862,
6864, 6866, 6868, 6870, 6872, 6874, 6876, 6878, 6880, 6882,
6884, 6886, 6888, 6890, 6892, 6894, 6896, 6898, 6900, 6902,
6904, 6906, 6908, 6910, 6912, 6914, 6916, 6918, 6920, 6922,
6924, 6926, 6928, 6930, 6932, 6934, 6936, 6938, 6940, 6942,
6944, 6946, 6948, 6950, 6952, 6954, 6956, 6958, 6960, 6962,
6964, 6966, 6968, 6970, 6972, 6974, 6976, 6978, 6980, 6982,
6984, 6986, 6988, 6990, 6992, 6994, 6996, 6998, 7000, 7002,
7004, 7006, 7008, 7010, 7012, 7014, 7016, 7018, 7020, 7022,
7024, 7026, 7028, 7030, 7032, 7034, 7036, 7038, 7040, 7042,
7044, 7046, 7048, 7050, 7052, 7054, 7056, 7058, 7060, 7062,
7064, 7066, 7068, 7070, 7072, 7074, 7076, 7078, 7080, 7082,
7084, 7086, 7088, 7090, 7092, 7094, 7096, 7098, 7100, 7102,
7104, 7106, 7108, 7110, 7112, 7114, 7116, 7118, 7120, 7122,
7124, 7126, 7128, 7130, 7132, 7134, 7136, 7138, 7140, 7142,
7144, 7146, 7148, 7150, 7152, 7154, 7156, 7158, 7160, 7162,
7164, 7166, 7168, 7170, 7172, 7174, 7176, 7178, 7180, 7182,
7184, 7186, 7188, 7190, 7192, 7194, 7196, 7198, 7200, 7202,
7204, 7206, 7208, 7210, 7212, 7214, 7216, 7218, 7220, 7222,
7224, 7226, 7228, 7230, 7232, 7234, 7236, 7238, 7240, 7242,
7244, 7246, 7248, 7250, 7252, 7254, 7256, 7258, 7260, 7262,
7264, 7266, 7268, 7270, 7272, 7274, 7276, 7278, 7280, 7282,
7284, 7286, 7288, 7290, 7292, 7294, 7296, 7298, 7300, 7302,
7304, 7306, 7308, 7310, 7312, 7314, 7316, 7318, 7320, 7322,
7324, 7326, 7328, 7330, 7332, 7334, 7336, 7338, 7340, 7342,
7344, 7346, 7348, 7350, 7352, 7354, 7356, 7358, 7360, 7362,
7364, 7366, 7368, 7370, 7372, 7374, 7376, 7378, 7380, 7382,
7384, 7386, 7388, 7390, 7392, 7394, 7396, 7398, 7400, 7402,
7404, 7406, 7408, 7410, 7412, 7414, 7416, 7418, 7420, 7422,
7424, 7426, 7428, 7430, 7432, 7434, 7436, 7438, 7440, 7442,
7444, 7446, 7448, 7450, 7452, 7454, 7456, 7458, 7460, 7462,
7464, 7466, 7468, 7470, 7472, 7474, 7476, 7478, 7480, 7482,
7484, 7486, 7488, 7490, 7492, 7494, 7496, 7498, 7500, 7502,
7504, 7506, 7508, 7510, 7512, 7514, 7516, 7518, 7520, 7522,
7524, 7526, 7528, 7530, 7532, 7534, 7536, 7538, 7540, 7542,
7544, 7546, 7548, 7550, 7552, 7554, 7556, 7558, 7560, 7562,
7564, 7566, 7568, 7570, 7572, 7574, 7576, 7578, 7580, 7582,
7584, 7586, 7588, 7590, 7592, 7594, 7596, 7598, 7600, 7602,
7604, 7606, 7608, 7610, 7612, 7614, 7616, 7618, 7620, 7622,
7624, 7626, 7628, 7630, 7632, 7634, 7636, 7638, 7640, 7642,
7644, 7646, 7648, 7650, 7652, 7654, 7656, 7658, 7660, 7662,
7664, 7666, 7668, 7670, 7672, 7674, 7676, 7678, 7680, 7682,
7684, 7686, 7688, 7690, 7692, 7694, 7696, 7698, 7700, 7702,
7704, 7706, 7708, 7710, 7712, 7714, 7716, 7718, 7720, 7722,
7724, 7726, 7728, 7730, 7732, 7734, 7736, 7738, 7740, 7742,
7744, 7746, 7748, 7750, 7752, 7754, 7756, 7758, 7760, 7762,
7764, 7766, 7768, 7770, 7772, 7774, 7776, 7778, 7780, 7782,
7784, 7786, 7788, 7790, 7792, 7794, 7796, 7798, 7800, 7802,
7804, 7806, 7808, 7810, 7812, 7814, 7816, 7818, 7820, 7822,
7824, 7826, 7828, 7830, 7832, 7834, 7836, 7838, 7840, 7842,
7844, 7846, 7848, 7850, 7852, 7854, 7856, 7858, 7860, 7862,
7864, 7866, 7868, 7870, 7872, 7874, 7876, 7878, 7880, 7882,
7884, 7886, 7888, 7890, 7892, 7894, 7896, 7898, 7900, 7902,
7904, 7906, 7908, 7910, 7912, 7914, 7916, 7918, 7920, 7922,
7924, 7926, 7928, 7930, 7932, 7934, 7936, 7938, 7940, 7942,
7944, 7946, 7948, 7950, 7952, 7954, 7956, 7958, 7960, 7962,
7964, 7966, 7968, 7970, 7972, 7974, 7976, 7978, 7980, 7982,
7984, 7986, 7988, 7990, 7992, 7994, 7996, 7998, 8000, 8002,
8004, 8006, 8008, 8010, 8012, 8014, 8016, 8018, 8020, 8022,
8024, 8026, 8028, 8030, 8032, 8034, 8036, 8038, 8040, 8042,
8044, 8046, 8048, 8050, 8052, 8054, 8056, 8058, 8060, 8062,
8064, 8066, 8068, 8070, 8072, 8074, 8076, 8078, 8080, 8082,
8084, 8086, 8088, 8090, 8092, 8094, 8096, 8098, 8100, 8102,
8104, 8106, 8108, 8110, 8112, 8114, 8116, 8118, 8120, 8122,
8124, 8126, 8128, 8130, 8132, 8134, 8136, 8138, 8140, 8142,
8144, 8146, 8148, 8150, 8152, 8154, 8156, 8158, 8160, 8162,
8164, 8166, 8168, 8170, 8172, 8174, 8176, 8178, 8180, 8182,
8184, 8186, 8188, 8190, 8192, 8194, 8196, 8198, 8200, 8202,
8204, 8206, 8208, 8210, 8212, 8214, 8216, 8218, 8220, 8222,
8224, 8226, 8228, 8230, 8232, 8234, 8236, 8238, 8240, 8242,
8244, 8246, 8248, 8250, 8252, 8254, 8256, 8258, 8260, 8262,
8264, 8266, 8268, 8270, 8272, 8274, 8276, 8278, 8280, 8282,
8284, 8286, 8288, 8290, 8292, 8294, 8296, 8298, 8300, 8302,
8304, 8306, 8308, 8310, 8312, 8314, 8316, 8318, 8320, 8322,
8324, 8326, 8328, 8330, 8332, 8334, 8336, 8338, 8340, 8342,
8344, 8346, 8348, 8350, 8352, 8354, 8356, 8358, 8360, 8362,
8364, 8366, 8368, 8370, 8372, 8374, 8376, 8378, 8380, 8382,
8384, 8386, 8388, 8390, 8392, 8394, 8396, 8398, 8400, 8402,
8404, 8406, 8408, 8410, 8412, 8414, 8416, 8418, 8420, 8422,
8424, 8426, 8428, 8430, 8432, 8434, 8436, 8438, 8440, 8442,
8444, 8446, 8448, 8450, 8452, 8454, 8456, 8458, 8460, 8462,
8464, 8466, 8468, 8470, 8472, 8474, 8476, 8478, 8480, 8482,
8484, 8486, 8488, 8490, 8492, 8494, 8496, 8498, 8500, 8502,
8504, 8506, 8508, 8510, 8512, 8514, 8516, 8518, 8520, 8522,
8524, 8526, 8528, 8530, 8532, 8534, 8536, 8538, 8540, 8542,
8544, 8546, 8548, 8550, 8552, 8554, 8556, 8558, 8560, 8562,
8564, 8566, 8568, 8570, 8572, 8574, 8576, 8578, 8580, 8582,
8584, 8586, 8588, 8590, 8592, 8594, 8596, 8598, 8600, 8602,
8604, 8606, 8608, 8610, 8612, 8614, 8616, 8618, 8620, 8622,
8624, 8626, 8628, 8630, 8632, 8634, 8636, 8638, 8640, 8642,
8644, 8646, 8648, 8650, 8652, 8654, 8656, 8658, 8660, 8662,
8664, 8666, 8668, 8670, 8672, 8674, 8676, 8678, 8680, 8682,
8684, 8686, 8688, 8690, 8692, 8694, 8696, 8698, 8700, 8702,
8704, 8706, 8708, 8710, 8712, 8714, 8716, 8718, 8720, 8722,
8724, 8726, 8728, 8730, 8732, 8734, 8736, 8738, 8740, 8742, 8744, 8746, 8748, 8750, 8752, 8754, 8756, 8758, 8760, 8762, 8764, 8766, 8768, 8770, 8772, 8774, 8776, 8778, 8780, 8782, 8784, 8786, 8788, 8790, 8792, 8794, 8796, 8798, 8800, 8802, 8804, 8806, 8808, 8810, 8812, 8814, 8816, 8818, 8820, 8822, 8824, 8826, 8828, 8830, 8832, 8834, 8836, 8838, 8840, 8842, 8844, 8846, 8848, 8850, 8852, 8854, 8856, 8858, 8860, 8862, 8864, 8866, 8868, 8870, 8872, 8874, 8876, 8878, 8880, 8882, 8884, 8886, 8888, 8890, 8892, 8894, 8896, 8898, 8900, 8902, 8904, 8906, 8908, 8910, 8912, 8914, 8916, 8918, 8920, 8922, 8924, 8926, 8928, 8930, 8932, 8934, 8936, 8938, 8940, 8942, 8944, 8946, 8988, 8950, 8952, 8954, 8956, 8958, 8960, 8962, 8964, 8966, 8968, 8970, 8972, 8974, 8976, 8978, 8980, 8982, 8984, 8986, 8988, 8990, 8992, 8994, 8996, 8998, 9000, 9002, 9004, 9006, 9008, 9010, 9012, 9014, 9016, 9018, 9020, 9022, 9024, 9026, 9028, 9030, 9032, 9034, 9036, 9038, 9040, 9042, 9044, 9046, 9048, 9050, 9052, 9054, 9056, 9058, 9060, 9062, 9064, 9066, 9068, 9070, 9072, 9074, 9076, 9078, 9080, 9082, 9084, 9086, 9088, 9090, 9092, 9094, 9096, 9098, 9100, 9102, 9104, 9106, 9108, 9110, 9112, 9114, 9116, 9118, 9120, 9122, 9124, 9126, 9128, 9130, 9132, 9134, 9136, 9138, 9140, 9142, 9144, 9146, 9148, 9150, 9152, 9154, 9156, 9158, 9160, 9162, 9164, 9166, 9168, 9170, 9172, 9174, 9176, 9178, 9180, 9182, 9184, 9186, 9188, 9190, 9192, 9194, 9196, 9198, 9200, 9202, 9204, 9206, 9208, 9210, 9212, 9214, 9216, 9218, 9220, 9222, 9224, 9226, 9228, 9230, 9232, 9234, 9236, 9238, 9240, 9242, 9244, 9246, 9248, 9250, 9252, 9254, 9256, 9258, 9260, 9262, 9264, 9266, 9268, 9270, 9272, 9274, 9276, 9278, 9280, 9282, 9284, 9286, 9288, 9290, 9292, 9294, 9296, 9298, 9300, 9302, 9304, 9306, 9308, 9310, 9312, 9314, 9316, 9318, 9320, 9322, 9324, 9326, 9328, 9330, 9332, 9334, 9336, 9338, 9340, 9342, 9344, 9346, 9348, 9350, 9352, 9354, 9356, 9358, 9360, 9362, 9364, 9366, 9368, 9370, 9372, 9374, 9376, 9378, 9380, 9382, 9384, 9386, 9388, 9390, 9392, 9394, 9396, 9398, 9400, 9402, 9404, 9406, 9408, 9410, 9412, 9414, 9416, 9418, 9420, 9422, 9424, 9426, 9428, 9430, 9432, 9434, 9436, 9438, 9440, 9442, 9444, 9446, 9448, 9450, 9452, 9454, 9456, 9458, 9460, 9462, 9464, 9466, 9468, 9470, 9472, 9474, 9476, 9478, 9480, 9482, 9484, 9486, 9488, 9490, 9492, 9494, 9496, 9498, 9500, 9502, 9504, 9506, 9508, 9510, 9512, 9514, 9516, 9518, 9520, 9522, 9524, 9526, 9528, 9530, 9532, 9534, 9536, 9538, 9540, 9542, 9544, 9546, 9548, 9550, 9552, 9554, 9556, 9558, 9560, 9562, 9564, 9566, 9568, 9570, 9572, 9574, 9576, 9578, 9580, 9582, 9584, 9586, 9588, 9590, 9592, 9594, 9596, 9598, 9600, 9602, 9604, 9606, 9608, 9610, 9612, 9614, 9616, 9618, 9620, 9622, 9624, 9626, 9628, 9630, 9632, 9634, 9636, 9638, 9640, 9642, 9644, 9646, 9648, 9650, 9652, 9654, 9656, 9658, 9660, 9662, 9664, 9666, 9668, 9670, 9672, 9674, 9676, 9678, 9680, 9682, 9684, 9686, 9688, 9690, 9692, 9694, 9696, 9698, 9700, 9702, 9704, 9706, 9708, 9710, 9712, 9714, 9716, 9718, 9720, 9722, 9724, 9726, 9728, 9730, 9732, 9734, 9736, 9738, 9740, 9742, 9744, 9746, 9748, 9750, 9752, 9754, 9756, 9758, 9760, 9762, 9764, 9766, 9768, 9770, 9772, 9774, 9776, 9778, 9780, 9782, 9784, 9786, 9788, 9790, 9792, 9794, 9796, 9798, 9800, 9802, 9804, 9806, 9808, 9810, 9812, 9814, 9816, 9818, 9820, 9822, 9824, 9826, 9828, 9830, 9832, 9834, 9836, 9838, 9840, 9842, 9844, 9846, 9848, 9850, 9852, 9854, 9856, 9858, 9860, 9862, 9864, 9866, 9868, 9870, 9872, 9874, 9876, 9878, 9880, 9882, 9884, 9886, 9888, 9890, 9892, 9894, 9896, 9898, 9900, 9902, 9904, 9906, 9908, 9910, 9912, 9914, 9916, 9918, 9920, 9922, 9924, 9926, 9928, 9930, 9932, 9934, 9936, 9938, 9940, 9942, 9944, 9946, 9948, 9950, 9952, 9954, 9956, 9958, 9960, 9962, 9964, 9966, 9968, 9970, 9972, 9974, 9976, 9978, 9980, 9982, 9984, 9986, 9988, 9990; (b) an amino acid sequence having at least 80% sequence identity to an amino acid sequence of (a); (c) an amino acid sequence which is a fragment of at least 10 consecutive amino acids from an amino acid sequence of (a); or (d) an amino acid sequence having at least 80% sequence identity to an amino acid sequence of (a) and including a fragment of at least 10 consecutive amino acids from an amino acid sequence of (a). In a particular embodiment, the polypeptides of this aspect of the invention comprise a fragment which comprises at least one B-cell epitope of (a).

In a second aspect, the invention relates to a polypeptide comprising: (a) an amino acid sequence selected from the group consisting of SEQ ID NOs 512, 2454, 2456, 2678, 2692, 4596, 4748, 7004, 7052, 8168, 4628 and 5700; (b) an amino acid sequence having at least 80% sequence identity to an amino acid sequence of (a); (c) an amino acid sequence which is a fragment of at least 10 consecutive amino acids from an amino acid sequence of (a); or (d) an amino acid sequence having at least 80% sequence identity to an amino acid sequence of (a) and including a fragment of at least 10 consecutive amino acids from an amino acid sequence of (a). In a particular embodiment, the polypeptides of this aspect of the invention comprise a fragment which comprises at least one B-cell epitope of (a).

In another aspect, the invention relates to a polypeptide comprising: (a) an amino acid sequence selected from the group consisting of SEQ ID NOs 8564, 2728, 9872, 4672, 5680, 534, 3222, 3226 and 7004; (b) an amino acid sequence having at least 80% sequence identity to an amino acid sequence of (a); (c) an amino acid sequence which is a fragment of at least 10 consecutive amino acids from an amino acid sequence of (a); or (d) an amino acid sequence having at least 80% sequence identity to an amino acid sequence of (a) and including a fragment of at least 10 consecutive amino acids from an amino acid sequence of (a). In a particular embodiment, the polypeptides of this aspect of the invention comprise a fragment which comprises at least one B-cell epitope of (a).

The present invention also relates to a nucleic acid comprising: (a) a nucleotide sequence selected from the group consisting of SEQ ID NOs 705, 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 635, 637, 639, 641, 643, 645, 647, 649, 651, 653, 655, 657, 659, 661, 663, 665, 667, 669, 671, 673, 675, 677, 679, 681, 683, 685, 687, 689, 691, 693, 695, 697, 699, 701, 703, 707, 709, 711, 713, 715, 717, 719, 721, 723, 725, 727, 729, 731, 733, 735, 737, 739, 741, 743, 745, 747, 749, 751, 753, 755, 757, 759, 761, 763, 765, 767, 769, 771, 773, 775, 777, 779, 781, 783, 785, 787, 789, 791, 793, 795, 797, 799, 801, 803, 805, 807, 809, 811, 813, 815, 817, 819, 821, 823, 825, 827, 829, 831, 833, 835, 837, 839, 841, 843, 845, 847, 849, 851, 853, 855, 857, 859, 861, 863, 865, 867, 869, 871, 873, 875, 877, 879, 881, 883, 885, 887, 889, 891, 893, 895, 897, 899, 901, 903, 905, 907, 909, 911, 913, 915, 917, 919, 921, 923, 925, 927, 929, 931, 933, 935, 937, 939, 941, 943, 945, 947, 949, 951, 953, 955, 957, 959, 961, 963, 965, 967, 969, 971, 973, 975, 977, 979, 981, 983, 985, 987, 989, 991, 993, 995, 997, 999, 1001, 1003, 1005, 1007, 1009, 1011, 1013, 1015, 1017, 1019, 1021, 1023, 1025, 1027, 1029, 1031, 1033, 1035, 1037, 1039, 1041, 1043, 1045, 1047, 1049, 1051, 1053, 1055, 1057, 1059, 1061, 1063, 1065, 1067, 1069, 1071, 1073, 1075, 1077, 1079, 1081, 1083, 1085, 1087, 1089, 1091, 1093, 1095, 1097, 1099, 1101, 1103, 1105, 1107, 1109, 1111, 1113, 1115, 1117, 1119, 1121, 1123, 1125, 1127, 1129, 1131, 1133, 1135, 1137, 1139, 1141, 1143, 1145, 1147, 1149, 1151, 1153, 1155, 1157, 1159, 1161, 1163, 1165, 1167, 1169, 1171, 1173, 1175, 1177, 1179, 1181, 1183, 1185, 1187, 1189, 1191, 1193, 1195, 1197, 1199, 1201, 1203, 1205, 1207, 1209, 1211, 1213, 1215, 1217, 1219, 1221, 1223, 1225, 1227, 1229, 1231, 1233, 1235, 1237, 1239, 1241, 1243, 1245, 1247, 1249, 1251, 1253, 1255, 1257, 1259, 1261, 1263, 1265, 1267, 1269, 1271, 1273, 1275, 1277, 1279, 1281, 1283, 1285, 1287, 1289, 1291, 1293, 1295, 1297, 1299, 1301, 1303, 1305, 1307, 1309, 1311, 1313, 1315, 1317, 1319, 1321, 1323, 1325, 1327, 1329, 1331, 1333, 1335, 1337, 1339, 1341, 1343, 1345, 1347, 1349, 1351, 1353, 1355, 1357, 1359, 1361, 1363, 1365, 1367, 1369, 1371, 1373, 1375, 1377, 1379, 1381, 1383, 1385, 1387, 1389, 1391, 1393, 1395, 1397, 1399, 1401, 1403, 1405, 1407, 1409, 1411, 1413, 1415, 1417, 1419, 1421, 1423, 1425, 1427, 1429, 1431, 1433, 1435, 1437, 1439, 1441, 1443, 1445, 1447, 1449, 1451, 1453, 1455, 1457, 1459, 1461, 1463, 1465, 1467, 1469, 1471, 1473, 1475, 1477, 1479, 1481, 1483, 1485, 1487, 1489, 1491, 1493, 1495, 1497, 1499, 1501, 1503, 1505, 1507, 1509, 1511, 1513, 1515, 1517, 1519, 1521, 1523, 1525, 1527, 1529, 1531, 1533, 1535, 1537, 1539, 1541, 1543, 1545, 1547, 1549, 1551, 1553, 1555, 1557, 1559, 1561, 1563, 1565, 1567, 1569, 1571, 1573, 1575, 1577, 1579, 1581, 1583, 1585, 1587, 1589, 1591, 1593, 1595, 1597, 1599, 1601, 1603, 1605, 1607, 1609, 1611, 1613, 1615, 1617, 1619, 1621, 1623, 1625, 1627, 1629, 1631, 1633, 1635, 1637, 1639, 1641, 1643, 1645, 1647, 1649, 1651, 1653, 1655, 1657, 1659, 1661, 1663, 1665, 1667, 1669, 1671, 1673, 1675, 1677, 1679, 1681, 1683, 1685, 1687, 1689, 1691, 1693, 1695, 1697, 1699, 1701, 1703, 1705, 1707, 1709, 1711, 1713, 1715, 1717, 1719, 1721, 1723, 1725, 1727, 1729, 1731, 1733, 1735, 1737, 1739, 1741, 1743, 1745, 1747, 1749, 1751, 1753, 1755, 1757, 1759, 1761, 1763, 1765, 1767, 1769, 1771, 1773, 1775, 1777, 1779, 1781, 1783, 1785, 1787, 1789, 1791, 1793, 1795, 1797, 1799, 1801, 1803, 1805, 1807, 1809, 1811, 1813, 1815, 1817, 1819, 1821, 1823, 1825, 1827, 1829, 1831, 1833, 1835, 1837, 1839, 1841, 1843, 1845, 1847, 1849, 1851, 1853, 1855, 1857, 1859, 1861, 1863, 1865, 1867, 1869, 1871, 1873, 1875, 1877, 1879, 1881, 1883, 1885, 1887, 1889, 1891, 1893, 1895, 1897, 1899, 1901, 1903, 1905, 1907, 1909, 1911, 1913, 1915, 1917, 1919, 1921, 1923, 1925, 1927, 1929, 1931, 1933, 1935, 1937, 1939, 1941, 1943, 1945, 1947, 1949, 1951, 1953, 1955, 1957, 1959, 1961, 1963, 1965, 1967, 1969, 1971, 1973, 1975, 1977, 1979, 1981, 1983, 1985, 1987, 1989, 1991, 1993, 1995, 1997, 1999, 2001, 2003, 2005, 2007, 2009, 2011, 2013, 2015, 2017, 2019, 2021, 2023, 2025, 2027, 2029, 2031, 2033, 2035, 2037, 2039, 2041, 2043, 2045, 2047, 2049, 2051, 2053, 2055, 2057, 2059, 2061, 2063, 2065, 2067, 2069, 2071, 2073, 2075, 2077, 2079, 2081, 2083, 2085, 2087, 2089, 2091, 2093, 2095, 2097, 2099, 2101, 2103, 2105, 2107, 2109, 2111, 2113, 2115, 2117, 2119, 2121, 2123, 2125, 2127, 2129, 2131, 2133, 2135, 2137, 2139, 2141, 2143, 2145, 2147, 2149, 2151, 2153, 2155, 2157, 2159, 2161, 2163, 2165, 2167, 2169, 2171, 2173, 2175, 2177, 2179, 2181, 2183, 2185, 2187, 2189, 2191, 2193, 2195, 2197, 2199, 2201, 2203, 2205, 2207, 2209, 2211, 2213, 2215, 2217, 2219, 2221, 2223, 2225, 2227, 2229, 2231, 2233, 2235, 2237, 2239, 2241, 2243, 2245, 2247, 2249, 2251, 2253, 2255, 2257, 2259, 2261, 2263, 2265, 2267, 2269, 2271, 2273, 2275, 2277, 2279, 2281, 2283, 2285, 2287, 2289, 2291, 2293, 2295, 2297, 2299, 2301, 2303, 2305, 2307, 2309, 2311, 2313, 2315, 2317, 2319, 2321, 2323, 2325, 2327, 2329, 2331, 2333, 2335, 2337, 2339, 2341, 2343, 2345, 2347, 2349, 2351, 2353, 2355, 2357, 2359, 2361, 2363, 2365, 2367, 2369, 2371, 2373, 2375, 2377, 2379, 2381, 2383, 2385, 2387, 2389, 2391, 2393, 2395, 2397, 2399, 2401, 2403, 2405, 2407, 2409, 2411, 2413, 2415, 2417, 2419, 2421, 2423, 2425, 2427, 2429, 2431, 2433, 2435, 2437, 2439, 2441, 2443, 2445, 2447, 2449, 2451, 2453, 2455, 2457, 2459, 2461, 2463, 2465, 2467, 2469, 2471, 2473, 2475, 2477, 2479, 2481, 2483, 2485, 2487, 2489, 2491, 2493, 2495, 2497, 2499, 2501, 2503, 2505, 2507, 2509, 2511, 2513, 2515, 2517, 2519, 2521, 2523, 2525, 2527, 2529, 2531, 2533, 2535, 2537, 2539, 2541, 2543, 2545, 2547, 2549, 2551, 2553, 2555, 2557, 2559, 2561, 2563, 2565, 2567, 2569, 2571, 2573, 2575, 2577, 2579, 2581, 2583, 2585, 2587, 2589, 2591, 2593, 2595, 2597, 2599, 2601, 2603, 2605, 2607, 2609, 2611, 2613, 2615, 2617, 2619, 2621, 2623, 2625, 2627, 2629, 2631, 2633, 2635, 2637, 2639, 2641, 2643, 2645, 2647, 2649, 2651, 2653, 2655, 2657, 2659, 2661, 2663, 2665, 2667, 2669, 2671, 2673, 2675, 2677, 2679, 2681, 2683, 2685, 2687, 2689, 2691, 2693, 2695, 2697, 2699, 2701, 2703, 2705, 2707, 2709, 2711, 2713, 2715, 2717, 2719, 2721, 2723, 2725, 2727, 2729, 2731, 2733, 2735, 2737, 2739, 2741, 2743, 2745, 2747, 2749, 2751, 2753, 2755, 2757, 2759, 2761, 2763, 2765, 2767, 2769, 2771, 2773, 2775, 2777, 2779, 2781, 2783, 2785, 2787, 2789, 2791, 2793, 2795, 2797, 2799, 2801, 2803, 2805, 2807, 2809, 2811, 2813, 2815, 2817, 2819, 2821, 2823, 2825, 2827, 2829, 2831, 2833, 2835, 2837, 2839, 2841, 2843, 2845, 2847, 2849, 2851, 2853, 2855, 2857, 2859, 2861, 2863, 2865, 2867, 2869, 2871, 2873, 2875, 2877, 2879, 2881, 2883, 2885, 2887, 2889, 2891, 2893, 2895, 2897, 2899, 2901, 2903, 2905, 2907, 2909, 2911, 2913, 2915, 2917, 2919, 2921, 2923, 2925, 2927, 2929, 2931, 2933, 2935, 2937, 2939, 2941, 2943, 2945, 2947, 2949, 2951, 2953, 2955, 2957, 2959, 2961, 2963, 2965, 2967, 2969, 2971, 2973, 2975, 2977, 2979, 2981, 2983, 2985, 2987, 2989, 2991, 2993, 2995, 2997, 2999, 3001, 3003, 3005, 3007, 3009, 3011, 3013, 3015, 3017, 3019, 3021, 3023, 3025, 3027, 3029, 3031, 3033, 3035, 3037, 3039, 3041, 3043, 3045, 3047, 3049, 3051, 3053, 3055, 3057, 3059, 3061, 3063, 3065, 3067, 3069, 3071, 3073, 3075, 3077, 3079, 3081, 3083, 3085, 3087, 3089, 3091, 3093, 3095, 3097, 3099, 3101, 3103, 3105, 3107, 3109, 3111, 3113, 3115, 3117, 3119, 3121, 3123, 3125, 3127, 3129, 3131, 3133, 3135, 3137, 3139, 3141, 3143, 3145, 3147, 3149, 3151, 3153, 3155, 3157, 3159, 3161, 3163, 3165, 3167, 3169, 3171, 3173, 3175, 3177, 3179, 3181, 3183, 3185, 3187, 3189, 3191, 3193, 3195, 3197, 3199, 3201, 3203, 3205, 3207, 3209, 3211, 3213, 3215, 3217, 3219, 3221, 3223, 3225, 3227, 3229, 3231, 3233, 3235, 3237, 3239, 3241, 3243, 3245, 3247, 3249, 3251, 3253, 3255, 3257, 3259, 3261, 3263, 3265, 3267, 3269, 3271, 3273, 3275, 3277, 3279, 3281, 3283, 3285, 3287, 3289, 3291, 3293, 3295, 3297, 3299, 3301, 3303, 3305, 3307, 3309, 3311, 3313, 3315, 3317, 3319, 3321, 3323, 3325, 3327, 3329, 3331, 3333, 3335, 3337, 3339, 3341, 3343, 3345, 3347, 3349, 3351, 3353, 3355, 3357, 3359, 3361, 3363, 3365, 3367, 3369, 3371, 3373, 3375, 3377, 3379, 3381, 3383, 3385, 3387, 3389, 3391, 3393, 3395, 3397, 3399, 3401, 3403, 3405, 3407, 3409, 3411, 3413, 3415, 3417, 3419, 3421, 3423, 3425, 3427, 3429, 3431, 3433, 3435, 3437, 3439, 3441, 3443, 3445, 3447, 3449, 3451, 3453, 3455, 3457, 3459, 3461, 3463, 3465, 3467, 3469, 3471, 3473, 3475, 3477, 3479, 3481, 3483, 3485, 3487, 3489, 3491, 3493, 3495, 3497, 3499, 3501, 3503, 3505, 3507, 3509, 3511, 3513, 3515, 3517, 3519, 3521, 3523, 3525, 3527, 3529, 3531, 3533, 3535, 3537, 3539, 3541, 3543, 3545, 3547, 3549, 3551, 3553, 3555, 3557, 3559, 3561, 3563, 3565, 3567, 3569, 3571, 3573, 3575, 3577, 3579, 3581, 3583, 3585, 3587, 3589, 3591, 3593, 3595, 3597, 3599, 3601, 3603, 3605, 3607, 3609, 3611, 3613, 3615, 3617, 3619, 3621, 3623, 3625, 3627, 3629, 3631, 3633, 3635, 3637, 3639, 3641, 3643, 3645, 3647, 3649, 3651, 3653, 3655, 3657, 3659, 3661, 3663, 3665, 3667, 3669, 3671, 3673, 3675, 3677, 3679, 3681, 3683, 3685, 3687, 3689, 3691, 3693, 3695, 3697, 3699, 3701, 3703, 3705, 3707, 3709, 3711, 3713, 3715, 3717, 3719, 3721, 3723, 3725, 3727, 3729, 3731, 3733, 3735, 3737, 3739, 3741, 3743, 3745, 3747, 3749, 3751, 3753, 3755, 3757, 3759, 3761, 3763, 3765, 3767, 3769, 3771, 3773, 3775, 3777, 3779, 3781, 3783, 3785, 3787, 3789, 3791, 3793, 3795, 3797, 3799, 3801, 3803, 3805, 3807, 3809, 3811, 3813, 3815, 3817, 3819, 3821, 3823, 3825, 3827, 3829, 3831, 3833, 3835, 3837, 3839, 3841, 3843, 3845, 3847, 3849, 3851, 3853, 3855, 3857, 3859, 3861, 3863, 3865, 3867, 3869, 3871, 3873, 3875, 3877, 3879, 3881, 3883, 3885, 3887, 3889, 3891, 3893, 3895, 3897, 3899, 3901, 3903, 3905, 3907, 3909, 3911, 3913, 3915, 3917, 3919, 3921, 3923, 3925, 3927, 3929, 3931, 3933, 3935, 3937, 3939, 3941, 3943, 3945, 3947, 3949, 3951, 3953, 3955, 3957, 3959, 3961, 3963, 3965, 3967, 3969, 3971, 3973, 3975, 3977, 3979, 3981, 3983, 3985, 3987, 3989, 3991, 3993, 3995, 3997, 3999, 4001, 4003, 4005, 4007, 4009, 4011, 4013, 4015, 4017, 4019, 4021, 4023, 4025, 4027, 4029, 4031, 4033, 4035, 4037, 4039, 4041, 4043, 4045, 4047, 4049, 4051, 4053, 4055, 4057, 4059, 4061, 4063, 4065, 4067, 4069, 4071, 4073, 4075, 4077, 4079, 4081, 4083, 4085, 4087, 4089, 4091, 4093, 4095, 4097, 4099, 4101, 4103, 4105, 4107, 4109, 4111, 4113, 4115, 4117, 4119, 4121, 4123, 4125, 4127, 4129, 4131, 4133, 4135, 4137, 4139, 4141, 4143, 4145, 4147, 4149, 4151, 4153, 4155, 4157, 4159, 4161, 4163, 4165, 4167, 4169, 4171, 4173, 4175, 4177, 4179, 4181, 4183, 4185, 4187, 4189, 4191, 4193, 4195, 4197, 4199, 4201, 4203, 4205, 4207, 4209, 4211, 4213, 4215, 4217, 4219, 4221, 4223, 4225, 4227, 4229, 4231, 4233, 4235, 4237, 4239, 4241, 4243, 4245, 4247, 4249, 4251, 4253, 4255, 4257, 4259, 4261, 4263, 4265, 4267, 4269, 4271, 4273, 4275, 4277, 4279, 4281, 4283, 4285, 4287, 4289, 4291, 4293, 4295, 4297, 4299, 4301, 4303, 4305, 4307, 4309, 4311, 4313, 4315, 4317, 4319, 4321, 4323, 4325, 4327, 4329, 4331, 4333, 4335, 4337, 4339, 4341, 4343, 4345, 4347, 4349, 4351, 4353, 4355, 4357, 4359, 4361, 4363, 4365, 4367, 4369, 4371, 4373, 4375, 4377, 4379, 4381, 4383, 4385, 4387, 4389, 4391, 4393, 4395, 4397, 4399, 4401, 4403, 4405, 4407, 4409, 4411, 4413, 4415, 4417, 4419, 4421, 4423, 4425, 4427, 4429, 4431, 4433, 4435, 4437, 4439, 4441, 4443, 4445, 4447, 4449, 4451, 4453, 4455, 4457, 4459, 4461, 4463, 4465, 4467, 4469, 4471, 4473, 4475, 4477, 4479, 4481, 4483, 4485, 4487, 4489, 4491, 4493, 4495, 4497, 4499, 4501, 4503, 4505, 4507, 4509, 4511, 4513, 4515, 4517, 4519, 4521, 4523, 4525, 4527, 4529, 4531, 4533, 4535, 4537, 4539, 4541, 4543, 4545, 4547, 4549, 4551, 4553, 4555, 4557, 4559, 4561, 4563, 4565, 4567, 4569, 4571, 4573, 4575, 4577, 4579, 4581, 4583, 4585, 4587, 4589, 4591, 4593, 4595, 4597, 4599, 4601, 4603, 4605, 4607, 4609, 4611, 4613, 4615, 4617, 4619, 4621, 4623, 4625, 4627, 4629, 4631, 4633, 4635, 4637, 4639, 4641, 4643, 4645, 4647, 4649, 4651, 4653, 4655, 4657, 4659, 4661, 4663, 4665, 4667, 4669, 4671, 4673, 4675, 4677, 4679, 4681, 4683, 4685, 4687, 4689, 4691, 4693, 4695, 4697, 4699, 4701, 4703, 4705, 4707, 4709, 4711, 4713, 4715, 4717, 4719, 4721, 4723, 4725, 4727, 4729, 4731, 4733, 4735, 4737, 4739, 4741, 4743, 4745, 4747, 4749, 4751, 4753, 4755, 4757, 4759, 4761, 4763, 4765, 4767, 4769, 4771, 4773, 4775, 4777, 4779, 4781, 4783, 4785, 4787, 4789, 4791, 4793, 4795, 4797, 4799, 4801, 4803, 4805, 4807, 4809, 4811, 4813, 4815, 4817, 4819, 4821, 4823, 4825, 4827, 4829, 4831, 4833, 4835, 4837, 4839, 4841, 4843, 4845, 4847, 4849, 4851, 4853, 4855, 4857, 4859, 4861, 4863, 4865, 4867, 4869, 4871, 4873, 4875, 4877, 4879, 4881, 4883, 4885, 4887, 4889, 4891, 4893, 4895, 4897, 4899, 4901, 4903, 4905, 4907, 4909, 4911, 4913, 4915, 4917, 4919, 4921, 4923, 4925, 4927, 4929, 4931, 4933, 4935, 4937, 4939, 4941, 4943, 4945, 4947, 4949, 4951, 4953, 4955, 4957, 4959, 4961, 4963, 4965, 4967, 4969, 4971, 4973, 4975, 4977, 4979, 4981, 4983, 4985, 4987, 4989, 4991, 4993, 4995, 4997, 4999, 5001, 5003, 5005, 5007, 5009, 5011, 5013, 5015, 5017, 5019, 5021, 5023, 5025, 5027, 5029, 5031, 5033, 5035, 5037, 5039, 5041, 5043, 5045, 5047, 5049, 5051, 5053, 5055, 5057, 5059, 5061, 5063, 5065, 5067, 5069, 5071, 5073, 5075, 5077, 5079, 5081, 5083, 5085, 5087, 5089, 5091, 5093, 5095, 5097, 5099, 5101, 5103, 5105, 5107, 5109, 5111, 5113, 5115, 5117, 5119, 5121, 5123, 5125, 5127, 5129, 5131, 5133, 5135, 5137, 5139, 5141, 5143, 5145, 5147, 5149, 5151, 5153, 5155, 5157, 5159, 5161, 5163, 5165, 5167, 5169, 5171, 5173, 5175, 5177, 5179, 5181, 5183, 5185, 5187, 5189, 5191, 5193, 5195, 5197, 5199, 5201, 5203, 5205, 5207, 5209, 5211, 5213, 5215, 5217, 5219, 5221, 5223, 5225, 5227, 5229, 5231, 5233, 5235, 5237, 5239, 5241, 5243, 5245, 5247, 5249, 5251, 5253, 5255, 5257, 5259, 5261, 5263, 5265, 5267, 5269, 5271, 5273, 5275, 5277, 5279, 5281, 5283, 5285, 5287, 5289, 5291, 5293, 5295, 5297, 5299, 5301, 5303, 5305, 5307, 5309, 5311, 5313, 5315, 5317, 5319, 5321, 5323, 5325, 5327, 5329, 5331, 5333, 5335, 5337, 5339, 5341, 5343, 5345, 5347, 5349, 5351, 5353, 5355, 5357, 5359, 5361, 5363, 5365, 5367, 5369, 5371, 5373, 5375, 5377, 5379, 5381, 5383, 5385, 5387, 5389, 5391, 5393, 5395, 5397, 5399, 5401, 5403, 5405, 5407, 5409, 5411, 5413, 5415, 5417, 5419, 5421, 5423, 5425, 5427, 5429, 5431, 5433, 5435, 5437, 5439, 5441, 5443, 5445, 5447, 5449, 5451, 5453, 5455, 5457, 5459, 5461, 5463, 5465, 5467, 5469, 5471, 5473, 5475, 5477, 5479, 5481, 5483, 5485, 5487, 5489, 5491, 5493, 5495, 5497, 5499, 5501, 5503, 5505, 5507, 5509, 5511, 5513, 5515, 5517, 5519, 5521, 5523, 5525, 5527, 5529, 5531, 5533, 5535, 5537, 5539, 5541, 5543, 5545, 5547, 5549, 5551, 5553, 5555, 5557, 5559, 5561, 5563, 5565, 5567, 5569, 5571, 5573, 5575, 5577, 5579, 5581, 5583, 5585, 5587, 5589, 5591, 5593, 5595, 5597, 5599, 5601, 5603, 5605, 5607, 5609, 5611, 5613, 5615, 5617, 5619, 5621, 5623, 5625, 5627, 5629, 5631, 5633, 5635, 5637, 5639, 5641, 5643, 5645, 5647, 5649, 5651, 5653, 5655, 5657, 5659, 5661, 5663, 5665, 5667, 5669, 5671, 5673, 5675, 5677, 5679, 5681, 5683, 5685, 5687, 5689, 5691, 5693, 5695, 5697, 5699, 5701, 5703, 5705, 5707, 5709, 5711, 5713, 5715, 5717, 5719, 5721, 5723, 5725, 5727, 5729, 5731, 5733, 5735, 5737, 5739, 5741, 5743, 5745, 5747, 5749, 5751, 5753, 5755, 5757, 5759, 5761, 5763, 5765, 5767, 5769, 5771, 5773, 5775, 5777, 5779, 5781, 5783, 5785, 5787, 5789, 5791, 5793, 5795, 5797, 5799, 5801, 5803, 5805, 5807, 5809, 5811, 5813, 5815, 5817, 5819, 5821, 5823, 5825, 5827, 5829, 5831, 5833, 5835, 5837, 5839, 5841, 5843, 5845, 5847, 5849, 5851, 5853, 5855, 5857, 5859, 5861, 5863, 5865, 5867, 5869, 5871, 5873, 5875, 5877, 5879, 5881, 5883, 5885, 5887, 5889, 5891, 5893, 5895, 5897, 5899, 5901, 5903, 5905, 5907, 5909, 5911, 5913, 5915, 5917, 5919, 5921, 5923, 5925, 5927, 5929, 5931, 5933, 5935, 5937, 5939, 5941, 5943, 5945, 5947, 5949, 5951, 5953, 5955, 5957, 5959, 5961, 5963, 5965, 5967, 5969, 5971, 5973, 5975, 5977, 5979, 5981, 5983, 5985, 5987, 5989, 5991, 5993, 5995, 5997, 5999, 6001, 6003, 6005, 6007, 6009, 6011, 6013, 6015, 6017, 6019, 6021, 6023, 6025, 6027, 6029, 6031, 6033, 6035, 6037, 6039, 6041, 6043, 6045, 6047, 6049, 6051, 6053, 6055, 6057, 6059, 6061, 6063, 6065, 6067, 6069, 6071, 6073, 6075, 6077, 6079, 6081, 6083, 6085, 6087, 6089, 6091, 6093, 6095, 6097, 6099, 6101, 6103, 6105, 6107, 6109, 6111, 6113, 6115, 6117, 6119, 6121, 6123, 6125, 6127, 6129, 6131, 6133, 6135, 6137, 6139, 6141, 6143, 6145, 6147, 6149, 6151, 6153, 6155, 6157, 6159, 6161, 6163, 6165, 6167, 6169, 6171, 6173, 6175, 6177, 6179, 6181, 6183, 6185, 6187, 6189, 6191, 6193, 6195, 6197, 6199, 6201, 6203,
6205, 6207, 6209, 6211, 6213, 6215, 6217, 6219, 6221, 6223,
6225, 6227, 6229, 6231, 6233, 6235, 6237, 6239, 6241, 6243,
6245, 6247, 6249, 6251, 6253, 6255, 6257, 6259, 6261, 6263,
6265, 6267, 6269, 6271, 6273, 6275, 6277, 6279, 6281, 6283,
6285, 6287, 6289, 6291, 6293, 6295, 6297, 6299, 6301, 6303,
6305, 6307, 6309, 6311, 6313, 6315, 6317, 6319, 6321, 6323,
6325, 6327, 6329, 6331, 6333, 6335, 6337, 6339, 6341, 6343,
6345, 6347, 6349, 6351, 6353, 6355, 6357, 6359, 6361, 6363,
6365, 6367, 6369, 6371, 6373, 6375, 6377, 6379, 6381, 6383,
6385, 6387, 6389, 6391, 6393, 6395, 6397, 6399, 6401, 6403,
6405, 6407, 6409, 6411, 6413, 6415, 6417, 6419, 6421, 6423,
6425, 6427, 6429, 6431, 6433, 6435, 6437, 6439, 6441, 6443,
6445, 6447, 6449, 6451, 6453, 6455, 6457, 6459, 6461, 6463,
6465, 6467, 6469, 6471, 6473, 6475, 6477, 6479, 6481, 6483,
6485, 6487, 6489, 6491, 6493, 6495, 6497, 6499, 6501, 6503,
6505, 6507, 6509, 6511, 6513, 6515, 6517, 6519, 6521, 6523,
6525, 6527, 6529, 6531, 6533, 6535, 6537, 6539, 6541, 6543,
6545, 6547, 6549, 6551, 6553, 6555, 6557, 6559, 6561, 6563,
6565, 6567, 6569, 6571, 6573, 6575, 6577, 6579, 6581, 6583,
6585, 6587, 6589, 6591, 6593, 6595, 6597, 6599, 6601, 6603,
6605, 6607, 6609, 6611, 6613, 6615, 6617, 6619, 6621, 6623,
6625, 6627, 6629, 6631, 6633, 6635, 6637, 6639, 6641, 6643,
6645, 6647, 6649, 6651, 6653, 6655, 6657, 6659, 6661, 6663,
6665, 6667, 6669, 6671, 6673, 6675, 6677, 6679, 6681, 6683,
6685, 6687, 6689, 6691, 6693, 6695, 6697, 6699, 6701, 6703,
6705, 6707, 6709, 6711, 6713, 6715, 6717, 6719, 6721, 6723,
6725, 6727, 6729, 6731, 6733, 6735, 6737, 6739, 6741, 6743,
6745, 6747, 6749, 6751, 6753, 6755, 6757, 6759, 6761, 6763,
6765, 6767, 6769, 6771, 6773, 6775, 6777, 6779, 6781, 6783,
6785, 6787, 6789, 6791, 6793, 6795, 6797, 6799, 6801, 6803,
6805, 6807, 6809, 6811, 6813, 6815, 6817, 6819, 6821, 6823,
6825, 6827, 6829, 6831, 6833, 6835, 6837, 6839, 6841, 6843,
6845, 6847, 6849, 6851, 6853, 6855, 6857, 6859, 6861, 6863,
6865, 6867, 6869, 6871, 6873, 6875, 6877, 6879, 6881, 6883,
6885, 6887, 6889, 6891, 6893, 6895, 6897, 6899, 6901, 6903,
6905, 6907, 6909, 6911, 6913, 6915, 6917, 6919, 6921, 6923,
6925, 6927, 6929, 6931, 6933, 6935, 6937, 6939, 6941, 6943,
6945, 6947, 6949, 6951, 6953, 6955, 6957, 6959, 6961, 6963,
6965, 6967, 6969, 6971, 6973, 6975, 6977, 6979, 6981, 6983,
6985, 6987, 6989, 6991, 6993, 6995, 6997, 6999, 7001, 7003,
7005, 7007, 7009, 7011, 7013, 7015, 7017, 7019, 7021, 7023,
7025, 7027, 7029, 7031, 7033, 7035, 7037, 7039, 7041, 7043,
7045, 7047, 7049, 7051, 7053, 7055, 7057, 7059, 7061, 7063,
7065, 7067, 7069, 7071, 7073, 7075, 7077, 7079, 7081, 7083,
7085, 7087, 7089, 7091, 7093, 7095, 7097, 7099, 7101, 7103,
7105, 7107, 7109, 7111, 7113, 7115, 7117, 7119, 7121, 7123,
7125, 7127, 7129, 7131, 7133, 7135, 7137, 7139, 7141, 7143,
7145, 7147, 7149, 7151, 7153, 7155, 7157, 7159, 7161, 7163,
7165, 7167, 7169, 7171, 7173, 7175, 7177, 7179, 7181, 7183,
7185, 7187, 7189, 7191, 7193, 7195, 7197, 7199, 7201, 7203,
7205, 7207, 7209, 7211, 7213, 7215, 7217, 7219, 7221, 7223,
7225, 7227, 7229, 7231, 7233, 7235, 7237, 7239, 7241, 7243,
7245, 7247, 7249, 7251, 7253, 7255, 7257, 7259, 7261, 7263,
7265, 7267, 7269, 7271, 7273, 7275, 7277, 7279, 7281, 7283,
7285, 7287, 7289, 7291, 7293, 7295, 7297, 7299, 7301, 7303,
7305, 7307, 7309, 7311, 7313, 7315, 7317, 7319, 7321, 7323,
7325, 7327, 7329, 7331, 7333, 7335, 7337, 7339, 7341, 7343,
7345, 7347, 7349, 7351, 7353, 7355, 7357, 7359, 7361, 7363,
7365, 7367, 7369, 7371, 7373, 7375, 7377, 7379, 7381, 7383,
7385, 7387, 7389, 7391, 7393, 7395, 7397, 7399, 7401, 7403,
7405, 7407, 7409, 7411, 7413, 7415, 7417, 7419, 7421, 7423,
7425, 7427, 7429, 7431, 7433, 7435, 7437, 7439, 7441, 7443,
7445, 7447, 7449, 7451, 7453, 7455, 7457, 7459, 7461, 7463,
7465, 7467, 7469, 7471, 7473, 7475, 7477, 7479, 7481, 7483,
7485, 7487, 7489, 7491, 7493, 7495, 7497, 7499, 7501, 7503,
7505, 7507, 7509, 7511, 7513, 7515, 7517, 7519, 7521, 7523,
7525, 7527, 7529, 7531, 7533, 7535, 7537, 7539, 7541, 7543,
7545, 7547, 7549, 7551, 7553, 7555, 7557, 7559, 7561, 7563,
7565, 7567, 7569, 7571, 7573, 7575, 7577, 7579, 7581, 7583,
7585, 7587, 7589, 7591, 7593, 7595, 7597, 7599, 7601, 7603,
7605, 7607, 7609, 7611, 7613, 7615, 7617, 7619, 7621, 7623,
7625, 7627, 7629, 7631, 7633, 7635, 7637, 7639, 7641, 7643,
7645, 7647, 7649, 7651, 7653, 7655, 7657, 7659, 7661, 7663,
7665, 7667, 7669, 7671, 7673, 7675, 7677, 7679, 7681, 7683,
7685, 7687, 7689, 7691, 7693, 7695, 7697, 7699, 7701, 7703,
7705, 7707, 7709, 7711, 7713, 7715, 7717, 7719, 7721, 7723,
7725, 7727, 7729, 7731, 7733, 7735, 7737, 7739, 7741, 7743,
7745, 7747, 7749, 7751, 7753, 7755, 7757, 7759, 7761, 7763,
7765, 7767, 7769, 7771, 7773, 7775, 7777, 7779, 7781, 7783,
7785, 7787, 7789, 7791, 7793, 7795, 7797, 7799, 7801, 7803,
7805, 7807, 7809, 7811, 7813, 7815, 7817, 7819, 7821, 7823,
7825, 7827, 7829, 7831, 7833, 7835, 7837, 7839, 7841, 7843,
7845, 7847, 7849, 7851, 7853, 7855, 7857, 7859, 7861, 7863,
7865, 7867, 7869, 7871, 7873, 7875, 7877, 7879, 7881, 7883,
7885, 7887, 7889, 7891, 7893, 7895, 7897, 7899, 7901, 7903,
7905, 7907, 7909, 7911, 7913, 7915, 7917, 7919, 7921, 7923,
7925, 7927, 7929, 7931, 7933, 7935, 7937, 7939, 7941, 7943,
7945, 7947, 7949, 7951, 7953, 7955, 7957, 7959, 7961, 7963,
7965, 7967, 7969, 7971, 7973, 7975, 7977, 7979, 7981, 7983,
7985, 7987, 7989, 7991, 7993, 7995, 7997, 7999, 8001, 8003,
8005, 8007, 8009, 8011, 8013, 8015, 8017, 8019, 8021, 8023,
8025, 8027, 8029, 8031, 8033, 8035, 8037, 8039, 8041, 8043,
8045, 8047, 8049, 8051, 8053, 8055, 8057, 8059, 8061, 8063,
8065, 8067, 8069, 8071, 8073, 8075, 8077, 8079, 8081, 8083,
8085, 8087, 8089, 8091, 8093, 8095, 8097, 8099, 8101, 8103,
8105, 8107, 8109, 8111, 8113, 8115, 8117, 8119, 8121, 8123,
8125, 8127, 8129, 8131, 8133, 8135, 8137, 8139, 8141, 8143,
8145, 8147, 8149, 8151, 8153, 8155, 8157, 8159, 8161, 8163,
8165, 8167, 8169, 8171, 8173, 8175, 8177, 8179, 8181, 8183,
8185, 8187, 8189, 8191, 8193, 8195, 8197, 8199, 8201, 8203,
8205, 8207, 8209, 8211, 8213, 8215, 8217, 8219, 8221, 8223,
8225, 8227, 8229, 8231, 8233, 8235, 8237, 8239, 8241, 8243,
8245, 8247, 8249, 8251, 8253, 8255, 8257, 8259, 8261, 8263,
8265, 8267, 8269, 8271, 8273, 8275, 8277, 8279, 8281, 8283,
8285, 8287, 8289, 8291, 8293, 8295, 8297, 8299, 8301, 8303,
8305, 8307, 8309, 8311, 8313, 8315, 8317, 8319, 8321, 8323,
8325, 8327, 8329, 8331, 8333, 8335, 8337, 8339, 8341, 8343,
8345, 8347, 8349, 8351, 8353, 8355, 8357, 8359, 8361, 8363,
8365, 8367, 8369, 8371, 8373, 8375, 8377, 8379, 8381, 8383,
8385, 8387, 8389, 8391, 8393, 8395, 8397, 8399, 8401, 8403,
8405, 8407, 8409, 8411, 8413, 8415, 8417, 8419, 8421, 8423,
8425, 8427, 8429, 8431, 8433, 8435, 8437, 8439, 8441, 8443,
8445, 8447, 8449, 8451, 8453, 8455, 8457, 8459, 8461, 8463,
8465, 8467, 8469, 8471, 8473, 8475, 8477, 8479, 8481, 8483,
8485, 8487, 8489, 8491, 8493, 8495, 8497, 8499, 8501, 8503,
8505, 8507, 8509, 8511, 8513, 8515, 8517, 8519, 8521, 8523,
8525, 8527, 8529, 8531, 8533, 8535, 8537, 8539, 8541, 8543,
8545, 8547, 8549, 8551, 8553, 8555, 8557, 8559, 8561, 8563,
8565, 8567, 8569, 8571, 8573, 8575, 8577, 8579, 8581, 8583,
8585, 8587, 8589, 8591, 8593, 8595, 8597, 8599, 8601, 8603,
8605, 8607, 8609, 8611, 8613, 8615, 8617, 8619, 8621, 8623,
8625, 8627, 8629, 8631, 8633, 8635, 8637, 8639, 8641, 8643,
8645, 8647, 8649, 8651, 8653, 8655, 8657, 8659, 8661, 8663,
8665, 8667, 8669, 8671, 8673, 8675, 8677, 8679, 8681, 8683,
8685, 8687, 8689, 8691, 8693, 8695, 8697, 8699, 8701, 8703,
8705, 8707, 8709, 8711, 8713, 8715, 8717, 8719, 8721, 8723,
8725, 8727, 8729, 8731, 8733, 8735, 8737, 8739, 8741, 8743,
8745, 8747, 8749, 8751, 8753, 8755, 8757, 8759, 8761, 8763,
8765, 8767, 8769, 8771, 8773, 8775, 8777, 8779, 8781, 8783,
8785, 8787, 8789, 8791, 8793, 8795, 8797, 8799, 8801, 8803,
8805, 8807, 8809, 8811, 8813, 8815, 8817, 8819, 8821, 8823,
8825, 8827, 8829, 8831, 8833, 8835, 8837, 8839, 8841, 8843,
8845, 8847, 8849, 8851, 8853, 8855, 8857, 8859, 8861, 8863, 8865, 8867, 8869, 8871, 8873, 8875, 8877, 8879, 8881, 8883, 8885, 8887, 8889, 8891, 8893, 8895, 8897, 8899, 8901, 8903, 8905, 8907, 8909, 8911, 8913, 8915, 8917, 8919, 8921, 8923, 8925, 8927, 8929, 8931, 8933, 8935, 8937, 8939, 8941, 8943, 8945, 8947, 8949, 8951, 8953, 8955, 8957, 8959, 8961, 8963, 8965, 8967, 8969, 8971, 8973, 8975, 8977, 8979, 8981, 8983, 8985, 8987, 8989, 8991, 8993, 8995, 8997, 8999, 9001, 9003, 9005, 9007, 9009, 9011, 9013, 9015, 9017, 9019, 9021, 9023, 9025, 9027, 9029, 9031, 9033, 9035, 9037, 9039, 9041, 9043, 9045, 9047, 9049, 9051, 9053, 9055, 9057, 9059, 9061, 9063, 9065, 9067, 9069, 9071, 9073, 9075, 9077, 9079, 9081, 9083, 9085, 9087, 9089, 9091, 9093, 9095, 9097, 9099, 9101, 9103, 9105, 9107, 9109, 9111, 9113, 9115, 9117, 9119, 9121, 9123, 9125, 9127, 9129, 9131, 9133, 9135, 9137, 9139, 9141, 9143, 9145, 9147, 9149, 9151, 9153, 9155, 9157, 9159, 9161, 9163, 9165, 9167, 9169, 9171, 9173, 9175, 9177, 9179, 9181, 9183, 9185, 9187, 9189, 9191, 9193, 9195, 9197, 9199, 9201, 9203, 9205, 9207, 9209, 9211, 9213, 9215, 9217, 9219, 9221, 9223, 9225, 9227, 9229, 9231, 9233, 9235, 9237, 9239, 9241, 9243, 9245, 9247, 9249, 9251, 9253, 9255, 9257, 9259, 9261, 9263, 9265, 9267, 9269, 9271, 9273, 9275, 9277, 9279, 9281, 9283, 9285, 9287, 9289, 9291, 9293, 9295, 9297, 9299, 9301, 9303, 9305, 9307, 9309, 9311, 9313, 9315, 9317, 9319, 9321, 9323, 9325, 9327, 9329, 9331, 9333, 9335, 9337, 9339, 9341, 9343, 9345, 9347, 9349, 9351, 9353, 9355, 9357, 9359, 9361, 9363, 9365, 9367, 9369, 9371, 9373, 9375, 9377, 9379, 9381, 9383, 9385, 9387, 9389, 9391, 9393, 9395, 9397, 9399, 9401, 9403, 9405, 9407, 9409, 9411, 9413, 9415, 9417, 9419, 9421, 9423, 9425, 9427, 9429, 9431, 9433, 9435, 9437, 9439, 9441, 9443, 9445, 9447, 9449, 9451, 9453, 9455, 9457, 9459, 9461, 9463, 9465, 9467, 9469, 9471, 9473, 9475, 9477, 9479, 9481, 9483, 9485, 9487, 9489, 9491, 9493, 9495, 9497, 9499, 9501, 9503, 9505, 9507, 9509, 9511, 9513, 9515, 9517, 9519, 9521, 9523, 9525, 9527, 9529, 9531, 9533, 9535, 9537, 9539, 9541, 9543, 9545, 9547, 9549, 9551, 9553, 9555, 9557, 9559, 9561, 9563, 9565, 9567, 9569, 9571, 9573, 9575, 9577, 9579, 9581, 9583, 9585, 9587, 9589, 9591, 9593, 9595, 9597, 9599, 9601, 9603, 9605, 9607, 9609, 9611, 9613, 9615, 9617, 9619, 9621, 9623, 9625, 9627, 9629, 9631, 9633, 9635, 9637, 9639, 9641, 9643, 9645, 9647, 9649, 9651, 9653, 9655, 9657, 9659, 9661, 9663, 9665, 9667, 9669, 9671, 9673, 9675, 9677, 9679, 9681, 9683, 9685, 9687, 9689, 9691, 9693, 9695, 9697, 9699, 9701, 9703, 9705, 9707, 9709, 9711, 9713, 9715, 9717, 9719, 9721, 9723, 9725, 9727, 9729, 9731, 9733, 9735, 9737, 9739, 9741, 9743, 9745, 9747, 9749, 9751, 9753, 9755, 9757, 9759, 9761, 9763, 9765, 9767, 9769, 9771, 9773, 9775, 9777, 9779, 9781, 9783, 9785, 9787, 9789, 9791, 9793, 9795, 9797, 9799, 9801, 9803, 9805, 9807, 9809, 9811, 9813, 9815, 9817, 9819, 9821, 9823, 9825, 9827, 9829, 9831, 9833, 9835, 9837, 9839, 9841, 9843, 9845, 9847, 9849, 9851, 9853, 9855, 9857, 9859, 9861, 9863, 9865, 9867, 9869, 9871, 9873, 9875, 9877, 9879, 9881, 9883, 9885, 9887, 9889, 9891, 9893, 9895, 9897, 9899, 9901, 9903, 9905, 9907, 9909, 9911, 9913, 9915, 9917, 9919, 9921, 9923, 9925, 9927, 9929, 9931, 9933, 9935, 9937, 9939, 9941, 9943, 9945, 9947, 9949, 9951, 9953, 9955, 9957, 9959, 9961, 9963, 9965, 9967, 9969, 9971, 9973, 9975, 9977, 9979, 9981, 9983, 9985, 9987, 9989; (b) a nucleotide sequence having at least 80% sequence identity to an amino acid sequence of (a); (c) a nucleotide sequence which is a fragment of at least 10 consecutive nucleotides from a nucleotide sequence of (a); or (d) a nucleotide sequence having at least 80% sequence identity to a nucleotide sequence of (a) and including a fragment of at least 10 consecutive nucleotides from a nucleotide sequence of (a).

In another aspect, the invention relates to a nucleic acid comprising: (a) a nucleotide sequence selected from the group consisting of SEQ ID NOs 511, 2453, 2455, 2677, 2691, 4595, 4747, 7003, 7051, 8167, 4627 and 5699; (b) a nucleotide sequence having at least 80% sequence identity to an amino acid sequence of (a); (c) a nucleotide sequence which is a fragment of at least 10 consecutive nucleotides from a nucleotide sequence of (a); or (d) a nucleotide sequence having at least 80% sequence identity to a nucleotide sequence of (a) and including a fragment of at least 10 consecutive nucleotides from a nucleotide sequence of (a).

In a further aspect, the invention relates to a nucleic acid comprising: (a) a nucleotide sequence selected from the group consisting of SEQ ID Nos 8563, 2727, 9871, 4671, 5679, 533, 3221, 3225 and 7003, (b) a nucleotide sequence having at least 80% sequence identity to an amino acid sequence of (a); (c) a nucleotide sequence which is a fragment of at least 10 consecutive nucleotides from a nucleotide sequence of (a); or (d) a nucleotide sequence having at least 80% sequence identity to a nucleotide sequence of (a) and including a fragment of at least 10 consecutive nucleotides from a nucleotide sequence of (a).

The present invention also relates to nucleic acids of the invention encoding a polypeptide the invention, and to monoclonal antibodies specific for a polypeptide of the invention.

The polypeptides, nucleic acids and antibodies of the invention can be used in medicine and in the manufacture of a medicament for raising an immune response in a patient.

The present invention also relates to pharmaceutical compositions comprising a polypeptide, nucleic acid or antibody of the invention, in admixture with a pharmaceutically acceptable carrier. The invention further relates to a pharmaceutical composition comprising two or more polypeptides of the invention, in admixture with a pharmaceutically acceptable carrier. In a particular embodiment, the pharmaceutical compositions of the invention further comprise a vaccine adjuvant. The present invention further relates to immunogenic compositions comprising one or more outer membrane vesicles (OMVs) expressing or overexpressing one or more polypeptides encoded by:

(a) a nucleotide sequence selected from the group consisting of SEQ ID NOs 511, 2453, 2455, 2677, 2691, 4595, 4747, 7003, 7051, 8167, 4627 and 5699; (b) a nucleotide sequence having at least 80% sequence identity to an amino acid sequence of (a); (c) a nucleotide sequence which is a fragment of at least 10 consecutive nucleotides from a nucleotide sequence of (a); or (d) a nucleotide sequence having at least 80% sequence identity to a nucleotide sequence of (a) and including a fragment of at least 10 consecutive nucleotides from a nucleotide sequence of (a).

The present invention also relates to immunogenic compositions comprising one or more OMVs expressing or overexpressing one or more polypeptides encoded by: (a) a nucleotide sequence selected from the group consisting of SEQ ID Nos 8563, 2727, 9871, 4671, 5679, 533, 3221, 3225 and 7003; (b) a nucleotide sequence having at least 80% sequence identity to an amino acid sequence of (a); (c) a nucleotide sequence which is a fragment of at least 10 consecutive nucleotides from a nucleotide sequence of (a); or (d) a nucleotide sequence having at least 80% sequence identity to a nucleotide sequence of (a) and including a fragment of at least 10 consecutive nucleotides from a nucleotide sequence of (a).

The present invention also relates to methods for raising an immune response in a patient, comprising the step of administering to the patient a pharmaceutical composition or immunogenic composition of the invention. In a particular embodiment, the immune response is protective against ExPEC infection, and in particular against a MNEC infection.

Further aspects of the invention are described below.

DETAILED DESCRIPTION OF THE INVENTION

Figure 1:
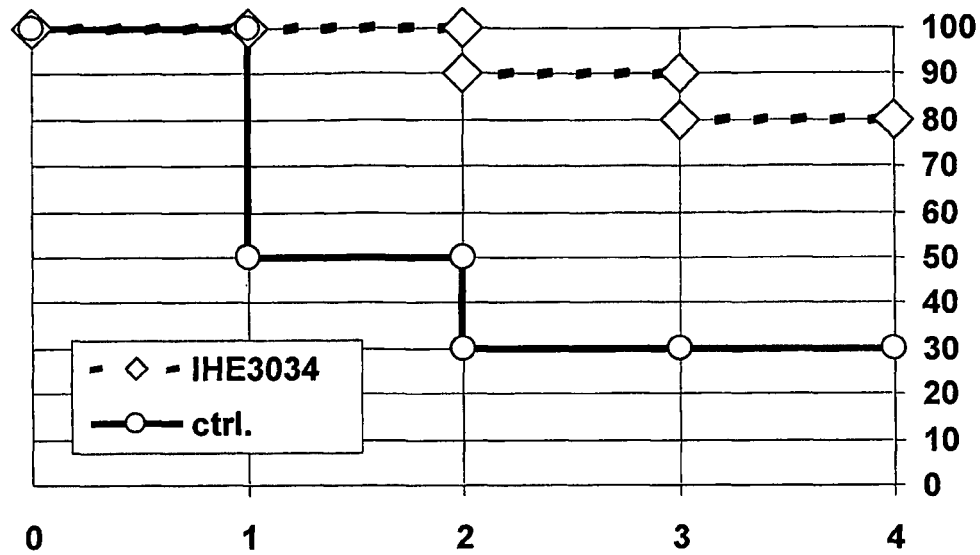
FIG. 1 shows the % survival of mice over time after challenge with IHE3034 following immunization with heat-inactivated IHE3034 or with a control ('fisiol'), and also bacteremia levels (cfa/ml) after 24 hours.
Figure 1:
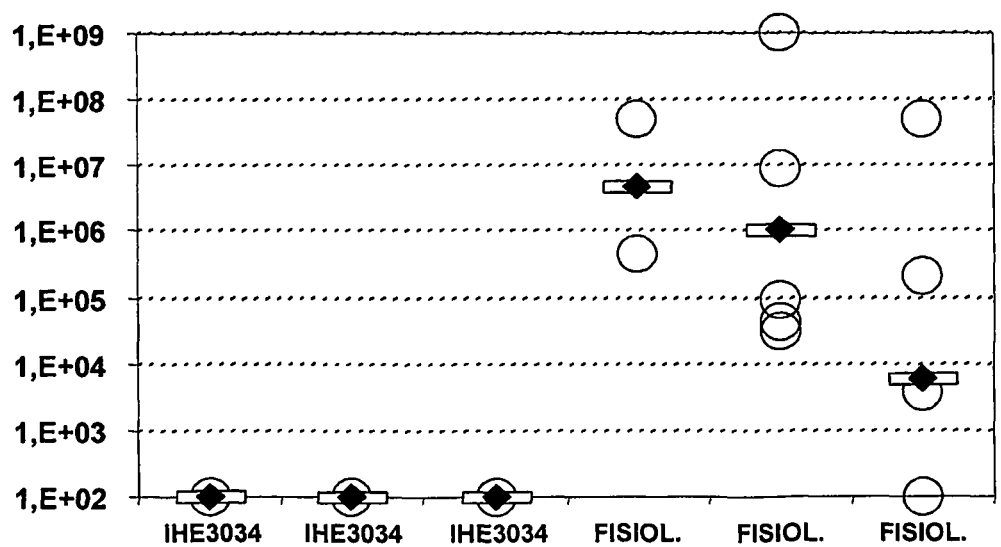

The inventors have identified 4995 open reading frames from a K1/B2 MNEC strain, and have identified a subset of these that is of particular interest for preparing immunogenic compositions against MNEC strains.

Polypeptides

The invention provides polypeptides comprising the amino acid sequences disclosed in the examples. These amino acid sequences are given in the sequence listing as the even-numbered sequences SEQ ID NOs 2 to 9990.

Preferred amino acid sequences from within SEQ ID NOs 2 to 9990 are given in Table 2. Further preferred amino acid sequences are those not identified in the prior art e.g. not identified in any of references 5, 6, 7, 8, 9, 10, 11 and 13.

The invention also provides a polypeptide encoded within any one of nucleic acid sequences SEQ ID NOs 9991 to 10273 or within SEQ ID NO: 10274. The coding sequence in the nucleic acid preferably begins with a start codon and ends with a stop codon. Preferred polypeptides are those not identified in the prior art e.g. not identified in any of references 5, 6, 8, 10 and 11.

The invention also provides polypeptides comprising amino acid sequences that have sequence identity to the amino acid sequences disclosed in the examples. Similarly, the invention provides polypeptides comprising amino acid sequences that have sequence identity to the amino acid sequences encoded within SEQ ID NOs 9991 to 10273 or within SEQ ID NO: 10274. Depending on the particular sequence, the degree of sequence identity is preferably greater than 50% (e.g. 60%, 70%, 75%, 80%, 85%, 90%, 91%, 92%, 93%, 94%, 95%, 96%, 97%, 98%, 99% or more). These polypeptides include homologs, orthologs, allelic variants and mutants. Typically, 50% identity or more between two polypeptide sequences is considered to be an indication of functional equivalence. Identity between polypeptides is preferably determined by the Smith-Waterman homology search algorithm as implemented in the MPSRCH program (Oxford Molecular), using an affine gap search with parameters gap open penalty=12 and gap extension penalty=1.

These polypeptide may, compared to the sequences of the examples, include one or more (e.g. 1, 2, 3, 4, 5, 6, 7, 8, 9, 10, etc.) conservative amino acid substitutions i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. Moreover, the polypeptides may have one or more (e.g. 1, 2, 3, 4, 5, 6, 7, 8, 9, 10, etc.) single amino acid deletions relative to a reference sequence. Furthermore, the polypeptides may include one or more (e.g. 1, 2, 3, 4, 5, 6, 7, 8, 9, 10, etc.) insertions (e.g. each of 1, 2, 3, 4 or 5 amino acids) relative to a reference sequence.

Preferred polypeptides include polypeptides that are lipidated, that are located in the outer membrane, that are located in the inner membrane, or that are located in the periplasm. Particularly preferred polypeptides are those that fall into more than one of these categories e.g. lipidated polypeptides that are located in the outer membrane. Lipoproteins may have a N-terminal cysteine to which lipid is covalently attached, following post-translational processing of the signal peptide.

Polypeptides that may be lipidated include SEQ ID NOs: 620, 630, 660, 724, 946, 1196, 1304, 1510, 1530, 1548, 1600, 1700, 1958, 2030, 2396, 2610, 3040, 3364, 3414, 3422, 3554, 3678, 3824, 4072, 4116, 4178, 4240, 4374, 4412, 4462, 4576, 4664, 4856, 5178, 5286, 5362, 5662, 5682, 5984, 6018, 6132, 6256, 6286, 6532, 6714, 6754, 6764, 6790, 6938, 7144, 7442, 7674, 7872, 8278, 8498, 8564, 8782, 8784, 9276 and 9580. SEQ ID NOs 5662 (ORF02831) and 8564 (ORF04282) are preferred lipoproteins.

Preferred polypeptides are those listed in Table 2.

The invention further provides polypeptides comprising fragments of the amino acid sequences disclosed in the examples. Similarly, the invention provides polypeptides comprising fragments of the amino acid sequences encoded within SEQ ID NOs 9991 to 10273 or within SEQ ID NO: 10274. The fragments should comprise at least n consecutive amino acids from the sequences and, depending on the particular sequence, n is 7 or more (e.g. 8, 10, 12, 14, 16, 18, 20, 22, 24, 26, 28, 30, 35, 40, 45, 50, 60, 70, 80, 90, 100 or more). The fragment may comprise at least one T-cell or, preferably, a B-cell epitope of the sequence. T- and B-cell epitopes can be identified empirically (e.g. using PEPSCAN [14,15] or similar methods), or they can be predicted (e.g. using the Jameson-Wolf antigenic index [16], matrix-based approaches [17], TEPITOPE [18], neural networks [19], OptiMer & EpiMer [20,21], ADEPT [22], Tsites [23], hydrophilicity [24], antigenic index [25] or the methods disclosed in reference 26, etc.). Other preferred fragments are (a) the N-terminal signal peptides of the polypeptides of the invention, (b) the polypeptides, but without their N-terminal signal peptides, (c) the polypeptides, but without 1, 2, 3, 4, 5, 6, 7, 8, 9 or 10 of their N-terminal amino acid residue(s).

Other preferred fragments are those that begin with an amino acid encoded by a potential start codon (ATG, GTG, TTG). Fragments starting at the methionine encoded by a start codon downstream of the indicated start codon are polypeptides of the invention.

Other preferred fragments are those that are common to a polypeptide of the invention and to a polypeptide identified in any of references 5, 6, 8, 10 and 11.

Polypeptides of the invention can be prepared in many ways e.g. by chemical synthesis (in whole or in part), by digesting longer polypeptides using proteases, by translation from RNA, by purification from cell culture (e.g. from recombinant expression), from the organism itself (e.g. after bacterial culture, or direct from patients), etc. A preferred method for production of peptides <40 amino acids long involves in vitro chemical synthesis [27,28]. Solid-phase peptide synthesis is particularly preferred, such as methods based on tboc or Fmoc [29] chemistry. Enzymatic synthesis [30] may also be used in part or in fall. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non natural amino acids, such as iodotyrosine or methylphenylalanine, azidohomoalanine, etc.) [31]. Where D-amino acids are included, however, it is preferred to use chemical synthesis. Polypeptides of the invention may have covalent modifications at the C-terminus and/or N-terminus.

Polypeptides of the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Polypeptides of the invention are preferably provided in purified or substantially purified form i.e. substantially free from other polypeptides (e.g. free from naturally-occurring polypeptides), particularly from other ExPEC or host cell polypeptides, and are generally at least about 50% pure (by weight), and usually at least about 90% pure i.e. less than about 50%, and more preferably less than about 10% (e.g. 5% or less) of a composition is made up of other expressed polypeptides. Polypeptides of the invention are preferably ExPEC, and more preferably MNEC, polypeptides.

Polypeptides of the invention may be attached to a solid support. Polypeptides of the invention may comprise a detectable label (e.g. a radioactive or fluorescent label, or a biotin label).

The term polypeptide refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains. Polypeptides of the invention can be naturally or non-naturally glycosylated (i.e. the polypeptide has a glycosylation pattern that differs from the glycosylation pattern found in the corresponding naturally occurring polypeptide).

Polypeptides of the invention may be at least 40 amino acids long (e.g. at least 40, 50, 60, 70, 80, 90, 100, 120, 140, 160, 180, 200, 220, 240, 260, 280, 300, 350, 400, 450, 500 or more). Polypeptides of the invention may be shorter than 500 amino acids (e.g. no longer than 40, 50, 60, 70, 80, 90, 100, 120, 140, 160, 180, 200, 220, 240, 260, 280, 300, 350, 400 or 450 amino acids).

The invention provides polypeptides comprising a sequence -X-Y- or -Y-X-, wherein: -X- is an amino acid sequence as defined above and -Y- is not a sequence as defined above i.e. the invention provides fusion proteins. Where the N-terminus codon of a polypeptide-coding sequence is not ATG then that codon will be translated as the standard amino acid for that codon rather than as a Met, which occurs when the codon is translated as a start codon.

The invention provides a process for producing polypeptides of the invention, comprising the step of culturing a host cell of to the invention under conditions which induce polypeptide expression.

The invention provides a process for producing a polypeptide of the invention, wherein the polypeptide is synthesised in part or in whole using chemical means.

The invention provides a composition comprising two or more (e.g. 2, 3, 4, 5, 6 or more) polypeptides of the invention. The different polypeptides may be selected such that they are involved in different bacterial metabolic and/or signalling pathways e.g. selection from 2, 3, 4, 5, 6 or more of the following categories: adhesins; autotransporter proteins; toxins; iron acquisitions proteins; and membrane-associated proteins, including in particular integral outer membrane proteins. Such combinations of antigens may target the immune response against different aspects of the bacterial life cycle, resulting in a more effective immune response.

The invention also provides a hybrid polypeptide represented by the formula $NH_2$-A-[-X-L-]$_n$-B—COOH, wherein X is a polypeptide of the invention as defined above, L is an optional linker amino acid sequence, A is an optional N-terminal amino acid sequence, B is an optional C-terminal amino acid sequence, and n is an integer greater than 1. The value of n is between 2 and x, and the value of x is typically 3, 4, 5, 6, 7, 8, 9 or 10. Preferably n is 2, 3 or 4; it is more preferably 2 or 3; most preferably, n=2. for each n instances, -X- may be the same or different. For each n instances of [-X-L-], linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples include short peptide sequences which facilitate cloning, poly-glycine linkers (i.e. $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. -A- and —B— are optional sequences which will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct polypeptide trafficking, or short peptide sequences which facilitate cloning or purification (e.g. histidine tags i.e. $His_n$ where n=3, 4, 5, 6, 7, 8, 9, 10 or more). Other suitable N-terminal and C-terminal amino acid sequences will be apparent to those skilled in the art.

Various tests can be used to assess the in vivo immunogenicity of polypeptides of the invention. For example, polypeptides can be expressed recombinantly and used to screen patient sera by immunoblot. A positive reaction between the polypeptide and patient serum indicates that the patient has previously mounted an immune response to the protein in question i.e. the protein is an immunogen. This method can also be used to identify immunodominant proteins.

Antibodies

The invention provides antibodies that bind to polypeptides of the invention. These may be polyclonal or monoclonal and may be produced by any suitable means (e.g. by recombinant expression). To increase compatibility with the human immune system, the antibodies may be chimeric or humanised [e.g. refs. 32 & 33], or fully human antibodies may be used. The antibodies may include a detectable label (e.g.

for diagnostic assays). Antibodies of the invention may be attached to a solid support. Antibodies of the invention are preferably neutralising antibodies.

Monoclonal antibodies are particularly useful in identification and purification of the individual polypeptides against which they are directed. Monoclonal antibodies of the invention may also be employed as reagents in immunoassays, radioimmunoassays (RIA) or enzyme-linked immunosorbent assays (ELISA), etc. In these applications, the antibodies can be labelled with an analytically-detectable reagent such as a radioisotope, a fluorescent molecule or an enzyme. The monoclonal antibodies produced by the above method may also be used for the molecular identification and characterization (epitope mapping) of polypeptides of the invention.

Antibodies of the invention are preferably specific to ExPEC strains of *E. coli*, i.e. they bind preferentially to ExPEC *E. coli* relative to other bacteria (e.g. relative to non-ExPEC *E. coli* and relative to non *E. coli* bacteria). More preferably, the antibodies are specific to MNEC strains i.e. they bind preferentially to MNEC bacteria relative to other bacteria, including relative to other ExPEC *E. coli*.

Antibodies of the invention are preferably provided in purified or substantially purified form. Typically, the antibody will be present in a composition that is substantially free of other polypeptides e.g. where less than 90% (by weight), usually less than 60% and more usually less than 50% of the composition is made up of other polypeptides.

Antibodies of the invention can be of any isotype (e.g. IgA, IgG, IgM i.e. an $\alpha$, $\gamma$ or $\mu$ heavy chain), but will generally be IgG. Within the IgG isotype, antibodies may be IgG1, IgG2, IgG3 or IgG4 subclass. Antibodies of the invention may have a $\kappa$ or a $\lambda$ light chain.

Antibodies of the invention can take various forms, including whole antibodies, antibody fragments such as $F(ab')_2$ and $F(ab)$ fragments, Fv fragments (non-covalent heterodimers), single-chain antibodies such as single chain Fv molecules (scFv), minibodies, oligobodies, etc. The term "antibody" does not imply any particular origin, and includes antibodies obtained through non-conventional processes, such as phage display.

The invention provides a process for detecting polypeptides of the invention, comprising the steps of: (a) contacting an antibody of the invention with a biological sample under conditions suitable for the formation of an antibody-antigen complexes; and (b) detecting said complexes.

The invention provides a process for detecting antibodies of the invention, comprising the steps of: (a) contacting a polypeptide of the invention with a biological sample (e.g. a blood or serum sample) under conditions suitable for the formation of an antibody-antigen complexes; and (b) detecting said complexes.

Preferred antibodies bind to a polypeptide of the invention with substantially greater affinity than antibodies known in the art. Preferably, the affinity is at least 1.5-fold, 2-fold, 5-fold 10-fold, 100-fold, $10^3$-fold, $10^4$-fold, $10^5$-fold, $10^6$-fold etc. stronger than antibodies known in the art.

Nucleic Acids

The invention also provides nucleic acid comprising a nucleotide sequence encoding the polypeptides of the invention (e.g. the odd-numbered SEQ ID NOs: 1 to 9989). The invention also provides nucleic acid comprising any one of SEQ ID NOs 9991 to 10273.

The invention also provides nucleic acid comprising nucleotide sequences having sequence identity to such nucleotide sequences. Identity between sequences is preferably determined by the Smith-Waterman homology search algorithm as described above. Depending on the particular sequence, the degree of sequence identity is preferably greater than 50% (e.g. 60%, 70%, 75%, 80%, 85%, 90%, 91%, 92%, 93%, 94%, 95%, 96%, 97%, 98%, 99% or more).

The invention also provides nucleic acid which can hybridize to these nucleic acids. Hybridization reactions can be performed under conditions of different "stringency". Conditions that increase stringency of a hybridization reaction of widely known and published in the art [e.g. page 7.52 of reference 34]. Examples of relevant conditions include (in order of increasing stringency): incubation temperatures of 25° C., 37° C., 50° C., 55° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art [e.g. see refs 34-37, etc.].

In some embodiments, nucleic acid of the invention hybridizes to a target under low stringency conditions; in other embodiments it hybridizes under intermediate stringency conditions; in preferred embodiments, it hybridizes under high stringency conditions. An exemplary set of low stringency hybridization conditions is 50° C. and 10×SSC. An exemplary set of intermediate stringency hybridization conditions is 55° C. and 1×SSC. An exemplary set of high stringency hybridization conditions is 68° C. and 0.1×SSC.

Nucleic acid comprising fragments of these sequences are also provided. These should comprise at least at consecutive nucleotides from the sequences and, depending on the particular sequence, n is 10 or more (e.g. 12, 14, 15, 18, 20, 25, 30, 35, 40, 50, 60, 70, 80, 90, 100, 150, 200 or more). Preferred fragments are those that are common to a nucleic acid sequence of the invention and to a nucleic acid sequence identified in any of references 5, 6, 8, 10 and 11.

The invention provides nucleic acid of formula 5'-X-Y-Z-3', wherein: -X- is a nucleotide sequence consisting of x nucleotides; -Z- is a nucleotide sequence consisting of z nucleotides; -Y- is a nucleotide sequence consisting of either (a) a fragment of a nucleic acid sequence selected from odd-numbered SEQ ID NOS: 1 to 9989, (b) a fragment of any one of SEQ ID NOs 9991 to 10273; (c) a fragment of SEQ ID NO: 10274; or (d) the complement of (a) or (b) or (c); and said nucleic acid 5'-X-Y-Z-3' is neither (i) a fragment of either an odd-numbered nucleic acid from SEQ ID NOS: 1 to 9989 or of SEQ ID NOs 9991 to 10273 or of SEQ ID NO: 10274, nor (ii) the complement of (i). The -X- and/or -Z- moieties may comprise a promoter sequence (or its complement).

The invention also provides nucleic acid comprising a fragment of at least n consecutive nucleotides from SEQ ID 10274, wherein n is 10 or more e.g. 12, 14, 15, 18, 20, 25, 30, 35, 40, 50, 60, 70, 80, 90, 100, 150, 200, 250, 300, 350, 400, 450, 500, 600, 700, 800, 900, 1000, 1500, 2000, 3000, 4000, 5000, 10000, 100000, 1000000 or more. This nucleic acid may be single-stranded, at least in part, such that it can act as a hybridisation probe and/or amplification primer. In some embodiments, the fragment is not, or does not include, a fragment of a prior art ExPEC sequence e.g. not a fragment of a nucleic acid sequence specifically disclosed in any of refs. 5, 6, 7, 8, 9, 10, 11 and 13. In other embodiments, the fragment is also a fragment of a prior art ExPEC sequence e.g. is identical to a fragment of a nucleic acid sequence specifically disclosed in any of refs. 5, 6, 7, 8, 9, 10, 11 and 13. The invention includes nucleic acid comprising sequences complementary to these sequences (e.g. for antisense or probing, or for use as primers).

Nucleic acids of the invention can be used in hybridisation reactions (e.g. Northern or Southern blots, or in nucleic acid microarrays or 'gene chips') and amplification reactions (e.g. PCR, SDA, SSSR, LCR, TMA, NASBA, etc.) and other nucleic acid techniques.

Nucleic acid according to the invention can take various forms (e.g. single-stranded, double-stranded, vectors, primers, probes, labelled etc.). Nucleic acids of the invention may be circular or branched, but will generally be linear. Unless otherwise specified or required, any embodiment of the invention that utilizes a nucleic acid may utilize both the double-stranded form and each of two complementary single-stranded forms which make up the double-stranded form. Primers and probes are generally single-stranded, as are antisense nucleic acids.

Nucleic acids of the invention are preferably provided in purified or substantially purified form i.e. substantially free from other nucleic acids (e.g. free from naturally-occurring nucleic acids), particularly from other ExPEC or host cell nucleic acids, generally being at least about 50% pure (by weight), and usually at least about 90% pure. Nucleic acids of the invention are preferably ExPEC nucleic acids.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acid of the invention may be attached to a solid support (e.g. a bead, plate, filter, film, slide, microarray support, resin, etc.). Nucleic acid of the invention may be labelled e.g. with a radioactive or fluorescent label, or a biotin label. This is particularly useful where the nucleic acid is to be used in detection techniques e.g. where the nucleic acid is a primer or as a probe.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids of the invention comprise sequences, but they may also comprise non-ExPEC sequences (e.g. in nucleic acids of formula 5'-X-Y-Z-3', as defined above). This is particularly useful for primers, which may thus comprise a first sequence complementary to a nucleic acid target and a second sequence which is not complementary to the nucleic acid target. Any such non-complementary sequences in the primer are preferably 5' to the complementary sequences. Typical non-complementary sequences comprise restriction sites or promoter sequences.

Nucleic acids of the invention can be prepared in many ways e.g. by chemical synthesis (at least in part), by digesting longer nucleic acids using nucleases (e.g. restriction enzymes), by joining shorter nucleic acids (e.g. using ligases or polymerases), from genomic or cDNA libraries, etc.

Nucleic acids of the invention may be part of a vector i.e. part of a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which is designed to result in the production of a recombinant virus or virus-like particle, or "shuttle vectors", which comprise the attributes of more than one type of vector. Preferred vectors are plasmids. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention.

Where a nucleic acid is DNA, it will be appreciated that "U" in a RNA sequence will be replaced by "T" in the DNA. Similarly, where a nucleic acid is RNA, it will be appreciated that "T" in a DNA sequence will be replaced by "U" in the RNA.

The term "complement" or "complementary" when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T). The terms also imply a direction—the complement of 5'-ACAGT-3' is 5'-ACTGT-3' rather than 5'-TGTCA-3'.

Nucleic acids of the invention can be used, for example: to produce polypeptides; as hybridization probes for the detection of nucleic acid in biological samples; to generate additional copies of the nucleic acids; to generate ribozymes or antisense oligonucleotides; as single-stranded DNA primers or probes; or as triple-strand forming oligonucleotides.

The invention provides a process for producing nucleic acid of the invention, wherein the nucleic acid is synthesised in part or in whole using chemical means.

The invention provides vectors comprising nucleotide sequences of the invention (e.g. cloning or expression vectors) and host cells transformed with such vectors.

The invention also provides a kit comprising primers (e.g. PCR primers) for amplifying a template sequence contained within an ExPEC nucleic acid sequence, the kit comprising a first primer and a second primer, wherein the first primer is substantially complementary to said template sequence and the second primer is substantially complementary to a complement of said template sequence, wherein the parts of said primers which have substantial complementarity define the termini of the template sequence to be amplified. The first primer and/or the second primer may include a detectable label (e.g. a fluorescent label).

The invention also provides a kit comprising first and second single-stranded oligonucleotides which allow amplification of a ExPEC template nucleic acid sequence contained in a single- or double-stranded nucleic acid (or mixture thereof), wherein: (a) the first oligonucleotide comprises a primer sequence which is substantially complementary to said template nucleic acid sequence; (b) the second oligonucleotide comprises a primer sequence which is substantially complementary to the complement of said template nucleic acid sequence; (c) the first oligonucleotide and/or the second oligonucleotide comprise(s) sequence which is not complementary to said template nucleic acid; and (d) said primer sequences define the termini of the template sequence to be amplified. The non-complementary sequence(s) of feature (c) are preferably upstream of (i.e. 5' to) the primer sequences. One or both of these (c) sequences may comprise a restriction site [e.g. ref. 38] or a promoter sequence [e.g. 39]. The first oligonucleotide and/or the second oligonucleotide may include a detectable label (e.g. a fluorescent label).

The template sequence may be any part of a genome sequence (e.g. SEQ ID NO: 10274). For example, it could be a rRNA gene (e.g. Turenne et al. (2000) *J. Clin. Microbiol.* 38:513-520) or a protein-coding gene. The template sequence is preferably specific to ExPEC, and more preferably to MNEC.

The invention also provides a computer-readable medium (e.g. a floppy disk, a hard disk, a CD-ROM, a DVD etc.) and/or a computer database containing one or more of the sequences in the sequence listing. The medium preferably contains SEQ ID NO: 10274.

The invention provides a process for detecting nucleic acid of the invention, comprising the steps of: (a) contacting a nucleic probe according to the invention with a biological sample under hybridising conditions to form duplexes; and (b) detecting said duplexes.

The invention provides a process for detecting in a biological sample (e.g. blood), comprising the step of contacting nucleic acid according to the invention with the biological sample under hybridising conditions. The process may involve nucleic acid amplification (e.g. PCR, SDA, SSSR, LCR, TMA, NASBA, etc.) or hybridisation (e.g. microarrays, blots, hybridisation with a probe in solution etc.). PCR detection of ExPEC in clinical samples has been reported [e.g. see ref. 40]. Clinical assays based on nucleic acid are described in general in ref. 41.

The invention provides a process for preparing a fragment of a target sequence, wherein the fragment is prepared by extension of a nucleic acid primer. The target sequence and/or the primer are nucleic acids of the invention. The primer extension reaction may involve nucleic acid amplification (e.g. PCR, SDA, SSSR, LCR, TMA, NASBA, etc.).

Nucleic acid amplification according to the invention may be quantitative and/or real-time.

For certain embodiments of the invention, nucleic acids are preferably at least 7 nucleotides in length (e.g. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 90, 100, 110, 120, 130, 140, 150, 160, 170, 180, 190, 200, 225, 250, 275, 300 nucleotides or longer).

For certain embodiments of the invention, nucleic acids are preferably at most 500 nucleotides in length (e.g. 450, 400, 350, 300, 250, 200, 150, 140, 130, 120, 110, 100, 90, 80, 75, 70, 65, 60, 55, 50, 45, 40, 39, 38, 37, 36, 35, 34, 33, 32, 31, 30, 29, 28, 27, 26, 25, 24, 23, 22, 21, 20, 19, 18, 17, 16, 15 nucleotides or shorter).

Primers and probes of the invention, and other nucleic acids used for hybridization, are preferably between 10 and 30 nucleotides in length (e.g. 10, 11, 12, 13, 14, 15, 16, 17, 18, 19, 20, 21, 22, 23, 24, 25, 26, 27, 28, 29, or 30 nucleotides).

Mutant Bacteria

The invention provides a *E. coli* bacterium in which expression of one or more of the genes identified herein has been knocked out. Techniques for gene knockout are well known, and knockout mutants of *E. coli* have been reported previously.

The knockout is preferably achieved using isogenic deletion of the coding region, but any other suitable technique may be used e.g. deletion or mutation of the promoter, deletion or mutation of the start codon, antisense inhibition, inhibitory RNA, etc. In the resulting bacterium, however, mRNA encoding the gene product will be absent and/or its translation will be inhibited (e.g. to less than 1% of wild-type levels).

The bacterium may contain a marker gene in place of the knocked out gene e.g. an antibiotic resistance marker.

Vesicles

Reference 42 describes the preparation of vesicles from a MNEC strain by the knockout of mltA (a murein lytic transglycosylase) or one or more of the components of the *E. coli* Tol-Pal complex [43], such as tolA, tolQ, tolB, pal and/or tolR. These vesicles can be improved by making one or more further genetic changes to the chromosome of the bacterium or through insertion of "ad-hoc" episomalic elements (e.g. expression vectors) in order to increase the amount of and/or immunoaccessibility "exposure" of protective antigens on the surface the vesicles.

One way of obtaining such improvements is to up-regulate the expression of the polypeptides protective antigens of the invention. Many different genetic strategies for increasing the expression of a target protein are well-known in the art and can be distinguished into two broad categories: one relying on modifications of the chromosome (e.g. replacement of the wild-type promoter with a stronger promoter, inactivation of natural repressor genes, etc.) to increase expression of an endogenous gene, and the other based on recombinant expression by episomalic elements (e.g. high-copy number plasmids, vectors harboring an engineered target gene, etc.) or integration of a exogenous protective target gene in the chromosome. Practical examples for each of these approaches can be found in references 44 to 50.

Another way of increasing vesicle immunogenicity and selectivity is to down-regulate the expression of immunodominant non-protective antigens or to down-regulate proteins that are homologous to proteins found in commensal strains. Further improvements can be achieved sought by reducing the potential vesicle toxicity through detoxification of the Lipid A moiety of LPS. Similar changes have been previously described to produce improved vesicles from other Gram-negative pathogens (see for example references 51 & 52).

All the above strategies can be used either alone or in combination to obtain improved vesicles for use in immunogenic compositions. The invention provides a pathogenic *Escherichia coli* bacterium (particularly a MNEC) having a knockout of mltA and/or of a component of its Tol-Pal complex, and one or more of: (i) a chromosomal gene encoding a polypeptide of the invention under the control of a promoter that provides higher expression levels of the polypeptide than the promoter that is naturally associated with the gene encoding the polypeptide; (ii) an autonomously-replicating extrachromosomal element encoding a polypeptide of the invention; and/or (iii) a genetic modification to reduce the toxicity of the Lipid A moiety of *E. coli* LPS relative to wild-type LPS.

The invention also provides vesicles obtainable by culturing such a bacterium, such as the vesicles that, during culture of the bacterium, are released into the culture medium.

Pharmaceutical Compositions

The invention provides compositions comprising: (a) polypeptide, antibody, vesicles, and/or nucleic acid of the invention; and (b) a pharmaceutically acceptable carrier. These compositions may be suitable as immunogenic compositions, for instance, or as diagnostic reagents, or as vaccines. Vaccines according to the invention may either be prophylactic (i.e. to prevent infection) or therapeutic (i.e. to treat infection), but will typically be prophylactic.

In a particular aspect, the invention provides immunogenic compositions comprising one or more outer membrane vesicles (OMVs) expressing or overexpressing one or more polypeptides encoded by: (a) a nucleotide sequence selected from the group consisting of SEQ ID NOs 511, 2453, 2455, 2677, 2691, 4595, 4747, 7003, 7051, 8167, 4627 and 5699; (b) a nucleotide sequence having at least 80% sequence identity to an amino acid sequence of (a); (c) a nucleotide sequence which is a fragment of at least 10 consecutive nucleotides from a nucleotide sequence of (a); or (d) a nucleotide sequence having at least 80% sequence identity to a nucleotide sequence of (a) and including a fragment of at least 10 consecutive nucleotides from a nucleotide sequence of (a).

In another aspect, the invention provides immunogenic compositions comprising one or more outer membrane vesicles (OMVs) expressing or overexpressing one or more polypeptides encoded by: (a) a nucleotide sequence selected from the group consisting of SEQ ID Nos 8563, 2727, 9871, 4671, 5679, 533, 3221, 3225 and 7003; (b) a nucleotide sequence having at least 80% sequence identity to an amino acid sequence of (a); (c) a nucleotide sequence which is a fragment of at least 10 consecutive nucleotides from a nucleotide sequence of (a); or (d) a nucleotide sequence having at least 80% sequence identity to a nucleotide sequence of (a) and including a fragment of at least 10 consecutive nucleotides from a nucleotide sequence of (a).

A 'pharmaceutically acceptable carrier' includes any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in ref. 289.

Compositions of the invention may include an antimicrobial, particularly if packaged in a multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

Polypeptides of the invention may be administered in conjunction with other immunoregulatory agents. In particular, compositions will usually include a vaccine adjuvant. The adjuvant may be selected from one or more of the group consisting of a TH1 adjuvant and TH2 adjuvant, farther discussed below. Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 53], or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. Mineral containing compositions may also be formulated as a particle of metal salt [54].

Aluminum salts may be included in vaccines of the invention such that the dose of $Al^{3+}$ is between 0.2 and 1.0 mg per dose.

In another embodiment the adjuvant of the invention comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, an aluminum phosphate adjuvant with pI ~4 electrostatically adsorbs lysozyme, but not albumin, at pH 7.4. Should albumin be the target, aluminum hydroxide adjuvant would be selected (e.g. with pH 11.4). Alternatively, pre-treatment of aluminum hydroxide with phosphate lowers its pI, making it a preferred adjuvant for more basic antigens.

A typical aluminium phosphate adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where an aluminium phosphate is used and it is desired not to adsorb an antigen to the adjuvant, this is favoured by including free phosphate ions in solution (e.g. by the use of a phosphate buffer).

B. Oil Emulsions

Oil emulsion compositions suitable for use as adjuvants in the invention include squalene-water emulsions, such as MF59 (5% Squalene, 0.5% Tween 80, and 0.5% Span 85, formulated into submicron particles using a microfluidizer) [Chapter 10 of ref. 53; see also refs. 55-57 chapter 12 of ref. 58.]. MF59 is used as the adjuvant in the FLUAD™ influenza virus trivalent subunit vaccine. The emulsion advantageously includes citrate ions e.g. 10 mM sodium citrate buffer.

Particularly preferred adjuvants for use in the compositions are submicron oil-in-water emulsions. Preferred submicron oil-in-water emulsions for use herein are squalene/water emulsions, optionally containing varying amounts of MTP-PE, such as a submicron oil-in-water emulsion containing 4-5% w/v squalene, 0.25-1.0% w/v Tween 80 (polyoxyethylenesorbitan monooleate), and/or 0.25-1.0% Span 85 (sorbitan trioleate), and, optionally, N-acetylmuramyl-L-alanyl-D-isogluatminyl-L-alanine-2-(1'-2'-dipalmitoyl-sn-glycero-3-hydroxyphosphophoryloxy)-ethylamine (MTP-PE). Submicron oil-in-water emulsions, methods of making the same and immunostimulating agents, such as muramyl peptides, for use in the compositions, are described in detail in references 55 & 59-60.

An emulsion of squalene, a tocopherol, and Tween 80 can be used. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100) can be used.

An emulsion of squalane, polysorbate 80 and poloxamer 401 ("Pluronic™ L121") can be used. The emulsion can be formulated in phosphate buffered saline, pH 7.4. This emulsion is a useful delivery vehicle for muramyl dipeptides, and has been used with threonyl-MDP in the "SAF-1" adjuvant [61] (0.05-1% Thr-MDP, 5% squalane, 2.5% Pluronic L121 and 0.2% polysorbate 80). It can also be used without the Thr-MDP, as in the "AF" adjuvant [62] (5% squalane, 1.25% Pluronic L121 and 0.2% polysorbate 80). Microfluidisation is preferred.

Complete Freund's adjuvant (CFA) and incomplete Freund's adjuvant (IFA) may also be used as adjuvants in the invention.

C. Saponin Formulations [Chapter 22 of ref. 53]

Saponin formulations may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponin can also be commercially obtained from *Smilax orizata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref 63. Saponin formulations may also comprise a sterol, such as cholesterol [64].

Combinations of saponins and cholesterols can be used to form unique particles called immunostimulating complexs (ISCOMs) [chapter 23 of ref. 53]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are farther described in refs. 64-66. Optionally, the ISCOMS may be devoid of additional detergent(s) [67].

A review of the development of saponin based adjuvants can be found in refs. 68 & 69.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed farther in refs. 70-75. Virosomes are discussed farther in, for example, ref. 76

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 77. Such "small particles" of 3dMPL are small enough to be sterile filtered through a 0.22 μm membrane [77]. Other non-toxic LPS derivatives include monophosphoryl lipid A mimics, such as aminoalkyl glucosaminide phosphate derivatives e.g. RC-529 [78,79].

Lipid A derivatives include derivatives of lipid A from *Escherichia coli* such as OM-174. OM-174 is described for example in refs. 80 & 81.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 82, 83 and 84 disclose possible analog substitutions e.g. replacement of guanosine with 2'-deoxy-7-deazaguanosine. The adjuvant effect of CpG oligonucleotides is further discussed in refs. 85-90.

The CpG sequence may be directed to TLR9, such as the motif GTCGTT or TTCGTT [91]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 92-94. Preferably, the CpG is a CpG-A ODN.

Preferably, the CpG oligonucleotide is constructed so that the 5' end is accessible for receptor recognition. Optionally, two CpG oligonucleotide sequences may be attached at their 3" ends to form "immunomers". See, for example, refs. 91 & 95-97.

Other immunostimulatory oligonucleotides include a double-stranded RNA, or an oligonucleotide containing a palindromic sequence, or an oligonucleotide containing a poly(dG) sequence.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 98 and as parenteral adjuvants in ref. 99. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 100-107. Numerical reference for amino acid substitutions is preferably based on the alignments of the A and B subunits of ADP-ribosylating toxins set forth in ref. 108, specifically incorporated herein by reference in its entirety.

Compounds of formula I, II or III, or salts thereof, can also be used as adjuvants:

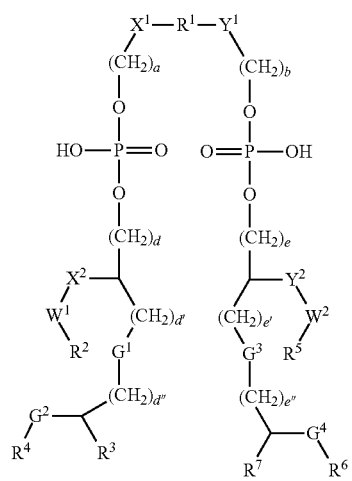

I

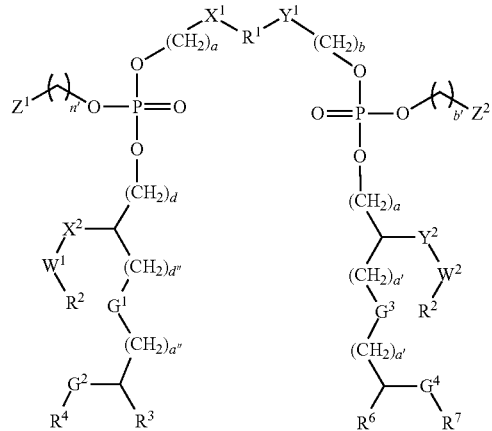

II

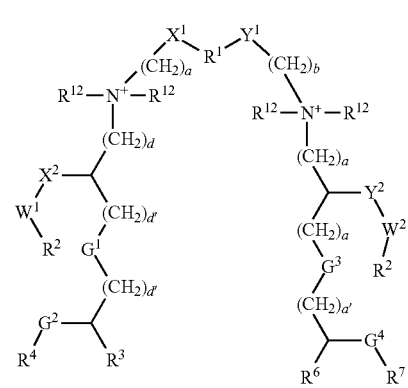

III as defined in reference 109, such as 'ER 803058', 'ER 803732', 'ER 804053', ER 804058', 'ER 804059', 'ER 804442', 'ER 804680', 'ER 804764', ER 803022 or 'ER 804057' e.g.:

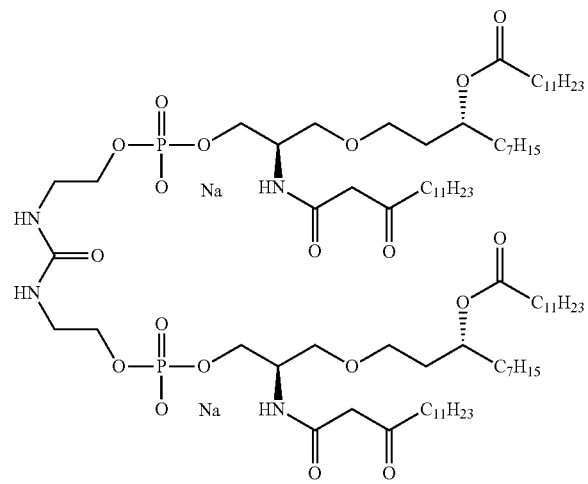

ER804057

ER-803022:

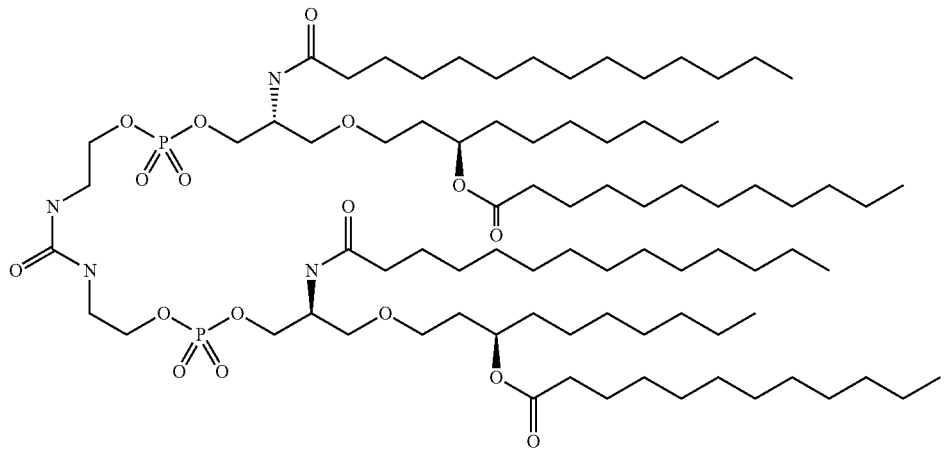

F. Human Immunomodulators

Human immunomodulators suitable for use as adjuvants in the invention include cytokines, such as interleukins (e.g. IL-1, IL-2, IL-4, IL-5, IL-6, IL-7, IL-12 [110], etc.) [111], interferons (e.g. interferon-γ), macrophage colony stimulating factor, tumor necrosis factor and macrophage inflammatory protein-1alpha (MIP-1alpha) and MIP-1beta [112].

G. Bioadhesives and Mucoadhesives

Bioadhesives and mucoadhesives may also be used as adjuvants in the invention. Suitable bioadhesives include esterified hyaluronic acid microspheres [113] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [114].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of ref. 53)

Examples of liposome formulations suitable for use as adjuvants are described in refs. 115-117.

J. Polyoxyethylene Ether and Polyoxyethylene Ester Formulations

Adjuvants suitable for use in the invention include polyoxyethylene ethers and polyoxyethylene esters [118]. Such formulations further include polyoxyethylene sorbitan ester surfactants in combination with an octoxynol [119] as well as polyoxyethylene alkyl ethers or ester surfactants in combination with at least one additional non-ionic surfactant such as an octoxynol [120]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Phosphazenes e.g. PCPP

Phosphazene adjuvants include poly[di(carboxylatophenoxy)phosphazene] ("PCPP") as described, for example, in refs. 121 and 122.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinoline Compounds.

Imidazoquinoline adjuvants include Imiquimod ("R-837") [123,124], Resiquimod ("R-848") [125], and their analogs; and salts thereof (e.g. the hydrochloride salts). Further details about immunostimulatory imidazoquinolines can be found in references 126 to 130.

N. Thiosemicarbazone Compounds.

Examples of thiosemicarbazone compounds, as well as methods of formulating, manufacturing, and screening for compounds all suitable for use as adjuvants in the invention include those described in ref. 131. The thiosemicarbazones are particularly effective in the stimulation of human peripheral blood mononuclear cells for the production of cytokines, such as TNF-α.

O. Tryptanthrin Compounds.

Examples of tryptanthrin compounds, as well as methods of formulating, manufacturing, and screening for compounds all suitable for use as adjuvants in the invention include those described in ref. 132. The tryptanthrin compounds are particularly effective in the stimulation of human peripheral blood mononuclear cells for the production of cytokines, such as TNF-α.

P. Nucleoside Analogs

Various nucleoside analogs can be used as adjuvants, such as (a) Isatorabine (ANA-245; 7-thia-8-oxoguanosine):

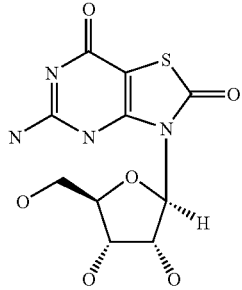 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 133 to 135; (f) a compound having the formula:

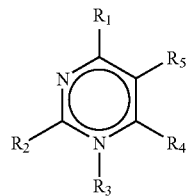

wherein:
- $R_1$ and $R_2$ are each independently H, halo, —$NR_aR_b$, —OH, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;
- $R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;
- $R_4$ and $R_5$ are each independently H, halo, heterocyclyl, substituted heterocyclyl, —C(O)—$R_d$, $C_{1-6}$ alkyl, substituted $C_{1-6}$ alkyl, or bound together to form a 5 membered ring as in $R_{4-5}$:

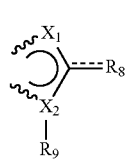

the binding being achieved at the bonds indicated by a ⌇

- $X_1$ and $X_2$ are each independently N, C, O, or S;
- $R_8$ is H, halo, —OH, $C_{1-6}$ alkyl, $C_{2-6}$ alkenyl, $C_{2-6}$ alkynyl, —OH, —$NR_aR_b$, —$(CH_2)_n$—O—$R_c$, —O—($C_{1-6}$ alkyl), —$S(O)_pR_e$, or —C(O)—$R_d$;
- $R_9$ is H, $C_{1-6}$ alkyl, substituted $C_{1-6}$ alkyl, heterocyclyl, substituted heterocyclyl or $R_{9a}$, wherein $R_{9a}$ is:

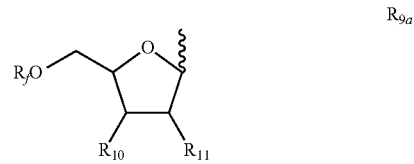

the binding being achieved at the bond indicated by a ⌇

- $R_{10}$ and $R_{11}$ are each independently H, halo, $C_{1-6}$ alkoxy, substituted $C_{1-6}$ alkoxy, —$NR_aR_b$, or —OH;
- each $R_a$ and $R_b$ is independently H, $C_{1-6}$ alkyl, substituted $C_{1-6}$ alkyl, —C(O)$R_d$, $C_{6-10}$ aryl;
- each $R_c$ is independently H, phosphate, diphosphate, triphosphate, $C_{1-6}$ alkyl, or substituted $C_{1-6}$ alkyl;
- each $R_d$ is independently H, halo, $C_{1-6}$ alkyl, substituted $C_{1-6}$ alkyl, $C_{1-6}$ alkoxy, substituted $C_{1-6}$ alkoxy, —$NH_2$, —NH($C_{1-6}$ alkyl), —NH(substituted $C_{1-6}$ alkyl), —N($C_{1-6}$ alkyl)$_2$, —N(substituted $C_{1-6}$ alkyl)$_2$, $C_{6-10}$ aryl, or heterocyclyl;
- each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;
- each $R_f$ is independently H, $C_{1-6}$ alkyl, substituted $C_{1-6}$ alkyl, —C(O)$R_d$, phosphate, diphosphate, or triphosphate;
- each n is independently 0, 1, 2, or 3;
- each p is independently 0, 1, or 2; or or (g) a pharmaceutically acceptable salt of any of (a) to (f), a tautomer of any of (a) to (f, or a pharmaceutically acceptable salt of the tautomer.

Q. Lipids Linked to a Phosphate-Containing Acyclic Backbone

Adjuvants containing lipids linked to a phosphate-containing acyclic backbone include the TLR4 antagonist E5564 [136,137]:

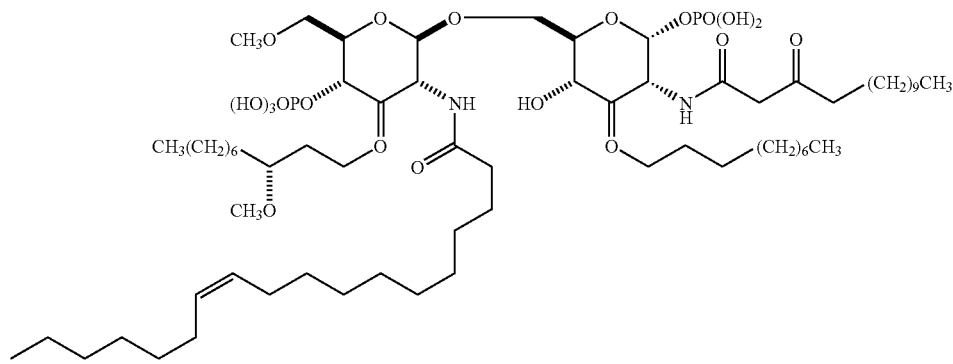

R. Small Molecule Immunopotentiators (SMIPs)

SMIPs include:

N2-methyl-1-(2-methylpropyl)-1H-imidazo[4,5-c]quinoline-2,4-diamine;
N2,N2-dimethyl-1-(2-methylpropyl)-1H-imidazo[4,5-c]quinoline-2,4-diamine;
N2-ethyl-N2-methyl-1-(2-methylpropyl)-1H-imidazo[4,5-c]quinoline-2,4-diamine;
N2-methyl-1-(2-methylpropyl)-N2-propyl-1H-imidazo[4,5-c]quinoline-2,4-diamine;
1-(2-methylpropyl)-N2-propyl-1H-imidazo[4,5-c]quinoline-2,4-diamine;
N2-butyl-1-(2-methylpropyl)-1H-imidazo[4,5-c]quinoline-2,4-diamine;
N2-butyl-N2-methyl-1-(2-methylpropyl)-1H-imidazo[4,5-c]quinoline-2,4-diamine;
N2-methyl-1-(2-methylpropyl)-N2-pentyl-1H-imidazo[4,5-c]quinoline-2,4-diamine;
N2-methyl-1-(2-methylpropyl)-N2-prop-2-enyl-1H-imidazo[4,5-c]quinoline-2,4-diamine;
1-(2-methylpropyl)-2-[(phenylmethyl)thio]-1H-imidazo[4,5-c]quinolin-4-amine;
1-(2-methylpropyl)-2-(propylthio)-1H-imidazo[4,5-c]quinolin-4-amine;
2-[[4-amino-1-(2-methylpropyl)-1H-imidazo[4,5-c]quinolin-2-yl](methyl)amino]ethanol;
2-[[4-amino-1-(2-methylpropyl)-1H-imidazo[4,5-c]quinolin-2-yl](methyl)amino]ethyl acetate;
4-amino-1-(2-methylpropyl)-1,3-dihydro-2H-imidazo[4,5-c]quinolin-2-one;
N2-butyl-1-(2-methylpropyl)-N4,N4-bis(phenylmethyl)-1H-imidazo[4,5-c]quinoline-2,4-diamine;
N2-butyl-N2-methyl-1-(2-methylpropyl)-N4,N4-bis(phenylmethyl)-1H-imidazo[4,5-c]quinoline-2,4-diamine;
N2-methyl-1-(2-methylpropyl)-N4,N4-bis(phenylmethyl)-1H-imidazo[4,5-c]quinoline-2,4-diamine;
N2,N2-dimethyl-1-(2-methylpropyl)-N4,N4-bis(phenylmethyl)-1H-imidazo[4,5-c]quinoline-2,4-diamine;
1-{4-amino-2-[methyl(propyl)amino]-1H-imidazo[4,5-c]quinolin-1-yl}-2-methylpropan-2-ol;
1-[4-amino-2-(propylamino)-1H-imidazo[4,5-c]quinolin-1-yl]-2-methylpropan-2-ol;
N4,N4-dibenzyl-1-(2-methoxy-2-methylpropyl)-N2-propyl-1H-imidazo[4,5-c]quinoline-2,4-diamine.

S. Proteosomes

One adjuvant is an outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of *Neisseria meningitidis* outer membrane and lipopolysaccharides. They have been used as adjuvants for influenza vaccines [138].

T. Other Adjuvants

Other substances that act as immunostimulating agents are disclosed in chapter 7 of ref. 53. references 53 and 58. Further useful adjuvant substances include:

Methyl inosine 5'-monophosphate ("MIMP") [139].

A polyhydroxlated pyrrolizidine compound [140], such as one having formula:

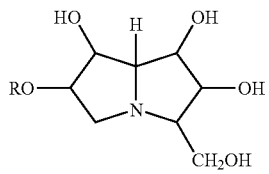

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A gamma inulin [141] or derivative thereof, such as algammulin.

Compounds disclosed in reference 142.

Compounds disclosed in reference 143, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [144,145], Hydrapthalamide compounds, Benzophenone compounds, Isoxazole compounds, Sterol compounds, Quinazilinone compounds, Pyrrole compounds [146], Anthraquinone compounds, Quinoxaline compounds, Triazine compounds, Pyrazalopyrimidine compounds, and Benzazole compounds [147].

Loxoribine (7-allyl-8-oxoguanosine) [148].

A formulation of a cationic lipid and a (usually neutral) co-lipid, such as aminopropyl-dimethyl-myristoleyloxy-propanaminium bromide-diphytanoylphosphatidyl-ethanolamine ("Vaxfectin™") or aminopropyl-dimethyl-bis-dodecyloxy-propanaminium bromide-dioleoylphosphatidyl-ethanolamine ("GAP-DLRIE: DOPE"). Formulations containing (±)-N-(3-aminopropyl)-N,N-dimethyl-2,3-bis(syn-9-tetradeceneyloxy)-1-propanaminium salts are preferred [149].

The invention may also comprise combinations of one or more of the adjuvants identified above. For example, the following combinations may be used as adjuvant compositions in the invention: (1) a saponin and an oil-in-water emulsion [150]; (2) a saponin (e.g. QS21)+a non-toxic LPS derivative (e.g. 3dMPL) [151]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [152]; (5) combinations of 3dMPL with, for example, QS21 and/or oil-in-water emulsions [153]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (8) one or more mineral salts (such as an aluminum salt)+a non-toxic derivative of LPS (such as 3dMPL); and (9) one or more mineral salts (such as an aluminum salt)+an immunostimulatory oligonucleotide (such as a nucleotide sequence including a CpG motif).

The compositions of the invention will preferably elicit both a cell mediated immune response as well as a humoral immune response in order to effectively address a uropathogenic infection. This immune response will preferably induce long lasting (e.g. neutralising) antibodies and a cell mediated immunity that can quickly respond upon exposure to MNEC-associated antigens.

Two types of T cells, CD4 and CD8 cells, are generally thought necessary to initiate and/or enhance cell mediated immunity and humoral immunity. CD8 T cells can express a CD8 co-receptor and are commonly referred to as cytotoxic T lymphocytes (CTLs). CD8 T cells are able to recognized or interact with antigens displayed on MHC Class I molecules. CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of particular value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response. An enhanced TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production. An enhanced TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives hereof. Mineral containing compositions, such as aluminium salts are preferred TH2 adjuvants for use in the invention.

Preferably, the invention includes a composition comprising a combination of a TH1 adjuvant and a TH2 adjuvant. Preferably, such a composition elicits an enhanced TH1 and an enhanced TH2 response i.e. an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e. relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

The use of an aluminium hydroxide or aluminium phosphate adjuvant is particularly preferred, and antigens are generally adsorbed to these salts. Calcium phosphate is another preferred adjuvant.

The pH of compositions of the invention is preferably between 6 and 8, preferably about 7. Stable pH may be maintained by the use of a buffer. Where a composition comprises an aluminium hydroxide salt, it is preferred to use a histidine buffer [154]. The composition may be sterile and/or pyrogen-free. Compositions of the invention may be isotonic with respect to humans.

Compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g. freeze-dried) for solution or suspension in liquid vehicles prior to injection.

Compositions of the invention may be packaged in unit dose form or in multiple dose form. For multiple dose forms, vials are preferred to pre-filled syringes. Effective dosage volumes can be routinely established, but a typical human dose of the composition for injection has a volume of 0.5 ml.

Where a composition of the invention is to be prepared extemporaneously prior to use (e.g. where a component is presented in lyophilised form) and is presented as a kit, the kit may comprise two vials, or it may comprise one ready filled syringe and one vial, with the contents of the syringe being used to reactivate the contents of the vial prior to injection.

Thus the invention provides for a kit comprising a first component and a second component, wherein: the first component comprises one or more polypeptide, antibody, vesicle and/or nucleic acid of the invention; and the second component comprises one or more of the following: instructions for administering a composition to a patient, a syringe or other delivery device, an adjuvant, and/or a pharmaceutically acceptable formulating solution.

The invention also provides a delivery device (e.g. a syringe) pre-filled with the immunogenic compositions of the invention.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials, and a typical quantity of each meningococcal saccharide antigen per dose is between 1 μg and 10 mg per antigen.

Pharmaceutical Uses

The invention also provides a method of treating a patient, comprising administering to the patient a therapeutically effective amount of a composition of the invention. The patient may either be at risk from the disease themselves or may be a pregnant woman ('maternal immunisation' [155]).

The invention provides nucleic acid, polypeptide, vesicle or antibody of the invention for use as medicaments (e.g. as immunogenic compositions or as vaccines) or as diagnostic reagents. It also provides the use of nucleic acid, polypeptide, vesicle or antibody of the invention in the manufacture of: (i) a medicament for treating or preventing disease and/or infection caused by an ExPEC bacterium; (ii) a diagnostic reagent for detecting the presence of or of antibodies raised against an ExPEC bacterium; and/or (iii) a reagent which can raise antibodies against an ExPEC bacterium. Said ExPEC bacterium can be of any serotype or strain, but are preferably MNEC bacteria e.g. K1 serotype and/or B2 MLEE type.

The invention is useful for the prevention and/or treatment of diseases such as bacteremia, meningitis, a urinary tract infection, pyelonephritis and/or cystitis. The invention is particularly useful for the treatment of sepsis and/or meningitis The patient is preferably a human. The human may be a child (e.g. aged between 0 and 18 years, or between 0-5 years), may be an adolescent (e.g. aged 15-19), an adult (e.g. aged 19-54) or may be elderly (e.g. 55 years or older). Female adolescents and adults are a preferred group of patients. A vaccine intended for children or adolescents may also be administered to adults e.g. to assess safety, dosage, immunogenicity, etc.

Other possible patient animals include dogs, which may be carriers of ExPEC [156,157].

One way of checking efficacy of therapeutic treatment involves monitoring infection after administration of the composition of the invention. One way of checking efficacy of prophylactic treatment involves monitoring immune responses against an administered polypeptide after administration. Immunogenicity of compositions of the invention can be determined by administering them to test subjects (e.g. children 12-16 months age, or animal models e.g. a murine model) and then determining standard parameters including ELISA titres (GMT) of IgG. These immune responses will generally be determined around 4 weeks after administration of the composition, and compared to values determined before administration of the composition. Where more than one dose of the composition is administered, more than one post-administration determination may be made. Efficacy may also be assessed using adult mice models of sepsis, mouse models of UTI, and passive protection from meningitis in infant rats.

Administration of polypeptide antigens is a preferred method of treatment for inducing immunity. Administration of antibodies of the invention is another preferred method of treatment. This method of passive immunisation is particularly useful for newborn children or for pregnant women. This method will typically use monoclonal antibodies, which will be humanised or fully human.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral (e.g. tablet, spray), vaginal, topical, transdermal, transcutaneous, intranasal, sublingual, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity. Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage treatment can be a single dose schedule or a multiple dose schedule. Multiple doses may be used in a primary immunisation schedule and/or in a booster immunisation schedule. A primary dose schedule may be followed by a booster dose schedule. In a multiple dose schedule the various doses may be given by the same or different routes e.g. a parenteral prime and mucosal boost, a mucosal prime and parenteral boost, etc. Suitable timing between priming doses (e.g. between 4-16 weeks), and between priming and boosting, can be routinely determined. For example, a primary course of vaccination may include 1-10 separate doses, followed by other doses given at subsequent time intervals required to maintain and/or reinforce an immune response, for example, at 1-4 months for a second dose, and if needed, a subsequent dose or doses after several months.

Bacterial infections affect various areas of the body and so compositions may be prepared in various forms. For example, the compositions may be prepared as injectables, either as liquid solutions or suspensions. Solid forms suitable for solution in, or suspension in, liquid vehicles prior to injection can also be prepared (e.g. a lyophilised or a spray-freeze dried composition). The composition may be prepared for topical administration e.g. as an ointment, cream or powder. The composition be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 158 & 159]. The composition may be in kit form, designed such that a combined composition is reconstituted just prior to administration to a patient. Such kits may comprise one or more antigens in liquid form and one or more lyophilised antigens.

Compositions of the invention may be administered to patients at substantially the same time as (e.g. during the same medical consultation or visit to a healthcare professional) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, a human papillomavirus vaccine, an inactivated poliovirus vaccine, a hepatitis B virus vaccine, a pneumococcal conjugate vaccine, a meningococcal conjugate vaccine, etc. Similarly they may be administered to patients at substantially the same time as (e.g. during the same medical consultation or visit to a healthcare professional) an antibiotic, and in particular an antibiotic compound active against MNEC.

Further Antigenic Components of Compositions of the Invention

The invention also provides a composition comprising a polypeptide or the invention and one or more of the following further antigens:

a saccharide antigen from *N. meningitidis* serogroup A, C, W135 and/or Y (preferably all four), such as the oligosaccharide disclosed in ref. 160 from serogroup C [see also ref. 161] or the oligosaccharides of ref. 162.

an antigen from *N. meningitidis* serogroup B such as those disclosed in refs. 163-171, etc.

a saccharide antigen from *Streptococcus pneumoniae* [e.g. 172, 173, 174].

an antigen from hepatitis A virus, such as inactivated virus [e.g. 175, 176].

an antigen from hepatitis B virus, such as the surface and/or core antigens [e.g. 176, 177].

a diphtheria antigen, such as a diphtheria toxoid [e.g. chapter 3 of ref. 178] e.g. the $CRM_{197}$ mutant [e.g. 179].

an antigen from hepatitis C virus [e.g. 180].

an antigen from HIV [181]

a tetanus antigen, such as a tetanus toxoid [e.g. chapter 4 of ref. 178].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 182 & 183].

a saccharide antigen from *Haemophilus influenzae* B [e.g. 161].

polio antigen(s) [e.g. 184, 185] such as IPV.

measles, mumps and/or rubella antigens [e.g. chapters 9, 10 & 11 of ref. 178].

varicella antigens.

influenza antigen(s) [e.g. chapter 19 of ref. 178], such as the haemagglutinin and/or neuraminidase surface proteins. Influenza antigens may be derived from interpandemic (annual) flu strains. Influenza antigens may be derived from strains with the potential to cause a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans). Influenza antigens may be derived from viruses grown in eggs or cell culture.

an antigen from *Moraxella catarrhalis* [e.g. 186].

a saccharide antigen from *Streptococcus agalactiae* (group B streptococcus).

an protein antigen from *Streptococcus agalactiae* (group B streptococcus) [e.g. 187, 188].

an antigen from *N. gonorrhoeae* [e.g. 189-192].

an antigen from *Chlamydia pneumoniae* [e.g. refs. 193 to 199] or a combination of antigens from *C. pneumoniae* [e.g. 200].

an antigen from *Chlamydia trachomatis*, or a combination of antigens from *C. trachomatis* [e.g. 201].

an antigen from *Porphyromonas gingivalis* [e.g. 202].

rabies antigen(s) [e.g. 203] such as lyophilised inactivated virus [e.g. 204, RabAvert™].

antigen(s) from a paramyxovirus such as respiratory syncytial virus (RSV [205, 206]) and/or parainfluenza virus (PIV3 [207]).

an antigen from *Bacillus anthracis* [e.g. 208, 209, 210].

an antigen from *Streptococcus pyogenes* (group A streptococcus) [e.g. 188, 211, 212].

an antigen from *Staphylococcus aureus* [e.g. 213].

an antigen from a virus in the flaviviridae family (genus *flavivirus*), such as from yellow fever virus, Japanese encephalitis virus, four serotypes of Dengue viruses, tick-borne encephalitis virus, West Nile virus.

a pestivirus antigen, such as from classical porcine fever virus, bovine viral diarrhoea virus, and/or border disease virus.

a parvovirus antigen e.g. from parvovirus B19.

a human papilloma virus (HPV) antigen [214]

The composition may comprise one or more of these further antigens.

Preferred Gonococcal antigens include one or more of ngs13 (OmpA), OmpH, ngs576 (peptidyl-prolyl cis/trans isomerase (PPIase) protein), ngs41 and ngs117.

Preferred HPV antigens include one or more of HPV 16, HPV 18, HPV 6 and HPV 11.

Preferred *Chlamydia trachomatis* antigens include one or more of: CT045, CT089, CT242, CT316, CT381. CT396, CT398, CT444, CT467, CT547, CT587, CT823, CT761 and specific combinations of these antigens as disclosed in WO 05/002619.

Preferred *Chlamydia pneumoniae* antigens include one or more of: CPn0324, Cpn0301, Cpn0482, Cpn0503, Cpn0525, Cpn0558, Cpn0584, Cpn0800, Cpn0979, Cpn0498, Cpn0300, Cpn0042, Cpn0013, Cpn450, Cpn0661, Cpn0557, Cpn0904, Clpn0795, Cpn0186 and Cpn0604 and specific combinations of these antigens as disclosed in WO 05/084306.

Preferred GBS antigens include one or more of GBS80, GBS 104, GBS 59, GBS 67, GBS 322 and GBS 276.

In another embodiment, antigens of the invention are combined with one or more additional, non-*E. coli* antigens suitable for use in a vaccine designed to protect females against genitourinary and/or sexually transmitted diseases. For example, the antigens may be combined with an antigen derived from the group consisting of *Streptococcus agalactiae, Chlamydia trachomatis, Neisseria gonorrhoeae*, papillomavirus and herpes simplex virus. Where human papillomavirus antigens are used, they may be from one or more of HPV 16, HPV 18, HPV 6 and/or HPV 11.

In another embodiment, the antigen combinations of the invention are combined with one or more additional, non-ExPEC antigens suitable for use in a vaccine designed to protect elderly or immunocompromised individuals. For example, the antigen combinations may be combined with an antigen derived from the group consisting of *Enterococcus faecalis, Staphylococcus aureus, Staphylococcus epidermis, Pseudomonas aeruginosa, Legionella pneumophila, Listeria monocytogenes, Neisseria meningitidies*, influenza, and parainfluenza virus ('PIV').

Toxic protein antigens may be detoxified where necessary (e.g. detoxification of pertussis toxin by chemical and/or genetic means [183]).

Where a dipptheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates include bacterial toxins (such as diphtheria toxoid or tetanus toxoid), the *N. meningitidis* outer membrane protein [215], synthetic peptides [216,217], heat shock proteins [218,219], pertussis proteins [220,221], protein D from *H. influenzae* [222,223], cytokines [224], lymphokines [224], *H. influenzae* proteins, hormones [224], growth factors [224], toxin A or B from *C. difficile* [225], iron-uptake proteins [226], artificial proteins comprising multiple human CD4+ T cell epitopes from various pathogen-derived antigens [227] such as the N19 protein [228], pneumococcal surface protein PspA [229], pneumolysin [230], etc. A preferred carrier protein is CRM197 protein [231].

Antigens in the composition will typically be present at a concentration of at least 1 µg/ml each. In general, the concentration of any given antigen will be sufficient to elicit an immune response against that antigen.

Antigens are preferably adsorbed to an aluminium salt.

Nucleic Acid Immunisation

The immunogenic compositions described above include polypeptide antigens from MNEC. As an alternative to using proteins antigens in the immunogenic compositions of the invention, nucleic acid (preferably DNA e.g. in the form of a plasmid) encoding the antigen may be used, to give compositions, methods and uses based on nucleic acid immunisation. Nucleic acid immunisation is now a developed field (e.g. see references 232 to 239 etc.), and has been applied to many vaccines.

The nucleic acid encoding the immunogen is expressed in vivo after delivery to a patient and the expressed immunogen then stimulates the immune system. The active ingredient will typically take the form of a nucleic acid vector comprising: (i) a promoter; (ii) a sequence encoding the immunogen, operably linked to the promoter; and optionally (iii) a selectable marker. Preferred vectors may further comprise (iv) an origin of replication; and (v) a transcription terminator downstream of and operably linked to (ii). In general, (i) & (v) will be eukaryotic and (iii) & (iv) will be prokaryotic.

Preferred promoters are viral promoters e.g. from cytomegalovirus (CMV). The vector may also include transcriptional regulatory sequences (e.g. enhancers) in addition to the promoter and which interact functionally with the promoter. Preferred vectors include the immediate-early CMV enhancer/promoter, and more preferred vectors also include CMV intron A. The promoter is operably linked to a downstream sequence encoding an immunogen, such that expression of the immunogen-encoding sequence is under the promoter's control.

Where a marker is used, it preferably functions in a microbial host (e.g. in a prokaryote, in a bacteria, in a yeast). The marker is preferably a prokaryotic selectable marker (e.g. transcribed under the control of a prokaryotic promoter). For convenience, typical markers are antibiotic resistance genes.

The vector of the invention is preferably an autonomously replicating episomal or extrachromosomal vector, such as a plasmid.

The vector of the invention preferably comprises an origin of replication. It is preferred that the origin of replication is active in prokaryotes but not in eukaryotes.

Preferred vectors thus include a prokaryotic marker for selection of the vector, a prokaryotic origin of replication, but a eukaryotic promoter for driving transcription of the immunogen-encoding sequence. The vectors will therefore (a) be amplified and selected in prokaryotic hosts without polypeptide expression, but (b) be expressed in eukaryotic hosts without being amplified. This arrangement is ideal for nucleic acid immunization vectors.

The vector of the invention may comprise a eukaryotic transcriptional terminator sequence downstream of the coding sequence. This can enhance transcription levels. Where the coding sequence does not have its own, the vector of the invention preferably comprises a polyadenylation sequence. A preferred polyadenylation sequence is from bovine growth hormone.

The vector of the invention may comprise a multiple cloning site.

In addition to sequences encoding the immunogen and a marker, the vector may comprise a second eukaryotic coding sequence. The vector may also comprise an IRES upstream of said second sequence in order to permit translation of a second eukaryotic polypeptide from the same transcript as the immunogen. Alternatively, the immunogen-coding sequence may be downstream of an IRES.

The vector of the invention may comprise unmethylated CpG motifs e.g. unmethylated DNA sequences which have in common a cytosine preceding a guanosine, flanked by two 5' purines and two 3' pyrimidines. In their unmethylated form these DNA motifs have been demonstrated to be potent stimulators of several types of immune cell.

Vectors may be delivered in a targeted way. Receptor-mediated DNA therapy techniques are described in, for example, references 240 to 245. Therapeutic compositions containing a nucleic acid are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. Factors such as method of action (e.g. for enhancing or inhibiting levels of the encoded gene product) and efficacy of transformation and expression are considerations which will affect the dosage required for ultimate efficacy. Where greater expression is desired over a larger area of tissue, larger amounts of vector or the same amounts re-administered in a successive protocol of administrations, or several administrations to different adjacent or close tissue portions may be required to effect a positive therapeutic outcome. In all cases, routine experimentation in clinical trials will determine specific ranges for optimal therapeutic effect.

Vectors can be delivered using gene delivery vehicles. The gene delivery vehicle can be of viral or non-viral origin (see generally references 246 to 249).

Viral-based vectors for delivery of a desired nucleic acid and expression in a desired cell are well known in the art. Exemplary viral-based vehicles include, but are not limited to, recombinant retroviruses (e.g. references 250 to 260), alphavirus-based vectors (e.g. Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532); hybrids or chimeras of these viruses may also be used), poxvirus vectors (e.g. vaccinia, fowlpox, canarypox, modified vaccinia Ankara, etc.), adenovirus vectors, and adeno-associated virus (AAV) vectors (e.g. see refs. 261 to 266). Administration of DNA linked to killed adenovirus [267] can also be employed.

Non-viral delivery vehicles and methods can also be employed, including, but not limited to, polycationic condensed DNA linked or unlinked to killed adenovirus alone [e.g. 267], ligand-linked DNA [268], eukaryotic cell delivery vehicles cells [e.g. refs. 269 to 273] and nucleic charge neutralization or fusion with cell membranes. Naked DNA can also be employed. Exemplary naked DNA introduction methods are described in refs. 274 and 275. Liposomes (e.g. immunoliposomes) that can act as gene delivery vehicles are described in refs. 276 to 280. Additional approaches are described in references 281 & 282.

Further non-viral delivery suitable for use includes mechanical delivery systems such as the approach described in ref. 282. Moreover, the coding sequence and the product of expression of such can be delivered through deposition of photopolymerized hydrogel materials or use of ionizing radiation [e.g. refs. 283 & 284]. Other conventional methods for gene delivery that can be used for delivery of the coding sequence include, for example, use of hand-held gene transfer particle gun [285] or use of ionizing radiation for activating transferred genes [283 & 286].

Delivery DNA using PLG {poly(lactide-co-glycolide)} microparticles is a particularly preferred method e.g. by adsorption to the microparticles, which are optionally treated to have a negatively-charged surface (e.g. treated with SDS) or a positively-charged surface (e.g. treated with a cationic detergent, such as CTAB).

General

The term "comprising" encompasses "including" as well as "consisting" e.g. a composition "comprising" X may consist exclusively of X or may include something additional e.g. X+Y.

The term "about" in relatation to numerical value x means, for example, x±10%.

The word "substantially" does not exclude "completely" e.g. a composition which is "substantially free" from Y may be completely free from Y. Where necessary, the word "substantially" may be omitted from the definition of the invention.

The N-terminus residues in the amino acid sequences in the sequence listing are generally given as the amino acid encoded by the first codon in the corresponding nucleotide sequence. Where the first codon is not ATG (e.g. SEQ ID NOs: 1, 7, 19, 39, 43, 49, 51, 55, 63, 73, 119, 127, 129, 137, 143, 145, 147, 149, 155, 159, 165, 173, 181, 183, 205, 209, 219, 221, 229, 235, 247, 263, 269, 271, 297, 303, 325, 327, 341, 345, 359, 363, 373, 395, 401, 413, 443, 447, 453, 459, 463, 465, 469, 473, 477, 479, 495, 505, 507, 517, 527, 533, 535, 537, 539, 549, 569, 575, 579, 581, 583, 587, 591, 593, 599, 613, 621, 635, 637, 643, 655, 661, 665, 669, 671, 681, 683, 687, 693, 707, 709, 721, 723, 729, 743, 757, 763, 765, 769, 781, 791, 793, 813, 817, 823, 837, 839, 855, 861, 865, 881, 885, 897, 907, 909, 911, 917, 921, 941, 949, 957, 965, 975, 977, 979, 981, 983, 989, 993, 997, 1001, 1005, 1011, 1015, 1017, 1019, 1027, 1029, 1033, 1037, 1043, 1051, 1053, 1073, 1087, 1097, 1101, 1103, 1107, 1113, 1115, 1117, 1121, 1123, 1135, 1143, 1147, 1149, 1175, 1181, 1227, 1263, 1271, 1287, 1295, 1305, 1307, 1311, 1317, 1323, 1331, 1341, 1345, 1349, 1351, 1355, 1359, 1363, 1373, 1375, 1383, 1399, 1411, 1415, 1417, 1423, 1433, 1451, 1477, 1483, 1485, 1493, 1495, 1501, 1503, 1511, 1519, 1521, 1525, 1529, 1553, 1559, 1579, 1585, 1603, 1609, 1611, 1619, 1621, 1623, 1629, 1631, 1643, 1653, 1669, 1675, 1677, 1687, 1693, 1705, 1713, 1717, 1727, 1739, 1751, 1763, 1769, 1785, 1789, 1799, 1801, 1817, 1819, 1825, 1827, 1829, 1831, 1833, 1839, 1857, 1867, 1911, 1919, 1925, 1929, 1939, 1947, 1955, 1957, 1979, 1981, 1985, 1989, 1993, 1995, 2003, 2005, 2009, 2027, 2035, 2037, 2047, 2049, 2059, 2063, 2079, 2093, 2123, 2135, 2139, 2141, 2163, 2165, 2173, 2177, 2189, 2195, 2197, 2203, 2209, 2211, 2241, 2247, 2275, 2291, 2321, 2327, 2357, 2361, 2373, 2377, 2379, 2397, 2399, 2405, 2433, 2437, 2443, 2447, 2451, 2455, 2457, 2487, 2491, 2503, 2505, 2507, 2513, 2515, 2521, 2541, 2545, 2549, 2553, 2565, 2577, 2579, 2591, 2613, 2623, 2629, 2631, 2633, 2635, 2639, 2641, 2649, 2657, 2659, 2661, 2663, 2665, 2667, 2669, 2671, 2681, 2687, 2689, 2699, 2701, 2705, 2713, 2719, 2721, 2729, 2735, 2743, 2745, 2759, 2781, 2785, 2787, 2789, 2795, 2801, 2809, 2813, 2815, 2823, 2825, 2845, 2847, 2869, 2885, 2891, 2897, 2905, 2907, 2911, 2913, 2915, 2925, 2939, 2945, 2947, 2975, 2993, 3015, 3043, 3055, 3061, 3063, 3075, 3107, 3117, 3127, 3131, 3175, 3179, 3191, 3193, 3207, 3209, 3213, 3221, 3229, 3243, 3253, 3259, 3261, 3267, 3283, 3289, 3307, 3313, 3331, 3337, 3339, 3353, 3357, 3361, 3367, 3379, 3381, 3383, 3411, 3419, 3429, 3433, 3435, 3437, 3445, 3449, 3453, 3471, 3491, 3501, 3507, 3515, 3559, 3563, 3571, 3573, 3577, 3579, 3583, 3595, 3607, 3619, 3621, 3623, 3625, 3629, 3633, 3635, 3637, 3663, 3671, 3679, 3685, 3687, 3699, 3701, 3707, 3713, 3721, 3723, 3739, 3741, 3743, 3759, 3763, 3777, 3797, 3807, 3811, 3821, 2829, 3833, 3855, 3857, 3863, 3865, 3867, 3869, 3873, 3881, 3891, 3893, 3901, 3919, 3925, 3931, 3937, 3949, 3951, 3955, 3959, 3969, 3973, 3981, 3991, 4003, 4013, 4029, 4033, 4049, 4057, 4069, 4071, 4077, 4081, 4089, 4107, 4131, 4139, 4171, 4193, 4195, 4199, 4201, 4223, 4225, 4245, 4249, 4273, 4279, 4281, 4287, 4293, 4301, 4319, 4321, 4327, 4337, 4351, 4353, 4361, 4363, 4365, 4369, 4377, 4379, 4387, 4395, 4403, 4411, 4417, 4423, 4429, 4443, 4463, 4479, 4483, 4485, 4493, 4495, 4523, 4527, 4529, 4541, 4549, 4553, 4563, 4577, 4583, 4585, 4595, 4619, 4635, 4651, 4677, 4683, 4685, 4699, 4703, 4709, 4711, 4719, 4751, 4753, 4761, 4789, 4803, 4805, 4819, 4829, 4833, 4837, 4839, 4847, 4851, 4857, 4863, 4869, 4887, 4891, 4893, 4909, 4925, 4927, 4931, 4935, 4939, 4943, 4949, 4957, 4963, 4965, 4973, 5019, 5033, 5063, 5073, 5081, 5083, 5085, 5089, 5093, 5113, 5167, 5179, 5183, 5193, 5209, 5211, 5213, 5227, 5231, 5237, 5245, 5273, 5281, 5283, 5297, 5299, 5301, 5305, 5309, 5329, 5333, 5347, 5353, 5365, 5367, 5369, 5385, 5389, 5401, 5435, 5437, 5439, 5453, 5465, 5475, 5515, 5517, 5525, 5543, 5545, 5559, 5571, 5605, 5611, 5619, 5639, 5651, 5655, 5665, 5685, 5701, 5715, 5761, 5769, 5771, 5775, 5781, 5793, 5795, 5801, 5817, 5819, 5831, 5855, 5861, 5865, 5873, 5887, 5889, 5909, 5911, 5927, 5945, 5949, 5957, 5959, 5965, 5973, 5987, 5997, 6003, 6013, 6015, 6023, 6025, 6027, 6037, 6063, 6091, 6093, 6095, 6097, 6111, 6117, 6119, 6135, 6143, 6147, 6165, 6177, 6187, 6189, 6191, 6195, 6197, 6199, 6203, 6223, 6227, 6229, 6237, 6245, 6247, 6249, 6253, 6255, 6259, 6267, 6297, 6305, 6311, 6317, 6345, 6361, 6389, 6419, 6421, 6435, 6457, 6461, 6463, 6467, 6471, 6487, 6499, 6535, 6553, 6559, 6561, 6565, 6617, 6631, 6633, 6643, 6677, 6699, 6707, 6733, 6745, 6781, 6783, 6789, 6799, 6813, 6843, 6847, 6851, 6861, 6885, 6893, 6899, 6901, 6905, 6915, 6917, 6919, 6933, 6941, 6943, 6957, 6961, 6967, 6973, 6985, 6993, 6995, 7021, 7023, 7045, 7047, 7051, 7063, 7065, 7069, 7077, 7085, 7089, 7091, 7097, 7099, 7107, 7113, 7123, 7129, 7131, 7167, 7191, 7199, 7219, 7223, 7241, 7247, 7263, 7277, 7289, 7309, 7339, 7345, 7383, 7401, 7409, 7411, 7413, 7429, 7439, 7443, 7455, 7459, 7461, 7465, 7477, 7489, 7497, 7499, 7513, 7523, 7525, 7527, 7533, 7549, 7555, 7557, 7567, 7581, 7601, 7611, 7615, 7617, 7623, 7633, 7641, 7651, 7653, 7659, 7665, 7687, 7693, 7701, 7709, 7723, 7727, 7779, 7789, 7797, 7809, 7849, 7859, 7869, 7877, 7885, 7891, 7893, 7905, 7907, 7917, 7929, 7933, 7937, 7943, 7945, 7951, 7953, 7969, 7971, 8015, 8017, 8027, 8055, 8059, 8061, 8069, 8107, 8137, 8145, 8149, 8151, 8153, 8171, 8179, 8217, 8219, 8231, 8239, 8245, 8247, 8261, 8269, 8301, 8313, 8341, 8365, 8371, 8381, 8387, 8393, 8421, 8447, 8453, 8455, 8457, 8461, 8465, 8471, 8493, 8501, 8505, 8515, 8523, 8531, 8545, 8575, 8579, 8581, 8617, 8645, 8647, 8655, 8667, 8677, 8679, 8683, 8689, 8691, 8697, 8709, 8715, 8721, 8727, 8731, 8739, 8745, 8775, 8793, 8797, 8807, 8815, 8823, 8827, 8833, 8859, 8863, 8869, 8889, 8899, 8901, 8909, 8913, 8915, 8929, 8933, 8935, 8949, 8951, 8955, 8967, 8993, 8995, 8997, 9003, 9009, 9013, 9019, 9033, 9037, 9061, 9065, 9067, 9079, 9101, 9103, 9123, 9153, 9157, 9163, 9185, 9189, 9197, 9201, 9223, 9225, 9227, 9241, 9243, 9247, 9273, 9275, 9281, 9297, 9313, 9321, 9331, 9339, 9369, 9383, 9385, 9387, 9409, 9413, 9435, 9449, 9469, 9471, 9491, 9495, 9497, 9499, 9503, 9527, 9529, 9545, 9547, 9557, 9559, 9565, 9577, 9589, 9599, 9601, 9603, 9605, 9607, 9621, 9633, 9635, 9653, 9655, 9663, 9681, 9701, 9705, 9717, 9731, 9747, 9765, 9797, 9807, 9809, 9811, 9831, 9851, 9853, 9855, 9875, 9899, 9915, 9929, 9931, 9939, 9941, 9945, 9949, 9953, 9959, 9989), it will be understood that it will be translated as methionine when the codon functions as a start codon, but will be translated as the indicated non-Met amino acid when the sequence is at the C-terminus of a fusion partner. The invention specifically discloses and encompasses each of the amino acid sequences of the sequence listing having a N-terminus methionine residue (e.g. a formyl-methionine residue) in place of any indicated non-Met residue (e.g. for SEQ ID NOS: 236, 662, 758, 770, 782, 792, 838, 918, 1182, 1312, 1374, 1632, 2064, 2378, 2400, 2456, 2516, 2636, 2670, 2682, 2688, 2744, 3384, 3702, 3714, 4058, 4678, 4704, 4804, 4806, 4848, 6026, 6112, 7022, 7242, 7710, 8582, 9682). It also specifically discloses and encompasses each of the amino acid sequences of the sequence listing starting at any internal methionine residues in the sequences.

As indicated in the above text, nucleic acids and polypeptides of the invention may include sequences that:
(a) are identical (i.e. 100% identical) to the sequences disclosed in the sequence listing;
(b) share sequence identity with the sequences disclosed in the sequence listing;
(c) have 1, 2, 3, 4, 5, 6, 7, 8, 9 or 10 single nucleotide or amino acid alterations (deletions, insertions, substitutions), which may be at separate locations or may be contiguous, as compared to the sequences of (a) or (b); and
(d) when aligned with a particular sequence from the sequence listing using a pairwise alignment algorithm, a moving window of x monomers (amino acids or nucleotides) moving from start (N-terminus or 5') to end (C-terminus of 3'), such that for an alignment that extends to p monomers (where p>x) there are p−x+1 such windows, each window has at least x•y identical aligned monomers, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x•y is not an integer then it is rounded up to the nearest integer. The preferred pairwise alignment algorithm is the Needleman-Wunsch global alignment algorithm [287], using default parameters (e.g. with Gap opening penalty=10.0, and with Gap extension penalty=0.5, using the EBLOSUM62 scoring matrix). This algorithm is conveniently implemented in the needle tool in the EMBOSS package [288].

The nucleic acids and polypeptides of the invention may additionally have further sequences to the N-terminus/5' and/or C-terminus/3' of these sequences (a) to (d).

The practice of the present invention will employ, unless otherwise indicated, conventional methods of chemistry, biochemistry, molecular biology, immunology and pharmacology, within the skill of the art. Such techniques are explained fully in the literature. See, e.g., references 289-296, etc.

EXPERIMENTAL

Below are examples of specific embodiments or modes for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

MODES FOR CARRYING OUT THE INVENTION

MNEC Strain IHE3034

IHE3034 is a known *E. coli* strain of the MNEC pathotype. Table 1 of reference 297 reports that IHE3034 is classified as O18:K1:H7/9 serotype, and falls into ECOR group B2. Known virulence-associated genes on horizontally transferred DNA elements are sfaII, ibeA, iro, kps (group II), fyuA and malX. It also carries the cdt gene cluster coding for the cytolethal distending toxin.

Sequencing of *E. coli* K1 strain IHE3034 led to 283 contigs. These are given as SEQ ID NOs 9991 to 10273, arranged in descending order of length.

Analysis of the genome sequence of *E. coli* K1 strain IHE3034 has identified 4995 open reading frames (ORFs), which are referred to by the nomenclature ORFnnnnn, where nnnnn is a number between 00001 and 04995. Sequences for these ORFs are given as SEQ ID NOs: 1 to 9990, with odd-numbered SEQ ID NOs being DNA sequences, and even-numbered IDs being amino acid sequences. The nnnnn numbering can be converted to the SEQ ID NO: numbering of the sequence listing as follows: for an amino acid sequence, SEQ ID NO:=nnnnn×2; for a nucleotide sequence, SEQ ID NO:=[nnnnn×2]−1. Thus ORF01234 is found as SEQ ID NOs: 2467 & 2468, as shown in Table 1.

Initial functional annotation of the 4995 ORFs is given in Table 1.

Table 3 shows the ORFs which have low homology with commensal strain ORFs (1194 in total). These ORFs are preferred for giving specificity to pathological *E. coli* strains vs. commensal strains, both in relation to nucleic acid testing and in relation to immunological cross-reactivity. Potential pathogenicity islands are located in the ranges ORF00028-70, ORF000330-353, ORF00655-687, ORF00883-910, ORF01031-1058, ORF1078-1119, ORF1186-1228, ORF01313-1376, ORF01479-1514, ORF01523-1543, ORF01550-1578, ORF01810-1865, ORF02295-02315, ORF02351-2375, ORF02382-2405, ORF02436-2472, ORF02788-02816, ORF02844-2891, ORF03011-3056, ORF03340-3365, ORF03499-3522, ORF04416-4439, ORF04661-4679, ORF04915-4930, and ORF04946-4966.

Based on various criteria applied by the inventors, a subset of 142 of the 4995 ORFs (2.8%) has been selected for immunogenic use. These 142 ORFs are listed in Table 2. The criteria for selection of the subset include, but are not limited to: low homology with ORFs from commensal *E. coli* strains; length>100 aa; and suitable cellular localisation (shown at bottom of Table 2).

The genes encoding these 142 proteins are cloned, expressed in bacteria (e.g. in a non-pathogenic laboratory *E. coli* host, or in a *Bacillus* such as *B. subtilis* or *B. megaterium*), purified, and then are used to immunise test animals (e.g. mice). The serum raised in the mice are then analysed in Western blot, ELISA and FACS assays, and are further tested in both in vitro and in vivo experiments. Suitable in vitro experiments include testing the ability of antibodies to induce complement-mediated bacterial killing and/or opsonophagocytosis activity, to block binding of MNEC strains (or the purified antigen) to human epithelial cells or other cell lines, and/or to inhibit adhesion/invasion of *E. coli* bacteria (e.g. K1 strain) to brain microvascular endothelial cells (BMEC). Suitable in vivo experiments for testing efficacy against bacteremia and meningitis include active and/or passive systemic immunisations and challenge in 5-day-old rats challenged with *E. coli* K1 strain, and immunisation and intraperitoneal infection of adult mice with MNEC strains.

The importance of the proteins to the bacterial life-cycle can be tested by creating isogenic knockout mutants. The mutants can also be used to ensure that sera raised by an antigen are specific for that antigen. Microarrays are used to study expression patterns. Conservation and/or variability is assessed by sequencing the genes from multiple different ExPEC strains.

Assays were carried out in order to select predicted surface-exposed proteins, which are specific for MNEC strains and absent in non-pathogenic strains (commensal and laboratory strains). Once selected these proteins are expressed and purified and used to immunize mice.

It is known from reference 43 that a mutation in any of the tol-pal genes of *E. coli* results in the formation of vesicles containing native outer membrane proteins. By comparing the proteins present in vesicles of MNEC strains and non-pathogenic strains it is possible to select a small group of proteins that could be used as potential antigens.

Lambda Red-Mediated Gene Manipulation in Commensal and Pathogenic *E. Coli*

This method is a rapid PCR-based method used to inactivate the tolR gene from the wild-type *E. coli* strains [298]. Briefly, the first step consists in amplifying independently the upstream and downstream regions of the target gene (tolR) and the resistance marker cassette. The two PCR products obtained in step 1 are mixed with the amplification producer of the AB cassette at equimolar concentrations and submitted to a second round of PCR (a three way PCR) to generate a resistance marker cassette flanked by upstream and downstream 500 bp (or more) regions homologous to the target gene. In the third step, large amounts (1 µg) of the desired linear DNA are electroporated into lamda-red competent cells.

Vesicle Preparation

1. Vesicle Preparation by Precipitation with TCA

LB media was inoculated with bacteria grown on plates and incubated overnight at 37° C. under gentle shaking. The culture was used to inoculate 200 ml of LB at OD600 0.1. Bacteria were grown to OD600 0.4 (or as specified). Culture was centrifuged for 10 minutes at 4000×g and the supernatant was filtered through a 0.22 mm filter to remove residual bacteria.

The same experiments were also performed under iron limiting conditions by adding Dipyridyl (0.25 mM) to the LB media.

Precipitation was performed by adding to the culture supernatant 10% final of a solution at 100% (w/v) TCA, 0.4% (w/v) deoxycholate. The precipitation was allowed to proceed for 30 minutes at 4° C. Precipitate was recovered by 10 minutes centrifugation at 20000×g at 4° C. The pellet was washed once with 10% TCA (w/v) and twice with absolute ethanol. The pellet was dried with speed vac, and stored at −20° C.

The wild type and mutated strains were subjected to SDS polyacrylamide gel electrophoresis from which it could be observed that there were many more bands in the supernatant of the mutated strains than the wildtype strains. Randomly picked bands demonstrated that all the proteins in the supernatant were membrane proteins.

2. Vesicle Preparation by Ultracentrifugation

Culture supernatant was ultracentrifuged at 200000×g for 2 hours at 4° C. The pellet was washed with PBS, resuspended in PBS, and stored at −20° C.

3. Guanidinium Denaturation of the Vesicles

Prior to the guanidinium denaturation, Vesicles were precipitated with ethanol. 10 µg of OMV in PBS were precipitate by adding cold absolute ethanol to 90% final. Precipitation was allowed to proceed for 20 minutes at −20° C. Precipitate was recovered by 10 minutes centrifugation at 13000×g. Pellet was resuspended with 50 ml, 6M guanidinium, 15 mM DTT, 200 mM Tris-HCl, pH 8.0.

Denaturation was allowed to proceed for 60 minutes at 60° C. Prior to digestion, solution was diluted 1/8 with a solution of 1.5M Tris pH 8.0 and 5 mg of trypsin were added to the diluted solution. Digestion was allowed to proceed overnight at 37° C. Reaction was stopped by adding 0.1% final of formic acid. Peptides were extracted using Oasis extraction cartridges. Peptides were analyzed by LC coupled MS-MS.

4. Surface Digestion 5 mg of trypsin were added to 10 mg of vesicles in PBS and incubated at 37° C. for 3 hours. Reaction was stopped by adding 0.1% final of formic acid. Peptides were recovered by filtration through a 30 Kda cut-off filter and extracted with Oasis extraction cartridge. Peptides were analyzed with LC coupled MSMS.

Vesicle Analysis

Protein Quantification

Proteins were quantified with the Bradford method, using the BSA as standard.

SDS-Page

Samples were analyzed with a sodium dodecyl sulfate (SDS) 4-12% polyacrylamide gel, using a Mini-Protean II electrophoresis apparatus. Samples were suspended in SDS sample buffer (0.06 M Tris-HCl pH 6.8, 10% (v/v) glycerol, 2% (w/v) SDS, 5% (v/v) 2-mercaptoethanol, 10 mg/ml bromophenol blue) and heated to 100° C. for 5 min before SDS-polyacrylamide gel electrophoreis. After the run, gels were stained with Coomassie Blue MALDI-TOF Mass Spectrometry.

Protein bands or spots were excised from gels, washed with 50 mM ammonium bicarbonate/acetonitrile (50/50, v/v), and dried with a Speed-Vac centrifuge (Savant). The dried spots were digested at 37° C. for 2 h by adding 7 to 10 ml of a solution containing 5 mM ammonium bicarbonate, 0.012 mg of sequencing-grade trypsin. After digestion 0.6 ml were loaded on a matrix pre-spotted target and air-dried. Spots were washed with 0.6 ml of a solution of 70% ethanol, 0.1% trifluoracetic acid. Mass spectra were acquired on an ultraflex MALDI TOF mass spectrometer. Spectra were externally calibrated by using a combination of standards pre-spotted on the target. Protein identification was carried out by both automatic and manual comparisons of experimentally generated monoisotopic peaks of peptides in the mass range of 700 to 3,000 Da with computer-generated fingerprints, using the Mascot program.

Bi-Dimensional Electrophoresis 200 mg of vesicles were resuspended in an Immobiline re-swelling solution (7M urea, 2M thiourea, 2% (w/v) CHAPS (2% w/v) ASB14, 2% (v/v) IPG buffer pH 3-10 NL, 2 mM TBP, 65 mM DTT), and adsorbed overnight on 7 cm Immobiline DryStrips (pH 3-10 NL). Proteins were then separated by 2D electrophoresis. The first dimension was run using a IPGphor Isoelectric Focusing Unit, applying sequentially 150 V for 35 minutes, 500 V for 35 minutes, 1,000 V for 30 minutes, 2,600 V for 10 minutes, 3,500 V for 15 minutes, 4,200 V for 15 minutes, and finally 5,000 V to reach 10 kVh. For the second dimension, the strips were equilibrated by two 10 minute-incubations in 4 M urea, 2 M thiourea, 30% glycerol, 2% SDS, 5 mM TBP, 50 Mm Tris HCl pH 8.8, 2.5% acrylamide, Bromo phenol Blue 0.2%: Proteins were then separated on linear 4-12% precasted polyacrylamide gels.

Gels were stained with colloidal Coomassie Blue and scanned with a Personal Densitometer SI. Images were analyzed with Image Master 2D Elite software.

Nano-LC/MS/MS

Peptides were separated by nano-LC on a CapLC HPLC system connected to a Q-TOF Micro ESI mass spectrometer equipped with a nanospray source. Samples were loaded onto an Atlantis C18 NanoEase column (100 µm i.d.×100 mm), through a C18 trap column (300 µm i.d.×5 mm). Peptides were eluted with a 50-min gradient from 2% to 60% of 95% ACN, in a solution of 0.1% formic acid at a flow rate of 400 nl/minute. The eluted peptides were subjected to an automated data-dependent acquisition program, using the MassLynx software, version 4.0, where a MS survey scan was used to automatically select multi-charged peptides over the m/z range of 400-2,000 for further MS/MS fragmentation. Up to three different components where subjected to MS/MS fragmentation at the same time. After data acquisition, the individual MS/MS spectra were combined, smoothed and centroided by MassLynx. Search and identification of peptides were performed in batch mode with a licensed version of MASCOT. The MASCOT search parameters were: (1) species: ExPEC (2) allowed number of missed cleavages (only for trypsin digestion): 6; (3) variable post-translational modifications: methionine oxidation; (4) peptide tolerance: ±500 ppm; (5) MS/MS tolerance: ±0.3 Da and (6): peptide charge: from +1 to +4. As for the previous platform, only significant hits as defined by MASCOT probability analysis were considered. The score thresholds for acceptance of protein identifications from at least one peptide were set by MASCOT as 18 for trypsin digestion and 36 for proteinase K digestion.

Results

As a result of the above analyses, 10 further preferred antigens were identified. Namely orf03526 (SEQ ID No: 7051+7052), orf01339 (SEQ ID No: 2677+2678), orf00256 (SEQ ID No: 511+512), orf01346 (SEQ ID No: 2691+2692), orf04084 (SEQ ID No: 8167+8168), orf02374 (SEQ ID No: 4747+4748), orf03502 (SEQ ID No: 7003+7004), orf02298 (SEQ ID No: 4595+4596), orf01228 (SEQ ID No: 2455+2456), orf01227 (SEQ ID No: 2453+2454), orf02314 (SEQ ID NO: 4627+4628) and orf02850 (SEQ ID NO: 5699+5700). These are listed in Table 4 where the identities of these proteins to proteins in the UPEC strain CFT073 are also given. Further preferred antigens are those which display greater than 60% identity to preferred antigens from the CFT073 strain which were identified using the same methods as above. These preferred antigens are orf04282 (SEQ ID No: 8563+8564), orf01364 (SEQ ID No: 2727+2728), orf04936 (SEQ ID No: 9871+9872), orf02336 (SEQ ID No: 4671+4672), orf02840 (SEQ ID No: 5679+5680), orf00267 (SEQ ID No: 533+534), orf01611 (SEQ ID No: 3221+3222), orf01613 (SEQ ID No: 3225+3226) and orf03502 (SEQ ID No: 7003+7004).

Antigen Analysis

Mouse Model of Systemic Infection

To screen a large number of antigens selected by comparative genome analysis between pathogenic and non pathogenic *E. coli* strains, a protection model based on a classical virulence assay has been established.

The experimental model (immunization and infection) uses 5 week old-CD1 outbreed mice which are challenged with intraperitoneal inoculation of virulent IHE3034 *E. coli* strain. The challenge dose has been experimentally determined as the amount of bacteria able to kill 80% of adult mice within 72 hours and corresponds to $1\times10^7$ cfU/mouse for the IHE3034 strain.

Two proteins, described as virulence factors and potential protective antigens were used as positive controls. These proteins are the IbeA [299] and the IroN (SEQ ID No:2691, 2692 and refs 300,301). The recombinant proteins were expressed and used in the immunization assays.

Immunization Protocol

Mice are immunized three times by subcutaneous injection of 150 µl of protein solution using freund's adjuvants as shown in the table below:

|  | Control mice: | Immunized mice: |
|---|---|---|
| Day 0 | 75 µl of saline solution<br>75 µl of complete freund's adjuvant | 75 µl of protein solution (20 µg)<br>75 µl of complete freund's adjuvant |
| Day 21 | 75 µl of saline solution<br>75 µl of incomplete freund's adjuvant | 75 µl of protein solution (20 µg)<br>75 µl of incomplete freund's adjuvant |
| Day 35 | 75 µl of saline solution<br>75 µl of incomplete freund's adjuvant | 75 µl of protein solution (20 µg)<br>75 µl of incomplete freund's adjuvant |

Blood samples are collected the day before the first immunization (preimmune serum), at day 34 and 48 (day before challenge). Sera from immunized animals are tested by western blot and ELISA to determine the antibodies titer.

Challenge

At day 48 *E. coli* IHE3034 strain is streaked on LB agar plate from frozen stock and incubated overnight (ON) at 37° C. in incubator. At Day 49 the ON plate-culture is used to inoculate 50 ml of LB medium to have an $O.D._{600}=0.1$, and grown for 1.5 hours at 37° C. under agitation until the bacteria culture reaches an $O.D._{600}=0.6$ corresponding to $5\times10^8$ cfu/ml for the IHE3034 strain. The culture is diluted in physiological solution until the concentration of bacteria is $1\times10^8$/ml (typically 2 ml of bacterial culture is diluted in 8 ml of physiological solution) and plated using a standard plate count method to verify the inoculum. 100 µl of the cell suspension containing $1\times10^7$ IHE3034 bacteria is injected intraperitoneally, using a 1 ml syringe, to control and immunized mice. The number of deaths in each animal group at 24, 48 and 72 hours after infection are recorded.

The protection due to vaccination is evaluated by comparison of the survival in the vaccinated group and the survival in control group of mice at 72 hours from the challenge. Percentage of survival relative to controls is calculated using the formula:

$$\frac{\text{rate of survival in vaccine group} - \text{rate of survival in control group}}{\text{rate of survival in control group}}$$

Results

Figure 3:
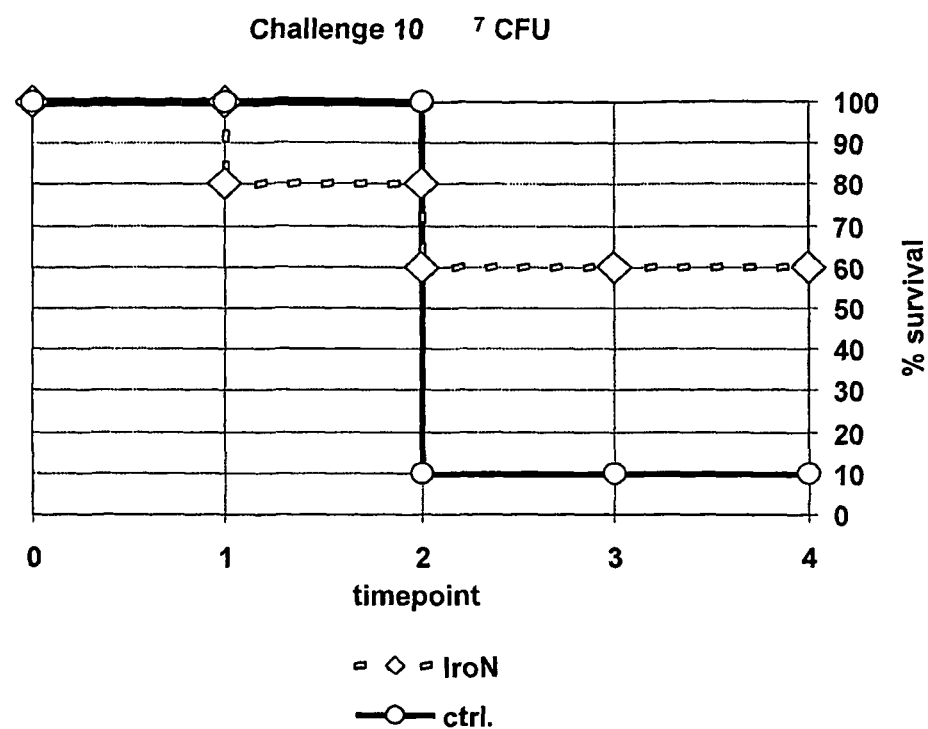
FIG. 3 shows the % survival of mice after challenge with IHE3034 following immunization with IroN or a control (top) and the serum anti-IroN Ig titer (bottom).
Figure 3:
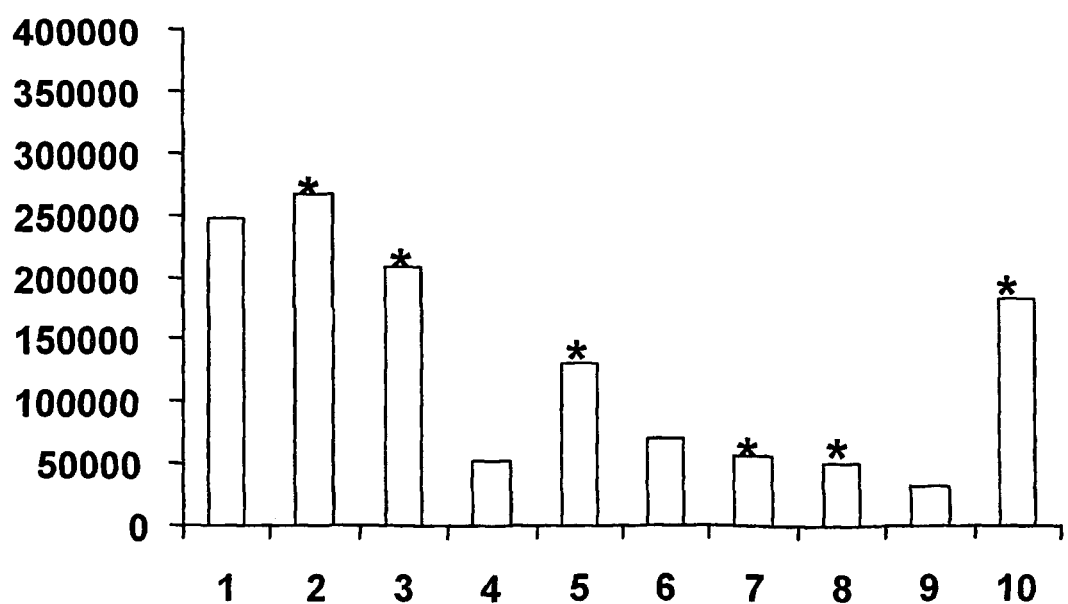
Figure 4:
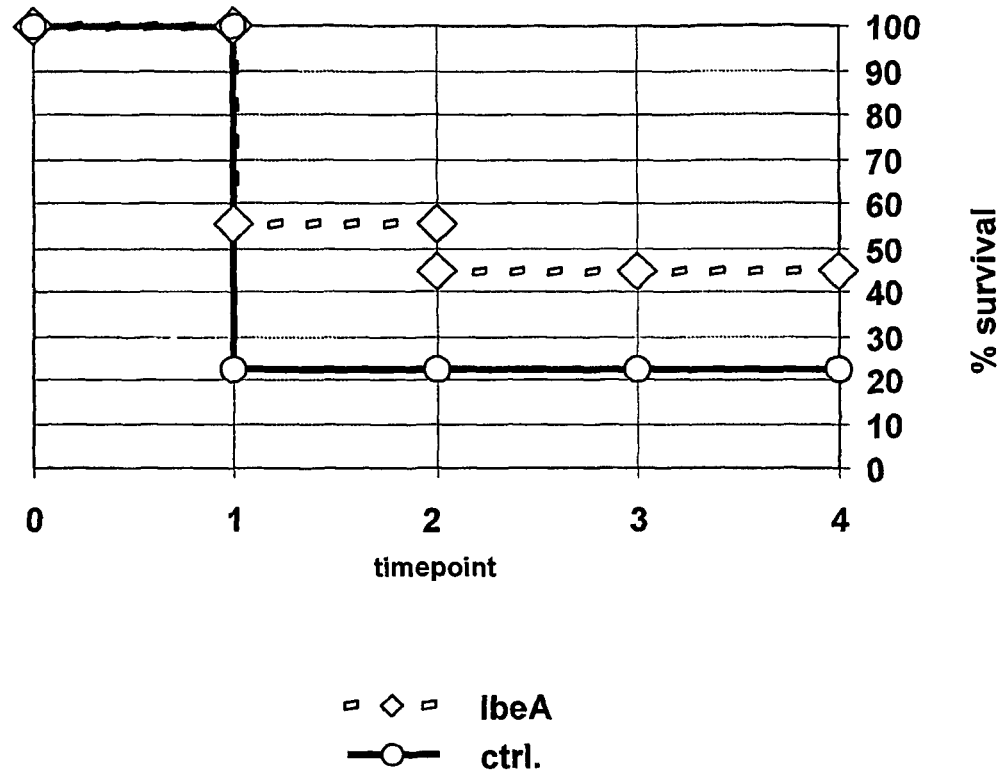
FIG. 4 is similar to FIG. 3, but for IbeA rather than IroN.
Figure 4:
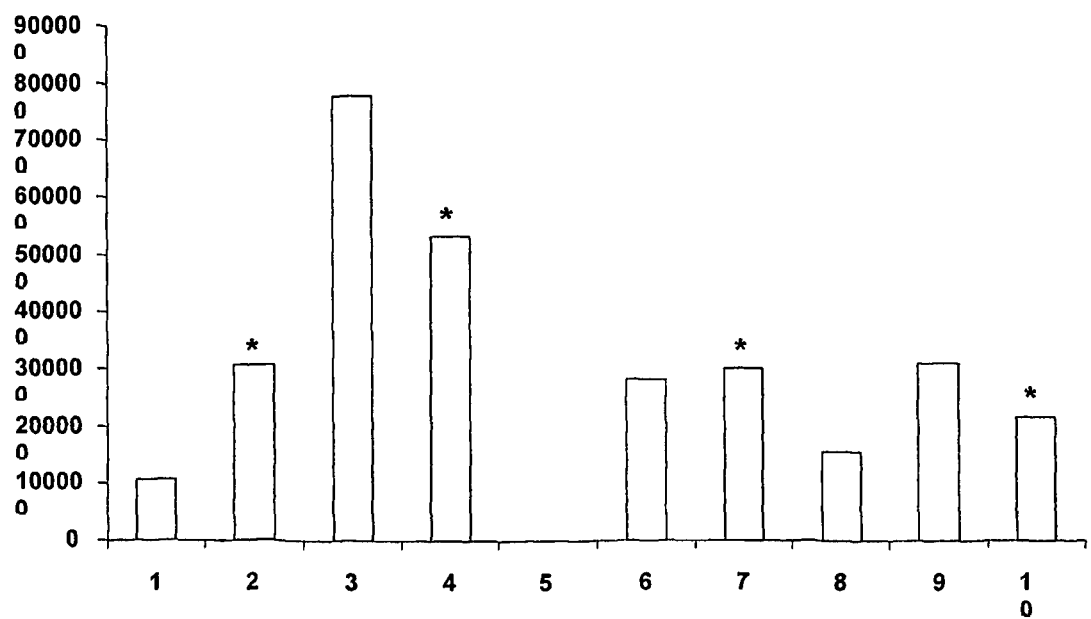

Immunization was carried out as above with positive controls IroN and IbeA. As can be seen in FIGS. 3 and 4 the % survival of the mice after challenge with IHE3034 is increased following immunization with either IroN or IbeA.

Immunization was then carried out with heat-inactivated IHE3034. As can be seen in FIG. 1, the % survival of the mice after challenge with IHE3034 is increased following immunization with heat-inactivated IHE3034.

Figure 2:
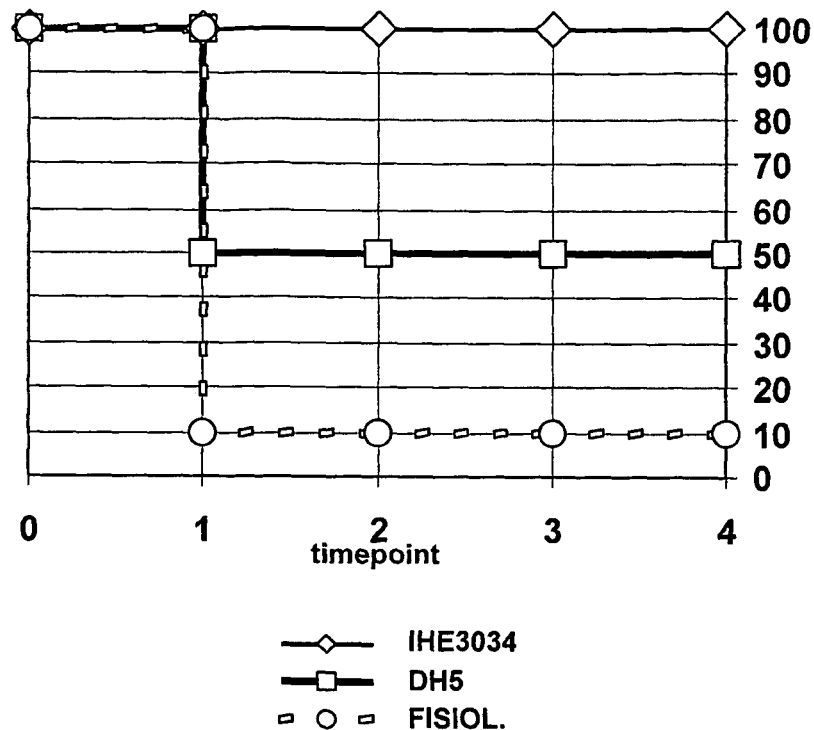
FIG. 2 shows the % survival of mice after challenge with IHE3034 following immunization either with heat-inactivated bacteria (top) or with vesicles (bottom) from ΔToIR mutants. Immunogens were prepared from the IHE3034 strain or from a control strain (DH5).
Figure 2:
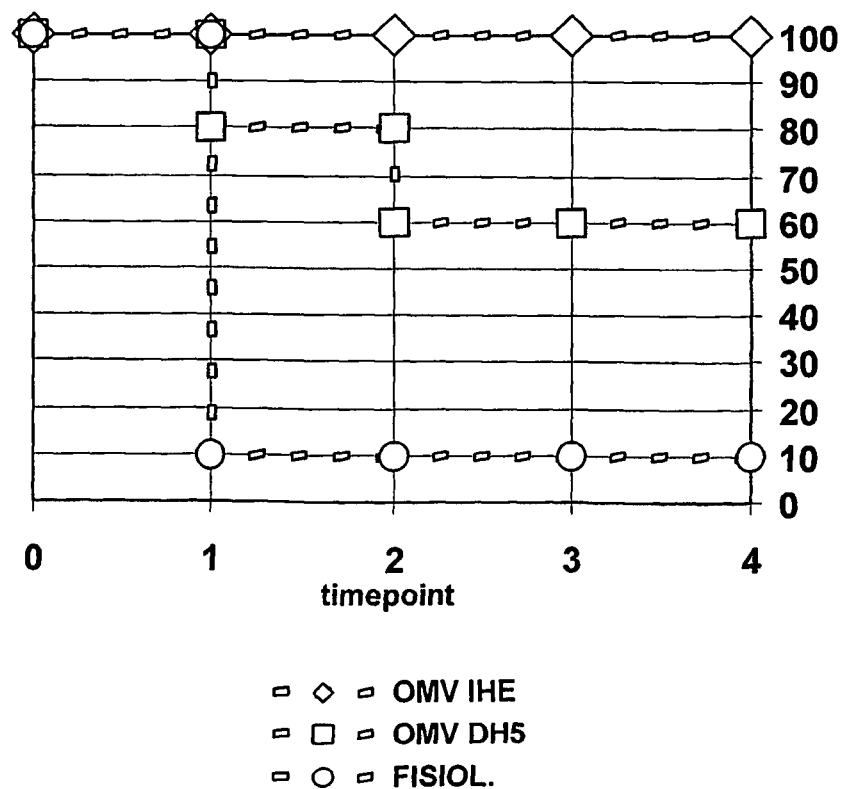

Immunization was also carried out with vesicles from IHE3034 ΔTol-R. As can be seen in FIG. 2, the % survival of the mice after challenge with IHE3034 is increased following immunization with IHE3034 ΔTol-R.

Immunisation Studies

Antigens are selected for combining to give a composition of the invention. BALB/c mice are divided into nine groups and immunized as follows:

| Group | Immunizing Composition | Route of Delivery |
|---|---|---|
| 1 | Mixture of antigens (10-20 μg protein/each) + CFA (Complete Freund's Adjuvant) | Intra-peritoneal or intra-nasal or subcutaneous |
| 2 | Mixture of antigens (5 μg/each) + Al-hydroxide (200 μg) | Intra-peritoneal or intra-nasal or subcutaneous |
| 3 | Mixture of antigens (10-20 μg protein/each) + CpG (10 ug) | Intra-peritoneal or intra-nasal or subcutaneous |
| 4 | Mixture of antigens (10-20 μg protein/each) + Al-hydroxide (200 μg) + CpG (10 μg) | Intra-peritoneal or intra-nasal or subcutaneous |
| 5 | CFA | Intra-peritoneal or intra-nasal or subcutaneous |
| 6 | Mixture of antigens (10-20 μg protein/each) + LTK63 (5 μg) | Intra-peritoneal or Intranasal or subcutaneous |
| 7 | Al-hydroxide (200 μg) + CpG (10 μg) | Intra-peritoneal or intra-nasal or subcutaneous |
| 8 | CpG (10 μg) | Intra-peritoneal or intra-nasal or subcutaneous |
| 9 | LTK63 (5 μg) | Intra-peritoneal or intra-nasal or subcutaneous |

Mice are immunized at two-week intervals. Two to three weeks after the last immunization, all mice are challenged with the appropriate MNEC strain. When mucosal immunization (e.g. intranasal) is used, the animal model is also challenged mucosally to test the protective effect of the mucosal immunogen. Immediately prior to challenge, mice are bled to determine antibody titre to the antigens that were administered.

For the mouse challenge, virulent bacteria will be grown in appropriate media. Bacteria are harvested by centrifugation, re-suspended, and serially diluted for the challenge inoculum. BALB/c mice are challenged and observed daily for 30 days post-exposure.

Total IgG and IgG1/IgG2A subtypes can be measured in mouse sera resulting from the different immunization regimens by using an ELISA assay on whole bacteria and on purified recombinant proteins. Furthermore, assessment of antigen-specific CD4+ and CD8+Th-cells in spleen cells and/or PBMC isolated from immunized mice can be carried out by multi-parametric FACS analysis, to evaluate the cytokine expression profiles of antigen-specific T-cells. In particular production of IFN-γ and IL-5 can be measured after in vitro stimulation of T cells with purified antigens. In addition, splenocytes and/or PBMC from mice immunized with each antigen/vaccine formulation may be collected 10-12 days after the last immunization dose and stimulated with MNEC bacteria. After 4 hours of stimulation, Brefeldin A is added to the cells for the following 12 hours, to block cytokine secretion. Afterwards cells are fixed and stained with antibodies to detect MNEC-specific T cells expressing IFN-γ and IL-5.

T cells can be isolated from peripheral blood lymphocytes (PBLs) by a variety of procedures known to those skilled in the art. For example, T cell populations can be "enriched" from a population of PBLs through the removal of accessory and B cells. In particular, T cell enrichment can be accomplished by the elimination of non-T cells using anti-MHC class II monoclonal antibodies. Similarly, other antibodies can be used to deplete specific populations of non-T cells. For example, anti-Ig antibody molecules can be used to deplete B cells and anti-MacI antibody molecules can be used to deplete macrophages.

T cells can be further fractionated into a number of different subpopulations by techniques known to those skilled in the art. Two major subpopulations can be isolated based on their differential expression of the cell surface markers CD4 and CD8. For example, following the enrichment of T cells as described above, CD4+ cells can be enriched using antibodies specific for CD4. The antibodies may be coupled to a solid support such as magnetic beads. Conversely, CD8+ cells can be enriched through the use of antibodies specific for CD4 (to remove CD4+ cells), or can be-isolated by the use of CD8 antibodies coupled to a solid support. CD4 lymphocytes from MNEC-infected patients can be expanded ex vivo, before or after transduction.

Following purification of T cells, the purified T cells are pre-stimulated with various cytokines including but not limited to rIL-2, IL-10, IL-12, and IL-15, which promote growth and activation of lymphocytes.

MNBC-specific T cells, may be activated by the above described immunogenic polypeptides. MNEC-specific T cells can be CD8+ or CD4+. MNEC-specific CD8+ T cells can be cytotoxic T lymphocytes (CTL) which can kill MNEC-infected cells that display any of the above described polypeptides or fragments thereof complexed with an MHC class I molecule. Chlamydia-specific CD8+ T cells can be detected by, for example, $^{51}$Cr release assays. $^{51}$Cr release assays measure the ability of MNEC-specific CD8+ T cells to lyse target cells displaying one or more of these epitopes. MNEC-specific CD8+ T cells which express antiviral agents, such as IFN γ, are also contemplated herein and can also be detected by immunological methods, preferably by intracellular staining for IFN-γ or alike cytokines after in vitro stimulation with one or more of the above described MNE polypeptides. MNEC-specific CD4+ T cells can be detected by a lymphoproliferation assay. Lymphoproliferation assays measure the ability of MNEC-specific CD4+ T cells to proliferate in response to one or more of the above described polypeptides.

It will be understood that the invention has been described by way of example only and modifications may be made whilst remaining within the scope and spirit of the invention.

TABLE 1

Annotation of ORF00001 to ORF04995

| ORFnnnnn | SEQ ID NOs | Annotation |
|---|---|---|
| ORF00001 | 1 & 2 | Phosphoglycerol transferase I |
| ORF00002 | 3 & 4 | primosomal operon 17.5K protein (mdob-dnac intergenic region) |
| ORF00003 | 5 & 6 | DNA replication protein dnaC |
| ORF00004 | 7 & 8 | Primosomal protein I |
| ORF00005 | 9 & 10 | probable integral membrane protein Cj1165c, putative |
| ORF00006 | 11 & 12 | probable integral membrane protein Cj1166c, putative |
| ORF00007 | 13 & 14 | transcriptional regulator, LuxR family domain protein |
| ORF00008 | 15 & 16 | Transcriptional activator protein bglJ |
| ORF00009 | 17 & 18 | Ferric iron reductase protein fhuF [1.6.99.—] |
| ORF00010 | 19 & 20 | Protein of unknown function (DUF1435) family |
| ORF00011 | 21 & 22 | conserved hypothetical protein |
| ORF00012 | 23 & 24 | Ribosomal RNA small subunit methyltransferase C (AE005668) [2.1.1.52] |
| ORF00013 | 25 & 26 | DNA polymerase III, psi subunit (holD) [2.7.7.7] |
| ORF00014 | 27 & 28 | ribosomal-protein-alanine acetyltransferase (rimI) [2.3.1.128] |
| ORF00015 | 29 & 30 | HAD superfamily (subfamily IA) hydrolase, TIGR02254 |
| ORF00016 | 31 & 32 | site-specific recombinase, phage integrase family |
| ORF00017 | 33 & 34 | hypothetical protein |
| ORF00018 | 35 & 36 | conserved hypothetical protein |
| ORF00019 | 37 & 38 | Hypothetical nin region protein (cysD) |
| ORF00020 | 39 & 40 | hypothetical protein |
| ORF00021 | 41 & 42 | conserved hypothetical protein |
| ORF00022 | 43 & 44 | Sb36 |
| ORF00023 | 45 & 46 | Sb36 |
| ORF00024 | 47 & 48 | hypothetical protein |
| ORF00025 | 49 & 50 | hypothetical protein |
| ORF00026 | 51 & 52 | conserved hypothetical protein |
| ORF00027 | 53 & 54 | repressor |
| ORF00028 | 55 & 56 | Sb40 |
| ORF00029 | 57 & 58 | immunity region |
| ORF00030 | 59 & 60 | conserved hypothetical protein |
| ORF00031 | 61 & 62 | replication protein |
| ORF00032 | 63 & 64 | hypothetical protein |
| ORF00033 | 65 & 66 | phage N-6-adenine-methyltransferase [2.1.1.72] |
| ORF00034 | 67 & 68 | LexA repressor |
| ORF00035 | 69 & 70 | crossover junction endodeoxyribonuclease [3.1.22.—] |
| ORF00036 | 71 & 72 | Sb46 |
| ORF00037 | 73 & 74 | Protein of unknown function (DUF1277) superfamily |
| ORF00038 | 75 & 76 | Antitermination protein Q homolog from lambdoid prophage |
| ORF00039 | 77 & 78 | lysis protein S.b1556 |
| ORF00040 | 79 & 80 | endolysin (lysozyme) [3.2.1.17] |
| ORF00041 | 81 & 82 | Bacteriophage lysis protein |
| ORF00042 | 83 & 84 | hypothetical protein |
| ORF00043 | 85 & 86 | Gifsy-2 prophage protein |
| ORF00044 | 87 & 88 | Phage terminase large subunit (GpA) |
| ORF00045 | 89 & 90 | conserved hypothetical protein |
| ORF00046 | 91 & 92 | phage portal protein, lambda family |
| ORF00047 | 93 & 94 | Gifsy-2 prophage resembles Clp protease |
| ORF00048 | 95 & 96 | conserved hypothetical protein |
| ORF00049 | 97 & 98 | Gifsy-2 prophage ATP-binding sugar transporter-like protein |
| ORF00050 | 99 & 100 | Gifsy 1 prophage: similar to minor tail protein Z |
| ORF00051 | 101 & 102 | Phage minor tail protein U |
| ORF00052 | 103 & 104 | putative tail component of prophage CP-933K |
| ORF00053 | 105 & 106 | phage minor tail protein G |
| ORF00054 | 107 & 108 | phage tail assembly protein T |
| ORF00055 | 109 & 110 | Gifsy-1 prophage protein |
| ORF00056 | 111 & 112 | Phage minor tail protein |
| ORF00057 | 113 & 114 | phage minor tail protein L |
| ORF00058 | 115 & 116 | Putative tail fiber component K of prophage |
| ORF00059 | 117 & 118 | Putative tail fiber component K of prophage |
| ORF00060 | 119 & 120 | Gifsy-1 prophage protein |
| ORF00061 | 121 & 122 | Gifsy-1 prophage protein |
| ORF00062 | 123 & 124 | host specificity protein (partial) |
| ORF00063 | 125 & 126 | Lom |
| ORF00064 | 127 & 128 | conserved hypothetical protein |
| ORF00065 | 129 & 130 | hypothetical protein |
| ORF00066 | 131 & 132 | conserved hypothetical protein |
| ORF00067 | 133 & 134 | conserved hypothetical protein |
| ORF00068 | 135 & 136 | conserved hypothetical protein |
| ORF00069 | 137 & 138 | maturase-related protein |
| ORF00070 | 139 & 140 | DinI-like protein Z3916-ECs3483 (AF175466) |
| ORF00071 | 141 & 142 | peptide chain release factor 3 (prfC) |
| ORF00072 | 143 & 144 | Osmotically inducible protein Y precursor |
| ORF00073 | 145 & 146 | Protein of unknown function (DUF1328) family |
| ORF00074 | 147 & 148 | unnamed protein product |
| ORF00075 | 149 & 150 | Mg-dependent DNase |
| ORF00076 | 151 & 152 | pyruvate formate lyase activating enzyme (act) [1.97.1.4] |

TABLE 1-continued

Annotation of ORF00001 to ORF04995

| ORFnnnnn | SEQ ID NOs | Annotation |
|---|---|---|
| ORF00077 | 153 & 154 | Protein |
| ORF00078 | 155 & 156 | conserved hypothetical protein |
| ORF00079 | 157 & 158 | deoxyribose-phosphate aldolase (deoC) [4.1.2.4] |
| ORF00080 | 159 & 160 | Thymidine phosphorylase (TDRPASE) |
| ORF00081 | 161 & 162 | phosphopentomutase (deoB) [5.4.2.7] |
| ORF00082 | 163 & 164 | purine nucleoside phosphorylase (deoD) [2.4.2.1] |
| ORF00083 | 165 & 166 | conserved hypothetical protein |
| ORF00084 | 167 & 168 | lipoate-protein ligase A [6.3.4.—] |
| ORF00085 | 169 & 170 | Protein smp precursor |
| ORF00086 | 171 & 172 | phosphoserine phosphatase (serB) [3.1.3.3] |
| ORF00087 | 173 & 174 | DNA repair protein RadA (radA) |
| ORF00088 | 175 & 176 | nicotinamide-nucleotide adenylyltransferase [2.7.7.1] |
| ORF00089 | 177 & 178 | conserved hypothetical protein |
| ORF00090 | 179 & 180 | Helix-turn-helix motif |
| ORF00091 | 181 & 182 | ABC transporter ATP-binding protein yjjK (atp_bind) |
| ORF00092 | 183 & 184 | soluble lytic murein transglycosylase [3.2.1.—] |
| ORF00093 | 185 & 186 | trp operon repressor (trpR) |
| ORF00094 | 187 & 188 | conserved hypothetical protein TIGR00258 |
| ORF00095 | 189 & 190 | phosphoglycerate mutase family protein, putative [5.4.2.1] |
| ORF00096 | 191 & 192 | Right origin-binding protein |
| ORF00097 | 193 & 194 | CreA protein |
| ORF00098 | 195 & 196 | Transcriptional Regulatory protein creB |
| ORF00099 | 197 & 198 | Sensor protein creC [2.7.3.—] |
| ORF00100 | 199 & 200 | Inner membrane protein creD (AE005671) |
| ORF00101 | 201 & 202 | Aerobic respiration control protein arcA (Dye resistance protein) (arcA) |
| ORF00102 | 203 & 204 | RNA methyltransferase, TrmH family, group 1 |
| ORF00103 | 205 & 206 | aspartokinase I, homoserine dehydrogenase I |
| ORF00104 | 207 & 208 | homoserine kinase (thrB) [2.7.1.39] |
| ORF00105 | 209 & 210 | threonine synthase (thrC) [4.2.3.1] |
| ORF00106 | 211 & 212 | unnamed protein product; ORF_ID: o101#5 |
| ORF00107 | 213 & 214 | conserved hypothetical protein |
| ORF00108 | 215 & 216 | UPF0246 protein yaaA |
| ORF00109 | 217 & 218 | unnamed protein product (ORF8) |
| ORF00110 | 219 & 220 | transaldolase (tal) [2.2.1.2] |
| ORF00111 | 221 & 222 | Molybdopterin biosynthesis mog protein |
| ORF00112 | 223 & 224 | gpr1-fun34-yaaH family protein |
| ORF00113 | 225 & 226 | unnamed protein product; ORF4 |
| ORF00114 | 227 & 228 | conserved hypothetical protein |
| ORF00115 | 229 & 230 | hypothetical protein |
| ORF00116 | 231 & 232 | chaperone protein DnaK (dnaK) |
| ORF00117 | 233 & 234 | chaperone protein DnaJ (dnaJ) |
| ORF00118 | 235 & 236 | gef protein-related protein |
| ORF00119 | 237 & 238 | Putative conserved protein |
| ORF00120 | 239 & 240 | Sulfatase, putative |
| ORF00121 | 241 & 242 | conserved hypothetical protein |
| ORF00122 | 243 & 244 | Na+-H+ antiporter NhaA (nhaA) |
| ORF00123 | 245 & 246 | Transcriptional activator protein nhaR |
| ORF00124 | 247 & 248 | riboflavin biosynthesis protein RibF (ribF) [2.7.1.26 2.7.7.2] |
| ORF00125 | 249 & 250 | isoleucyl-tRNA synthetase (ileS) [6.1.1.5] |
| ORF00126 | 251 & 252 | lipoprotein signal peptidase (lspA) [3.4.23.36] |
| ORF00127 | 253 & 254 | 5.2.1.8 [5.2.1.8] |
| ORF00128 | 255 & 256 | 4-hydroxy-3-methylbut-2-enyl diphosphate reductase (ispH) [1.17.1.2] |
| ORF00129 | 257 & 258 | inosine-uridine preferring nucleoside hydrolase [3.2.—.—] |
| ORF00130 | 259 & 260 | hyopthetical protein DUF805 |
| ORF00131 | 261 & 262 | dihydrodipicolinate reductase (dapB) [1.3.1.26] |
| ORF00132 | 263 & 264 | carbamoyl-phosphate synthase, small subunit (carA) [6.3.5.5] |
| ORF00133 | 265 & 266 | carbamoyl-phosphate synthase, large subunit (carB) [6.3.5.5] |
| ORF00134 | 267 & 268 | Transposase |
| ORF00135 | 269 & 270 | Transcriptional activatory protein caiF |
| ORF00136 | 271 & 272 | Carnitine operon protein caiE |
| ORF00137 | 273 & 274 | echA1 [5.—.—.—] |
| ORF00138 | 275 & 276 | caiC (fadD) [6.3.2.—] |
| ORF00139 | 277 & 278 | CAIB-BAIF family protein, putative [2.8.3.—] |
| ORF00140 | 279 & 280 | Crotonobetainyl-CoA dehydrogenase (Crotonobetainyl-CoAreductase) (acd) [1.3.99.—] |
| ORF00141 | 281 & 282 | L-carnitine-gamma-butyrobetaine antiporter |
| ORF00142 | 283 & 284 | electron transfer flavoprotein, beta subunit, putative |
| ORF00143 | 285 & 286 | electron transfer flavoprotein, alpha subunit, putative |
| ORF00144 | 287 & 288 | FixC protein [1.5.5.—] |
| ORF00145 | 289 & 290 | Ferredoxin-like protein |
| ORF00146 | 291 & 292 | sugar transporter, putative |
| ORF00147 | 293 & 294 | Glutathione-regulated potassium-efflux system ancillary protein kefF (QUINONE) [1.6.99.2] |
| ORF00148 | 295 & 296 | Glutathione-regulated potassium-efflux system protein kefC (K(+)-H(+)antiporter) |
| ORF00149 | 297 & 298 | dihydrofolate reductase (folA) [1.5.1.3] |
| ORF00150 | 299 & 300 | CcdB antidote CcdA |

TABLE 1-continued

Annotation of ORF00001 to ORF04995

| ORFnnnnn | SEQ ID NOs | Annotation |
|---|---|---|
| ORF00151 | 301 & 302 | CcdB-like protein |
| ORF00152 | 303 & 304 | CcdB-like protein |
| ORF00153 | 305 & 306 | bis(5'-nucleosyl)-tetraphosphatase (symmetrical) [3.6.1.41] |
| ORF00154 | 307 & 308 | Protein apaG (AJ012295) |
| ORF00155 | 309 & 310 | dimethyladenosine transferase (ksgA) [2.1.1.—] |
| ORF00156 | 311 & 312 | 4-hydroxythreonine-4-phosphate dehydrogenase (pdxA) [1.1.1.262] |
| ORF00157 | 313 & 314 | Survival protein surA precursor (Peptidyl-prolyl cis-trans isomerasesurA) (PPIase) (Rotamase C) (PPIase) [5.2.1.8] |
| ORF00158 | 315 & 316 | Organic solvent tolerance protein precursor |
| ORF00159 | 317 & 318 | Organic solvent tolerance protein precursor |
| ORF00160 | 319 & 320 | DnaJ-like protein djlA (AE005182) |
| ORF00161 | 321 & 322 | ribosomal large subunit pseudouridine synthase A |
| ORF00162 | 323 & 324 | RNA polymerase associated protein (hepA) [3.6.1.—] |
| ORF00163 | 325 & 326 | hypothetical protein |
| ORF00164 | 327 & 328 | DNA polymerase II |
| ORF00165 | 329 & 330 | L-ribulose-5-phosphate 4-epimerase (araD) [5.1.3.4] |
| ORF00166 | 331 & 332 | L-arabinose isomerase (araA) [5.3.1.4] |
| ORF00167 | 333 & 334 | L-ribulokinase (araB) [2.7.1.16] |
| ORF00168 | 335 & 336 | transcriptional regulator, AraC family |
| ORF00169 | 337 & 338 | conserved hypothetical protein |
| ORF00170 | 339 & 340 | DedA family integral membrane protein |
| ORF00171 | 341 & 342 | thiamine ABC transporter, ATP-binding protein |
| ORF00172 | 343 & 344 | thiamine-thiamine pyrophosphate ABC transporter, permease protein (thiP) |
| ORF00173 | 345 & 346 | thiamin-thiamin pyrophosphate ABC transporter, thiamin-thiamin pyrophospate-binding protein (thiB) |
| ORF00174 | 347 & 348 | Bacterial extracellular solute-binding proteins, family 5 family |
| ORF00175 | 349 & 350 | 3-isopropylmalate dehydratase, small subunit (leuD) [4.2.1.33] |
| ORF00176 | 351 & 352 | 3-isopropylmalate dehydratase, large subunit (leuC) [4.2.1.33] |
| ORF00177 | 353 & 354 | 3-isopropylmalate dehydrogenase (leuB) [1.1.1.85] |
| ORF00178 | 355 & 356 | 2-isopropylmalate synthase (leuA) [2.3.3.13] |
| ORF00179 | 357 & 358 | LeuO protein. |
| ORF00180 | 359 & 360 | acetolactate synthase, large subunit, biosynthetic type (ilvB) [2.2.1.6] |
| ORF00181 | 361 & 362 | acetolactate synthase, small subunit (ilvN) [2.2.1.6] |
| ORF00182 | 363 & 364 | transcriptional repressor of fru operon and others |
| ORF00183 | 365 & 366 | mraZ protein (mraZ) |
| ORF00184 | 367 & 368 | S-adenosyl-methyltransferase MraW (mraW) [2.1.1.—] |
| ORF00185 | 369 & 370 | Cell division protein ftsL |
| ORF00186 | 371 & 372 | Peptidoglycan synthetase ftsI precursor (PBP) [2.4.1.129] |
| ORF00187 | 373 & 374 | UDP-N-acetylmuramoylalanyl-D-glutamate--2,6-diaminopimelate ligase |
| ORF00188 | 375 & 376 | UDP-N-acetylmuramoylalanyl-D-glutamyl-2,6-diaminopimelate--D-alanyl-D-alanyl ligase (murF) [6.3.2.10] |
| ORF00189 | 377 & 378 | phospho-N-acetylmuramoyl-pentapeptide-transferase (mraY) [2.7.8.13] |
| ORF00190 | 379 & 380 | UDP-N-acetylmuramoylalanine--D-glutamate ligase (murD) [6.3.2.9] |
| ORF00191 | 381 & 382 | Cell division protein ftsW |
| ORF00192 | 383 & 384 | undecaprenyldiphospho-muramoylpentapeptide beta-N-acetylglucosaminyltransferase (murG) [2.4.1.227] |
| ORF00193 | 385 & 386 | UDP-N-acetylmuramate--alanine ligase (murC) [6.3.2.8] |
| ORF00194 | 387 & 388 | D-alanine--D-alanine ligase B (ddlB) [6.3.2.4] |
| ORF00195 | 389 & 390 | Acetolactate synthase isozyme III large subunit [4.1.3.18] |
| ORF00196 | 391 & 392 | acetolactate synthase, small subunit (ilvN) [2.2.1.6] |
| ORF00197 | 393 & 394 | fructose repressor (catabolite repressor-activator) |
| ORF00198 | 395 & 396 | fructose repressor (catabolite repressor-activator) |
| ORF00199 | 397 & 398 | Acetolactate synthase isozyme III large subunit [4.1.3.18] |
| ORF00200 | 399 & 400 | acetolactate synthase, small subunit (ilvN) [2.2.1.6] |
| ORF00201 | 401 & 402 | fructose repressor (catabolite repressor-activator) |
| ORF00202 | 403 & 404 | D-alanine-D-alanine ligase B (ddlB) [6.3.2.4] |
| ORF00203 | 405 & 406 | cell division protein ftsQ |
| ORF00204 | 407 & 408 | cell division protein FtsA (ftsA) |
| ORF00205 | 409 & 410 | Cell division protein ftsZ |
| ORF00206 | 411 & 412 | UDP-3-0-acyl N-acetylglucosamine deacetylase (lpxC) [3.5.1.—] |
| ORF00207 | 413 & 414 | Secretion monitor precursor |
| ORF00208 | 415 & 416 | secA protein |
| ORF00209 | 417 & 418 | preprotein translocase, SecA subunit (secA) |
| ORF00210 | 419 & 420 | Mutator mutT protein (mutT) [3.6.1.—] |
| ORF00211 | 421 & 422 | UPF0243 zinc-binding protein yacG-related protein |
| ORF00212 | 423 & 424 | Hypothetical UPF0289 protein yacF |
| ORF00213 | 425 & 426 | dephospho-CoA kinase (coaE) [2.7.1.24] |
| ORF00214 | 427 & 428 | guanosine monophosphate reductase (guaC) [1.7.1.7] |
| ORF00215 | 429 & 430 | Protein transport protein hofC (MTB) |
| ORF00216 | 431 & 432 | Protein transport protein hofB (MTB) |
| ORF00217 | 433 & 434 | Prepilin peptidase dependent protein D precursor |
| ORF00218 | 435 & 436 | nicotinate-nucleotide pyrophosphorylase (nadC) [2.4.2.19] |
| ORF00219 | 437 & 438 | AmpD protein (ampD) |
| ORF00220 | 439 & 440 | regulates ampC |
| ORF00221 | 441 & 442 | Aromatic amino acid transport protein aroP (General aromatic aminoacid permease) |

TABLE 1-continued

Annotation of ORF00001 to ORF04995

| ORFnnnnn | SEQ ID NOs | Annotation |
|---|---|---|
| ORF00222 | 443 & 444 | uropathogenic specific protein |
| ORF00223 | 445 & 446 | unnamed protein product; 9 bp deletion at the 3' end OrfU2 |
| ORF00224 | 447 & 448 | uropathogenic specific protein (partial) [3.1.—.—] |
| ORF00225 | 449 & 450 | unnamed protein product; OrfU3 |
| ORF00226 | 451 & 452 | unnamed protein product; OrfU1 |
| ORF00227 | 453 & 454 | Pyruvate dehydrogenase complex repressor |
| ORF00228 | 455 & 456 | Pyruvate dehydrogenase E1 component (aceE) [1.2.4.1] |
| ORF00229 | 457 & 458 | pyruvate dehydrogenase complex dihydrolipoamide acetyltransferase (aceF) [2.3.1.12] |
| ORF00230 | 459 & 460 | dihydrolipoamide dehydrogenase (lpdA) [1.8.1.4] |
| ORF00231 | 461 & 462 | conserved hypothetical protein |
| ORF00232 | 463 & 464 | hypothetical protein |
| ORF00233 | 465 & 466 | hypothetical protein |
| ORF00234 | 467 & 468 | aconitate hydratase 2 (acnB) [4.2.1.3] |
| ORF00235 | 469 & 470 | S-adenosylmethionine decarboxylase proenzyme |
| ORF00236 | 471 & 472 | spermidine synthase (speE) [2.5.1.16] |
| ORF00237 | 473 & 474 | yacC |
| ORF00238 | 475 & 476 | Blue copper oxidase cueO precursor |
| ORF00239 | 477 & 478 | Glucose dehydrogenase |
| ORF00240 | 479 & 480 | hypoxanthine phosphoribosyltransferase (hpt) [2.4.2.8] |
| ORF00241 | 481 & 482 | Protein yadF [4.2.1.1] |
| ORF00242 | 483 & 484 | ABC transporter ATP-binding protein |
| ORF00243 | 485 & 486 | ABC transporter integral membrane protein STY0195 (membrane) |
| ORF00244 | 487 & 488 | Fructose-specific phosphotransferase system component homolog. (PTS) [2.7.1.69] |
| ORF00245 | 489 & 490 | Polysaccharide deacetylase domain protein |
| ORF00246 | 491 & 492 | aspartate 1-decarboxylase (panD) [4.1.1.11] |
| ORF00247 | 493 & 494 | transposase |
| ORF00248 | 495 & 496 | pantoate--beta-alanine ligase (panC) [6.3.2.1] |
| ORF00249 | 497 & 498 | 3-methyl-2-oxobutanoate hydroxymethyltransferase (panB) [2.1.2.11] |
| ORF00250 | 499 & 500 | Hypothetical fimbrial-like protein yadC precursor |
| ORF00251 | 501 & 502 | Protein yadK |
| ORF00252 | 503 & 504 | Fimbrial protein subfamily |
| ORF00253 | 505 & 506 | hypothetical protein |
| ORF00254 | 507 & 508 | Outer membrane usher protein htrE precursor |
| ORF00255 | 509 & 510 | Chaperone protein ecpD precursor |
| ORF00256 | 511 & 512 | pilin chaperone ecpD2 |
| ORF00257 | 513 & 514 | 2-amino-4-hydroxy-6-hydroxymethyldihydropteridine pyrophosphokinase (folK) [2.7.6.3] |
| ORF00258 | 515 & 516 | Poly(A) polymerase (PAP) (Plasmid copy number protein) (PAP) [2.7.7.19] |
| ORF00259 | 517 & 518 | poly(A) polymerase (PAP) |
| ORF00260 | 519 & 520 | glutamate-tRNA ligase homolog yadB |
| ORF00261 | 521 & 522 | dnaK suppressor protein |
| ORF00262 | 523 & 524 | sugar fermentation stimulation protein (sfsA) |
| ORF00263 | 525 & 526 | 2-5 RNA ligase |
| ORF00264 | 527 & 528 | ATP-dependent helicase HrpB (hrpB) |
| ORF00265 | 529 & 530 | peptidoglycan synthetase penicillin-binding protein 1B |
| ORF00266 | 531 & 532 | penicillin-binding protein 1B (mrcB) |
| ORF00267 | 533 & 534 | Ferrichrome-iron receptor precursor (Ferric hydroxamate uptake)(Ferric hydroxamate receptor) |
| ORF00268 | 535 & 536 | Ferrichrome transport ATP-binding protein fhuC |
| ORF00269 | 537 & 538 | Ferrichrome-binding periplasmic protein precursor |
| ORF00270 | 539 & 540 | Ferrichrome transport system permease protein fhuB (membrane) |
| ORF00271 | 541 & 542 | glutamate-1-semialdehyde-2,1-aminomutase (hemL) [5.4.3.8] |
| ORF00272 | 543 & 544 | H(+)-Cl(−) exchange transporter clcA |
| ORF00273 | 545 & 546 | HesB family protein |
| ORF00274 | 547 & 548 | predicted membrane protein |
| ORF00275 | 549 & 550 | Vitamin B12 transport protein btuF precursor (PBP) |
| ORF00276 | 551 & 552 | MTA-SAH nucleosidase |
| ORF00277 | 553 & 554 | deoxyguanosinetriphosphate triphosphohydrolase, putative subfamily [3.1.5.1] |
| ORF00278 | 555 & 556 | htrA product [3.4.21.—] |
| ORF00279 | 557 & 558 | Carbohydrate diacid regulator |
| ORF00280 | 559 & 560 | Hypothetical UPF0325 protein yaeH |
| ORF00281 | 561 & 562 | 2,3,4,5-tetrahydropyridine-2,6-dicarboxylate N-succinyltransferase (dapD) [2.3.1.117] |
| ORF00282 | 563 & 564 | protein-P-II uridylyltransferase (glnD) [2.7.7.59] |
| ORF00283 | 565 & 566 | methionine aminopeptidase, type I (map) [3.4.11.18] |
| ORF00284 | 567 & 568 | conserved hypothetical protein |
| ORF00285 | 569 & 570 | 30S ribosomal protein S2 |
| ORF00286 | 571 & 572 | translation elongation factor Ts (tsf) |
| ORF00287 | 573 & 574 | uridylate kinase (pyrH) [2.7.4.—] |
| ORF00288 | 575 & 576 | ribosome recycling factor (frr) |
| ORF00289 | 577 & 578 | 1-deoxy-D-xylulose 5-phosphate reductoisomerase (dxr) [1.1.1.267] |
| ORF00290 | 579 & 580 | undecaprenyl diphosphate synthase (uppS) [2.5.1.31] |
| ORF00291 | 581 & 582 | phosphatidate cytidylyltransferase (cdsA) [2.7.7.41] |
| ORF00292 | 583 & 584 | membrane-associated zinc metalloprotease, putative |
| ORF00293 | 585 & 586 | outer membrane protein precursor yaeT (D15) |

TABLE 1-continued

Annotation of ORF00001 to ORF04995

| ORFnnnnn | SEQ ID NOs | Annotation |
|---|---|---|
| ORF00294 | 587 & 588 | histone-like protein, located in outer membrane or |
| ORF00295 | 589 & 590 | UDP-3-O-[3-hydroxymyristoyl] glucosamine N-acyltransferase (lpxD) [2.3.1.—] |
| ORF00296 | 591 & 592 | (3R)-hydroxymyristol acyl carrier protein dehydratase [4.2.1.—] |
| ORF00297 | 593 & 594 | acyl-[acyl-carrier-protein]--UDP-N-acetylglucosamine O-acyltransferase (lpxA) [2.3.1.129] |
| ORF00298 | 595 & 596 | lipid-A-disaccharide synthase (lpxB) [2.4.1.182] |
| ORF00299 | 597 & 598 | ribonuclease HII (rnhB) [3.1.26.4] |
| ORF00300 | 599 & 600 | DNA polymerase III alpha subunit (dnaE) [2.7.7.7] |
| ORF00301 | 601 & 602 | acetyl-CoA carboxylase, carboxyl transferase, alpha subunit (accA) [6.4.1.2] |
| ORF00302 | 603 & 604 | Lysine decarboxylase, constitutive (ldc) [4.1.1.18] |
| ORF00303 | 605 & 606 | Lysine decarboxylase, constitutive (ldc) [4.1.1.18] |
| ORF00304 | 607 & 608 | lactoylglutathione lyase |
| ORF00305 | 609 & 610 | cell cycle protein (Ile) |
| ORF00306 | 611 & 612 | Rof protein |
| ORF00307 | 613 & 614 | putative cytoplasmic protein |
| ORF00308 | 615 & 616 | YaeQ protein |
| ORF00309 | 617 & 618 | Peptidyl-tRNA hydrolase domain, putative |
| ORF00310 | 619 & 620 | Copper homeostasis protein cutF precursor (lipoprotein) |
| ORF00311 | 621 & 622 | yaeF protein |
| ORF00312 | 623 & 624 | prolyl-tRNA synthetase (proS) [6.1.1.15] |
| ORF00313 | 625 & 626 | UPF0066 protein rcsF (orf3) |
| ORF00314 | 627 & 628 | Protein rcsF |
| ORF00315 | 629 & 630 | D-methionine-binding lipoprotein metQ precursor (hlpA) |
| ORF00316 | 631 & 632 | D-methionine transport system permease protein metI (membrane) |
| ORF00317 | 633 & 634 | D-methionine ABC transporter, ATP-binding protein (metN) |
| ORF00318 | 635 & 636 | unnamed protein product |
| ORF00319 | 637 & 638 | hypothetical protein |
| ORF00320 | 639 & 640 | 2,5-diketo-D-gluconic acid reductase B (orf267) [1.1.1.274] |
| ORF00321 | 641 & 642 | unnamed protein product; Highly similar to LysR-family transcriptional regulator, YafC protein of Escherichia coli (orf304) |
| ORF00322 | 643 & 644 | unnamed protein product |
| ORF00323 | 645 & 646 | methlytransferase, UbiE-COQ5 family |
| ORF00324 | 647 & 648 | Membrane-bound lytic murein transglycosylase D precursor(Murein hydrolase D) (Regulatory protein dniR) [3.2.1.—] |
| ORF00325 | 649 & 650 | hydroxyacylglutathione hydrolase [3.1.2.6] |
| ORF00326 | 651 & 652 | hypothetical protein |
| ORF00327 | 653 & 654 | conserved hypothetical protein |
| ORF00328 | 655 & 656 | RNase HI, degrades RNA of DNA-RNA hybrids |
| ORF00329 | 657 & 658 | DNA polymerase III, epsilon subunit (dnaQ) [2.7.7.7] |
| ORF00330 | 659 & 660 | Hypothetical lipoprotein yafT precursor |
| ORF00331 | 661 & 662 | Aec32 |
| ORF00332 | 663 & 664 | Aec31 |
| ORF00333 | 665 & 666 | Aec30 |
| ORF00334 | 667 & 668 | Aec29 |
| ORF00335 | 669 & 670 | hypothetical protein |
| ORF00336 | 671 & 672 | Aec28 |
| ORF00337 | 673 & 674 | Aec27 |
| ORF00338 | 675 & 676 | Aec26 |
| ORF00339 | 677 & 678 | Aec25 |
| ORF00340 | 679 & 680 | Aec24 |
| ORF00341 | 681 & 682 | Aec23 |
| ORF00342 | 683 & 684 | hypothetical protein |
| ORF00343 | 685 & 686 | Aec22 |
| ORF00344 | 687 & 688 | Aec20 |
| ORF00345 | 689 & 690 | Aec19 |
| ORF00346 | 691 & 692 | Aec18 |
| ORF00347 | 693 & 694 | Aec17 |
| ORF00348 | 695 & 696 | Aec16 |
| ORF00349 | 697 & 698 | Aec15 (AF044503) |
| ORF00350 | 699 & 700 | Aec14 |
| ORF00351 | 701 & 702 | Aec13 |
| ORF00352 | 703 & 704 | Transposase (IS4 family) |
| ORF00353 | 705 & 706 | Aec7 |
| ORF00354 | 707 & 708 | possible hydrolase |
| ORF00355 | 709 & 710 | hypothetical protein |
| ORF00356 | 711 & 712 | Inhibitor of vertebrate lysozyme precursor |
| ORF00357 | 713 & 714 | Acyl-CoA dehydrogenase (EC 1.3.99.—). [1.3.99.—] |
| ORF00358 | 715 & 716 | Phosphoheptose isomerase (gmhA) [5.—.—.—] |
| ORF00359 | 717 & 718 | Bacterial protein of unknown function (DUF949) superfamily |
| ORF00360 | 719 & 720 | Predicted glutamine amidotransferase |
| ORF00361 | 721 & 722 | conserved hypothetical protein |
| ORF00362 | 723 & 724 | Hypothetical lipoprotein yafL precursor |
| ORF00363 | 725 & 726 | Protein of unknown function (DUF1568) domain protein |
| ORF00364 | 727 & 728 | FhiA protein |
| ORF00365 | 729 & 730 | MbhA protein |
| ORF00366 | 731 & 732 | DNA polymerase IV (Pol IV) [2.7.7.7] |

TABLE 1-continued

Annotation of ORF00001 to ORF04995

| ORFnnnnn | SEQ ID NOs | Annotation |
|---|---|---|
| ORF00367 | 733 & 734 | prevent-host-death family protein |
| ORF00368 | 735 & 736 | unnamed protein product |
| ORF00369 | 737 & 738 | Hypothetical acetyltransferase yafP [2.3.1.—] |
| ORF00370 | 739 & 740 | uncharacterized conserved protein, RtcB-UPF0027 family CAC3383 |
| ORF00371 | 741 & 742 | Peptide chain release factor homolog (RF) |
| ORF00372 | 743 & 744 | aminoacyl-histidine dipeptidase PepD |
| ORF00373 | 745 & 746 | Xanthine-guanine phosphoribosyltransferase (XGPRT) [2.4.2.22] |
| ORF00374 | 747 & 748 | Hydrolases of the alpha-beta superfamily |
| ORF00375 | 749 & 750 | Curlin genes transcriptional activatory protein |
| ORF00376 | 751 & 752 | Outer membrane pore protein E precursor |
| ORF00377 | 753 & 754 | glutamate 5-kinase (proB) [2.7.2.11] |
| ORF00378 | 755 & 756 | gamma-glutamyl phosphate reductase (proA) [1.2.1.41] |
| ORF00379 | 757 & 758 | HTH-type transcriptional regulator prsX |
| ORF00380 | 759 & 760 | Haemoglobin protease |
| ORF00381 | 761 & 762 | InsA |
| ORF00382 | 763 & 764 | InsB |
| ORF00383 | 765 & 766 | conserved hypothetical protein |
| ORF00384 | 767 & 768 | YagU |
| ORF00385 | 769 & 770 | Uncharacterised protein family (UPF0153) superfamily |
| ORF00386 | 771 & 772 | conserved hypothetical protein |
| ORF00387 | 773 & 774 | conserved hypothetical protein |
| ORF00388 | 775 & 776 | conserved hypothetical protein |
| ORF00389 | 777 & 778 | conserved hypothetical protein |
| ORF00390 | 779 & 780 | MatB precursor |
| ORF00391 | 781 & 782 | transcriptional regulator, LuxR family domain protein |
| ORF00392 | 783 & 784 | ribosomal protein L36 (rpmJ) |
| ORF00393 | 785 & 786 | tail protein |
| ORF00394 | 787 & 788 | Sb24 |
| ORF00395 | 789 & 790 | tail fiber assembly protein |
| ORF00396 | 791 & 792 | T4-exclusion protein gpIBEGd |
| ORF00397 | 793 & 794 | hypothetical protein |
| ORF00398 | 795 & 796 | hypothetical protein |
| ORF00399 | 797 & 798 | NADH-dependent flavin oxidoreductase, Oye family [1.—.—.—] |
| ORF00400 | 799 & 800 | dienelactone hydrolase domain protein (AE000230) |
| ORF00401 | 801 & 802 | transcription regulator, LysR family Atu5241 |
| ORF00402 | 803 & 804 | transcriptional regulator (LysR family) |
| ORF00403 | 805 & 806 | oxidoreductase, aldo-keto reductase family |
| ORF00404 | 807 & 808 | 2,5-diketo-D-gluconic acid reductase A [1.1.1.—] |
| ORF00405 | 809 & 810 | Putative adhesin |
| ORF00406 | 811 & 812 | Hypothetical transcriptional regulator ykgA |
| ORF00407 | 813 & 814 | 2,5-diketo-D-gluconic acid reductase A |
| ORF00408 | 815 & 816 | MC21 |
| ORF00409 | 817 & 818 | Protein of unknown function (DUF1471) superfamily |
| ORF00410 | 819 & 820 | pyridine nucleotide-disulfide oxidoreductase [1.16.1.1] |
| ORF00411 | 821 & 822 | Hypothetical transcriptional regulator ykgD |
| ORF00412 | 823 & 824 | Cysteine-rich domain protein |
| ORF00413 | 825 & 826 | iron-sulfur cluster binding protein |
| ORF00414 | 827 & 828 | Uncharacterized ACR, YkgG family COG1556 family |
| ORF00415 | 829 & 830 | hypothetical protein |
| ORF00416 | 831 & 832 | outer membrane autotransporter barrel domain protein |
| ORF00417 | 833 & 834 | conserved hypothetical protein |
| ORF00418 | 835 & 836 | conserved hypothetical protein |
| ORF00419 | 837 & 838 | Type 1 fimbriae Regulatory protein fimB |
| ORF00420 | 839 & 840 | choline dehydrogenase (betA) [1.1.99.1] |
| ORF00421 | 841 & 842 | betaine aldehyde dehydrogenase (betB) [1.2.1.8] |
| ORF00422 | 843 & 844 | Regulatory protein betI (U73857) |
| ORF00423 | 845 & 846 | High-affinity choline transport protein |
| ORF00424 | 847 & 848 | EAL domain protein |
| ORF00425 | 849 & 850 | allS |
| ORF00426 | 851 & 852 | glutathione-regulated potassium-efflux system protein |
| ORF00427 | 853 & 854 | ankyrin repeat domain protein |
| ORF00428 | 855 & 856 | conserved hypothetical protein |
| ORF00429 | 857 & 858 | YahF-FdrA-like protein |
| ORF00430 | 859 & 860 | YahG-YlbE-like protein |
| ORF00431 | 861 & 862 | Carbamate kinase-like protein yahI [2.7.2.2] |
| ORF00432 | 863 & 864 | Cytosine deaminase |
| ORF00433 | 865 & 866 | Protein of unknown function (DUF984) superfamily |
| ORF00434 | 867 & 868 | ABC transporter, substrate binding protein [sugar] (AE005211) |
| ORF00435 | 869 & 870 | ribose ABC transporter (ATP-binding protein) |
| ORF00436 | 871 & 872 | ribose ABC transporter, permease protein, putative |
| ORF00437 | 873 & 874 | ABC sugar transporter, permease subunit (permease) |
| ORF00438 | 875 & 876 | oxidoreductase, zinc-binding [1.1.1.2] |
| ORF00439 | 877 & 878 | RhtC-like transporter STY0397 (RhtC) |
| ORF00440 | 879 & 880 | Protein of unknown function (DUF1471) superfamily |
| ORF00441 | 881 & 882 | propionate catabolism operon regulatory protein PrpR (prpR) |
| ORF00442 | 883 & 884 | hypothetical protein |

TABLE 1-continued

Annotation of ORF00001 to ORF04995

| ORFnnnnn | SEQ ID NOs | Annotation |
|---|---|---|
| ORF00443 | 885 & 886 | regulator for prp operon |
| ORF00444 | 887 & 888 | hypothetical protein |
| ORF00445 | 889 & 890 | methylisocitrate lyase (prpB) [4.1.3.30] |
| ORF00446 | 891 & 892 | 2-methylcitrate synthase (Methylcitrate synthase)(Citrate synthase 2) [2.3.3.5] |
| ORF00447 | 893 & 894 | 2-methylcitrate dehydratase (prpD) [4.2.1.79] |
| ORF00448 | 895 & 896 | propionate--CoA ligase (prpE) [6.2.1.17] |
| ORF00449 | 897 & 898 | cytosine transporter, putative |
| ORF00450 | 899 & 900 | Cytosine deaminase |
| ORF00451 | 901 & 902 | Galactoside O-acetyltransferase [2.3.1.18] |
| ORF00452 | 903 & 904 | Lactose permease (Lactose-proton symport) |
| ORF00453 | 905 & 906 | Beta-galactosidase (lacZ) [3.2.1.23] |
| ORF00454 | 907 & 908 | transcriptional regulator, lacI family domain protein, putative |
| ORF00455 | 909 & 910 | Arac-family transcriptional regulator |
| ORF00456 | 911 & 912 | nucleoprotein-polynucleotide-associated enzyme |
| ORF00457 | 913 & 914 | carboxylesterase [3.1.1.1] |
| ORF00458 | 915 & 916 | alcohol dehydrogenase [similarity] (adhC) [1.—.—.—] |
| ORF00459 | 917 & 918 | putative alpha helix chain |
| ORF00460 | 919 & 920 | conserved hypothetical protein |
| ORF00461 | 921 & 922 | Sugar phosphate nucleotydyl transferase |
| ORF00462 | 923 & 924 | glucosaminyltransferase |
| ORF00463 | 925 & 926 | Putative conserved protein |
| ORF00464 | 927 & 928 | taurine ABC transporter, periplasmic binding protein (tauA) |
| ORF00465 | 929 & 930 | taurine ABC transporter, ATP-binding protein (cmpC) |
| ORF00466 | 931 & 932 | Taurine transport system permease protein tauC |
| ORF00467 | 933 & 934 | alpha-ketoglutarate-dependent taurine dioxygenase [1.—.—.—] |
| ORF00468 | 935 & 936 | delta-aminolevulinic acid dehydratase (hemB) [4.2.1.24] |
| ORF00469 | 937 & 938 | puative autotransporter-virulence factor STY0405 (partial) |
| ORF00470 | 939 & 940 | conserved hypothetical protein |
| ORF00471 | 941 & 942 | beta-lactamase |
| ORF00472 | 943 & 944 | SbmA protein |
| ORF00473 | 945 & 946 | lipoprotein, putative |
| ORF00474 | 947 & 948 | conserved hypothetical protein |
| ORF00475 | 949 & 950 | conserved hypothetical protein |
| ORF00476 | 951 & 952 | D-alanine--D-alanine ligase A (D-alanylalanine synthetaseA) (D-Ala-D-Ala ligase A) [6.3.2.4] |
| ORF00477 | 953 & 954 | conserved hypothetical protein |
| ORF00478 | 955 & 956 | LD01705p |
| ORF00479 | 957 & 958 | Alkaline phosphatase precursor |
| ORF00480 | 959 & 960 | induced by phosphate starvation |
| ORF00481 | 961 & 962 | AdrA protein (GGDEF) |
| ORF00482 | 963 & 964 | pyrroline-5-carboxylate reductase (proC) [1.5.1.2] |
| ORF00483 | 965 & 966 | YaiI-YqxD family protein family |
| ORF00484 | 967 & 968 | shikimate kinase (aroK) [2.7.1.71] |
| ORF00485 | 969 & 970 | conserved hypothetical protein |
| ORF00486 | 971 & 972 | AroM protein |
| ORF00487 | 973 & 974 | uncharacterized protein conserved in bacteria |
| ORF00488 | 975 & 976 | conserved hypothetical protein |
| ORF00489 | 977 & 978 | conserved hypothetical protein |
| ORF00490 | 979 & 980 | Recombination associated protein rdgC |
| ORF00491 | 981 & 982 | possible NAGC-like transcriptional regulator |
| ORF00492 | 983 & 984 | major facilitator family transporter |
| ORF00493 | 985 & 986 | Exonuclease sbcC (P-loop) [3.1.15.—] |
| ORF00494 | 987 & 988 | exonuclease SbcD (SbcD) [3.1.—.—] |
| ORF00495 | 989 & 990 | conserved hypothetical protein |
| ORF00496 | 991 & 992 | phosphate regulon transcriptional regulatory protein PhoB (phoB) |
| ORF00497 | 993 & 994 | Phosphate regulon sensor protein phoR |
| ORF00498 | 995 & 996 | hypothetical protein |
| ORF00499 | 997 & 998 | conserved hypothetical protein |
| ORF00500 | 999 & 1000 | branched-chain amino acid transport system II carrier protein (brnQ) |
| ORF00501 | 1001 & 1002 | Proline-specific permease proY |
| ORF00502 | 1003 & 1004 | maltodextrin glucosidase [3.2.1.20] |
| ORF00503 | 1005 & 1006 | Protein of unknown function, DUF479 superfamily |
| ORF00504 | 1007 & 1008 | S-adenosylmethionine:tRNA ribosyltransferase-isomerase (queA) [5.—.—.—] |
| ORF00505 | 1009 & 1010 | queuine tRNA-ribosyltransferase (tgt) [2.4.2.29] |
| ORF00506 | 1011 & 1012 | preprotein translocase, YajC subunit, putative |
| ORF00507 | 1013 & 1014 | Protein-export membrane protein secD |
| ORF00508 | 1015 & 1016 | protein-export membrane protein secF |
| ORF00509 | 1017 & 1018 | HNH endonuclease domain protein |
| ORF00510 | 1019 & 1020 | Nucleoside-specific channel-forming protein tsx precursor |
| ORF00511 | 1021 & 1022 | yajI protein |
| ORF00512 | 1023 & 1024 | conserved hypothetical protein TIGR00244 |
| ORF00513 | 1025 & 1026 | riboflavin biosynthesis protein RibD (ribD) [3.5.4.26 1.1.1.193] |
| ORF00514 | 1027 & 1028 | 6,7-dimethyl-8-ribityllumazine synthase |
| ORF00515 | 1029 & 1030 | transcription antitermination factor NusB (nusB) |
| ORF00516 | 1031 & 1032 | thiamine-monophosphate kinase (thiL) [2.7.4.16] |
| ORF00517 | 1033 & 1034 | Phosphatidylglycerophosphatase A |

TABLE 1-continued

Annotation of ORF00001 to ORF04995

| ORFnnnnn | SEQ ID NOs | Annotation |
|---|---|---|
| ORF00518 | 1035 & 1036 | probable oxidoreductase yajO [1.—.—.—] |
| ORF00519 | 1037 & 1038 | 1-deoxy-D-xylulose-5-phosphate synthase (dxs) [2.2.1.7] |
| ORF00520 | 1039 & 1040 | Geranyltranstransferase (Farnesyl-diphosphate synthase)(FPP synthase) (ispA) [2.5.1.10] |
| ORF00521 | 1041 & 1042 | exodeoxyribonuclease VII, small subunit (xseB) [3.1.11.6] |
| ORF00522 | 1043 & 1044 | hypothetical protein |
| ORF00523 | 1045 & 1046 | Thiamine biosynthesis protein thiI (thiI) |
| ORF00524 | 1047 & 1048 | 4-methyl-5(B-hydroxyethyl)-thiazole monophosphate biosynthesis enzyme (ThiJ) |
| ORF00525 | 1049 & 1050 | 2-dehydropantoate 2-reductase (panE) [1.1.1.169] |
| ORF00526 | 1051 & 1052 | Protein yajQ |
| ORF00527 | 1053 & 1054 | Hypothetical transport protein yajR |
| ORF00528 | 1055 & 1056 | protoheme IX farnesyltransferase (cyoE) [2.5.1.—] |
| ORF00529 | 1057 & 1058 | cytochrome o ubiquinol oxidase C subunit [1.10.3.—] |
| ORF00530 | 1059 & 1060 | Cytochrome c oxidase subunit III |
| ORF00531 | 1061 & 1062 | Ubiquinol oxidase polypeptide I (Cytochrome o subunit 1)(Oxidase BO(3) subunit 1) (Cytochrome o ubiquinol oxidase subunit 1)(Ubiquinol oxidase chain A) [1.10.3.—] |
| ORF00532 | 1063 & 1064 | Ubiquinol oxidase polypeptide II precursor (Cytochrome osubunit 2) (Oxidase BO(3) subunit 2) (Cytochrome o ubiquinol oxidasesubunit 2) (Ubiquinol oxidase chain B) [1.10.3.—] |
| ORF00533 | 1065 & 1066 | beta-lactamase induction signal transducer AmpG |
| ORF00534 | 1067 & 1068 | AmpG-signal transducer |
| ORF00535 | 1069 & 1070 | putative polymerase-proteinase |
| ORF00536 | 1071 & 1072 | BolA protein |
| ORF00537 | 1073 & 1074 | conserved hypothetical protein |
| ORF00538 | 1075 & 1076 | Trigger factor (TF) (tig) |
| ORF00539 | 1077 & 1078 | conserved hypothetical protein |
| ORF00540 | 1079 & 1080 | trigger factor (tig) [5.2.1.8] |
| ORF00541 | 1081 & 1082 | ATP-dependent Clp protease, proteolytic subunit ClpP (clpP) [3.4.21.92] |
| ORF00542 | 1083 & 1084 | ATP-dependent Clp protease, ATP-binding subunit ClpX (clpX) |
| ORF00543 | 1085 & 1086 | ATP-dependent protease La (lon) [3.4.21.53] |
| ORF00544 | 1087 & 1088 | DNA-binding protein HU-beta, NS1 (HU) |
| ORF00545 | 1089 & 1090 | Peptidyl-prolyl cis-trans isomerase D (PPlase D)(Rotamase D) [5.2.1.8] |
| ORF00546 | 1091 & 1092 | DNA uptake protein |
| ORF00547 | 1093 & 1094 | Predicted thioesterase |
| ORF00548 | 1095 & 1096 | exsB protein |
| ORF00549 | 1097 & 1098 | conserved hypothetical protein |
| ORF00550 | 1099 & 1100 | Cof protein |
| ORF00551 | 1101 & 1102 | transcriptional regulator, AsnC family |
| ORF00552 | 1103 & 1104 | Multidrug resistance-like ATP-binding protein mdlA (atp) |
| ORF00553 | 1105 & 1106 | multidrug resistance-like ATP-binding protein Mdl |
| ORF00554 | 1107 & 1108 | glutamine synthetase activity regulation protein |
| ORF00555 | 1109 & 1110 | ammonium transporter (amt) |
| ORF00556 | 1111 & 1112 | acyl-CoA thioesterase II (tesB) [3.1.2.—] |
| ORF00557 | 1113 & 1114 | hypothetical protein |
| ORF00558 | 1115 & 1116 | glycoprotein-polysaccharide metabolism |
| ORF00559 | 1117 & 1118 | predicted methylated DNA-protein cysteine methyltransferase |
| ORF00560 | 1119 & 1120 | Protein of unknown function (DUF1428) superfamily |
| ORF00561 | 1121 & 1122 | EAL domain protein |
| ORF00562 | 1123 & 1124 | conserved hypothetical protein |
| ORF00563 | 1125 & 1126 | Maltose O-acetyltransferase [2.3.1.79] |
| ORF00564 | 1127 & 1128 | hypothetical protein |
| ORF00565 | 1129 & 1130 | Hha protein |
| ORF00566 | 1131 & 1132 | YmoB |
| ORF00567 | 1133 & 1134 | Acriflavine resistance protein B |
| ORF00568 | 1135 & 1136 | Acriflavine resistance protein A precursor |
| ORF00569 | 1137 & 1138 | HTH-type transcriptional regulator acrR (Potential acrAB operonrepressor) (acrEF) |
| ORF00570 | 1139 & 1140 | Potassium efflux system kefA |
| ORF00571 | 1141 & 1142 | conserved hypothetical protein |
| ORF00572 | 1143 & 1144 | primosomal replication protein N |
| ORF00573 | 1145 & 1146 | Protein of unknown function (DUF454) family |
| ORF00574 | 1147 & 1148 | hypothetical protein |
| ORF00575 | 1149 & 1150 | adenine phosphoribosyltransferase (apt) [2.4.2.7] |
| ORF00576 | 1151 & 1152 | DNA polymerase III, subunits gamma and tau, programmed (dnaX) [2.7.7.7] |
| ORF00577 | 1153 & 1154 | conserved hypothetical protein TIGR00103 |
| ORF00578 | 1155 & 1156 | recombination protein RecR (recR) |
| ORF00579 | 1157 & 1158 | Chaperone protein htpG (Heat shock protein htpG) (High temperatureprotein G) (Heat shock protein C62.5) (htpG) |
| ORF00580 | 1159 & 1160 | Adenylate kinase |
| ORF00581 | 1161 & 1162 | ferrochelatase (hemH) [4.99.1.1] |
| ORF00582 | 1163 & 1164 | Acetyl esterase [3.1.1.—] |
| ORF00583 | 1165 & 1166 | Inosine-guanosine kinase [2.7.1.73] |
| ORF00584 | 1167 & 1168 | RosB |
| ORF00585 | 1169 & 1170 | fosmidomycin resistance protein (CAMPs) |
| ORF00586 | 1171 & 1172 | Protein ushA precursor [Includes: UDP-sugar hydrolase(UDP-sugar diphosphatase) (UDP-sugar pyrophosphatase); 5'-nucleotidase(EC 3.1.3.5) (5'-NT)] (5-NT) [3.6.1.45] |

TABLE 1-continued

Annotation of ORF00001 to ORF04995

| ORFnnnnn | SEQ ID NOs | Annotation |
| --- | --- | --- |
| ORF00587 | 1173 & 1174 | hypothetical protein |
| ORF00588 | 1175 & 1176 | hypothetical protein |
| ORF00589 | 1177 & 1178 | ybaK-ebsC protein (ybaK) |
| ORF00590 | 1179 & 1180 | GumN protein superfamily |
| ORF00591 | 1181 & 1182 | probable killer protein VCA0391 |
| ORF00592 | 1183 & 1184 | unnamed protein product; Some similarities with virulence associated protein A (vapA) |
| ORF00593 | 1185 & 1186 | Copper-transporting P-type ATPase [3.6.1.—] |
| ORF00594 | 1187 & 1188 | K-3-type glutaminase [3.5.1.2] |
| ORF00595 | 1189 & 1190 | amino acid permease family protein, putative |
| ORF00596 | 1191 & 1192 | Cu(I)-responsive transcriptional regulator (cueR) |
| ORF00597 | 1193 & 1194 | hypothetical protein |
| ORF00598 | 1195 & 1196 | lipoprotein, putative |
| ORF00599 | 1197 & 1198 | adhesin-invasin-like protein |
| ORF00600 | 1199 & 1200 | conserved hypothetical protein |
| ORF00601 | 1201 & 1202 | membrane protein |
| ORF00602 | 1203 & 1204 | band 7-Mec-2 family protein |
| ORF00603 | 1205 & 1206 | ABC transporter, ATP-binding protein |
| ORF00604 | 1207 & 1208 | membrane protein, putative |
| ORF00605 | 1209 & 1210 | ybbN protein |
| ORF00606 | 1211 & 1212 | oxidoreductase, short-chain dehydrogenase-reductase family (SDR) [1.—.—.—] |
| ORF00607 | 1213 & 1214 | acyl-coA thioesterase I precursor [3.1.2.—] |
| ORF00608 | 1215 & 1216 | ABC transporter, ATP-binding protein |
| ORF00609 | 1217 & 1218 | permease, putative domain protein |
| ORF00610 | 1219 & 1220 | YbbB |
| ORF00611 | 1221 & 1222 | allS |
| ORF00612 | 1223 & 1224 | Ureidoglycolate hydrolase (allA) [3.5.3.19] |
| ORF00613 | 1225 & 1226 | Negative regulator of allantoin and glyoxylate utilization operons(Transcriptional regulator allR) |
| ORF00614 | 1227 & 1228 | glyoxylate carboligase (gcl) [4.1.1.47] |
| ORF00615 | 1229 & 1230 | Hydroxypyruvate isomerase [5.3.1.22] |
| ORF00616 | 1231 & 1232 | 2-hydroxy-3-oxopropionate reductase [1.1.1.60] |
| ORF00617 | 1233 & 1234 | cytosine-purine-uracil-thiamine-allantoin permease family protein, putative |
| ORF00618 | 1235 & 1236 | Allantoinase [3.5.2.5] |
| ORF00619 | 1237 & 1238 | Putative purine permease ybbY |
| ORF00620 | 1239 & 1240 | Glycerate kinase 1 |
| ORF00621 | 1241 & 1242 | GlxB6 |
| ORF00622 | 1243 & 1244 | Allantoate amidohydrolase (partial) |
| ORF00623 | 1245 & 1246 | Ureidoglycolate dehydrogenase [1.1.1.154] |
| ORF00624 | 1247 & 1248 | Protein fdrA |
| ORF00625 | 1249 & 1250 | conserved hypothetical protein |
| ORF00626 | 1251 & 1252 | Protein of unknown function (DUF1116) superfamily |
| ORF00627 | 1253 & 1254 | conserved hypothetical protein |
| ORF00628 | 1255 & 1256 | carbamate kinase (arcC) [2.7.2.2] |
| ORF00629 | 1257 & 1258 | phosphoribosylaminoimidazole carboxylase, ATPase subunit (purK) [4.1.1.21] |
| ORF00630 | 1259 & 1260 | phosphoribosylaminoimidazole carboxylase, catalytic subunit (purE) [4.1.1.21] |
| ORF00631 | 1261 & 1262 | conserved hypothetical protein |
| ORF00632 | 1263 & 1264 | UDP-2,3-diacylglucosamine hydrolase (lpxH) [3.6.1.—] |
| ORF00633 | 1265 & 1266 | peptidyl-prolyl cis-trans isomerase B (ppiB) [5.2.1.8] |
| ORF00634 | 1267 & 1268 | cysteinyl-tRNA synthetase (cysS) [6.1.1.16] |
| ORF00635 | 1269 & 1270 | Predicted membrane-bound metal-dependent hydrolase (DUF457) family |
| ORF00636 | 1271 & 1272 | Uncharacterized ACR-related protein |
| ORF00637 | 1273 & 1274 | 5,10-methylene-tetrahydrofolate dehydrogenase (folD) [1.5.1.5] |
| ORF00638 | 1275 & 1276 | Prophage DLP12 integrase (Prophage QSR' integrase) |
| ORF00639 | 1277 & 1278 | conserved hypothetical protein |
| ORF00640 | 1279 & 1280 | Gp37 |
| ORF00641 | 1281 & 1282 | conserved hypothetical protein |
| ORF00642 | 1283 & 1284 | Sb36 |
| ORF00643 | 1285 & 1286 | conserved hypothetical protein |
| ORF00644 | 1287 & 1288 | unknown protein encoded by prophage CP-933N |
| ORF00645 | 1289 & 1290 | antitermination protein Q |
| ORF00646 | 1291 & 1292 | unknown protein encoded by prophage CP-933O |
| ORF00647 | 1293 & 1294 | DNA adenine-methylase |
| ORF00648 | 1295 & 1296 | lysis protein |
| ORF00649 | 1297 & 1298 | conserved hypothetical protein |
| ORF00650 | 1299 & 1300 | Protein of unknown function (DUF1327) superfamily |
| ORF00651 | 1301 & 1302 | Lysozyme (Lysis protein) (Muramidase) (Endolysin) [3.2.1.17] |
| ORF00652 | 1303 & 1304 | lipoprotein Rz1 precursor-related protein |
| ORF00653 | 1305 & 1306 | Bacteriophage lysis protein |
| ORF00654 | 1307 & 1308 | Bor protein homolog from lambdoid prophage DLP12 |
| ORF00655 | 1309 & 1310 | hypothetical protein |
| ORF00656 | 1311 & 1312 | Partial tonB-like membrane protein encoded within prophage |
| ORF00657 | 1313 & 1314 | conserved hypothetical protein |
| ORF00658 | 1315 & 1316 | Terminase small subunit (DNA packaging protein NU1) (fragment) |
| ORF00659 | 1317 & 1318 | Phage terminase large subunit (GpA) |
| ORF00660 | 1319 & 1320 | gpW |

TABLE 1-continued

Annotation of ORF00001 to ORF04995

| ORFnnnnn | SEQ ID NOs | Annotation |
|---|---|---|
| ORF00661 | 1321 & 1322 | phage portal protein, lambda family |
| ORF00662 | 1323 & 1324 | head-tail preconnector protein GP5 |
| ORF00663 | 1325 & 1326 | Bacteriophage lambda head decoration protein D |
| ORF00664 | 1327 & 1328 | Phage major capsid protein E |
| ORF00665 | 1329 & 1330 | DNA packaging protein FI |
| ORF00666 | 1331 & 1332 | Phage Head-Tail Attachment |
| ORF00667 | 1333 & 1334 | Prophage minor tail protein Z (GPZ) |
| ORF00668 | 1335 & 1336 | Phage minor tail protein U |
| ORF00669 | 1337 & 1338 | Major tail protein V |
| ORF00670 | 1339 & 1340 | phage minor tail protein G |
| ORF00671 | 1341 & 1342 | minor tail protein |
| ORF00672 | 1343 & 1344 | tail length tape measure protein precursor |
| ORF00673 | 1345 & 1346 | phage tail tape measure protein, lambda family |
| ORF00674 | 1347 & 1348 | phage minor tail protein L |
| ORF00675 | 1349 & 1350 | Putative tail fiber component K of prophage |
| ORF00676 | 1351 & 1352 | Bacteriophage lambda tail assembly protein I |
| ORF00677 | 1353 & 1354 | host specificity protein (partial) |
| ORF00678 | 1355 & 1356 | host specificity protein (partial) |
| ORF00679 | 1357 & 1358 | Lom |
| ORF00680 | 1359 & 1360 | conserved hypothetical protein |
| ORF00681 | 1361 & 1362 | conserved hypothetical protein |
| ORF00682 | 1363 & 1364 | conserved hypothetical protein |
| ORF00683 | 1365 & 1366 | conserved hypothetical protein |
| ORF00684 | 1367 & 1368 | Tail fiber assembly protein homolog from lambdoid prophage |
| ORF00685 | 1369 & 1370 | proteinase, putative |
| ORF00686 | 1371 & 1372 | Protease VII precursor (Omptin) (Outer membrane protein3B) (Protease A) (SopA) [3.4.21.87] |
| ORF00687 | 1373 & 1374 | Prophage DLP12 integrase (Prophage QSR' integrase) |
| ORF00688 | 1375 & 1376 | Tail fiber assembly protein homolog from lambdoid |
| ORF00689 | 1377 & 1378 | Protease VII precursor (Omptin) (Outer membrane protein3B) (Protease A) (SopA) [3.4.21.87] |
| ORF00690 | 1379 & 1380 | conserved hypothetical protein |
| ORF00690 | 1381 & 1382 | Bacteriophage N4 adsorption protein A precursor |
| ORF00692 | 1383 & 1384 | bacteriophage N4 adsorption protein NfrB |
| ORF00693 | 1385 & 1386 | hypothetical protein |
| ORF00694 | 1387 & 1388 | Sensor kinase cusS [2.7.3.—] |
| ORF00695 | 1389 & 1390 | Transcriptional regulatory protein cusR |
| ORF00696 | 1391 & 1392 | Cation efflux system protein cusC precursor |
| ORF00697 | 1393 & 1394 | Cation efflux system protein cusF precursor |
| ORF00698 | 1395 & 1396 | Cation efflux system protein cusB precursor |
| ORF00699 | 1397 & 1398 | Cation efflux system protein cusA (CzcA) |
| ORF00700 | 1399 & 1400 | Phenylalanine-specific permease |
| ORF00701 | 1401 & 1402 | putative transport |
| ORF00702 | 1403 & 1404 | Oxygen-insensitive NAD(P)H nitroreductase [1.—.—.—] |
| ORF00703 | 1405 & 1406 | Uncharacterized protein conserved in bacteria |
| ORF00704 | 1407 & 1408 | Protein of unknown function (DUF1158) superfamily |
| ORF00705 | 1409 & 1410 | Glutamate-cysteine ligase family 2, putative |
| ORF00706 | 1411 & 1412 | 4-phosphopantetheinyl transferase entD |
| ORF00707 | 1413 & 1414 | ferrienterobactin receptor precursor |
| ORF00708 | 1415 & 1416 | conserved hypothetical protein |
| ORF00709 | 1417 & 1418 | Enterochelin esterase |
| ORF00710 | 1419 & 1420 | mbtH protein-related protein |
| ORF00711 | 1421 & 1422 | enterobactin synthetase component F [2.7.7.—] |
| ORF00712 | 1423 & 1424 | Ferric enterobactin transport protein fepE (enterochelin) |
| ORF00713 | 1425 & 1426 | ferric exochelin uptake (fxuB) |
| ORF00714 | 1427 & 1428 | ferric exochelin uptake (fxuA) |
| ORF00715 | 1429 & 1430 | ferric exochelin uptake (fxuC) |
| ORF00716 | 1431 & 1432 | membrane protein, putative |
| ORF00717 | 1433 & 1434 | ferric enterobactin (enterochelin) binding protein; periplasmic component |
| ORF00718 | 1435 & 1436 | isochorismate synthase [5.4.99.6] |
| ORF00719 | 1437 & 1438 | 2,3-dihydroxybenzoate-AMP ligase [2.7.7.58] |
| ORF00720 | 1439 & 1440 | Isochorismatase (Isochorismate lyase) (2,3 dihydro-2,3dihydroxybenzoate synthase) (Enterobactin synthetase component B)(Enterochelin synthase B) (EntB) [3.3.2.1] |
| ORF00721 | 1441 & 1442 | oxidoreductase, short-chain dehydrogenase-reductase family [1.3.1.28] |
| ORF00722 | 1443 & 1444 | Hypothetical UPF0152 protein ybdB (p15) |
| ORF00723 | 1445 & 1446 | Carbon starvation protein A |
| ORF00724 | 1447 & 1448 | Uncharacterized small protein |
| ORF00725 | 1449 & 1450 | glycerol dehydrogenase [1.1.—.—] |
| ORF00726 | 1451 & 1452 | aminotransferase, class I [2.6.1.—] |
| ORF00727 | 1453 & 1454 | unnamed protein product; ORF_ID: o166#4 |
| ORF00728 | 1455 & 1456 | conserved hypothetical protein |
| ORF00729 | 1457 & 1458 | Hypothetical transcriptional regulator ybdO (orf2) |
| ORF00730 | 1459 & 1460 | Thiol:disulfide interchange protein dsbG precursor |
| ORF00731 | 1461 & 1462 | alkyl hydroperoxide reductase c22 protein [1.6.4.—] |
| ORF00732 | 1463 & 1464 | alkyl hydroperoxide reductase F52A protein [1.6.4.—] |

TABLE 1-continued

Annotation of ORF00001 to ORF04995

| ORFnnnnn | SEQ ID NOs | Annotation |
|---|---|---|
| ORF00733 | 1465 & 1466 | Universal stress protein G |
| ORF00734 | 1467 & 1468 | Regulator of nucleoside diphosphate kinase |
| ORF00735 | 1469 & 1470 | Ribonuclease I precursor [3.1.27.6] |
| ORF00736 | 1471 & 1472 | Citrate carrier-transporter (antiport) |
| ORF00737 | 1473 & 1474 | triphosphoribosyl-dephospho-CoA synthase (citG) [2.7.8.25] |
| ORF00738 | 1475 & 1476 | Apo-citrate lyase phosphoribosyl-dephospho-CoA transferase (citX) [2.7.7.—] |
| ORF00739 | 1477 & 1478 | citrate lyase, alpha subunit (citF) [2.8.3.10] |
| ORF00740 | 1479 & 1480 | citrate lyase, beta subunit (citE) [4.1.3.6] |
| ORF00741 | 1481 & 1482 | citrate lyase acyl carrier protein (citD) |
| ORF00742 | 1483 & 1484 | citrate lyase ligase (citC) [6.2.1.22] |
| ORF00743 | 1485 & 1486 | Sensor kinase dpiB |
| ORF00744 | 1487 & 1488 | Transcriptional regulatory protein dpiA (Destabilizer of plasmidinheritance) |
| ORF00745 | 1489 & 1490 | transport of dicarboxylates |
| ORF00746 | 1491 & 1492 | CrcA protein |
| ORF00747 | 1493 & 1494 | Cold shock-like protein cspE |
| ORF00748 | 1495 & 1496 | crcB protein (crcB) |
| ORF00749 | 1497 & 1498 | nitrilase |
| ORF00750 | 1499 & 1500 | Sec-independent protein translocase protein tatA (YIGT) |
| ORF00751 | 1501 & 1502 | lipoic acid synthetase (lipA) |
| ORF00752 | 1503 & 1504 | lipoate-protein ligase B (lipB) |
| ORF00753 | 1505 & 1506 | UPF0250 protein |
| ORF00754 | 1507 & 1508 | penicillin-binding protein 5 (PBP) [3.4.16.4] |
| ORF00755 | 1509 & 1510 | Rare lipoprotein A precursor (rlpA) |
| ORF00756 | 1511 & 1512 | conserved hypothetical protein |
| ORF00757 | 1513 & 1514 | rod shape-determining protein RodA (rodA) |
| ORF00758 | 1515 & 1516 | Penicillin-binding protein 2 (PBP-2)(PBP) |
| ORF00759 | 1517 & 1518 | Penicillin-binding protein 2 (PBP-2) (PBP) |
| ORF00760 | 1519 & 1520 | conserved hypothetical protein TIGR00246 |
| ORF00761 | 1521 & 1522 | unnamed protein product |
| ORF00762 | 1523 & 1524 | phosphoglycerate mutase family protein, putative [3.1.3.73] |
| ORF00763 | 1525 & 1526 | nicotinate (nicotinamide) nucleotide adenylyltransferase (nadD) [2.7.7.18] |
| ORF00764 | 1527 & 1528 | DNA polymerase III, delta subunit (holA) [2.7.7.7] |
| ORF00765 | 1529 & 1530 | a minor lipoprotein |
| ORF00766 | 1531 & 1532 | leucyl-tRNA synthetase (leuS) [6.1.1.4] |
| ORF00767 | 1533 & 1534 | Methyl-accepting chemotaxis protein |
| ORF00768 | 1535 & 1536 | Inosine-uridine nucleoside N-ribohydrolase (AL355920) |
| ORF00769 | 1537 & 1538 | Glutamate-aspartate transport ATP-binding protein gltL |
| ORF00770 | 1539 & 1540 | Glutamate-aspartate transport system permease protein gltK (membrane) |
| ORF00771 | 1541 & 1542 | Glutamate-aspartate transport system permease protein gltJ |
| ORF00772 | 1543 & 1544 | glutamate-aspartate ABC transporter, periplasmic glutamate-aspartate-binding protein, truncation |
| ORF00773 | 1545 & 1546 | Rhomboid family family |
| ORF00774 | 1547 & 1548 | Apolipoprotein N-acyltransferase (ALP N-acyltransferase)(Copper homeostasis protein cutE) [2.3.1.—] |
| ORF00775 | 1549 & 1550 | Magnesium and cobalt efflux protein corC (tlyC) |
| ORF00776 | 1551 & 1552 | predicted metal-dependent hydrolase |
| ORF00777 | 1553 & 1554 | PhoH-like protein |
| ORF00778 | 1555 & 1556 | tRNA-i(6)A37 thiotransferase enzyme MiaB (miaB) |
| ORF00779 | 1557 & 1558 | 2-octaprenyl-3-methyl-6-methoxy-1,4-benzoquinol hydroxylase |
| ORF00780 | 1559 & 1560 | Asparagine synthetase B [glutamine-hydrolyzing] |
| ORF00781 | 1561 & 1562 | nagD protein, degenerate |
| ORF00782 | 1563 & 1564 | N-acetylglucosamine repressor |
| ORF00783 | 1565 & 1566 | N-acetylglucosamine-6-phosphate deacetylase (nagA) [3.5.1.25] |
| ORF00784 | 1567 & 1568 | glucosamine-6-phosphate isomerase (nagB) [3.5.99.6] |
| ORF00785 | 1569 & 1570 | PTS system, N-acetylglucosamine-specific IIABC component (EII-Nag) [2.7.1.69] |
| ORF00786 | 1571 & 1572 | membrane protein, putative |
| ORF00787 | 1573 & 1574 | hypothetical protein |
| ORF00788 | 1575 & 1576 | Hypthetical protein |
| ORF00789 | 1577 & 1578 | Hypthetical protein |
| ORF00790 | 1579 & 1580 | TerC protein |
| ORF00791 | 1581 & 1582 | TerC protein |
| ORF00792 | 1583 & 1584 | dihydrodipicolinate synthase (AE004999) [4.2.1.52] |
| ORF00793 | 1585 & 1586 | Putative alcohol dehydrogenase (U59485) |
| ORF00794 | 1587 & 1588 | Putative inner membrane protein |
| ORF00795 | 1589 & 1590 | 4-hydroxythreonine-4-phosphate dehydrogenase (pdxA) [1.1.1.262] |
| ORF00796 | 1591 & 1592 | Transcriptional regulator of sugar metabolism, putative |
| ORF00797 | 1593 & 1594 | glutaminyl-tRNA synthetase (glnS) [6.1.1.18] |
| ORF00798 | 1595 & 1596 | hypothetical protein |
| ORF00799 | 1597 & 1598 | unnamed protein product; ORF_ID: o172#6 |
| ORF00800 | 1599 & 1600 | Hypothetical lipoprotein ybfN precursor |
| ORF00801 | 1601 & 1602 | Ferric uptake regulation protein (Ferric uptake regulator) |
| ORF00802 | 1603 & 1604 | Flavodoxin 1 |
| ORF00803 | 1605 & 1606 | urea amidolyase-related protein |
| ORF00804 | 1607 & 1608 | urea amidolyase-related protein |
| ORF00805 | 1609 & 1610 | SeqA protein |
| ORF00806 | 1611 & 1612 | phosphoglucomutase, alpha-D-glucose phosphate-specific (pgm) [5.4.2.2] |

TABLE 1-continued

Annotation of ORF00001 to ORF04995

| ORFnnnnn | SEQ ID NOs | Annotation |
| --- | --- | --- |
| ORF00807 | 1613 & 1614 | Putrescine-ornithine antiporter (Putrescine transport protein) (potE) |
| ORF00808 | 1615 & 1616 | Ornithine decarboxylase, inducible (speF) [4.1.1.17] |
| ORF00809 | 1617 & 1618 | conserved hypothetical protein |
| ORF00810 | 1619 & 1620 | hypothetical protein |
| ORF00811 | 1621 & 1622 | kdpE |
| ORF00812 | 1623 & 1624 | sensor histidine kinase KdpD, putative |
| ORF00813 | 1625 & 1626 | K+-transporting ATPase, C subunit (kdpC) [3.6.3.12] |
| ORF00814 | 1627 & 1628 | K+-transporting ATPase, B subunit (kdpB) [3.6.3.12] |
| ORF00815 | 1629 & 1630 | K+-transporting ATPase, A subunit (kdpA) [3.6.3.12] |
| ORF00816 | 1631 & 1632 | K+-transporting ATPase, F subunit (kdpF) [3.6.3.12] |
| ORF00817 | 1633 & 1634 | conserved hypothetical protein |
| ORF00818 | 1635 & 1636 | uncharacterized conserved protein (orf169) |
| ORF00819 | 1637 & 1638 | Deoxyribodipyrimidine photolyase [4.1.99.3] |
| ORF00820 | 1639 & 1640 | PTR2-family transport protein STY0750 |
| ORF00821 | 1641 & 1642 | conserved hypothetical protein TIGR00486 |
| ORF00822 | 1643 & 1644 | conserved hypothetical protein TIGR00370 |
| ORF00823 | 1645 & 1646 | urea amidolyase-related protein |
| ORF00824 | 1647 & 1648 | LamB-YcsF family protein (lamB) |
| ORF00825 | 1649 & 1650 | formamidopyrimidine-DNA glycosylase, putative [3.2.—.—] |
| ORF00826 | 1651 & 1652 | membrane protein, putative |
| ORF00827 | 1653 & 1654 | ybgO protein |
| ORF00828 | 1655 & 1656 | citrate synthase I (gltA) [2.3.3.1] |
| ORF00829 | 1657 & 1658 | succinate dehydrogenase cytochrome b-556 subunit (AF007569) |
| ORF00830 | 1659 & 1660 | Succinate dehydrogenase hydrophobic membrane anchor protein (sdhD) [1.3.99.1] |
| ORF00831 | 1661 & 1662 | succinate dehydrogenase, flavoprotein subunit (sdhA) |
| ORF00832 | 1663 & 1664 | succinate dehydrogenase, iron sulfur protein [1.3.99.1] |
| ORF00833 | 1665 & 1666 | 2-oxoglutarate dehydrogenase, E1 component (sucA) [1.2.4.2] |
| ORF00834 | 1667 & 1668 | 2-oxoglutarate dehydrogenase, E2 component, dihydrolipoamide succinyltransferase (sucB) [2.3.1.61] |
| ORF00835 | 1669 & 1670 | Dihydrolipoamide succinyltransferase component of 2-oxoglutarate dehydrogenase complex [2.3.1.61] |
| ORF00836 | 1671 & 1672 | Succinyl-CoA synthetase beta chain (SCS-beta) (sucC) [6.2.1.5] |
| ORF00837 | 1673 & 1674 | succinyl-CoA synthetase, alpha subunit (sucD) [6.2.1.5] |
| ORF00838 | 1675 & 1676 | uncharacterized protein, probably surface-located |
| ORF00839 | 1677 & 1678 | hypothetical protein |
| ORF00840 | 1679 & 1680 | cytochrome d ubiquinol oxidase chain I [similarity] [1.10.3.—] |
| ORF00841 | 1681 & 1682 | cytochrome d ubiquinol oxidase, subunit II (cydB) [1.10.3.—] |
| ORF00842 | 1683 & 1684 | cyd operon protein YbgT-related protein |
| ORF00843 | 1685 & 1686 | cyd operon protein YbgE |
| ORF00844 | 1687 & 1688 | Predicted thioesterase |
| ORF00845 | 1689 & 1690 | TolQ protein |
| ORF00846 | 1691 & 1692 | TolR protein (tolR) |
| ORF00847 | 1693 & 1694 | TolA protein |
| ORF00848 | 1695 & 1696 | TolA protein |
| ORF00849 | 1697 & 1698 | tolB (tolB) |
| ORF00850 | 1699 & 1700 | Peptidoglycan-associated lipoprotein precursor |
| ORF00851 | 1701 & 1702 | YbgF protein |
| ORF00852 | 1703 & 1704 | quinolinate synthetase complex, A subunit (nadA) |
| ORF00853 | 1705 & 1706 | Protein pnuC |
| ORF00854 | 1707 & 1708 | cation efflux family protein (efflux) |
| ORF00855 | 1709 & 1710 | conserved hypothetical protein |
| ORF00856 | 1711 & 1712 | phospho-2-dehydro-3-deoxyheptonate aldolase [2.5.1.54] |
| ORF00857 | 1713 & 1714 | hypothetical protein |
| ORF00858 | 1715 & 1716 | Phosphoglycerate mutase 1 |
| ORF00859 | 1717 & 1718 | Aldose 1-epimerase |
| ORF00860 | 1719 & 1720 | galactokinase (galK) [2.7.1.6] |
| ORF00861 | 1721 & 1722 | galactose-1-phosphate uridylyltransferase (galT) [2.7.7.10] |
| ORF00862 | 1723 & 1724 | UDP-glucose 4-epimerase (galE) [5.1.3.2] |
| ORF00863 | 1725 & 1726 | ATP-binding component of molybdate transport system (atp_bind) |
| ORF00864 | 1727 & 1728 | hypothetical protein |
| ORF00865 | 1729 & 1730 | Transcriptional regulator modE (modE) |
| ORF00866 | 1731 & 1732 | conserved hypothetical protein |
| ORF00867 | 1733 & 1734 | molybdate ABC transporter, periplasmic molybdate-binding protein (modA) |
| ORF00868 | 1735 & 1736 | molybdate ABC transporter, permease protein (modB) |
| ORF00869 | 1737 & 1738 | molybdate ABC transporter, ATP-binding protein (modC) [3.6.3.29] |
| ORF00870 | 1739 & 1740 | putative phosphatase |
| ORF00871 | 1741 & 1742 | conserved hypothetical protein |
| ORF00872 | 1743 & 1744 | ybhD protein |
| ORF00873 | 1745 & 1746 | FldA protein |
| ORF00874 | 1747 & 1748 | 2-oxoglutarate-malate translocator homolog yflS (SODiT1) |
| ORF00875 | 1749 & 1750 | aconitate hydratase, putative |
| ORF00876 | 1751 & 1752 | possible pectinesterase precursor |
| ORF00877 | 1753 & 1754 | conserved hypothetical protein TIGR00481 |
| ORF00878 | 1755 & 1756 | adenosylmethionine-8-amino-7-oxononanoate aminotransferase (bioA) [2.6.1.62] |
| ORF00879 | 1757 & 1758 | biotin synthase (bioB) [2.8.1.6] |
| ORF00880 | 1759 & 1760 | 8-amino-7-oxononanoate synthase (bioF) [2.3.1.47] |

TABLE 1-continued

Annotation of ORF00001 to ORF04995

| ORFnnnnn | SEQ ID NOs | Annotation |
|---|---|---|
| ORF00881 | 1761 & 1762 | biotin biosynthesis protein BioC (bioC) |
| ORF00882 | 1763 & 1764 | Dethiobiotin synthetase (DTBS) |
| ORF00883 | 1765 & 1766 | Phage minor tail protein |
| ORF00884 | 1767 & 1768 | phage minor tail protein L |
| ORF00885 | 1769 & 1770 | Putative tail fiber component K of prophage |
| ORF00886 | 1771 & 1772 | Minor tail protein precursor H |
| ORF00887 | 1773 & 1774 | Phage minor tail protein |
| ORF00888 | 1775 & 1776 | phage minor tail protein L |
| ORF00889 | 1777 & 1778 | Putative tail component of prophage |
| ORF00890 | 1779 & 1780 | Phage minor tail protein L |
| ORF00891 | 1781 & 1782 | Putative tail component of prophage |
| ORF00892 | 1783 & 1784 | Phage minor tail protein L |
| ORF00893 | 1785 & 1786 | Putative tail fiber component K of prophage |
| ORF00894 | 1787 & 1788 | Putative tail fiber component K of prophage |
| ORF00895 | 1789 & 1790 | Bacteriophage lambda tail assembly protein I |
| ORF00896 | 1791 & 1792 | host specificity protein (partial) |
| ORF00897 | 1793 & 1794 | tail assembly protein |
| ORF00898 | 1795 & 1796 | Bacteriophage lambda tail assembly protein I |
| ORF00899 | 1797 & 1798 | host specificity protein (partial) |
| ORF00900 | 1799 & 1800 | Putative tail component of prophage (partial) |
| ORF00901 | 1801 & 1802 | hypothetical protein |
| ORF00902 | 1803 & 1804 | conserved hypothetical protein |
| ORF00903 | 1805 & 1806 | conserved hypothetical protein |
| ORF00904 | 1807 & 1808 | conserved hypothetical protein |
| ORF00905 | 1809 & 1810 | SitD protein (AF128999) |
| ORF00906 | 1811 & 1812 | SitC protein (AF128999) |
| ORF00907 | 1813 & 1814 | SitB protein (AF128999) |
| ORF00908 | 1815 & 1816 | periplasmic binding protein (chelated) |
| ORF00909 | 1817 & 1818 | putative transposase |
| ORF00910 | 1819 & 1820 | conserved hypothetical protein |
| ORF00911 | 1821 & 1822 | isocitrate dehydrogenase [1.1.1.42] |
| ORF00912 | 1823 & 1824 | ydfO protein |
| ORF00913 | 1825 & 1826 | Hypothetical transcriptional regulator ycgE |
| ORF00914 | 1827 & 1828 | conserved hypothetical protein |
| ORF00915 | 1829 & 1830 | Sensors of blue-light using FAD family |
| ORF00916 | 1831 & 1832 | probable membrane protein b1168 (o528) |
| ORF00917 | 1833 & 1834 | conserved hypothetical protein |
| ORF00918 | 1835 & 1836 | conserved hypothetical protein |
| ORF00919 | 1837 & 1838 | conserved hypothetical protein |
| ORF00920 | 1839 & 1840 | conserved hypothetical protein |
| ORF00921 | 1841 & 1842 | putative ATP-binding component of a transport system |
| ORF00922 | 1843 & 1844 | cell division topological specificity factor MinE (minE) |
| ORF00923 | 1845 & 1846 | cell division inhibitor MinD |
| ORF00924 | 1847 & 1848 | tail assembly protein |
| ORF00925 | 1849 & 1850 | Host specificity protein J (partial) |
| ORF00926 | 1851 & 1852 | host specificity protein (partial) |
| ORF00927 | 1853 & 1854 | excinuclease ABC, B subunit (uvrB) |
| ORF00928 | 1855 & 1856 | Uncharacterized conserved membrane-associated protein |
| ORF00929 | 1857 & 1858 | Molybdenum cofactor biosynthesis protein A |
| ORF00930 | 1859 & 1860 | molybdenum cofactor biosynthesis protein B |
| ORF00931 | 1861 & 1862 | molybdenum cofactor biosynthesis protein C (moaC) |
| ORF00932 | 1863 & 1864 | Molybdopterin converting factor subunit 1 (MPT) |
| ORF00933 | 1865 & 1866 | Molybdopterin converting factor subunit 2 |
| ORF00934 | 1867 & 1868 | conserved hypothetical protein |
| ORF00935 | 1869 & 1870 | membrane protein (SAD) |
| ORF00936 | 1871 & 1872 | hypothetical protein |
| ORF00937 | 1873 & 1874 | Uncharacterized protein family UPF0005, putative |
| ORF00938 | 1875 & 1876 | membrane protein, putative |
| ORF00939 | 1877 & 1878 | phospholipase family protein [2.7.8.—] |
| ORF00940 | 1879 & 1880 | endonuclease-exonuclease-phosphatase family protein |
| ORF00941 | 1881 & 1882 | ABC transporter, permease protein, putative |
| ORF00942 | 1883 & 1884 | conserved hypothetical protein |
| ORF00943 | 1885 & 1886 | ElsD (membrane) |
| ORF00944 | 1887 & 1888 | ABC transporter, ATP binding-permease protein |
| ORF00945 | 1889 & 1890 | Hypothetical membrane protein ybhG |
| ORF00946 | 1891 & 1892 | probable transcription regulator ybiH |
| ORF00947 | 1893 & 1894 | Superfamily II DNA and RNA helicases |
| ORF00948 | 1895 & 1896 | GTP cyclohydrolase II (F160) |
| ORF00949 | 1897 & 1898 | probably ATP-dependent helicase |
| ORF00950 | 1899 & 1900 | glycosyl transferase family protein (o320) [2.4.2.18] |
| ORF00951 | 1901 & 1902 | YbiC (o361) [1.1.1.—] |
| ORF00952 | 1903 & 1904 | Protein of unknown function (DUF1471) superfamily |
| ORF00953 | 1905 & 1906 | TraR |
| ORF00954 | 1907 & 1908 | iron-regulated outer membrane protein |
| ORF00955 | 1909 & 1910 | TonB-dependent receptor for iron transport XF0599 (III) |
| ORF00956 | 1911 & 1912 | hypothetical protein |

TABLE 1-continued

Annotation of ORF00001 to ORF04995

| ORFnnnnn | SEQ ID NOs | Annotation |
|---|---|---|
| ORF00957 | 1913 & 1914 | Protein of unknown function (DUF1471) family |
| ORF00958 | 1915 & 1916 | Protein of unknown function (DUF890) superfamily |
| ORF00959 | 1917 & 1918 | putative transport protein |
| ORF00960 | 1919 & 1920 | ATP-binding component of glutamine high-affinity transport system (atp_bind) |
| ORF00961 | 1921 & 1922 | amino acid ABC transporter, amino acid-binding-permease protein |
| ORF00962 | 1923 & 1924 | amino acid ABC transporter, amino acid-binding-permease protein (GlnH) |
| ORF00963 | 1925 & 1926 | global regulator, starvation conditions |
| ORF00964 | 1927 & 1928 | transporter, EamA family |
| ORF00965 | 1929 & 1930 | outer membrane protein X |
| ORF00966 | 1931 & 1932 | Dca |
| ORF00967 | 1933 & 1934 | Transcriptional regulator mntR (Manganese transport regulator) |
| ORF00968 | 1935 & 1936 | transporter, NadC-P-Pho87 family, putative |
| ORF00969 | 1937 & 1938 | Protein ybiS precursor |
| ORF00970 | 1939 & 1940 | ABC transporter ATP-binding protein |
| ORF00971 | 1941 & 1942 | hydrolase, haloacid dehalogenase-like family |
| ORF00972 | 1943 & 1944 | pyruvate formate-lyase [2.3.1.54] |
| ORF00973 | 1945 & 1946 | Iron-dependent pyruvate formate-lyase-activating enzyme (pflC) [1.97.1.4] |
| ORF00974 | 1947 & 1948 | transaldolase, putative |
| ORF00975 | 1949 & 1950 | molybdopterin synthase sulfurylase MoeB (moeB) |
| ORF00976 | 1951 & 1952 | Molybdopterin biosynthesis protein moeA (moeA) |
| ORF00977 | 1953 & 1954 | asparaginase [3.5.1.1] |
| ORF00978 | 1955 & 1956 | Hypothetical ABC transporter ATP-binding protein in bcr 5'region. (D90720) |
| ORF00979 | 1957 & 1958 | Heme-binding protein a precursor (hemin-binding lipoprotein). |
| ORF00980 | 1959 & 1960 | ABC transporter permease protein (permease) |
| ORF00981 | 1961 & 1962 | peptide ABC transporter, permease protein |
| ORF00982 | 1963 & 1964 | EAL domain protein |
| ORF00983 | 1965 & 1966 | Hypothetical membrane protein yliF |
| ORF00984 | 1967 & 1968 | MiaB-like tRNA modifying enzyme YliG, TIGR01125 |
| ORF00985 | 1969 & 1970 | conserved hypothetical protein |
| ORF00986 | 1971 & 1972 | IppZ |
| ORF00987 | 1973 & 1974 | glutathione S-transferase |
| ORF00988 | 1975 & 1976 | Penicillin-binding protein 6 precursor (PBP) [3.4.16.4] |
| ORF00989 | 1977 & 1978 | Deoxyribose operon repressor (AE006172) |
| ORF00990 | 1979 & 1980 | unnamed protein product |
| ORF00991 | 1981 & 1982 | hypothetical protein |
| ORF00992 | 1983 & 1984 | Multidrug translocase mdfA |
| ORF00993 | 1985 & 1986 | conserved hypothetical protein |
| ORF00994 | 1987 & 1988 | hydrolase, haloacid dehalogenase-like family |
| ORF00995 | 1989 & 1990 | Major Facilitator Superfamily subfamily |
| ORF00996 | 1991 & 1992 | transcription regulator, TetR family, putative |
| ORF00997 | 1993 & 1994 | TrkA, Potassium channel-family protein |
| ORF00998 | 1995 & 1996 | conserved hypothetical protein |
| ORF00999 | 1997 & 1998 | Glutaredoxin, GrxA family (grxA) |
| ORF01000 | 1999 & 2000 | Protein of unknown function (DUF1418) superfamily |
| ORF01001 | 2001 & 2002 | Oxygen-insensitive NADPH nitroreductase [1.—.—.—] |
| ORF01002 | 2003 & 2004 | ribosomal protein S6 modification protein |
| ORF01003 | 2005 & 2006 | putative sensory transduction regulator |
| ORF01004 | 2007 & 2008 | Putrescine-binding periplasmic protein precursor |
| ORF01005 | 2009 & 2010 | Putrescine transport ATP-binding protein potG (atp_bind) |
| ORF01006 | 2011 & 2012 | putrescine ABC transporter, permease protein (membrane) |
| ORF01007 | 2013 & 2014 | Putrescine transport system permease protein potI |
| ORF01008 | 2015 & 2016 | conserved hypothetical protein |
| ORF01009 | 2017 & 2018 | 23S rRNA (uracil-5-)-methyltransferase RumB (rumB) [2.1.1.—] |
| ORF01010 | 2019 & 2020 | Arginine-binding periplasmic protein 2 precursor |
| ORF01011 | 2021 & 2022 | Arginine transport system permease protein artM (membrane) |
| ORF01012 | 2023 & 2024 | Arginine transport system permease protein artQ (artQ) |
| ORF01013 | 2025 & 2026 | Arginine-binding periplasmic protein 1 precursor |
| ORF01014 | 2027 & 2028 | Arginine transport ATP-binding protein artP |
| ORF01015 | 2029 & 2030 | Putative lipoprotein ybjP precursor |
| ORF01016 | 2031 & 2032 | conserved protein |
| ORF01017 | 2033 & 2034 | N-acetylmuramoyl-L-alanine amidase domain protein [3.5.1.28] |
| ORF01018 | 2035 & 2036 | conserved hypothetical protein |
| ORF01019 | 2037 & 2038 | COG0702: Predicted nucleoside-diphosphate-sugar epimerases, putative |
| ORF01020 | 2039 & 2040 | Low-specificity L-threonine aldolase [4.1.2.5] |
| ORF01021 | 2041 & 2042 | pyruvate dehydrogenase [1.2.2.2] |
| ORF01022 | 2043 & 2044 | iron-sulfur cluster-binding protein |
| ORF01023 | 2045 & 2046 | hybrid cluster protein |
| ORF01024 | 2047 & 2048 | putative surface protein |
| ORF01025 | 2049 & 2050 | aquaporin Z |
| ORF01026 | 2051 & 2052 | homology with RecF protein |
| ORF01027 | 2053 & 2054 | SomA (VirG) |
| ORF01028 | 2055 & 2056 | Macrolide-specific efflux protein macA precursor |
| ORF01029 | 2057 & 2058 | Macrolide-specific ABC-type efflux carrier (efflux) |
| ORF01030 | 2059 & 2060 | Cold shock-like protein cspD |
| ORF01031 | 2061 & 2062 | site-specific recombinase, phage integrase family, truncation |
| ORF01032 | 2063 & 2064 | probable DNA binding protein-related protein |

TABLE 1-continued

Annotation of ORF00001 to ORF04995

| ORFnnnnn | SEQ ID NOs | Annotation |
|---|---|---|
| ORF01033 | 2065 & 2066 | hypothetical protein |
| ORF01034 | 2067 & 2068 | conserved hypothetical protein |
| ORF01035 | 2069 & 2070 | conserved hypothetical protein |
| ORF01036 | 2071 & 2072 | hypothetical bacteriophage protein |
| ORF01037 | 2073 & 2074 | Bacteriophage P4 DNA primase |
| ORF01038 | 2075 & 2076 | Unknown protein encoded by prophage |
| ORF01039 | 2077 & 2078 | Single-strand binding protein (SSB) (Helix-destabilizing protein) (ssb) |
| ORF01040 | 2079 & 2080 | hypothetical protein |
| ORF01041 | 2081 & 2082 | conserved hypothetical protein |
| ORF01042 | 2083 & 2084 | Gifsy-1 prophage protein |
| ORF01043 | 2085 & 2086 | Head decoration protein (Head protein GPSHP) |
| ORF01044 | 2087 & 2088 | hypothetical protein |
| ORF01045 | 2089 & 2090 | head-tail preconnector protein GP5 |
| ORF01046 | 2091 & 2092 | gp1 |
| ORF01047 | 2093 & 2094 | Unknown protein encoded by prophage |
| ORF01048 | 2095 & 2096 | Unknown protein encoded by prophage |
| ORF01049 | 2097 & 2098 | ATP-dependent Clp protease adaptor protein clpS |
| ORF01050 | 2099 & 2100 | ATP-binding component of serine protease |
| ORF01051 | 2101 & 2102 | ATP-dependent clp protease ATP-binding subunit clpA |
| ORF01052 | 2103 & 2104 | CRISPR-associated protein Cas1 (cas1) |
| ORF01053 | 2105 & 2106 | unnamed protein product; Similar to unknown protein |
| ORF01054 | 2107 & 2108 | conserved hypothetical protein |
| ORF01055 | 2109 & 2110 | conserved hypothetical protein |
| ORF01056 | 2111 & 2112 | conserved hypothetical protein |
| ORF01057 | 2113 & 2114 | conserved hypothetical protein |
| ORF01058 | 2115 & 2116 | conserved hypothetical protein |
| ORF01059 | 2117 & 2118 | translation initiation factor IF-1 (infA) |
| ORF01060 | 2119 & 2120 | leucyl-phenylalanyl-tRNA--protein transferase (aat) [2.3.2.—] |
| ORF01061 | 2121 & 2122 | Transport ATP-binding protein cydC |
| ORF01062 | 2123 & 2124 | Transport ATP-binding protein cydD |
| ORF01063 | 2125 & 2126 | Antirestriction protein family |
| ORF01064 | 2127 & 2128 | YeeS protein (o160) |
| ORF01065 | 2129 & 2130 | Transport ATP-binding protein cydD |
| ORF01066 | 2131 & 2132 | thioredoxin-disulfide reductase (trxB) [1.8.1.9] |
| ORF01067 | 2133 & 2134 | Leucine-responsive Regulatory protein |
| ORF01068 | 2135 & 2136 | Cell division protein ftsK |
| ORF01069 | 2137 & 2138 | outer membrane lipoprotein carrier protein LolA (lolA) |
| ORF01070 | 2139 & 2140 | unnamed protein product |
| ORF01071 | 2141 & 2142 | seryl-tRNA synthetase (serS) [6.1.1.11] |
| ORF01072 | 2143 & 2144 | Anaerobic dimethyl sulfoxide reductase chain A precursor (dmsA) [1.8.99.—] |
| ORF01073 | 2145 & 2146 | anaerobic dimethylsulfoxide reductase chain B (dmsB) [1.—.—.—] |
| ORF01074 | 2147 & 2148 | DMSO reductase anchor subunit (DmsC) (dmsC) [1.8.99.—] |
| ORF01075 | 2149 & 2150 | Protein ycaC |
| ORF01076 | 2151 & 2152 | Hypothetical MFS-type transporter protein ycaD |
| ORF01077 | 2153 & 2154 | pyruvate formate lyase activating enzyme 1 [1.97.1.4] |
| ORF01078 | 2155 & 2156 | phage integrase |
| ORF01079 | 2157 & 2158 | phage regulatory protein |
| ORF01080 | 2159 & 2160 | gpB |
| ORF01081 | 2161 & 2162 | gp80-related protein |
| ORF01082 | 2163 & 2164 | InsAB' protein |
| ORF01083 | 2165 & 2166 | InsA protein |
| ORF01084 | 2167 & 2168 | gp81 |
| ORF01085 | 2169 & 2170 | TraR protein |
| ORF01086 | 2171 & 2172 | gp83 |
| ORF01087 | 2173 & 2174 | Replication gene A protein (GPA) |
| ORF01088 | 2175 & 2176 | gp91 |
| ORF01089 | 2177 & 2178 | conserved hypothetical protein |
| ORF01090 | 2179 & 2180 | hypothetical protein |
| ORF01091 | 2181 & 2182 | hypothetical protein |
| ORF01092 | 2183 & 2184 | phage portal protein, PBSX family |
| ORF01093 | 2185 & 2186 | Putative ATPase subunit of terminase (gpP-like) |
| ORF01094 | 2187 & 2188 | Phage capsid scaffolding protein (GPO) |
| ORF01095 | 2189 & 2190 | capsid scaffolding protein |
| ORF01096 | 2191 & 2192 | phage major capsid protein, P2 family |
| ORF01097 | 2193 & 2194 | Phage small terminase subunit |
| ORF01098 | 2195 & 2196 | Phage head completion protein (GPL) |
| ORF01099 | 2197 & 2198 | Tail protein X (GPX)-related protein |
| ORF01100 | 2199 & 2200 | Phage holin family 2 |
| ORF01101 | 2201 & 2202 | Lysozyme (Lysis protein) (Muramidase) (Endolysin)(Protein gpK) [3.2.1.17] |
| ORF01102 | 2203 & 2204 | hypothetical protein |
| ORF01103 | 2205 & 2206 | Protein lysA |
| ORF01104 | 2207 & 2208 | Protein lysB (AB008550) |
| ORF01105 | 2209 & 2210 | LysC |
| ORF01106 | 2211 & 2212 | Tail completion protein R (GPR) |
| ORF01107 | 2213 & 2214 | phage virion morphogenesis protein |
| ORF01108 | 2215 & 2216 | gpV (gpV) |

TABLE 1-continued

Annotation of ORF00001 to ORF04995

| ORFnnnnn | SEQ ID NOs | Annotation |
|---|---|---|
| ORF01109 | 2217 & 2218 | Baseplate assembly protein W (GPW) (gpW) |
| ORF01110 | 2219 & 2220 | Baseplate J-like protein |
| ORF01111 | 2221 & 2222 | gpI (gpI) |
| ORF01112 | 2223 & 2224 | gpH |
| ORF01113 | 2225 & 2226 | gpG (gpG) |
| ORF01114 | 2227 & 2228 | hypothetical protein |
| ORF01115 | 2229 & 2230 | Phage tail sheath protein |
| ORF01116 | 2231 & 2232 | phage major tail tube protein |
| ORF01117 | 2233 & 2234 | Phage tail protein E |
| ORF01118 | 2235 & 2236 | phage tail tape meausure protein, TP901 family, putative |
| ORF01119 | 2237 & 2238 | gpU (gpU) |
| ORF01120 | 2239 & 2240 | Gene D protein (GPD) |
| ORF01121 | 2241 & 2242 | Ogr |
| ORF01122 | 2243 & 2244 | formate acetyltransferase (pflB) [2.3.1.54] |
| ORF01123 | 2245 & 2246 | Probable formate transporter 1 |
| ORF01124 | 2247 & 2248 | unnamed protein product |
| ORF01125 | 2249 & 2250 | Protein of unknown function (DUF421) family |
| ORF01126 | 2251 & 2252 | phosphoserine aminotransferase (serC) [2.6.1.52] |
| ORF01127 | 2253 & 2254 | 3-phosphoshikimate 1-carboxyvinyltransferase (aroA) [2.5.1.19] |
| ORF01128 | 2255 & 2256 | cmk protein precursor [3.4.24.—] |
| ORF01129 | 2257 & 2258 | cytidylate kinase (cmk) [2.7.4.14] |
| ORF01130 | 2259 & 2260 | ribosomal protein S1 (rpsA) |
| ORF01131 | 2261 & 2262 | integration host factor, beta subunit (ihfB) |
| ORF01132 | 2263 & 2264 | DNA internalization-related competence protein ComEC-Rec2 |
| ORF01133 | 2265 & 2266 | lipid A export ATP-binding-permease protein MsbA (msbA) |
| ORF01134 | 2267 & 2268 | tetraacyldisaccharide 4'-kinase (lpxK) [2.7.1.130] |
| ORF01135 | 2269 & 2270 | Protein of unknown function (DUF1006) superfamily |
| ORF01136 | 2271 & 2272 | Tetraacyldisaccharide-1-P 4'-kinase |
| ORF01137 | 2273 & 2274 | 3-deoxy-D-manno-octulosonate cytidylyltransferase (kdsB) [2.7.7.38] |
| ORF01138 | 2275 & 2276 | Uncharacterized ACR, COG1434 family |
| ORF01139 | 2277 & 2278 | mukF protein (killing factor KicB) |
| ORF01140 | 2279 & 2280 | conserved hypothetical protein |
| ORF01141 | 2281 & 2282 | Protein smtA |
| ORF01142 | 2283 & 2284 | Chromosome partition protein mukF (kicB) |
| ORF01143 | 2285 & 2286 | Chromosome partition protein mukE |
| ORF01144 | 2287 & 2288 | cell division protein mukB (mukB) |
| ORF01145 | 2289 & 2290 | conserved hypothetical protein |
| ORF01146 | 2291 & 2292 | Bacterial protein of unknown function (DUF882) superfamily |
| ORF01147 | 2293 & 2294 | metallo-beta-lactamase superfamily protein [3.—.—.—] |
| ORF01148 | 2295 & 2296 | Aspartate aminotransferase (aspC) [2.6.1.1] |
| ORF01149 | 2297 & 2298 | Outer membrane protein F precursor (GBP) |
| ORF01150 | 2299 & 2300 | asparaginyl-tRNA synthetase (asnS) [6.1.1.22] |
| ORF01151 | 2301 & 2302 | nicotinate phosphoribosyltransferase (pncB) [2.4.2.11] |
| ORF01152 | 2303 & 2304 | aminopeptidase N (pepN) [3.4.11.2] |
| ORF01153 | 2305 & 2306 | sulfonate ABC transporter, ATP-binding subunit SsuB (AF075709) |
| ORF01154 | 2307 & 2308 | sulfonate ABC transporter, permease protein SsuC |
| ORF01155 | 2309 & 2310 | Alkanesulfonate monooxygenase [1.14.14.5] |
| ORF01156 | 2311 & 2312 | hypothetical protein |
| ORF01157 | 2313 & 2314 | ABC transporter, aliphatic sulfonates binding protein |
| ORF01158 | 2315 & 2316 | FMN reductase [1.5.1.29] |
| ORF01159 | 2317 & 2318 | dihydroorotate oxidase (pyrD) [1.3.3.1] |
| ORF01160 | 2319 & 2320 | Protein of unknown function (DUF1379) superfamily |
| ORF01161 | 2321 & 2322 | flavodoxin reductase (ferredoxin-NADPH reductase) family 1 |
| ORF01162 | 2323 & 2324 | predicted N6-adenine-specific DNA methylase |
| ORF01163 | 2325 & 2326 | ABC transporter ATP-binding protein uup |
| ORF01164 | 2327 & 2328 | hypothetical protein |
| ORF01165 | 2329 & 2330 | Paraquat-inducible protein A |
| ORF01166 | 2331 & 2332 | paraquat-inducible protein B |
| ORF01167 | 2333 & 2334 | Protein of unknown function (DUF330) superfamily |
| ORF01168 | 2335 & 2336 | Ribosome modulation factor (Protein E)-related protein |
| ORF01169 | 2337 & 2338 | beta-hydroxyacyl-(acyl-carrier-protein) dehydratase FabA (fabA) [4.2.1.—] |
| ORF01170 | 2339 & 2340 | unnamed protein product |
| ORF01171 | 2341 & 2342 | Outer membrane protein A precursor |
| ORF01172 | 2343 & 2344 | Cell division inhibitor |
| ORF01173 | 2345 & 2346 | hypothetical membrane protein, TIGR01666 (yccS) |
| ORF01174 | 2347 & 2348 | Regulator of competence-specific genes |
| ORF01175 | 2349 & 2350 | Domain of unknown function |
| ORF01176 | 2351 & 2352 | DNA helicase IV [3.6.1.—] |
| ORF01177 | 2353 & 2354 | methylglyoxal synthase (mgsA) [4.2.3.3] |
| ORF01178 | 2355 & 2356 | Hypothetical UPF0319 protein yccT precursor |
| ORF01179 | 2357 & 2358 | Protein yccU |
| ORF01180 | 2359 & 2360 | hemimethylated DNA binding domain, putative |
| ORF01181 | 2361 & 2362 | predicted SAM-dependent methyltransferase |
| ORF01182 | 2363 & 2364 | Acylphosphatase |
| ORF01183 | 2365 & 2366 | probable sulfite reductase gamma chain [1.8.—.—] |
| ORF01184 | 2367 & 2368 | Integral membrane protein |

TABLE 1-continued

Annotation of ORF00001 to ORF04995

| ORFnnnnn | SEQ ID NOs | Annotation |
|---|---|---|
| ORF01185 | 2369 & 2370 | Hydrogenase-1 small chain precursor |
| ORF01186 | 2371 & 2372 | conserved hypothetical protein |
| ORF01187 | 2373 & 2374 | Unknown protein encoded within prophage |
| ORF01188 | 2375 & 2376 | Uncharacterized BCR, COG1636 family |
| ORF01189 | 2377 & 2378 | putative cell killing protein of prophage (gef) |
| ORF01190 | 2379 & 2380 | Protein of unknown function (DUF1277) superfamily |
| ORF01191 | 2381 & 2382 | endodeoxyribonuclease RUS (Holliday junction resolvase) [3.1.22.—] |
| ORF01192 | 2383 & 2384 | Antitermination protein Q homolog of cryptic prophage |
| ORF01193 | 2385 & 2386 | hypothetical protein |
| ORF01194 | 2387 & 2388 | unnamed protein product; ORF137, length |
| ORF01195 | 2389 & 2390 | lysis protein S.b1556 |
| ORF01196 | 2391 & 2392 | hypothetical bacteriophage protein |
| ORF01197 | 2393 & 2394 | Lysozyme (Lysis protein) (Muramidase) (Endolysin) [3.2.1.17] |
| ORF01198 | 2395 & 2396 | lipoprotein Rz1 precursor-related protein |
| ORF01199 | 2397 & 2398 | Bacteriophage lysis protein |
| ORF01200 | 2399 & 2400 | Sb56 |
| ORF01201 | 2401 & 2402 | phage terminase, small subunit, putative, P27 family, putative |
| ORF01202 | 2403 & 2404 | phage terminase, large subunit, putative |
| ORF01203 | 2405 & 2406 | hypothetical protein |
| ORF01204 | 2407 & 2408 | phage portal protein, HK97 family |
| ORF01205 | 2409 & 2410 | Caudovirus prohead protease |
| ORF01206 | 2411 & 2412 | phage major capsid protein, HK97 family |
| ORF01207 | 2413 & 2414 | uncharacterized phage protein (possible DNA packaging) |
| ORF01208 | 2415 & 2416 | phage head-tail adaptor, putative |
| ORF01209 | 2417 & 2418 | phage protein, HK97 gp10 family |
| ORF01210 | 2419 & 2420 | Gp11 |
| ORF01211 | 2421 & 2422 | major tail subunit |
| ORF01212 | 2423 & 2424 | Phage tail assembly chaperone |
| ORF01213 | 2425 & 2426 | Gp14 |
| ORF01214 | 2427 & 2428 | tail length tape measure protein |
| ORF01215 | 2429 & 2430 | phage minor tail protein L |
| ORF01216 | 2431 & 2432 | Putative tail fiber component K of prophage |
| ORF01217 | 2433 & 2434 | Bacteriophage lambda tail assembly protein I |
| ORF01218 | 2435 & 2436 | Host specificity protein J (partial) |
| ORF01219 | 2437 & 2438 | Host specificity protein J (partial) |
| ORF01220 | 2439 & 2440 | host specificity protein (partial) |
| ORF01221 | 2441 & 2442 | Lom |
| ORF01222 | 2443 & 2444 | conserved hypothetical protein |
| ORF01223 | 2445 & 2446 | conserved hypothetical protein |
| ORF01224 | 2447 & 2448 | conserved hypothetical protein |
| ORF01225 | 2449 & 2450 | conserved hypothetical protein |
| ORF01226 | 2451 & 2452 | CdtA |
| ORF01227 | 2453 & 2454 | CdtB |
| ORF01228 | 2455 & 2456 | CdtC |
| ORF01229 | 2457 & 2458 | Periplasmic solute binding protein family family |
| ORF01230 | 2459 & 2460 | MEMBRANE PROTEIN |
| ORF01231 | 2461 & 2462 | Hypothetical UPF0190 protein yedY (AE005419) |
| ORF01232 | 2463 & 2464 | transthyretin family protein |
| ORF01233 | 2465 & 2466 | Transcriptional activator protein CopR. |
| ORF01234 | 2467 & 2468 | histidine kinase [2.7.3.—] |
| ORF01235 | 2469 & 2470 | H-NS-repressed protein, 30K (Hsp31) |
| ORF01236 | 2471 & 2472 | Outer membrane protein N precursor (OmpF) |
| ORF01237 | 2473 & 2474 | HD domain protein |
| ORF01238 | 2475 & 2476 | DNA-cytosine methyltransferase (M.EcoDcm) [2.1.1.37] |
| ORF01239 | 2477 & 2478 | integral membrane protein |
| ORF01240 | 2479 & 2480 | patch repair protein [3.1.—.—] |
| ORF01241 | 2481 & 2482 | Protein of unknown function |
| ORF01242 | 2483 & 2484 | conserved hypothetical protein |
| ORF01243 | 2485 & 2486 | conserved hypothetical protein |
| ORF01244 | 2487 & 2488 | diguanylate cyclase (GGDEF) domain protein |
| ORF01245 | 2489 & 2490 | mannosyl-3-phosphoglycerate phosphatase-related protein [3.1.3.—] |
| ORF01246 | 2491 & 2492 | conserved hypothetical protein |
| ORF01247 | 2493 & 2494 | conserved hypothetical protein |
| ORF01248 | 2495 & 2496 | Colanic acid capsular biosynthesis activation protein A |
| ORF01249 | 2497 & 2498 | flagellar biosynthetic protein FliR (fliR) |
| ORF01250 | 2499 & 2500 | flagellar biosynthetic protein FliQ (fliQ) |
| ORF01251 | 2501 & 2502 | flagellar biosynthetic protein FliP (fliP) |
| ORF01252 | 2503 & 2504 | terminase large subunit |
| ORF01253 | 2505 & 2506 | phage terminase family protein, putative |
| ORF01254 | 2507 & 2508 | hypothetical protein |
| ORF01255 | 2509 & 2510 | Gp45 |
| ORF01256 | 2511 & 2512 | conserved hypothetical protein |
| ORF01257 | 2513 & 2514 | CI protein |
| ORF01258 | 2515 & 2516 | transcriptional regulator, Cro-CI family-related protein |
| ORF01259 | 2517 & 2518 | repressor (cII) |
| ORF01260 | 2519 & 2520 | O (DNA replication; 299) |

TABLE 1-continued

Annotation of ORF00001 to ORF04995

| ORFnnnnn | SEQ ID NOs | Annotation |
|---|---|---|
| ORF01261 | 2521 & 2522 | P protein |
| ORF01262 | 2523 & 2524 | hydrogenase |
| ORF01263 | 2525 & 2526 | Hydrogenase-1 large chain (NiFe hydrogenase) (Membrane-bound hydrogenase 1 large subunit) (HYD1) (hyaB) [1.12.99.6] |
| ORF01264 | 2527 & 2528 | Ni—Fe-hydrogenase, b-type cytochrome subunit (CybH) |
| ORF01265 | 2529 & 2530 | Hydrogenase 1 maturation protease [3.4.24.—] |
| ORF01266 | 2531 & 2532 | Hydrogenase-1 operon protein hyaE |
| ORF01267 | 2533 & 2534 | Hydrogenase-1 operon protein hyaF |
| ORF01268 | 2535 & 2536 | cytochrome d ubiquinol oxidase, subunit I |
| ORF01269 | 2537 & 2538 | cytochrome d ubiquinol oxidase, subunit II (cydB) [1.10.3.—] |
| ORF01270 | 2539 & 2540 | conserved hypothetical protein |
| ORF01271 | 2541 & 2542 | cold shock-like protein |
| ORF01272 | 2543 & 2544 | Periplasmic appA protein precursor (agp) [3.1.3.2] |
| ORF01273 | 2545 & 2546 | hypothetical protein |
| ORF01274 | 2547 & 2548 | cold shock-like protein |
| ORF01275 | 2549 & 2550 | GnsB protein |
| ORF01276 | 2551 & 2552 | Putative electron transport protein yccM |
| ORF01277 | 2553 & 2554 | 2.7.3.—[2.7.3.—] |
| ORF01278 | 2555 & 2556 | TorCAD operon transcriptional Regulatory protein torR |
| ORF01279 | 2557 & 2558 | Periplasmic protein torT precursor |
| ORF01280 | 2559 & 2560 | trimethylamine-N-oxide reductase c-type cytochrome TorC (torC) |
| ORF01281 | 2561 & 2562 | trimethylamine-N-oxide reductase TorA (torA) [1.7.2.3] |
| ORF01282 | 2563 & 2564 | Chaperone protein torD |
| ORF01283 | 2565 & 2566 | conserved hypothetical protein |
| ORF01284 | 2567 & 2568 | conserved hypothetical protein |
| ORF01285 | 2569 & 2570 | dnaJ protein |
| ORF01286 | 2571 & 2572 | periplasmic glucose-1-phosphatase |
| ORF01287 | 2573 & 2574 | conserved hypothetical protein |
| ORF01288 | 2575 & 2576 | trp repressor-binding protein |
| ORF01289 | 2577 & 2578 | conserved hypothetical protein |
| ORF01290 | 2579 & 2580 | uracil-xanthine permease |
| ORF01291 | 2581 & 2582 | conserved hypothetical protein |
| ORF01292 | 2583 & 2584 | uracil-xanthine permease |
| ORF01293 | 2585 & 2586 | 4-hydroxyphenylacetate 3-monooxygenase (EC 1.14.13.3) small chain [1.14.13.3] |
| ORF01294 | 2587 & 2588 | putative nitroreductase (AE005300) [1.—.—.—] |
| ORF01295 | 2589 & 2590 | 3-oxoadipate enol-lactone hydrolase-4-carboxymuconolactone decarboxylase, putative |
| ORF01296 | 2591 & 2592 | hypothetical protein |
| ORF01297 | 2593 & 2594 | endoribonuclease L-PSP, putative |
| ORF01298 | 2595 & 2596 | Hypothetical isochorismatase family protein ycdL |
| ORF01299 | 2597 & 2598 | bacterial luciferase family protein, putative |
| ORF01300 | 2599 & 2600 | transcriptional regulator, TetR family, |
| ORF01301 | 2601 & 2602 | proline dehydrogenase-delta-1-pyrroline-5-carboxylate dehydrogenase |
| ORF01302 | 2603 & 2604 | conserved hypothetical protein |
| ORF01303 | 2605 & 2606 | sodium-proline symporter (putP) |
| ORF01304 | 2607 & 2608 | membrane protein, putative |
| ORF01305 | 2609 & 2610 | putative lipoprotein |
| ORF01306 | 2611 & 2612 | Tat-translocated enzyme |
| ORF01307 | 2613 & 2614 | PhoH family protein |
| ORF01308 | 2615 & 2616 | conserved hypothetical protein |
| ORF01309 | 2617 & 2618 | haemin storage system, HmsR protein (lgtD) |
| ORF01310 | 2619 & 2620 | HmsF (HmsF) |
| ORF01311 | 2621 & 2622 | haemin storage system, HmsH protein |
| ORF01312 | 2623 & 2624 | GGDEF domain protein |
| ORF01313 | 2625 & 2626 | integrase |
| ORF01314 | 2627 & 2628 | probable membrane protein |
| ORF01315 | 2629 & 2630 | INSA |
| ORF01316 | 2631 & 2632 | transposase |
| ORF01317 | 2633 & 2634 | hypothetical protein |
| ORF01318 | 2635 & 2636 | Prophage CP4-57 Regulatory protein alpA |
| ORF01319 | 2637 & 2638 | conserved hypothetical protein |
| ORF01320 | 2639 & 2640 | predicted methyltransferase |
| ORF01321 | 2641 & 2642 | predicted methyltransferase |
| ORF01322 | 2643 & 2644 | enterotoxin |
| ORF01323 | 2645 & 2646 | aminotransferase, class II, putative |
| ORF01324 | 2647 & 2648 | KbaY [4.1.2.—] |
| ORF01325 | 2649 & 2650 | PUTATIVE TAGATOSE 6-PHOSPHATE KINASE PROTEIN |
| ORF01326 | 2651 & 2652 | DeoR-family regulatory protein |
| ORF01327 | 2653 & 2654 | Transcriptional regulator of sugar metabolism |
| ORF01328 | 2655 & 2656 | D-galactarate dehydratase [4.2.1.42] |
| ORF01329 | 2657 & 2658 | D-GALACTARATE DEHYDRATASE [4.2.1.7] |
| ORF01330 | 2659 & 2660 | putative hydrolase |
| ORF01331 | 2661 & 2662 | galactarate dehydrogenase [4.2.1.42] |
| ORF01332 | 2663 & 2664 | hypothetical protein |
| ORF01333 | 2665 & 2666 | conserved hypothetical protein |
| ORF01334 | 2667 & 2668 | Putative F1C and S fimbrial switch Regulatory |

TABLE 1-continued

Annotation of ORF00001 to ORF04995

| ORFnnnnn | SEQ ID NOs | Annotation |
|---|---|---|
| ORF01335 | 2669 & 2670 | SfaB protein |
| ORF01336 | 2671 & 2672 | hypothetical protein |
| ORF01337 | 2673 & 2674 | SfaD protein |
| ORF01338 | 2675 & 2676 | SfaE protein |
| ORF01339 | 2677 & 2678 | F1C fimbrial usher |
| ORF01340 | 2679 & 2680 | S fimbrial adhesin minor subunit SfaG |
| ORF01341 | 2681 & 2682 | S fimbrial adhesin minor subunit SfaS (pilin) |
| ORF01342 | 2683 & 2684 | S fimbrial adhesin minor subunit SfaH |
| ORF01343 | 2685 & 2686 | EAL domain, putative |
| ORF01344 | 2687 & 2688 | PapX protein |
| ORF01345 | 2689 & 2690 | hypothetical protein |
| ORF01346 | 2691 & 2692 | IroN protein |
| ORF01347 | 2693 & 2694 | IroE |
| ORF01348 | 2695 & 2696 | IroD protein (Fes) |
| ORF01349 | 2697 & 2698 | IroC (ABC) |
| ORF01350 | 2699 & 2700 | Putative glucosyltransferase |
| ORF01351 | 2701 & 2702 | conserved hypothetical protein |
| ORF01352 | 2703 & 2704 | conserved hypothetical protein |
| ORF01353 | 2705 & 2706 | unnamed protein product; ORF94, length (ISPlu9-p) |
| ORF01354 | 2707 & 2708 | Transposase, IS4 family |
| ORF01355 | 2709 & 2710 | tonB dependent outer membrane hemin receptor, hmuR (Y08983) |
| ORF01356 | 2711 & 2712 | conserved hypothetical protein |
| ORF01357 | 2713 & 2714 | cobalamin synthesis protein, putative |
| ORF01358 | 2715 & 2716 | ECs1339 |
| ORF01359 | 2717 & 2718 | conserved hypothetical protein |
| ORF01360 | 2719 & 2720 | hypothetical protein |
| ORF01361 | 2721 & 2722 | replication protein (Rep) |
| ORF01362 | 2723 & 2724 | hypothetical protein |
| ORF01363 | 2725 & 2726 | YeeP protein |
| ORF01364 | 2727 & 2728 | antigen43 protein orthologue |
| ORF01365 | 2729 & 2730 | conserved hypothetical protein |
| ORF01366 | 2731 & 2732 | Z1215 protein (o273) |
| ORF01367 | 2733 & 2734 | conserved hypothetical protein |
| ORF01368 | 2735 & 2736 | Antirestriction protein family |
| ORF01369 | 2737 & 2738 | YeeS protein (o160) |
| ORF01370 | 2739 & 2740 | intergenic-region protein-related protein |
| ORF01371 | 2741 & 2742 | conserved hypothetical protein |
| ORF01372 | 2743 & 2744 | intergenic-region protein |
| ORF01373 | 2745 & 2746 | YeeV protein |
| ORF01374 | 2747 & 2748 | L0008-like protein |
| ORF01375 | 2749 & 2750 | Z1225 protein (AF071034) |
| ORF01376 | 2751 & 2752 | Z1226 protein |
| ORF01377 | 2753 & 2754 | putative dehydrogenase (AE005314) |
| ORF01378 | 2755 & 2756 | PHP family protein |
| ORF01379 | 2757 & 2758 | TorD protein |
| ORF01380 | 2759 & 2760 | Protein of unknown function (DUF1097) superfamily |
| ORF01381 | 2761 & 2762 | Curli production assembly-transport component csgG precursor |
| ORF01382 | 2763 & 2764 | Curli production assembly-transport component csgF precursor |
| ORF01383 | 2765 & 2766 | Curli production assembly-transport component csgE precursor |
| ORF01384 | 2767 & 2768 | transcriptional regulator, LuxR family |
| ORF01385 | 2769 & 2770 | curli fiber major subunit CsgA, degenerate |
| ORF01386 | 2771 & 2772 | curli fiber major subunit CsgA, degenerate, putative |
| ORF01387 | 2773 & 2774 | conserved hypothetical protein |
| ORF01388 | 2775 & 2776 | Appr-1-p processing enzyme family protein |
| ORF01389 | 2777 & 2778 | cardiolipin synthase |
| ORF01390 | 2779 & 2780 | Glucans biosynthesis protein C [2.1.—.—] |
| ORF01391 | 2781 & 2782 | conserved hypothetical protein |
| ORF01392 | 2783 & 2784 | Periplasmic glucans biosynthesis protein mdoG precursor |
| ORF01393 | 2785 & 2786 | Periplasmic glucans biosynthesis protein mdoH |
| ORF01394 | 2787 & 2788 | conserved hypothetical protein |
| ORF01395 | 2789 & 2790 | Protein of unknown function (DUF1375) superfamily |
| ORF01396 | 2791 & 2792 | Acidic protein msyB |
| ORF01397 | 2793 & 2794 | major facilitator family transporter |
| ORF01398 | 2795 & 2796 | Lipid A biosynthesis lauroyl acyltransferase |
| ORF01399 | 2797 & 2798 | rhodanese-like domain protein, putative |
| ORF01400 | 2799 & 2800 | Protein yceI precursor |
| ORF01401 | 2801 & 2802 | Cytochrome b561 homolog 2 |
| ORF01402 | 2803 & 2804 | conserved hypothetical protein |
| ORF01403 | 2805 & 2806 | N-methyl-L-tryptophan oxidase (MTOX) [1.5.3.—] |
| ORF01404 | 2807 & 2808 | unnamed protein product; ORF_ID: o233#8 |
| ORF01405 | 2809 & 2810 | unnamed protein product; ORF_ID: o233#9 |
| ORF01406 | 2811 & 2812 | dihydroorotase, homodimeric type (pyrC) [3.5.2.3] |
| ORF01407 | 2813 & 2814 | Protein of unknown function (DUF1439) superfamily |
| ORF01408 | 2815 & 2816 | Glutaredoxin, GrxB family (grxB) |
| ORF01409 | 2817 & 2818 | Major Facilitator Superfamily subfamily |
| ORF01410 | 2819 & 2820 | Ribosomal-protein-alanine acetyltransferase [2.3.1.128] |

TABLE 1-continued

Annotation of ORF00001 to ORF04995

| ORFnnnnn | SEQ ID NOs | Annotation |
|---|---|---|
| ORF01411 | 2821 & 2822 | g20.3 |
| ORF01412 | 2823 & 2824 | putative virulence factor |
| ORF01413 | 2825 & 2826 | integral membrane protein MviN (mviN) |
| ORF01414 | 2827 & 2828 | Flagella synthesis protein flgN |
| ORF01415 | 2829 & 2830 | Negative regulator of flagellin synthesis (Anti-sigma-28 factor) |
| ORF01416 | 2831 & 2832 | flagellar basal body P-ring protein FlgA precursor |
| ORF01417 | 2833 & 2834 | flagellar basal-body rod protein FlgB (flgB) |
| ORF01418 | 2835 & 2836 | flagellar basal-body rod protein FlgC (flgC) |
| ORF01419 | 2837 & 2838 | flagellar biosynthesis, hook protein |
| ORF01420 | 2839 & 2840 | flagellar biosynthesis, hook protein |
| ORF01421 | 2841 & 2842 | Flagellar basal-body rod protein flgF |
| ORF01422 | 2843 & 2844 | Flagellar basal-body rod protein flgG (Distal rod protein) |
| ORF01423 | 2845 & 2846 | flagellar L-ring protein FlgH (flgH) |
| ORF01424 | 2847 & 2848 | flagellar P-ring protein FlgI (flgI) |
| ORF01425 | 2849 & 2850 | Peptidoglycan hydrolase flgJ [3.2.1.—] |
| ORF01426 | 2851 & 2852 | flagellar hook-associated protein 1 (hap1) |
| ORF01427 | 2853 & 2854 | Flagellar hook-associated protein 3 (hap3) |
| ORF01428 | 2855 & 2856 | Ribonuclease E (RNase E) (rne) [3.1.4.—] |
| ORF01429 | 2857 & 2858 | hypothetical protein |
| ORF01430 | 2859 & 2860 | ribosomal large subunit pseudouridine synthase C (orfx) [4.2.1.70] |
| ORF01431 | 2861 & 2862 | ribosomal large subunit pseudouridine synthase C (orfx) [4.2.1.70] |
| ORF01432 | 2863 & 2864 | maf protein (maf) |
| ORF01433 | 2865 & 2866 | Uncharacterized ACR, COG1399 |
| ORF01434 | 2867 & 2868 | ribosomal protein L32 (rpmF) |
| ORF01435 | 2869 & 2870 | 3-oxoacyl-[acyl-carrier-protein] synthase II |
| ORF01436 | 2871 & 2872 | Aminodeoxychorismate lyase (4-amino-4-deoxychorismatelyase) (ADC lyase) (ADCL) (ADCL) [4.1.3.38] |
| ORF01437 | 2873 & 2874 | conserved hypothetical protein TIGR00247 |
| ORF01438 | 2875 & 2876 | thymidylate kinase (tmk) [2.7.4.9] |
| ORF01439 | 2877 & 2878 | DNA polymerase III, delta' subunit [2.7.7.7] |
| ORF01440 | 2879 & 2880 | Putative deoxyribonuclease ycfH |
| ORF01441 | 2881 & 2882 | PTS system, glucose-specific IIBC component (ptsG) [2.7.1.69] |
| ORF01442 | 2883 & 2884 | FhuE receptor precursor (III) |
| ORF01443 | 2885 & 2886 | HIT-like protein ycfF (Ap4A) |
| ORF01444 | 2887 & 2888 | Protein of unknown function (DUF1425) superfamily |
| ORF01445 | 2889 & 2890 | Fibronectin-binding protein B |
| ORF01446 | 2891 & 2892 | unnamed protein product [3.2.1.21] |
| ORF01447 | 2893 & 2894 | Beta-hexosaminidase |
| ORF01448 | 2895 & 2896 | ycfP protein |
| ORF01449 | 2897 & 2898 | NADH dehydrogenase |
| ORF01450 | 2899 & 2900 | conserved hypothetical protein |
| ORF01451 | 2901 & 2902 | transcriptional regulator, TetR family |
| ORF01452 | 2903 & 2904 | Protein of unknown function (DUF1471) superfamily |
| ORF01453 | 2905 & 2906 | ErfK-YbiS-YcfS-YnhG family |
| ORF01454 | 2907 & 2908 | transcription-repair coupling factor mutation frequency decline |
| ORF01455 | 2909 & 2910 | Acyltransferase family, putative |
| ORF01456 | 2911 & 2912 | hypothetical protein |
| ORF01457 | 2913 & 2914 | ABC transporter, integral membrane protein |
| ORF01458 | 2915 & 2916 | lipoprotein releasing system, ATP-binding protein (lolD) |
| ORF01459 | 2917 & 2918 | lipoprotein releasing system, transmembrane protein LolE (lolE) |
| ORF01460 | 2919 & 2920 | ROK family protein |
| ORF01461 | 2921 & 2922 | NAD-dependent deacetylase (Regulatory protein SIR2homolog) (DMB) [3.5.1.—] |
| ORF01462 | 2923 & 2924 | conserved hypothetical protein |
| ORF01463 | 2925 & 2926 | conserved hypothetical protein |
| ORF01464 | 2927 & 2928 | Spermidine-putrescine-binding periplasmic protein precursor (potD) |
| ORF01465 | 2929 & 2930 | Spermidine-putrescine transport system permease protein potC (potC) |
| ORF01466 | 2931 & 2932 | spermidine-putrescine transport system permease |
| ORF01467 | 2933 & 2934 | ABC transporter, polyamine transport protein, ATP-binding protein (atp_bind) |
| ORF01468 | 2935 & 2936 | peptidase T (pepT) [3.4.11.14] |
| ORF01469 | 2937 & 2938 | ycfD protein |
| ORF01470 | 2939 & 2940 | Sensor protein phoQ [2.7.3.—] |
| ORF01471 | 2941 & 2942 | transcriptional regulatory protein |
| ORF01472 | 2943 & 2944 | adenylosuccinate lyase (purB) [4.3.2.2] |
| ORF01473 | 2945 & 2946 | Uncharacterized protein involved in purine metabolism |
| ORF01474 | 2947 & 2948 | tRNA (5-methylaminomethyl-2-thiouridylate)-methyltransferase (trmU) [2.1.1.61] |
| ORF01475 | 2949 & 2950 | unnamed protein product [3.6.—.—] |
| ORF01476 | 2951 & 2952 | RNA pseudouridylate synthase family protein [4.2.1.70] |
| ORF01477 | 2953 & 2954 | conserved hypothetical protein |
| ORF01478 | 2955 & 2956 | isocitrate dehydrogenase, NADP-dependent (icd) [1.1.1.42] |
| ORF01479 | 2957 & 2958 | Prophage lambda integrase |
| ORF01480 | 2959 & 2960 | conserved hypothetical protein |
| ORF01481 | 2961 & 2962 | unnamed protein product; Some similarities with bacteriophage protein |
| ORF01482 | 2963 & 2964 | exonuclease Z0951 [similarity] [3.1.11.3] |
| ORF01483 | 2965 & 2966 | recombination protein Bet |
| ORF01484 | 2967 & 2968 | Host-nuclease inhibitor protein Gam |
| ORF01485 | 2969 & 2970 | Kil protein |

TABLE 1-continued

Annotation of ORF00001 to ORF04995

| ORFnnnnn | SEQ ID NOs | Annotation |
|---|---|---|
| ORF01486 | 2971 & 2972 | Lambda Regulatory protein CIII-related protein |
| ORF01487 | 2973 & 2974 | Ea10 gene protein |
| ORF01488 | 2975 & 2976 | conserved hypothetical protein |
| ORF01489 | 2977 & 2978 | antitermination protein Q |
| ORF01490 | 2979 & 2980 | lysozyme [3.2.1.17] |
| ORF01491 | 2981 & 2982 | Bacteriophage lysis protein |
| ORF01492 | 2983 & 2984 | hypothetical protein |
| ORF01493 | 2985 & 2986 | prophage L54a, HNH endonuclease family protein |
| ORF01494 | 2987 & 2988 | small terminase subunit |
| ORF01495 | 2989 & 2990 | phage terminase, large subunit, putative |
| ORF01496 | 2991 & 2992 | conserved hypothetical protein |
| ORF01497 | 2993 & 2994 | phage portal protein, HK97 family |
| ORF01498 | 2995 & 2996 | Sb5 (AF181080) |
| ORF01499 | 2997 & 2998 | phage major capsid protein, HK97 family |
| ORF01500 | 2999 & 3000 | Sb7-related protein |
| ORF01501 | 3001 & 3002 | Sb8 |
| ORF01502 | 3003 & 3004 | Sb9 |
| ORF01503 | 3005 & 3006 | hypothetical protein |
| ORF01504 | 3007 & 3008 | Sb11 |
| ORF01505 | 3009 & 3010 | conserved hypothetical protein |
| ORF01506 | 3011 & 3012 | Bacteriophage Mu tail sheath protein (GpL) |
| ORF01507 | 3013 & 3014 | Sb14 |
| ORF01508 | 3015 & 3016 | hypothetical protein |
| ORF01509 | 3017 & 3018 | Sb15 |
| ORF01510 | 3019 & 3020 | tail protein |
| ORF01511 | 3021 & 3022 | tail-DNA circulation protein (muN) |
| ORF01512 | 3023 & 3024 | Bacteriophage Mu P protein |
| ORF01513 | 3025 & 3026 | Bacteriophage Mu Gp45 protein |
| ORF01514 | 3027 & 3028 | Phage protein GP46 |
| ORF01515 | 3029 & 3030 | tail protein |
| ORF01516 | 3031 & 3032 | tail protein |
| ORF01517 | 3033 & 3034 | ycfE protein (fragment) |
| ORF01518 | 3035 & 3036 | Domain of unknown function DUF144 superfamily |
| ORF01519 | 3037 & 3038 | unnamed protein product; unidentified reading frame P-293 |
| ORF01520 | 3039 & 3040 | lipoprotein Rz1 precursor-related protein |
| ORF01521 | 3041 & 3042 | Bacteriophage lysis protein |
| ORF01522 | 3043 & 3044 | Bor protein homolog from lambdoid prophage DLP12 |
| ORF01523 | 3045 & 3046 | hypothetical protein |
| ORF01524 | 3047 & 3048 | conserved hypothetical protein |
| ORF01525 | 3049 & 3050 | Bacteriophage lambda head decoration protein D |
| ORF01526 | 3051 & 3052 | Phage major capsid protein E |
| ORF01527 | 3053 & 3054 | conserved hypothetical protein |
| ORF01528 | 3055 & 3056 | Phage Head-Tail Attachment |
| ORF01529 | 3057 & 3058 | Prophage minor tail protein Z (GPZ) |
| ORF01530 | 3059 & 3060 | Minor tail protein U |
| ORF01531 | 3061 & 3062 | hypothetical protein |
| ORF01532 | 3063 & 3064 | Minor tail protein Z (GPZ) |
| ORF01533 | 3065 & 3066 | Phage minor tail protein U |
| ORF01534 | 3067 & 3068 | minor tail protein |
| ORF01535 | 3069 & 3070 | Phage minor tail protein U |
| ORF01536 | 3071 & 3072 | major tail protein |
| ORF01537 | 3073 & 3074 | phage minor tail protein G |
| ORF01538 | 3075 & 3076 | minor tail protein |
| ORF01539 | 3077 & 3078 | minor tail protein |
| ORF01540 | 3079 & 3080 | tail length tape measure protein precursor |
| ORF01541 | 3081 & 3082 | minor tail protein |
| ORF01542 | 3083 & 3084 | Minor tail protein precursor H |
| ORF01543 | 3085 & 3086 | Minor tail protein precursor H |
| ORF01544 | 3087 & 3088 | hypothetical bacteriophage protein |
| ORF01545 | 3089 & 3090 | unnamed protein product; Similar to tail fiber assembly protein |
| ORF01546 | 3091 & 3092 | Protease VII precursor (Omptin) (Outer membrane protein3B) (Protease A) (SopA) [3.4.21.87] |
| ORF01547 | 3093 & 3094 | Protease VII precursor (Omptin) (Outer membrane protein3B) (Protease A) (SopA) [3.4.21.87] |
| ORF01548 | 3095 & 3096 | Protease VII precursor (Omptin) (Outer membrane protein3B) (Protease A) (SopA) [3.4.21.87] |
| ORF01549 | 3097 & 3098 | ydfE protein (35 kD) |
| ORF01550 | 3099 & 3100 | Phage terminase large subunit (GpA) |
| ORF01551 | 3101 & 3102 | Phage terminase large subunit (GpA) |
| ORF01552 | 3103 & 3104 | Phage terminase large subunit (GpA) |
| ORF01553 | 3105 & 3106 | Portal protein (Head protein GP4) |
| ORF01554 | 3107 & 3108 | head-tail preconnector protein GP5 |
| ORF01555 | 3109 & 3110 | Head-tail preconnector protein GP5 [Contains: Scaffold protein GP6(Head protein GP6)] |
| ORF01556 | 3111 & 3112 | Bacteriophage lambda head decoration protein D |
| ORF01557 | 3113 & 3114 | Phage major capsid protein E |

TABLE 1-continued

Annotation of ORF00001 to ORF04995

| ORFnnnnn | SEQ ID NOs | Annotation |
|---|---|---|
| ORF01558 | 3115 & 3116 | conserved hypothetical protein |
| ORF01559 | 3117 & 3118 | Phage Head-Tail Attachment |
| ORF01560 | 3119 & 3120 | Prophage minor tail protein Z (GPZ) |
| ORF01561 | 3121 & 3122 | Phage minor tail protein U |
| ORF01562 | 3123 & 3124 | major tail protein |
| ORF01563 | 3125 & 3126 | phage minor tail protein G |
| ORF01564 | 3127 & 3128 | minor tail protein |
| ORF01565 | 3129 & 3130 | Portal protein (Head protein GP4) |
| ORF01566 | 3131 & 3132 | head-tail preconnector protein GP5 |
| ORF01567 | 3133 & 3134 | Head-tail preconnector protein GP5 [Contains: Scaffold protein GP6(Head protein GP6)] |
| ORF01568 | 3135 & 3136 | Head-tail preconnector protein GP5 [Contains: Scaffold protein GP6(Head protein GP6)] |
| ORF01569 | 3137 & 3138 | Bacteriophage lambda head decoration protein D |
| ORF01570 | 3139 & 3140 | phage tail tape measure protein, lambda family |
| ORF01571 | 3141 & 3142 | Phage minor tail protein |
| ORF01572 | 3143 & 3144 | minor tail protein |
| ORF01573 | 3145 & 3146 | Putative tail component of prophage |
| ORF01574 | 3147 & 3148 | Phage minor tail protein |
| ORF01575 | 3149 & 3150 | Phage minor tail protein L |
| ORF01576 | 3151 & 3152 | Putative tail component of prophage |
| ORF01577 | 3153 & 3154 | Phage minor tail protein |
| ORF01578 | 3155 & 3156 | Phage minor tail protein L |
| ORF01579 | 3157 & 3158 | transcriptional regulator, GntR family |
| ORF01580 | 3159 & 3160 | Probable oxidoreductase ydfG |
| ORF01581 | 3161 & 3162 | peptidyl-dipeptidase Dcp, putative |
| ORF01582 | 3163 & 3164 | peptidyl-dipeptidase Dcp |
| ORF01583 | 3165 & 3166 | hypothetical protein |
| ORF01584 | 3167 & 3168 | GGDEF domain protein |
| ORF01585 | 3169 & 3170 | hypothetical protein |
| ORF01586 | 3171 & 3172 | Major Facilitator Superfamily subfamily |
| ORF01587 | 3173 & 3174 | YdeD |
| ORF01588 | 3175 & 3176 | Putative conserved protein |
| ORF01589 | 3177 & 3178 | PTS system, cellobiose-specific IIB component (PTS) [2.7.1.69] |
| ORF01590 | 3179 & 3180 | Putative conserved protein |
| ORF01591 | 3181 & 3182 | PTS system, cellobiose-specific IIA component |
| ORF01592 | 3183 & 3184 | f538 |
| ORF01593 | 3185 & 3186 | 6-phospho-beta-glucosidase |
| ORF01594 | 3187 & 3188 | Multiple antibiotic resistance protein marB-related protein |
| ORF01595 | 3189 & 3190 | multiple antibiotic resistance protein MarA |
| ORF01596 | 3191 & 3192 | Multiple antibiotic resistance protein marR (AL359989) |
| ORF01597 | 3193 & 3194 | conserved hypothetical protein TIGR00427 |
| ORF01598 | 3195 & 3196 | Sugar efflux transporter |
| ORF01599 | 3197 & 3198 | transcriptional regulator, LysR family |
| ORF01600 | 3199 & 3200 | Aldehyde-dehydrogenase like protein ynel (SSDH) [1.2.1.—] |
| ORF01601 | 3201 & 3202 | glutaminase family protein, interruption-N |
| ORF01602 | 3203 & 3204 | conserved hypothetical protein |
| ORF01603 | 3205 & 3206 | GGDEF domain protein |
| ORF01604 | 3207 & 3208 | altronate oxidoreductase |
| ORF01605 | 3209 & 3210 | Uncharacterised protein family (UPF0187) superfamily |
| ORF01606 | 3211 & 3212 | trans-aconitate methyltransferase [2.1.1.144] |
| ORF01607 | 3213 & 3214 | Protein hipB |
| ORF01608 | 3215 & 3216 | Protein hipA |
| ORF01609 | 3217 & 3218 | conserved hypothetical protein |
| ORF01610 | 3219 & 3220 | short chain dehydrogenase |
| ORF01611 | 3221 & 3222 | Type-1 fimbrial protein, A chain precursor |
| ORF01612 | 3223 & 3224 | Chaperone protein fimC precursor |
| ORF01613 | 3225 & 3226 | Outer membrane usher protein fimD precursor |
| ORF01614 | 3227 & 3228 | fimbrial morphology |
| ORF01615 | 3229 & 3230 | Hypothetical fimbrial-like protein ydeQ precursor |
| ORF01616 | 3231 & 3232 | oxidoreductase alpha (molybdopterin) subunit |
| ORF01617 | 3233 & 3234 | HTH-type transcriptional regulator ydeO |
| ORF01618 | 3235 & 3236 | arylsulfatase B (GALNS) |
| ORF01619 | 3237 & 3238 | radical SAM domain protein protein |
| ORF01620 | 3239 & 3240 | ABC efflux transporter, permease-ATP-binding protein, putative |
| ORF01621 | 3241 & 3242 | cds103 |
| ORF01622 | 3243 & 3244 | cds103 |
| ORF01623 | 3245 & 3246 | peptidase, M16 family, putative [3.4.99.—] |
| ORF01624 | 3247 & 3248 | glutamate decarboxylase [4.1.1.15] |
| ORF01625 | 3249 & 3250 | Amino acid antiporter |
| ORF01626 | 3251 & 3252 | yngK protein |
| ORF01627 | 3253 & 3254 | Putative conserved protein-related protein |
| ORF01628 | 3255 & 3256 | Sensor protein FixL (EC 2.7.3.—). (nifL) [2.7.3.—] |
| ORF01629 | 3257 & 3258 | protein C, osmotically inducible |
| ORF01630 | 3259 & 3260 | hypothetical protein |
| ORF01631 | 3261 & 3262 | conserved hypothetical protein |

TABLE 1-continued

Annotation of ORF00001 to ORF04995

| ORFnnnnn | SEQ ID NOs | Annotation |
|---|---|---|
| ORF01632 | 3263 & 3264 | conserved hypothetical protein |
| ORF01633 | 3265 & 3266 | 30S ribosomal protein S22 (Stationary-phase-induced ribosome-associated protein) (SRA) (Protein D)-related protein |
| ORF01634 | 3267 & 3268 | hypothetical protein |
| ORF01635 | 3269 & 3270 | NAD-linked malate dehydrogenase (malic enzyme) |
| ORF01636 | 3271 & 3272 | alcohol dehydrogenase, propanol-preferring (adhA) [1.—.—.—] |
| ORF01637 | 3273 & 3274 | proteic killer suppression protein hig A |
| ORF01638 | 3275 & 3276 | conserved hypothetical protein |
| ORF01639 | 3277 & 3278 | proteic killer active protein hig B |
| ORF01640 | 3279 & 3280 | formate dehydrogenase, gamma subunit [1.2.1.2] |
| ORF01641 | 3281 & 3282 | formate dehydrogenase, beta subunit (FdxH) [1.2.1.2] |
| ORF01642 | 3283 & 3284 | formate dehydrogenase, alpha subunit, selenocysteine-containing [1.2.1.2] |
| ORF01643 | 3285 & 3286 | formate dehydrogenase, alpha subunit, selenocysteine-containing [1.2.1.2] |
| ORF01644 | 3287 & 3288 | formate dehydrogenase, alpha subunit, selenocysteine-containing [1.2.1.2] |
| ORF01645 | 3289 & 3290 | hypothetical protein |
| ORF01646 | 3291 & 3292 | membrane protein yddG |
| ORF01647 | 3293 & 3294 | nitrite extrusion protein 2 |
| ORF01648 | 3295 & 3296 | nitrate reductase, alpha subunit [1.7.99.4] |
| ORF01649 | 3297 & 3298 | nitrate reductase, beta subunit (narH) [1.7.99.4] |
| ORF01650 | 3299 & 3300 | Respiratory nitrate reductase 2 delta chain [1.7.99.4] |
| ORF01651 | 3301 & 3302 | respiratory nitrate reductase, gamma subunit (narI) [1.7.99.4] |
| ORF01652 | 3303 & 3304 | phenazine biosynthesis protein PhzF family subfamily |
| ORF01653 | 3305 & 3306 | Chain D, M. Smegmatis Arylamine N-Acetyl Transferase [2.3.1.118] |
| ORF01654 | 3307 & 3308 | Flavin reductase like domain protein |
| ORF01655 | 3309 & 3310 | H repeat-associated protein (ORF-H) |
| ORF01656 | 3311 & 3312 | conserved hypothetical protein |
| ORF01657 | 3313 & 3314 | conserved hypothetical protein |
| ORF01658 | 3315 & 3316 | Aec15 (AF044503) |
| ORF01659 | 3317 & 3318 | Uncharacterized conserved protein |
| ORF01660 | 3319 & 3320 | probable transferase (U59485) |
| ORF01661 | 3321 & 3322 | glutathione S-transferase gst |
| ORF01662 | 3323 & 3324 | L-asparagine permease (516aa) |
| ORF01663 | 3325 & 3326 | conserved hypothetical protein |
| ORF01664 | 3327 & 3328 | TonB-dependent receptor protein |
| ORF01665 | 3329 & 3330 | Putative conserved protein-related protein |
| ORF01666 | 3331 & 3332 | acetyltransferase, GNAT family [2.3.1.—] |
| ORF01667 | 3333 & 3334 | Protein of unknown function, DUF606 superfamily |
| ORF01668 | 3335 & 3336 | conserved hypothetical protein |
| ORF01669 | 3337 & 3338 | conserved hypothetical protein |
| ORF01670 | 3339 & 3340 | hypothetical protein |
| ORF01671 | 3341 & 3342 | aldehyde dehydrogenase family protein (BADH) [1.2.1.8] |
| ORF01672 | 3343 & 3344 | polyamine ABC transporter, permease protein |
| ORF01673 | 3345 & 3346 | polyamine ABC transporter, permease protein |
| ORF01674 | 3347 & 3348 | polyamine ABC transporter, ATP-binding protein |
| ORF01675 | 3349 & 3350 | polyamine ABC transporter, periplasmic polyamine-binding protein |
| ORF01676 | 3351 & 3352 | unnamed protein product (TAT) [2.6.1.5] |
| ORF01677 | 3353 & 3354 | unnamed protein product |
| ORF01678 | 3355 & 3356 | conserved hypothetical protein |
| ORF01679 | 3357 & 3358 | peptidase, U32 family |
| ORF01680 | 3359 & 3360 | transcriptional regulator, Cro-Cl family, putative |
| ORF01681 | 3361 & 3362 | similar to benzoate transport protein |
| ORF01682 | 3363 & 3364 | Hypothetical lipoprotein ydcL precursor |
| ORF01683 | 3365 & 3366 | tellurite resistance protein TehB (tehB) |
| ORF01684 | 3367 & 3368 | Tellurite resistance protein tehA |
| ORF01685 | 3369 & 3370 | ribosomal-protein-serine acetyltransferase, putative |
| ORF01686 | 3371 & 3372 | conserved hypothetical protein |
| ORF01687 | 3373 & 3374 | Protein of unknown function (DUF465) family |
| ORF01688 | 3375 & 3376 | Glucans biosynthesis protein D precursor |
| ORF01689 | 3377 & 3378 | Protein of unknown function (DUF1338) family |
| ORF01690 | 3379 & 3380 | transcriptional regulator PcaQ |
| ORF01691 | 3381 & 3382 | methyl-accepting chemotaxis protein II, aspartate sensor receptor |
| ORF01692 | 3383 & 3384 | Hok protein.-related protein |
| ORF01693 | 3385 & 3386 | conserved hypothetical protein |
| ORF01694 | 3387 & 3388 | Cytochrome b561 (561) |
| ORF01695 | 3389 & 3390 | glyceraldehyde-3-phosphate dehydrogenase, type I (gap) [1.2.1.—] |
| ORF01696 | 3391 & 3392 | Aldehyde dehydrogenase A (NAD) [1.2.1.22] |
| ORF01697 | 3393 & 3394 | Protein ydcF |
| ORF01698 | 3395 & 3396 | ATP-dependent helicase HrpA (hrpA) |
| ORF01699 | 3397 & 3398 | [acyl-carrier-protein] phosphodiesterase acpD (fragment) [3.1.4.14] |
| ORF01700 | 3399 & 3400 | Dual specificity phosphatase, catalytic domain protein |
| ORF01701 | 3401 & 3402 | Lysophospholipase |
| ORF01702 | 3403 & 3404 | phosphatidate cytidylyltransferase (cdsA) [2.7.7.41] |
| ORF01703 | 3405 & 3406 | CDP-alcohol phosphatidyltransferase family |
| ORF01704 | 3407 & 3408 | oxidoreductase, aldo-keto reductase family [1.—.—.—] |
| ORF01705 | 3409 & 3410 | split orf |
| ORF01706 | 3411 & 3412 | Protein of unknown function (DUF1318) family |

TABLE 1-continued

Annotation of ORF00001 to ORF04995

| ORFnnnnn | SEQ ID NOs | Annotation |
|---|---|---|
| ORF01707 | 3413 & 3414 | lipoprotein, putative |
| ORF01708 | 3415 & 3416 | unnamed protein product; Similar to membrane protein YdbH of *Escherichia coli* |
| ORF01709 | 3417 & 3418 | fermentative D-lactate dehydrogenase (D-LDH) [1.1.1.28] |
| ORF01710 | 3419 & 3420 | Heat shock protein hslJ |
| ORF01711 | 3421 & 3422 | lipoprotein, putative |
| ORF01712 | 3423 & 3424 | pyruvate:ferredoxin (flavodoxin) oxidoreductase (nifJ) [1.2.7.1] |
| ORF01713 | 3425 & 3426 | Outer membrane protein N precursor (lbc) |
| ORF01714 | 3427 & 3428 | putative filament protein |
| ORF01715 | 3429 & 3430 | integrase for bacteriophage BP-933W |
| ORF01716 | 3431 & 3432 | YdaO protein |
| ORF01717 | 3433 & 3434 | ATP-independent RNA helicase dbpA |
| ORF01718 | 3435 & 3436 | hypothetical protein |
| ORF01719 | 3437 & 3438 | CorA-like Mg2+ transporter protein |
| ORF01720 | 3439 & 3440 | Diguanylate cyclase-phosphodiesterase domain 1 (GGDEF) |
| ORF01721 | 3441 & 3442 | Smr domain protein |
| ORF01722 | 3443 & 3444 | drug resistance transporter, Bcr-CflA family (emrB) |
| ORF01723 | 3445 & 3446 | HlyD family secretion protein |
| ORF01724 | 3447 & 3448 | transcriptional regulator, AraC family |
| ORF01725 | 3449 & 3450 | conserved hypothetical protein |
| ORF01726 | 3451 & 3452 | Methylated-DNA--protein-cysteine methyltransferase (6-O-methylguanine-DNA methyltransferase) (MGMT) (O-6-methylguanine-DNA-alkyltransferase) [2.1.1.63] |
| ORF01727 | 3453 & 3454 | Fumarate and nitrate reduction Regulatory protein |
| ORF01728 | 3455 & 3456 | universal stress protein family domain protein |
| ORF01729 | 3457 & 3458 | conserved hypothetical protein |
| ORF01730 | 3459 & 3460 | small-conductance mechanosensitive channel |
| ORF01731 | 3461 & 3462 | Periplasmic murein peptide-binding protein precursor |
| ORF01732 | 3463 & 3464 | Xanthosine operon regulatory protein. |
| ORF01733 | 3465 & 3466 | dienelactone hydrolase domain protein |
| ORF01734 | 3467 & 3468 | conserved hypothetical protein |
| ORF01735 | 3469 & 3470 | Mandelate racemase —muconate lactonizing enzyme, C-terminal domain protein |
| ORF01736 | 3471 & 3472 | YcjI |
| ORF01737 | 3473 & 3474 | thiol peroxidase (P20) [1.11.1.—] |
| ORF01738 | 3475 & 3476 | Transcriptional Regulatory protein tyrR |
| ORF01739 | 3477 & 3478 | conserved hypothetical protein TIGR01620 |
| ORF01740 | 3479 & 3480 | YcjX (AY008264) |
| ORF01741 | 3481 & 3482 | transcription regulator homolog lin2974 |
| ORF01742 | 3483 & 3484 | Outer membrane protein G precursor |
| ORF01743 | 3485 & 3486 | ABC transporter domain protein |
| ORF01744 | 3487 & 3488 | beta-phosphoglucomutase (pgmB) [5.4.2.6] |
| ORF01745 | 3489 & 3490 | maltose phosphorylase homolog lin2966 (phosphorylase) [3.2.1.—] |
| ORF01746 | 3491 & 3492 | oxidoreductase, Gfo-Idh-MocA family |
| ORF01747 | 3493 & 3494 | an *E. coli* protein homolog lin2968 [5.3.1.—] |
| ORF01748 | 3495 & 3496 | Alcohol dehydrogenase (EC 1.1.1.1). [1.1.1.—] |
| ORF01749 | 3497 & 3498 | ABC transporter, permease protein (AF175299) |
| ORF01750 | 3499 & 3500 | Sn-glycerol-3-phosphate transport system permease protein UgpA. (AF307052) |
| ORF01751 | 3501 & 3502 | ABC transporter, substrate-binding protein |
| ORF01752 | 3503 & 3504 | dextransucrase (EC 2.4.1.5), putative [2.4.1.5] |
| ORF01753 | 3505 & 3506 | rhodanese-like domain protein |
| ORF01754 | 3507 & 3508 | phage shock protein-related protein |
| ORF01755 | 3509 & 3510 | Phage shock protein C |
| ORF01756 | 3511 & 3512 | phage shock protein B |
| ORF01757 | 3513 & 3514 | Phage shock protein A |
| ORF01758 | 3515 & 3516 | Psp operon transcriptional activator |
| ORF01759 | 3517 & 3518 | probable amino acid permease ycjJ |
| ORF01760 | 3519 & 3520 | conserved hypothetical protein |
| ORF01761 | 3521 & 3522 | Peptide transport periplasmic protein sapA precursor |
| ORF01762 | 3523 & 3524 | Peptide transport system permease protein sapB |
| ORF01763 | 3525 & 3526 | Peptide transport system permease protein sapC (sapC) |
| ORF01764 | 3527 & 3528 | Peptide transport system ATP-binding protein sapD |
| ORF01765 | 3529 & 3530 | Peptide transport system ATP-binding protein sapF |
| ORF01766 | 3531 & 3532 | drug resistance transporter, Bcr-CflA family protein |
| ORF01767 | 3533 & 3534 | EefC outer membrane protein |
| ORF01768 | 3535 & 3536 | Acriflavine resistance protein B |
| ORF01769 | 3537 & 3538 | Acriflavine resistance protein A precursor (MFP) |
| ORF01770 | 3539 & 3540 | transcriptional regulator, TetR family |
| ORF01771 | 3541 & 3542 | enoyl-[acyl-carrier-protein] reductase ECs1861 (NADH) [1.3.1.9] |
| ORF01772 | 3543 & 3544 | conserved hypothetical protein |
| ORF01773 | 3545 & 3546 | exoribonuclease II (rnb) [3.1.13.1] |
| ORF01774 | 3547 & 3548 | sensory box protein |
| ORF01775 | 3549 & 3550 | conserved hypothetical protein |
| ORF01776 | 3551 & 3552 | glycerol-3-phosphate regulon repressor, putative |
| ORF01777 | 3553 & 3554 | Osmotically inducible lipoprotein B precursor-related protein |
| ORF01778 | 3555 & 3556 | translation initation factor SUI1, putative |
| ORF01779 | 3557 & 3558 | orotidine 5'-phosphate decarboxylase (pyrF) [4.1.1.23] |
| ORF01780 | 3559 & 3560 | hypothetical protein |
| ORF01781 | 3561 & 3562 | predicted N-acetylglucosaminyl transferase |

TABLE 1-continued

Annotation of ORF00001 to ORF04995

| ORFnnnnn | SEQ ID NOs | Annotation |
|---|---|---|
| ORF01782 | 3563 & 3564 | unnamed protein product |
| ORF01783 | 3565 & 3566 | Phosphatidylglycerophosphatase B (pgpB) [3.1.3.27] |
| ORF01784 | 3567 & 3568 | GTP cyclohydrolase II (ribA) [3.5.4.25] |
| ORF01785 | 3569 & 3570 | aconitate hydratase 1 (acnA) [4.2.1.3] |
| ORF01786 | 3571 & 3572 | conserved hypothetical protein |
| ORF01787 | 3573 & 3574 | conserved hypothetical protein |
| ORF01788 | 3575 & 3576 | HTH-type transcriptional regulator cysB (Cys regulon transcriptionalactivator) |
| ORF01789 | 3577 & 3578 | DNA topoisomerase I |
| ORF01790 | 3579 & 3580 | hypothetical protein |
| ORF01791 | 3581 & 3582 | Protein yciN |
| ORF01792 | 3583 & 3584 | Possible protease sohB |
| ORF01793 | 3585 & 3586 | Oxidoreductase [1.—.—.—] |
| ORF01794 | 3587 & 3588 | cob(I)alamin adenosyltransferase (cobO) [2.5.1.17] |
| ORF01795 | 3589 & 3590 | RNA pseudouridylate synthase family protein [4.2.1.70] |
| ORF01796 | 3591 & 3592 | conserved hypothetical protein |
| ORF01797 | 3593 & 3594 | Sua5-YciO-YrdC-YwlC family protein |
| ORF01798 | 3595 & 3596 | Protein trpH |
| ORF01799 | 3597 & 3598 | anthranilate synthase component I (trpE) [4.1.3.27] |
| ORF01800 | 3599 & 3600 | Anthranilate synthase component II [4.1.3.27] |
| ORF01801 | 3601 & 3602 | anthranilate isomerase (PRAI) [4.1.1.48] |
| ORF01802 | 3603 & 3604 | tryptophan synthase, beta subunit (trpB) [4.2.1.20] |
| ORF01803 | 3605 & 3606 | tryptophan synthase, alpha subunit (trpA) [4.2.1.20] |
| ORF01804 | 3607 & 3608 | conserved hypothetical protein |
| ORF01805 | 3609 & 3610 | Protein yciF |
| ORF01806 | 3611 & 3612 | yciE |
| ORF01807 | 3613 & 3614 | Outer membrane protein W precursor |
| ORF01808 | 3615 & 3616 | Tail fiber assembly protein homolog from lambdoid prophage |
| ORF01809 | 3617 & 3618 | Tail fiber assembly protein homolog from lambdoid prophage Qin |
| ORF01810 | 3619 & 3620 | probable membrane protein of prophage CP-933X Z1918 |
| ORF01811 | 3621 & 3622 | probable membrane protein of prophage CP-933X Z1918 |
| ORF01812 | 3623 & 3624 | unknown protein encoded by prophage CP-933X |
| ORF01813 | 3625 & 3626 | hypothetical protein |
| ORF01814 | 3627 & 3628 | Lom |
| ORF01815 | 3629 & 3630 | host specificity protein (partial) |
| ORF01816 | 3631 & 3632 | Host specificity protein J (partial) |
| ORF01817 | 3633 & 3634 | Bacteriophage lambda tail assembly protein I |
| ORF01818 | 3635 & 3636 | Putative tail fiber component K of prophage |
| ORF01819 | 3637 & 3638 | minor tail protein |
| ORF01820 | 3639 & 3640 | minor tail protein |
| ORF01821 | 3641 & 3642 | Phage minor tail protein |
| ORF01822 | 3643 & 3644 | Minor tail protein precursor H |
| ORF01823 | 3645 & 3646 | minor tail protein |
| ORF01824 | 3647 & 3648 | phage minor tail protein G |
| ORF01825 | 3649 & 3650 | Bacterial Ig-like domain (group 2) family |
| ORF01826 | 3651 & 3652 | Phage minor tail protein U |
| ORF01827 | 3653 & 3654 | Prophage minor tail protein Z (GPZ) |
| ORF01828 | 3655 & 3656 | Phage Head-Tail Attachment |
| ORF01829 | 3657 & 3658 | conserved hypothetical protein |
| ORF01830 | 3659 & 3660 | Phage major capsid protein E |
| ORF01831 | 3661 & 3662 | Bacteriophage lambda head decoration protein D |
| ORF01832 | 3663 & 3664 | head-tail preconnector protein GP5 |
| ORF01833 | 3665 & 3666 | phage portal protein, lambda family |
| ORF01834 | 3667 & 3668 | gpW |
| ORF01835 | 3669 & 3670 | Phage terminase large subunit (GpA) |
| ORF01836 | 3671 & 3672 | Terminase small subunit (GP1) (fragment) |
| ORF01837 | 3673 & 3674 | hypothetical protein |
| ORF01838 | 3675 & 3676 | Bacteriophage lysis protein |
| ORF01839 | 3677 & 3678 | lipoprotein Rz1 precursor-related protein |
| ORF01840 | 3679 & 3680 | putative bacteriophage protein |
| ORF01841 | 3681 & 3682 | Lysozyme (Lysis protein) (Muramidase) (Endolysin) [3.2.1.17] |
| ORF01842 | 3683 & 3684 | Protein of unknown function (DUF1327) superfamily |
| ORF01843 | 3685 & 3686 | Lysis protein S homolog from lambdoid prophage |
| ORF01844 | 3687 & 3688 | unnamed protein product; ORF616 |
| ORF01845 | 3689 & 3690 | unnamed protein product; ORF616 |
| ORF01846 | 3691 & 3692 | DNA adenine-methylase |
| ORF01847 | 3693 & 3694 | unknown protein encoded by prophage CP-933O |
| ORF01848 | 3695 & 3696 | Antitermination protein Q homolog of cryptic prophage |
| ORF01849 | 3697 & 3698 | endodeoxyribonuclease RUS (Holliday junction resolvase) [3.1.22.—] |
| ORF01850 | 3699 & 3700 | Protein of unknown function (DUF1277) superfamily |
| ORF01851 | 3701 & 3702 | prophage maintenance protein [similarity]-related protein |
| ORF01852 | 3703 & 3704 | hypothetical protein |
| ORF01853 | 3705 & 3706 | conserved hypothetical protein |
| ORF01854 | 3707 & 3708 | Unknown protein encoded within prophage |
| ORF01855 | 3709 & 3710 | conserved hypothetical protein |
| ORF01856 | 3711 & 3712 | Unknown protein encoded by cryptic prophage |
| ORF01857 | 3713 & 3714 | Peptidase S24-like domain, putative |

TABLE 1-continued

Annotation of ORF00001 to ORF04995

| ORFnnnnn | SEQ ID NOs | Annotation |
|---|---|---|
| ORF01858 | 3715 & 3716 | Protein of unknown function (DUF1391) family |
| ORF01859 | 3717 & 3718 | ydfB protein-related protein |
| ORF01860 | 3719 & 3720 | conserved hypothetical protein |
| ORF01861 | 3721 & 3722 | hypothetical protein |
| ORF01862 | 3723 & 3724 | Division inhibition protein dicB |
| ORF01863 | 3725 & 3726 | unknown protein encoded by prophage CP-933O-related protein |
| ORF01864 | 3727 & 3728 | Exodeoxyribonuclease VIII (35 kD) [3.1.11.—] |
| ORF01865 | 3729 & 3730 | integrase |
| ORF01866 | 3731 & 3732 | Outer membrane protein W precursor |
| ORF01867 | 3733 & 3734 | yciC |
| ORF01868 | 3735 & 3736 | intracellular septation protein A (ispZ) |
| ORF01869 | 3737 & 3738 | acyl-CoA hydrolase [3.1.2.—] |
| ORF01870 | 3739 & 3740 | TonB protein |
| ORF01871 | 3741 & 3742 | ycil protein |
| ORF01872 | 3743 & 3744 | Putative potassium channel protein |
| ORF01873 | 3745 & 3746 | Cardiolipin synthetase (Cardiolipin synthase) (CLsynthase) [2.7.8.—] |
| ORF01874 | 3747 & 3748 | Protein of unknown function, DUF440 superfamily |
| ORF01875 | 3749 & 3750 | peptide ABC transporter, ATP-binding protein (AA1) |
| ORF01876 | 3751 & 3752 | oligopeptide ABC transporter, ATP-binding protein (AA1) |
| ORF01877 | 3753 & 3754 | oligopeptide ABC transporter, permease protein (AA1) |
| ORF01878 | 3755 & 3756 | Oligopeptide transport system permease protein oppB (AA1) |
| ORF01879 | 3757 & 3758 | Periplasmic oligopeptide-binding protein precursor |
| ORF01880 | 3759 & 3760 | membrane protein, putative |
| ORF01881 | 3761 & 3762 | acetaldehyde dehydrogenase (acetylating) —alcohol dehydrogenase (EC 1.1.1.1) (ACDH) [1.2.1.10] |
| ORF01882 | 3763 & 3764 | Transposase insG for insertion sequence element IS4 |
| ORF01883 | 3765 & 3766 | thymidine kinase [2.7.1.21] |
| ORF01884 | 3767 & 3768 | conserved hypothetical protein |
| ORF01885 | 3769 & 3770 | DNA-binding protein H-NS homolog virR |
| ORF01886 | 3771 & 3772 | UTP-glucose-1-phosphate uridylyltransferase (galU) [2.7.7.9] |
| ORF01887 | 3773 & 3774 | Hnr protein |
| ORF01888 | 3775 & 3776 | drug transporter |
| ORF01889 | 3777 & 3778 | unnamed protein product |
| ORF01890 | 3779 & 3780 | formyltetrahydrofolate deformylase (purU) [3.5.1.10] |
| ORF01891 | 3781 & 3782 | Tpn1330 protein |
| ORF01892 | 3783 & 3784 | respiratory nitrate reductase, gamma subunit (narI) [1.7.99.4] |
| ORF01893 | 3785 & 3786 | Respiratory nitrate reductase 1 delta chain [1.7.99.4] |
| ORF01894 | 3787 & 3788 | nitrate reductase, beta subunit (narH) [1.7.99.4] |
| ORF01895 | 3789 & 3790 | nitrate reductase, alpha subunit [1.7.99.4] |
| ORF01896 | 3791 & 3792 | Nitrite extrusion protein 1 |
| ORF01897 | 3793 & 3794 | Nitrate-nitrite sensor protein narX [2.7.3.—] |
| ORF01898 | 3795 & 3796 | narL |
| ORF01899 | 3797 & 3798 | conserved hypothetical protein |
| ORF01900 | 3799 & 3800 | YchN protein |
| ORF01901 | 3801 & 3802 | Cation transport protein chaC |
| ORF01902 | 3803 & 3804 | Cation transport regulator chaB-related protein |
| ORF01903 | 3805 & 3806 | Calcium-proton antiporter |
| ORF01904 | 3807 & 3808 | conserved hypothetical protein |
| ORF01905 | 3809 & 3810 | 3-deoxy-8-phosphooctulonate synthase (kdsA) [2.5.1.55] |
| ORF01906 | 3811 & 3812 | Protein sirB1 |
| ORF01907 | 3813 & 3814 | Protein sirB1 |
| ORF01908 | 3815 & 3816 | Protein sirB2 |
| ORF01909 | 3817 & 3818 | Protein methyltransferase hemK (hemK) [2.1.1.—] |
| ORF01910 | 3819 & 3820 | peptide chain release factor 1 (prfA) |
| ORF01911 | 3821 & 3822 | glutamyl-tRNA reductase (hemA) [1.2.1.—] |
| ORF01912 | 3823 & 3824 | outer membrane lipoprotein LolB (lolB) |
| ORF01913 | 3825 & 3826 | 4-diphosphocytidyl-2C-methyl-D-erythritol kinase (ispE) [2.7.1.148] |
| ORF01914 | 3827 & 3828 | Ribose-phosphate pyrophosphokinase |
| ORF01915 | 3829 & 3830 | sulfate permease family protein |
| ORF01916 | 3831 & 3832 | conserved hypothetical protein |
| ORF01917 | 3833 & 3834 | peptidyl-tRNA hydrolase (pth) [3.1.1.29] |
| ORF01918 | 3835 & 3836 | GTP-binding protein YchF (ychF) |
| ORF01919 | 3837 & 3838 | Glycerol metabolism operon Regulatory protein |
| ORF01920 | 3839 & 3840 | dihydroxyacetone kinase, DhaK subunit (dhaK) [2.7.1.—] |
| ORF01921 | 3841 & 3842 | dihydroxyacetone kinase, L subunit [2.7.1.—] |
| ORF01922 | 3843 & 3844 | phosphoenolpyruvate-protein phosphotransferase, EI-HPr-EIIA components |
| ORF01923 | 3845 & 3846 | hypothetical protein |
| ORF01924 | 3847 & 3848 | conserved hypothetical protein |
| ORF01925 | 3849 & 3850 | Trehalase [3.2.1.28] |
| ORF01926 | 3851 & 3852 | Periplasmic binding protein family |
| ORF01927 | 3853 & 3854 | Iron (III) |
| ORF01928 | 3855 & 3856 | conserved hypothetical protein |
| ORF01929 | 3857 & 3858 | possible ABC-type iron-siderophore transport system ATP-binding protein (III) |
| ORF01930 | 3859 & 3860 | conserved hypothetical protein |
| ORF01931 | 3861 & 3862 | modD protein (modD) |
| ORF01932 | 3863 & 3864 | Putative outer membrane receptor, probably tonB dependent |

TABLE 1-continued

Annotation of ORF00001 to ORF04995

| ORFnnnnn | SEQ ID NOs | Annotation |
|---|---|---|
| ORF01933 | 3865 & 3866 | Transglycosylase associated protein |
| ORF01934 | 3867 & 3868 | YcgR protein superfamily |
| ORF01935 | 3869 & 3870 | murein transglycosylase E |
| ORF01936 | 3871 & 3872 | Muramoyltetrapeptide carboxypeptidase (LD-carboxypeptidase A) [3.4.17.13] |
| ORF01937 | 3873 & 3874 | Na+-H+ antiporter |
| ORF01938 | 3875 & 3876 | alanine racemase (alr) [5.1.1.1] |
| ORF01939 | 3877 & 3878 | D-amino acid dehydrogenase small subunit |
| ORF01940 | 3879 & 3880 | unidentified protein |
| ORF01941 | 3881 & 3882 | negative regulator for fad regulon, and positive |
| ORF01942 | 3883 & 3884 | Na+-H+ antiporter NhaB (nhaB) |
| ORF01943 | 3885 & 3886 | Disulfide bond formation protein B [1.8.4.—] |
| ORF01944 | 3887 & 3888 | UmuC protein |
| ORF01945 | 3889 & 3890 | UmuD protein (R391) [3.4.21.—] |
| ORF01946 | 3891 & 3892 | cytolysin A |
| ORF01947 | 3893 & 3894 | Bacterial protein of unknown function (DUF838) superfamily |
| ORF01948 | 3895 & 3896 | Protein ycgM (FAA) |
| ORF01949 | 3897 & 3898 | Protein ycgL |
| ORF01950 | 3899 & 3900 | Fels-1 Prophage Protein-like family |
| ORF01951 | 3901 & 3902 | septum site-determining protein MinC (minC) |
| ORF01952 | 3903 & 3904 | Lom |
| ORF01953 | 3905 & 3906 | Putative tail component of prophage (partial) |
| ORF01954 | 3907 & 3908 | Lom |
| ORF01955 | 3909 & 3910 | Putative tail component of prophage (partial) |
| ORF01956 | 3911 & 3912 | hypothetical protein |
| ORF01957 | 3913 & 3914 | GntR-family transcriptional regulator |
| ORF01958 | 3915 & 3916 | conserved hypothetical protein |
| ORF01959 | 3917 & 3918 | fructuronate reductase [1.—.—.—] |
| ORF01960 | 3919 & 3920 | metabolite-proton symporter (PPII) |
| ORF01961 | 3921 & 3922 | L-iditol 2-dehydrogenase |
| ORF01962 | 3923 & 3924 | Starvation sensing protein rspA |
| ORF01963 | 3925 & 3926 | Uncharacterized BCR, YnfA-UPF0060 family superfamily |
| ORF01964 | 3927 & 3928 | Protein of unknown function (DUF1283) superfamily |
| ORF01965 | 3929 & 3930 | Spermidine N(1)-acetyltransferase (SAT) [2.3.1.57] |
| ORF01966 | 3931 & 3932 | ynfC protein |
| ORF01967 | 3933 & 3934 | Protein of unknown function (DUF1161) family |
| ORF01968 | 3935 & 3936 | DmsA [1.8.99.—] |
| ORF01969 | 3937 & 3938 | DmsA [1.8.99.—] |
| ORF01970 | 3939 & 3940 | dimethylsulfoxide reductase chain A2 precursor, anaerobic [1.8.—.—] |
| ORF01971 | 3941 & 3942 | Anaerobic dimethyl sulfoxide reductase chain B (dmsB) [1.8.—.—] |
| ORF01972 | 3943 & 3944 | DMSO reductase anchor subunit (DmsC) (dmsC) [1.8.99.—] |
| ORF01973 | 3945 & 3946 | TorD protein |
| ORF01974 | 3947 & 3948 | dethiobiotin synthetase (DTBS) |
| ORF01975 | 3949 & 3950 | Putative chloride channel protein eriC-like |
| ORF01976 | 3951 & 3952 | Mlc protein |
| ORF01977 | 3953 & 3954 | transcriptional regulator, LysR family |
| ORF01978 | 3955 & 3956 | unnamed protein product |
| ORF01979 | 3957 & 3958 | Acid shock protein repeat family |
| ORF01980 | 3959 & 3960 | glutamyl endopeptidase [3.4.21.—] |
| ORF01981 | 3961 & 3962 | possible chaperone |
| ORF01982 | 3963 & 3964 | DMT Superfamily drug efflux pump |
| ORF01983 | 3965 & 3966 | Domain of unknown function, putative |
| ORF01984 | 3967 & 3968 | NAD(P) transhydrogenase, beta subunit (pntB) [1.6.1.2] |
| ORF01985 | 3969 & 3970 | NAD(P) transhydrogenase, alpha subunit (pntA) [1.6.1.1] |
| ORF01986 | 3971 & 3972 | Protein ydgH precursor |
| ORF01987 | 3973 & 3974 | hypothetical protein |
| ORF01988 | 3975 & 3976 | unnamed protein product |
| ORF01989 | 3977 & 3978 | fabG5, putative [1.—.—.—] |
| ORF01990 | 3979 & 3980 | Membrane protein glpM |
| ORF01991 | 3981 & 3982 | Transcriptional Regulatory protein rstA |
| ORF01992 | 3983 & 3984 | Sensor protein rstB [2.7.3.—] |
| ORF01993 | 3985 & 3986 | DNA replication terminus site-binding protein |
| ORF01994 | 3987 & 3988 | fumarate hydratase, class II (fumC) [4.2.1.2] |
| ORF01995 | 3989 & 3990 | fumarate hydratase class I, anaerobic [4.2.1.2] |
| ORF01996 | 3991 & 3992 | mannose-6-phosphate isomerase, class I (manA) [5.3.1.8] |
| ORF01997 | 3993 & 3994 | Bacterial protein of unknown function (DUF945) superfamily |
| ORF01998 | 3995 & 3996 | membrane-associated protein |
| ORF01999 | 3997 & 3998 | Glucuronide carrier protein |
| ORF02000 | 3999 & 4000 | Beta-glucuronidase (GUS) [3.2.1.31] |
| ORF02001 | 4001 & 4002 | transcriptional regulator, TetR family domain protein, putative |
| ORF02002 | 4003 & 4004 | 7-alpha-hydroxysteroid dehydrogenase |
| ORF02003 | 4005 & 4006 | Maltose regulon Regulatory protein malI |
| ORF02004 | 4007 & 4008 | PTS system, maltose and glucose-specific IIBC component (malX) [2.7.1.69] |
| ORF02005 | 4009 & 4010 | aminotransferase, class II, putative [4.4.1.8] |
| ORF02006 | 4011 & 4012 | adenosine deaminase (add) [3.5.4.4] |
| ORF02007 | 4013 & 4014 | predicted dehydrogenase |
| ORF02008 | 4015 & 4016 | Hha protein |

TABLE 1-continued

Annotation of ORF00001 to ORF04995

| ORFnnnnn | SEQ ID NOs | Annotation |
|---|---|---|
| ORF02009 | 4017 & 4018 | conserved hypothetical protein |
| ORF02010 | 4019 & 4020 | Electron transport complex protein rnfA |
| ORF02011 | 4021 & 4022 | Electron transport complex protein rnfB |
| ORF02012 | 4023 & 4024 | Electron transport complex protein rnfC |
| ORF02013 | 4025 & 4026 | Electron transport complex protein rnfD |
| ORF02014 | 4027 & 4028 | Electron transport complex protein rnfG (rnfG) |
| ORF02015 | 4029 & 4030 | Electron transport complex protein rnfE |
| ORF02016 | 4031 & 4032 | endonuclease III (nth) [4.2.99.18] |
| ORF02017 | 4033 & 4034 | Hypothetical transporter ydgR |
| ORF02018 | 4035 & 4036 | Glutathione S-transferase [2.5.1.18] |
| ORF02019 | 4037 & 4038 | pyridoxal kinase [2.7.1.35] |
| ORF02020 | 4039 & 4040 | tyrosyl-tRNA synthetase (tyrS) [6.1.1.1] |
| ORF02021 | 4041 & 4042 | pyridoxamine 5'-phosphate oxidase (pdxH) [1.4.3.5] |
| ORF02022 | 4043 & 4044 | ydhA protein |
| ORF02023 | 4045 & 4046 | Hypothetical UPF0075 protein ydhH |
| ORF02024 | 4047 & 4048 | SlyA |
| ORF02025 | 4049 & 4050 | Fusaric acid resistance protein FusE. |
| ORF02026 | 4051 & 4052 | Fusaric acid resistance protein conserved region family |
| ORF02027 | 4053 & 4054 | Copper-zinc superoxide dismutase (sodC) |
| ORF02028 | 4055 & 4056 | oxidoreductase, aldo-keto reductase family [1.—.—.—] |
| ORF02029 | 4057 & 4058 | unnamed protein product |
| ORF02030 | 4059 & 4060 | transcriptional regulatory protein |
| ORF02031 | 4061 & 4062 | N-ethylmaleimide reductase (Y13942) [1.—.—.—] |
| ORF02032 | 4063 & 4064 | lactoylglutathione lyase (gloA) [4.4.1.5] |
| ORF02033 | 4065 & 4066 | ribonuclease T (rnt) [3.1.13.—] |
| ORF02034 | 4067 & 4068 | glutaredoxin-related protein |
| ORF02035 | 4069 & 4070 | hypothetical protein |
| ORF02036 | 4071 & 4072 | putative lipoprotein |
| ORF02037 | 4073 & 4074 | superoxide dismutase, iron [1.15.1.1] |
| ORF02038 | 4075 & 4076 | major facilitator family transporter (AL136500) |
| ORF02039 | 4077 & 4078 | hypothetical protein |
| ORF02040 | 4079 & 4080 | Purine nucleotide synthesis repressor (purR) |
| ORF02041 | 4081 & 4082 | cyn operon transcriptional activator. |
| ORF02042 | 4083 & 4084 | Bicyclomycin resistance protein (Sulfonamide resistance protein). |
| ORF02043 | 4085 & 4086 | cyclopropane-fatty-acyl-phospholipid synthase [2.1.1.79] |
| ORF02044 | 4087 & 4088 | riboflavin synthase, alpha subunit (ribE) [2.5.1.9] |
| ORF02045 | 4089 & 4090 | Multidrug resistance protein norM |
| ORF02046 | 4091 & 4092 | possible enzyme |
| ORF02047 | 4093 & 4094 | Protein ydhR precursor |
| ORF02048 | 4095 & 4096 | conserved hypothetical protein |
| ORF02049 | 4097 & 4098 | conserved hypothetical protein |
| ORF02050 | 4099 & 4100 | PhsC protein homolog [2.8.1.5] |
| ORF02051 | 4101 & 4102 | nrfC protein homolog b1671 (nrfC) [2.8.1.5] |
| ORF02052 | 4103 & 4104 | conserved hypothetical protein |
| ORF02053 | 4105 & 4106 | aldehyde-ferredoxin oxidoreductase PH0892 (aor) [1.—.—.—] |
| ORF02054 | 4107 & 4108 | aldehyde oxidoreductase (aor) [1.—.—.—] |
| ORF02055 | 4109 & 4110 | iron-sulfur cluster-binding protein [2.8.1.5] |
| ORF02056 | 4111 & 4112 | conserved hypothetical protein |
| ORF02057 | 4113 & 4114 | pyruvate kinase (pyk) [2.7.1.40] |
| ORF02058 | 4115 & 4116 | major outer membrane lipoprotein |
| ORF02059 | 4117 & 4118 | ErfK-YbiS-YcfS-YnhG family |
| ORF02060 | 4119 & 4120 | SufE protein (orf5) |
| ORF02061 | 4121 & 4122 | aminotransferase, class-V [4.4.1.16] |
| ORF02062 | 4123 & 4124 | FeS assembly protein SufD (sufD) |
| ORF02063 | 4125 & 4126 | FeS assembly ATPase SufC (sufC) |
| ORF02064 | 4127 & 4128 | FeS assembly protein SufB (sufB) |
| ORF02065 | 4129 & 4130 | FeS assembly scaffold SufA (sufA) |
| ORF02066 | 4131 & 4132 | unnamed protein product |
| ORF02067 | 4133 & 4134 | uncharacterized domain 1, putative |
| ORF02068 | 4135 & 4136 | oxidoreductase, FAD-binding, putative |
| ORF02069 | 4137 & 4138 | Hypothetical UPF0118 protein ydiK |
| ORF02070 | 4139 & 4140 | conserved hypothetical protein |
| ORF02071 | 4141 & 4142 | transport system permease protein homolog lin2340 |
| ORF02072 | 4143 & 4144 | Hypothetical transport protein ydiN |
| ORF02073 | 4145 & 4146 | shikimate 5-dehydrogenase [1.1.1.—] |
| ORF02074 | 4147 & 4148 | 3-dehydroquinate dehydratase, type I (aroD) [4.2.1.10] |
| ORF02075 | 4149 & 4150 | acetyl-CoA-transferase subunit, putative [2.8.3.—] |
| ORF02076 | 4151 & 4152 | acyl-CoA dehydrogenase family protein, putative [1.3.99.—] |
| ORF02077 | 4153 & 4154 | Hypothetical transcriptional regulator ydiP |
| ORF02078 | 4155 & 4156 | FixA protein |
| ORF02079 | 4157 & 4158 | electron transfer flavoprotein, alpha subunit, putative |
| ORF02080 | 4159 & 4160 | flavoprotein, probably electron transport [1.5.5.—] |
| ORF02081 | 4161 & 4162 | Ferredoxin-like protein ydiT |
| ORF02082 | 4163 & 4164 | substrate--CoA ligase, putative [6.2.1.—] |
| ORF02083 | 4165 & 4166 | phosphoenolpyruvate synthase (ppsA) [2.7.9.2] |
| ORF02084 | 4167 & 4168 | Hypothetical UPF0085 protein ydiA |

TABLE 1-continued

Annotation of ORF00001 to ORF04995

| ORFnnnnn | SEQ ID NOs | Annotation |
|---|---|---|
| ORF02085 | 4169 & 4170 | phospho-2-dehydro-3-deoxyheptonate aldolase [2.5.1.54] |
| ORF02086 | 4171 & 4172 | conserved hypothetical protein |
| ORF02087 | 4173 & 4174 | Hypothetical UPF0061 protein ydiU (AP001520) |
| ORF02088 | 4175 & 4176 | conserved hypothetical protein |
| ORF02089 | 4177 & 4178 | lipoprotein (ORF) |
| ORF02090 | 4179 & 4180 | Vitamin B12 transport ATP-binding protein btuD (VitaminB12-transporting ATPase) [3.6.3.33] |
| ORF02091 | 4181 & 4182 | Glutathione peroxidase |
| ORF02092 | 4183 & 4184 | Vitamin B12 transport system permease protein btuC (membrane) |
| ORF02093 | 4185 & 4186 | integration host factor, alpha subunit (ihfA) |
| ORF02094 | 4187 & 4188 | phenylalanyl-tRNA synthetase, beta subunit (pheT) [6.1.1.20] |
| ORF02095 | 4189 & 4190 | phenylalanyl-tRNA synthetase, alpha subunit (pheS) [6.1.1.20] |
| ORF02096 | 4191 & 4192 | ribosomal protein L20 (rplT) |
| ORF02097 | 4193 & 4194 | ribosomal protein L35 (rpmI) |
| ORF02098 | 4195 & 4196 | translation initiation factor IF-3 (infC) |
| ORF02099 | 4197 & 4198 | threonyl-tRNA synthetase (thrS) [6.1.1.3] |
| ORF02100 | 4199 & 4200 | InsAB' protein |
| ORF02101 | 4201 & 4202 | InsA protein |
| ORF02102 | 4203 & 4204 | hypothetical protein |
| ORF02103 | 4205 & 4206 | Protein of unknown function, DUF481 superfamily |
| ORF02104 | 4207 & 4208 | pfkB (pfkB) [2.7.1.11] |
| ORF02105 | 4209 & 4210 | conserved hypothetical protein |
| ORF02106 | 4211 & 4212 | Fructosamine kinase subfamily |
| ORF02107 | 4213 & 4214 | conserved hypothetical protein |
| ORF02108 | 4215 & 4216 | Protein yniC (YniC) [3.1.3.18] |
| ORF02109 | 4217 & 4218 | Predicted membrane-bound metal-dependent hydrolase (DUF457) family |
| ORF02110 | 4219 & 4220 | sodium:dicarboxylate symporter family protein |
| ORF02111 | 4221 & 4222 | Cell division activator cedA |
| ORF02112 | 4223 & 4224 | conserved hypothetical protein |
| ORF02113 | 4225 & 4226 | Catalase HPII (III) [1.11.1.6] |
| ORF02114 | 4227 & 4228 | unnamed protein product; ORF 28.5 |
| ORF02115 | 4229 & 4230 | 6-phospho-beta-glucosidase [3.2.1.86] |
| ORF02116 | 4231 & 4232 | Cel operon repressor |
| ORF02117 | 4233 & 4234 | PEP-dependent phosphotransferase enzyme III for cellobiose, arbutin, and salicin (PTS) [2.7.1.69] |
| ORF02118 | 4235 & 4236 | PTS system, cellobiose-specific IIC component (celB) |
| ORF02119 | 4237 & 4238 | PTS system, N,N'-diacetylchitobiose-specific IIB component (EIIB-Chb)(N,N'-diacetylchitobiose-permease IIB component) (Phosphotransferaseenzyme II, B component) [2.7.1.69] |
| ORF02120 | 4239 & 4240 | Osmotically inducible lipoprotein E precursor |
| ORF02121 | 4241 & 4242 | NAD+ synthetase (nadE) [6.3.1.5] |
| ORF02122 | 4243 & 4244 | Bacterial protein of unknown function (DUF886) superfamily |
| ORF02123 | 4245 & 4246 | excinuclease ABC subunit C homolog |
| ORF02124 | 4247 & 4248 | Spheroplast protein Y precursor |
| ORF02125 | 4249 & 4250 | conserved hypothetical protein |
| ORF02126 | 4251 & 4252 | Succinylglutamate desuccinylase [3.1.—.—] |
| ORF02127 | 4253 & 4254 | Succinylarginine dihydrolase (astB) |
| ORF02128 | 4255 & 4256 | Succinate semialdehyde dehydrogenase (EC 1.2.1.24) (NAD(+)-dependent succinic semialdehyde dehydrogenase). (retinol) [1.2.1.24] |
| ORF02129 | 4257 & 4258 | Arginine N-succinyltransferase beta subunit (astA) [2.3.1.109] |
| ORF02130 | 4259 & 4260 | Succinylornithine transaminase (Succinylornithineaminotransferase) (ACOAT) [2.6.1.—] |
| ORF02131 | 4261 & 4262 | exodeoxyribonuclease III (xth) [3.1.11.2] |
| ORF02132 | 4263 & 4264 | membrane protein, probable, putative |
| ORF02133 | 4265 & 4266 | conserved hypothetical protein |
| ORF02134 | 4267 & 4268 | DedA family family |
| ORF02135 | 4269 & 4270 | IS110 family transposase, truncation, putative |
| ORF02136 | 4271 & 4272 | Protein ynjB |
| ORF02137 | 4273 & 4274 | Hypothetical ABC transporter permease protein ynjC |
| ORF02138 | 4275 & 4276 | Inner membrane protein Malk (P-loop) |
| ORF02139 | 4277 & 4278 | 2.8.1.1 [2.8.1.1] |
| ORF02140 | 4279 & 4280 | phosphatidylglycerophosphate synthase |
| ORF02141 | 4281 & 4282 | Protein of unknown function (DUF1496) superfamily |
| ORF02142 | 4283 & 4284 | mutT2 [3.6.1.—] |
| ORF02143 | 4285 & 4286 | NADP-specific glutamate dehydrogenase (NADP-GDH) [1.4.1.4] |
| ORF02144 | 4287 & 4288 | DNA topoisomerase III |
| ORF02145 | 4289 & 4290 | selenide, water dikinase (selD) [2.7.9.3] |
| ORF02146 | 4291 & 4292 | Protein ydjA |
| ORF02147 | 4293 & 4294 | hypothetical protein |
| ORF02148 | 4295 & 4296 | signal peptide peptidase SppA, 67K type (sppA) [3.4.—.—] |
| ORF02149 | 4297 & 4298 | L-asparaginase (ansA) [3.5.1.1] |
| ORF02150 | 4299 & 4300 | Pyrazinamidase-nicotinamidase (PZASE) [3.5.1.—] |
| ORF02151 | 4301 & 4302 | putative transport protein |
| ORF02152 | 4303 & 4304 | similar to transcription regulator DeoR family |
| ORF02153 | 4305 & 4306 | aldo-keto reductase Atu3877 (gsp69) [1.—.—.—] |
| ORF02154 | 4307 & 4308 | putative kinase |

TABLE 1-continued

Annotation of ORF00001 to ORF04995

| ORFnnnnn | SEQ ID NOs | Annotation |
|---|---|---|
| ORF02155 | 4309 & 4310 | Fructose-tagatose bisphosphate aldolase [4.1.2.—] |
| ORF02156 | 4311 & 4312 | Sorbitol dehydrogenase (EC 1.1.1.14) (L-iditol 2-dehydrogenase). (sorbitol) [1.1.1.14] |
| ORF02157 | 4313 & 4314 | Membrane transporter D1. |
| ORF02158 | 4315 & 4316 | sorbitol dehydrogenase, putative [1.1.1.—] |
| ORF02159 | 4317 & 4318 | Protein of unknown function (DUF1315) superfamily |
| ORF02160 | 4319 & 4320 | methionine-R-sulfoxide reductase (msrB) [1.8.4.6] |
| ORF02161 | 4321 & 4322 | glyceraldehyde-3-phosphate dehydrogenase, type I (gap) [1.2.1.—] |
| ORF02162 | 4323 & 4324 | transglycolase (fragment) |
| ORF02163 | 4325 & 4326 | Morphine 6-dehydrogenase (EC 1.1.1.218) (Naloxone reductase). (PA0804) [1.1.1.—] |
| ORF02164 | 4327 & 4328 | MltA-interacting protein precursor |
| ORF02165 | 4329 & 4330 | hypothetical protein |
| ORF02166 | 4331 & 4332 | protein kinase |
| ORF02167 | 4333 & 4334 | Hypothetical UPF0229 protein yeaH |
| ORF02168 | 4335 & 4336 | GGDEF domain protein |
| ORF02169 | 4337 & 4338 | GGDEF domain protein |
| ORF02170 | 4339 & 4340 | unnamed protein product |
| ORF02171 | 4341 & 4342 | transcriptional regulator araC family |
| ORF02172 | 4343 & 4344 | Protein of unknown function (DUF441) superfamily |
| ORF02173 | 4345 & 4346 | cyanate MFS transporter (permease) |
| ORF02174 | 4347 & 4348 | Protein of unknown function, DUF488 superfamily |
| ORF02175 | 4349 & 4350 | hemolysin VCA0594 |
| ORF02176 | 4351 & 4352 | GGDEF domain protein |
| ORF02177 | 4353 & 4354 | hypothetical protein |
| ORF02178 | 4355 & 4356 | Transglycosylase associated protein |
| ORF02179 | 4357 & 4358 | conserved hypothetical protein |
| ORF02180 | 4359 & 4360 | tellurite resistance protein TehB, putative |
| ORF02181 | 4361 & 4362 | hypothetical protein |
| ORF02182 | 4363 & 4364 | translocator protein, LysE family superfamily |
| ORF02183 | 4365 & 4366 | conserved hypothetical protein |
| ORF02184 | 4367 & 4368 | tartrate dehydrogenase (3-IPM-DH) [1.1.1.93] |
| ORF02185 | 4369 & 4370 | ribonuclease D (rnd) [3.1.26.3] |
| ORF02186 | 4371 & 4372 | Long-chain-fatty-acid--CoA ligase |
| ORF02187 | 4373 & 4374 | outer membrane lipoprotein |
| ORF02188 | 4375 & 4376 | Hypothetical M22 peptidase homolog yeaZ [3.4.24.57] |
| ORF02189 | 4377 & 4378 | unnamed protein product |
| ORF02190 | 4379 & 4380 | Endoribonuclease L-PSP superfamily |
| ORF02191 | 4381 & 4382 | conserved hypothetical protein |
| ORF02192 | 4383 & 4384 | Hypothetical UPF0181 protein yoaH-related protein |
| ORF02193 | 4385 & 4386 | Para-aminobenzoate synthase component I [6.3.5.8] |
| ORF02194 | 4387 & 4388 | MutT-family protein |
| ORF02195 | 4389 & 4390 | L-serine ammonia-lyase (sdaA) [4.3.1.17] |
| ORF02196 | 4391 & 4392 | EAL domain protein |
| ORF02197 | 4393 & 4394 | possible CorC-HlyC family of Mg+2-Co+2-heavy metal efflux pumps |
| ORF02198 | 4395 & 4396 | PTS enzyme IIAB, mannose-specific (EIII-MAN) |
| ORF02199 | 4397 & 4398 | PTS system, mannose-specific IIC component |
| ORF02200 | 4399 & 4400 | PTS system, mannose-specific IID component |
| ORF02201 | 4401 & 4402 | Hypothetical UPF0266 protein yobD |
| ORF02202 | 4403 & 4404 | Domain of unknown function DUF family |
| ORF02203 | 4405 & 4406 | 23S rRNA m1G745 methyltransferase, putative [2.1.1.51] |
| ORF02204 | 4407 & 4408 | Cold shock-like protein cspE |
| ORF02205 | 4409 & 4410 | conserved hypothetical protein |
| ORF02206 | 4411 & 4412 | lipoprotein, putative |
| ORF02207 | 4413 & 4414 | conserved hypothetical protein |
| ORF02208 | 4415 & 4416 | Transcriptional regulator kdgR |
| ORF02209 | 4417 & 4418 | MULTIDRUG RESISTANCE PROTEIN B |
| ORF02210 | 4419 & 4420 | heat shock protein, integral membrane protein (htpX) [3.4.24.—] |
| ORF02211 | 4421 & 4422 | Tail-specific protease precursor [3.4.21.102] |
| ORF02212 | 4423 & 4424 | carboxy-terminal protease for penicillin-binding protein 3 |
| ORF02213 | 4425 & 4426 | ProP effector |
| ORF02214 | 4427 & 4428 | GAF domain protein |
| ORF02215 | 4429 & 4430 | PqiA protein |
| ORF02216 | 4431 & 4432 | PqiA protein |
| ORF02217 | 4433 & 4434 | mce related protein family |
| ORF02218 | 4435 & 4436 | Sun-nucleolar protein family protein |
| ORF02219 | 4437 & 4438 | Protein of unknown function (DUF1480) superfamily |
| ORF02220 | 4439 & 4440 | Protein of unknown function (DUF1482) family |
| ORF02221 | 4441 & 4442 | Serine-threonine protein phosphatase 1 |
| ORF02222 | 4443 & 4444 | conserved hypothetical protein |
| ORF02223 | 4445 & 4446 | unnamed protein product |
| ORF02224 | 4447 & 4448 | Copper resistance protein D family, putative |
| ORF02225 | 4449 & 4450 | Protein yobA precursor |
| ORF02226 | 4451 & 4452 | DNA polymerase III, theta subunit [2.7.7.7] |
| ORF02227 | 4453 & 4454 | hydrolase, carbon-nitrogen family family |
| ORF02228 | 4455 & 4456 | DNA polymerase III, alpha subunit, Gram-positive type, putative |
| ORF02229 | 4457 & 4458 | protease II (AB004795) [3.4.21.83] |

TABLE 1-continued

Annotation of ORF00001 to ORF04995

| ORFnnnnn | SEQ ID NOs | Annotation |
|---|---|---|
| ORF02230 | 4459 & 4460 | unidentified reading frame |
| ORF02231 | 4461 & 4462 | unnamed protein product; Similar to lipoprotein YebF precursor of *Escherichia coli* |
| ORF02232 | 4463 & 4464 | hypothetical protein |
| ORF02233 | 4465 & 4466 | DNA damage-inducible gene in SOS regulon, dependent on cyclic AMP and H-NS |
| ORF02234 | 4467 & 4468 | phosphoribosylglycinamide formyltransferase 2 (purT) [2.1.2.—] |
| ORF02235 | 4469 & 4470 | 2-deydro-3-deoxyphosphogluconate aldolase-4-hydroxy-2-oxoglutarate aldolase (eda) [4.1.3.16] |
| ORF02236 | 4471 & 4472 | phoshogluconate dehydratase (edd) [4.2.1.12] |
| ORF02237 | 4473 & 4474 | glucose-6-phosphate 1-dehydrogenase (zwf) [1.1.1.49] |
| ORF02238 | 4475 & 4476 | conserved hypothetical protein |
| ORF02239 | 4477 & 4478 | Hex regulon repressor |
| ORF02240 | 4479 & 4480 | pyruvate kinase (pyk) [2.7.1.40] |
| ORF02241 | 4481 & 4482 | lipid A biosynthesis (KDO)2-(lauroyl)-lipid IVA acyltransferase (msbB) [2.3.1.—] |
| ORF02242 | 4483 & 4484 | Cell envelope |
| ORF02243 | 4485 & 4486 | High-affinity zinc uptake system protein znuA precursor (AE005408) |
| ORF02244 | 4487 & 4488 | ABC superfamily high affinity Zn transport protein (atp_bind) |
| ORF02245 | 4489 & 4490 | High-affinity zinc uptake system membrane protein znuB (atp_bind) |
| ORF02246 | 4491 & 4492 | Holliday junction DNA helicase RuvB (ruvB) |
| ORF02247 | 4493 & 4494 | Holliday junction DNA helicase RuvA (ruvA) |
| ORF02248 | 4495 & 4496 | Protein of unknown function (DUF1105) superfamily |
| ORF02249 | 4497 & 4498 | crossover junction endodeoxyribonuclease RuvC (ruvC) [3.1.22.4] |
| ORF02250 | 4499 & 4500 | conserved hypothetical protein TIGR01033 |
| ORF02251 | 4501 & 4502 | dATP pyrophosphohydrolase |
| ORF02252 | 4503 & 4504 | aspartyl-tRNA synthetase (aspS) [6.1.1.12] |
| ORF02253 | 4505 & 4506 | Hypothetical isochorismatase family protein yecD |
| ORF02254 | 4507 & 4508 | Protein of unknown function superfamily |
| ORF02255 | 4509 & 4510 | conserved hypothetical protein |
| ORF02256 | 4511 & 4512 | methyltransferase, putative |
| ORF02257 | 4513 & 4514 | methyltransferase, putative |
| ORF02258 | 4515 & 4516 | Trimethylamine-N-oxide reductase 2 precursor |
| ORF02259 | 4517 & 4518 | Cytochrome c-type protein torY |
| ORF02260 | 4519 & 4520 | copper homeostasis protein VC0730 |
| ORF02261 | 4521 & 4522 | Protein yecM |
| ORF02262 | 4523 & 4524 | arginyl-tRNA synthetase (argS) [6.1.1.19] |
| ORF02263 | 4525 & 4526 | Flagellar protein flhE precursor |
| ORF02264 | 4527 & 4528 | flagellar biosynthesis protein FlhA (flhA) |
| ORF02265 | 4529 & 4530 | flagellar biosynthetic protein FlhB (flhB) |
| ORF02266 | 4531 & 4532 | conserved hypothetical protein |
| ORF02267 | 4533 & 4534 | Chemotaxis protein cheZ |
| ORF02268 | 4535 & 4536 | Chemotaxis protein cheY |
| ORF02269 | 4537 & 4538 | Chemotaxis response regulator protein-glutamate methylesterase(EC 3.1.1.61) [3.1.1.61] |
| ORF02270 | 4539 & 4540 | Chemotaxis protein methyltransferase [2.1.1.80] |
| ORF02271 | 4541 & 4542 | methyl-accepting chemotaxis protein IV, peptide sensor receptor |
| ORF02272 | 4543 & 4544 | conserved hypothetical protein |
| ORF02273 | 4545 & 4546 | Methyl-accepting chemotaxis protein II |
| ORF02274 | 4547 & 4548 | Chemotaxis protein cheW |
| ORF02275 | 4549 & 4550 | Chemotaxis protein cheA |
| ORF02276 | 4551 & 4552 | Chemotaxis motB protein |
| ORF02277 | 4553 & 4554 | Chemotaxis motA protein |
| ORF02278 | 4555 & 4556 | Flagellar transcriptional activator flhC |
| ORF02279 | 4557 & 4558 | regulator of flagellar biosynthesis, acting on class 2 operons; transcriptional initiation factor |
| ORF02280 | 4559 & 4560 | Universal stress protein C (UspA) |
| ORF02281 | 4561 & 4562 | alpha,alpha-trehalose-phosphate synthase [UDP-forming] (otsA) [2.4.1.15] |
| ORF02282 | 4563 & 4564 | trehalose-phosphatase (otsB) [3.1.3.12] |
| ORF02283 | 4565 & 4566 | L-arabinose transport system permease protein araH |
| ORF02284 | 4567 & 4568 | L-arabinose transport ATP-binding protein araG |
| ORF02285 | 4569 & 4570 | L-arabinose-binding periplasmic protein precursor (PBP) |
| ORF02286 | 4571 & 4572 | Ferritin-like protein 2 |
| ORF02287 | 4573 & 4574 | conserved hypothetical protein |
| ORF02288 | 4575 & 4576 | lipoprotein, putative |
| ORF02289 | 4577 & 4578 | conserved hypothetical protein |
| ORF02290 | 4579 & 4580 | cytoplasmic ferritin (an iron storage protein) |
| ORF02291 | 4581 & 4582 | conserved hypothetical protein |
| ORF02292 | 4583 & 4584 | Tyrosine-specific transport protein |
| ORF02293 | 4585 & 4586 | preprotein translocase, SecA subunit |
| ORF02294 | 4587 & 4588 | conserved hypothetical protein |
| ORF02295 | 4589 & 4590 | Fels-2 prophage: similar to retron in E |
| ORF02296 | 4591 & 4592 | ParA |
| ORF02297 | 4593 & 4594 | Sb32 |
| ORF02298 | 4595 & 4596 | hypothetical protein |
| ORF02299 | 4597 & 4598 | phage portal protein, PBSX family |
| ORF02300 | 4599 & 4600 | Putative ATPase subunit of terminase (gpP-like) |
| ORF02301 | 4601 & 4602 | Phage capsid scaffolding protein (GPO) |
| ORF02302 | 4603 & 4604 | phage major capsid protein, P2 family |

TABLE 1-continued

Annotation of ORF00001 to ORF04995

| ORFnnnnn | SEQ ID NOs | Annotation |
|---|---|---|
| ORF02303 | 4605 & 4606 | Phage small terminase subunit |
| ORF02304 | 4607 & 4608 | head completion-stabilization protein L |
| ORF02305 | 4609 & 4610 | Phage Tail Protein X |
| ORF02306 | 4611 & 4612 | Bbp2 |
| ORF02307 | 4613 & 4614 | conserved hypothetical protein |
| ORF02308 | 4615 & 4616 | phage tail completion protein R |
| ORF02309 | 4617 & 4618 | Fels-2 prophage: similar to gpS for completion |
| ORF02310 | 4619 & 4620 | baseplate assembly protein V (gpV) |
| ORF02311 | 4621 & 4622 | phage baseplate assembly protein W (gpW) |
| ORF02312 | 4623 & 4624 | Baseplate J-like protein |
| ORF02313 | 4625 & 4626 | gpI (gpI) |
| ORF02314 | 4627 & 4628 | gpH (gpH) |
| ORF02315 | 4629 & 4630 | gpU prime (gpG) |
| ORF02316 | 4631 & 4632 | CDP-diacylglycerol--glycerol-3-phosphate 3-phosphatidyltransferase (pgsA) [2.7.8.5] |
| ORF02317 | 4633 & 4634 | excinuclease ABC, C subunit (uvrC) |
| ORF02318 | 4635 & 4636 | response regulator protein |
| ORF02319 | 4637 & 4638 | conserved hypothetical protein |
| ORF02320 | 4639 & 4640 | Regulatory protein sdiA |
| ORF02321 | 4641 & 4642 | amino acid ABC transporter, ATP-binding protein |
| ORF02322 | 4643 & 4644 | amino acid ABC transporter, permease protein (permease) |
| ORF02323 | 4645 & 4646 | 4.4.1.15 [3.5.99.7] |
| ORF02324 | 4647 & 4648 | Cystine-binding periplasmic protein precursor |
| ORF02325 | 4649 & 4650 | FliZ protein |
| ORF02326 | 4651 & 4652 | transcription initiation factor alternative sigma factor 28 (Sigma) |
| ORF02327 | 4653 & 4654 | FliC |
| ORF02328 | 4655 & 4656 | Flagellar hook-associated protein 2 (HAP2) |
| ORF02329 | 4657 & 4658 | flagellar protein FliS (fliS) |
| ORF02330 | 4659 & 4660 | flagellar protein FliT |
| ORF02331 | 4661 & 4662 | Cytoplasmic alpha-amylase [3.2.1.1] |
| ORF02332 | 4663 & 4664 | Hypothetical lipoprotein yedD precursor |
| ORF02333 | 4665 & 4666 | YeeE-YedE family protein family |
| ORF02334 | 4667 & 4668 | Hypothetical UPF0033 protein yedF-related protein |
| ORF02335 | 4669 & 4670 | Uncharacterized ACR, COG2135 superfamily |
| ORF02336 | 4671 & 4672 | Outer membrane porin protein nmpC precursor |
| ORF02337 | 4673 & 4674 | Hypothetical transcriptional regulator ybcM |
| ORF02338 | 4675 & 4676 | conserved hypothetical protein |
| ORF02339 | 4677 & 4678 | EmrE protein |
| ORF02340 | 4679 & 4680 | flagellar hook-basal body complex protein (FliE) (fliE) |
| ORF02341 | 4681 & 4682 | flagellar M-ring protein FliF (fliF) |
| ORF02342 | 4683 & 4684 | flagellar motor switch protein FliG (fliG) |
| ORF02343 | 4685 & 4686 | Flagellar assembly protein FliH (fliH) |
| ORF02344 | 4687 & 4688 | flagellum-specific ATP synthase |
| ORF02345 | 4689 & 4690 | flagellar export protein FliJ (fliJ) |
| ORF02346 | 4691 & 4692 | flagellar hook-length control protein |
| ORF02347 | 4693 & 4694 | Flagellar basal body-associated protein FliL (fliL) |
| ORF02348 | 4695 & 4696 | flagellar motor switch protein FliM (fliM) |
| ORF02349 | 4697 & 4698 | Flagellar motor switch protein fliN |
| ORF02350 | 4699 & 4700 | Flagellar protein fliO |
| ORF02351 | 4701 & 4702 | Unknown protein encoded by cryptic prophage |
| ORF02352 | 4703 & 4704 | Helix-turn-helix domain protein |
| ORF02353 | 4705 & 4706 | stability determinant |
| ORF02354 | 4707 & 4708 | unknown protein encoded by prophage CP-933N-related protein |
| ORF02355 | 4709 & 4710 | Division inhibition protein dicB |
| ORF02356 | 4711 & 4712 | conserved hypothetical protein |
| ORF02357 | 4713 & 4714 | Exodeoxyribonuclease VIII (35 kD) [3.1.11.—] |
| ORF02358 | 4715 & 4716 | conserved hypothetical protein |
| ORF02359 | 4717 & 4718 | Sb28 (AE005423) |
| ORF02360 | 4719 & 4720 | Protein of unknown function (DUF980) superfamily |
| ORF02361 | 4721 & 4722 | hypothetical protein |
| ORF02362 | 4723 & 4724 | integrase |
| ORF02363 | 4725 & 4726 | trpE2 |
| ORF02364 | 4727 & 4728 | Putative cytoplasmic transmembrane protein |
| ORF02365 | 4729 & 4730 | ABC transporter, ATP-binding-permease protein, putative |
| ORF02366 | 4731 & 4732 | EF0101 |
| ORF02367 | 4733 & 4734 | hypothetical protein |
| ORF02368 | 4735 & 4736 | Putataive AraC type regulator |
| ORF02369 | 4737 & 4738 | dihydroaeruginoic acid synthetase |
| ORF02370 | 4739 & 4740 | yersiniabactin biosynthetic protein |
| ORF02371 | 4741 & 4742 | yersiniabactin biosynthetic protein YbtU |
| ORF02372 | 4743 & 4744 | yersiniabactin biosynthetic protein YbtT |
| ORF02373 | 4745 & 4746 | mbtA [6.2.1.—] |
| ORF02374 | 4747 & 4748 | OMR family pesticin-yersiniabactin receptor protein (IRPC) |
| ORF02375 | 4749 & 4750 | conserved hypothetical protein |
| ORF02376 | 4751 & 4752 | putative factor |
| ORF02377 | 4753 & 4754 | putative factor |

TABLE 1-continued

Annotation of ORF00001 to ORF04995

| ORFnnnnn | SEQ ID NOs | Annotation |
|---|---|---|
| ORF02378 | 4755 & 4756 | conserved hypothetical protein |
| ORF02379 | 4757 & 4758 | major facilitator family transporter (PPII) |
| ORF02380 | 4759 & 4760 | AMP nucleosidase (amn) [3.2.2.4] |
| ORF02381 | 4761 & 4762 | Domain of unknown function, putative |
| ORF02382 | 4763 & 4764 | MelD protein |
| ORF02383 | 4765 & 4766 | amidase family protein, putative |
| ORF02384 | 4767 & 4768 | MATE efflux family protein subfamily |
| ORF02385 | 4769 & 4770 | Putative peptide synthetase |
| ORF02386 | 4771 & 4772 | NosB (AF183408) |
| ORF02387 | 4773 & 4774 | fmtA-like protein, putative |
| ORF02388 | 4775 & 4776 | thioesterase |
| ORF02389 | 4777 & 4778 | Prophage P4 integrase |
| ORF02390 | 4779 & 4780 | hypothetical protein |
| ORF02391 | 4781 & 4782 | MATE efflux family protein subfamily |
| ORF02392 | 4783 & 4784 | TubD protein [6.3.2.—] |
| ORF02393 | 4785 & 4786 | BarG |
| ORF02394 | 4787 & 4788 | NosB |
| ORF02395 | 4789 & 4790 | AMP-binding enzyme domain protein |
| ORF02396 | 4791 & 4792 | [acyl-carrier-protein] S-malonyltransferase [2.3.1.39] |
| ORF02397 | 4793 & 4794 | Putative acyl-coa dehydrogenase |
| ORF02398 | 4795 & 4796 | acyl carrier protein |
| ORF02399 | 4797 & 4798 | 3-hydroxyacyl CoA dehydrogenase (BHBD) [1.1.1.157] |
| ORF02400 | 4799 & 4800 | JamP |
| ORF02401 | 4801 & 4802 | oxidoreductase, zinc-binding dehydrogenase family family |
| ORF02402 | 4803 & 4804 | possible DNA-binding response regulator |
| ORF02403 | 4805 & 4806 | EntD-Gsp-HetI-Sfp family protein [2.7.8.—] |
| ORF02404 | 4807 & 4808 | transposase |
| ORF02405 | 4809 & 4810 | ISSo2, transposase OrfB, truncation |
| ORF02406 | 4811 & 4812 | Protein erfK-srfK precursor |
| ORF02407 | 4813 & 4814 | Nicotinate-nucleotide--dimethylbenzimidazole phosphoribosyltransferase(EC 2.4.2.21) (NN:DBI PRT) (N(1)-alpha-phosphoribosyltransferase) [2.4.2.21] |
| ORF02408 | 4815 & 4816 | cobalamin 5'-phosphate synthase (cobS) [2.7.8.26] |
| ORF02409 | 4817 & 4818 | Cobalamin biosynthesis protein cobU [2.7.1.156] |
| ORF02410 | 4819 & 4820 | conserved hypothetical protein |
| ORF02411 | 4821 & 4822 | conserved hypothetical protein |
| ORF02412 | 4823 & 4824 | TonB dependent receptor, putative |
| ORF02413 | 4825 & 4826 | conserved hypothetical protein |
| ORF02414 | 4827 & 4828 | Z1204 protein |
| ORF02415 | 4829 & 4830 | conserved hypothetical protein |
| ORF02416 | 4831 & 4832 | glucosaminyltransferase |
| ORF02417 | 4833 & 4834 | Sugar phosphate nucleotydyl transferase |
| ORF02418 | 4835 & 4836 | conserved hypothetical protein |
| ORF02419 | 4837 & 4838 | host specificity protein J, truncation, putative |
| ORF02420 | 4839 & 4840 | host specificity protein (partial) |
| ORF02421 | 4841 & 4842 | host specificity protein (partial) |
| ORF02422 | 4843 & 4844 | Terminase small subunit (GP1) (fragment) |
| ORF02423 | 4845 & 4846 | conserved hypothetical protein |
| ORF02424 | 4847 & 4848 | Partial tonB-like membrane protein encoded within prophage |
| ORF02425 | 4849 & 4850 | hypothetical protein |
| ORF02426 | 4851 & 4852 | Bor protein homolog from lambdoid prophage DLP12 |
| ORF02427 | 4853 & 4854 | Bacteriophage lysis protein |
| ORF02428 | 4855 & 4856 | lipoprotein Rz1 precursor-related protein |
| ORF02429 | 4857 & 4858 | hypothetical protein |
| ORF02430 | 4859 & 4860 | Lysozyme (Lysis protein) (Muramidase) (Endolysin) (lysozyme) [3.2.1.17] |
| ORF02431 | 4861 & 4862 | lysis protein S.b1556 |
| ORF02432 | 4863 & 4864 | hypothetical protein |
| ORF02433 | 4865 & 4866 | Outer membrane porin protein nmpC precursor (lbc) |
| ORF02434 | 4867 & 4868 | Antitermination protein Q homolog from lambdoid prophage |
| ORF02435 | 4869 & 4870 | endodeoxyribonuclease RUS (Holliday junction resolvase) |
| ORF02436 | 4871 & 4872 | Protein ninE-related protein |
| ORF02437 | 4873 & 4874 | phage N-6-adenine-methyltransferase [2.1.1.72] |
| ORF02438 | 4875 & 4876 | Protein ninB |
| ORF02439 | 4877 & 4878 | replication protein P |
| ORF02440 | 4879 & 4880 | transposase |
| ORF02441 | 4881 & 4882 | ECs1339 |
| ORF02442 | 4883 & 4884 | ribokinase |
| ORF02443 | 4885 & 4886 | Protein of unknown function (DUF1355) superfamily |
| ORF02444 | 4887 & 4888 | membrane protein, putative |
| ORF02445 | 4889 & 4890 | puative phophotriesterase (PTE) [3.1.8.1] |
| ORF02446 | 4891 & 4892 | gamma-glutamyltranspeptidase |
| ORF02447 | 4893 & 4894 | gamma-glutamyltranspeptidase |
| ORF02448 | 4895 & 4896 | ST55 protein |
| ORF02449 | 4897 & 4898 | conserved hypothetical protein |
| ORF02450 | 4899 & 4900 | conserved hypothetical protein |
| ORF02451 | 4901 & 4902 | ISBma3, transposase, truncation |
| ORF02452 | 4903 & 4904 | Prophage CP4-57 regulatory protein (AlpA) family |

TABLE 1-continued

Annotation of ORF00001 to ORF04995

| ORFnnnnn | SEQ ID NOs | Annotation |
|---|---|---|
| ORF02453 | 4905 & 4906 | hypothetical protein |
| ORF02454 | 4907 & 4908 | conserved hypothetical protein |
| ORF02455 | 4909 & 4910 | hypothetical protein |
| ORF02456 | 4911 & 4912 | Insertion sequence ATP-binding protein |
| ORF02457 | 4913 & 4914 | Transposase |
| ORF02458 | 4915 & 4916 | conserved hypothetical protein |
| ORF02459 | 4917 & 4918 | ferric-enterobactin-transport protein (III) |
| ORF02460 | 4919 & 4920 | ABC transporter permease STY0802 (FecCD_family) |
| ORF02461 | 4921 & 4922 | Periplasmic binding protein (III) |
| ORF02462 | 4923 & 4924 | TonB dependent receptor |
| ORF02463 | 4925 & 4926 | YeeP protein |
| ORF02464 | 4927 & 4928 | conserved hypothetical protein |
| ORF02465 | 4929 & 4930 | conserved hypothetical protein |
| ORF02466 | 4931 & 4932 | conserved hypothetical protein |
| ORF02467 | 4933 & 4934 | Patatin-like phospholipase family |
| ORF02468 | 4935 & 4936 | conserved hypothetical protein |
| ORF02469 | 4937 & 4938 | conserved hypothetical protein |
| ORF02470 | 4939 & 4940 | conserved hypothetical protein |
| ORF02471 | 4941 & 4942 | Z1215 protein (o273) |
| ORF02472 | 4943 & 4944 | Antirestriction protein family |
| ORF02473 | 4945 & 4946 | YeeS protein (o160) |
| ORF02474 | 4947 & 4948 | Protein of unknown function (DUF987) superfamily |
| ORF02475 | 4949 & 4950 | YeeU protein |
| ORF02476 | 4951 & 4952 | L0007-like protein |
| ORF02477 | 4953 & 4954 | YeeW protein |
| ORF02478 | 4955 & 4956 | Protein of unknown function (DUF496) superfamily |
| ORF02479 | 4957 & 4958 | conserved hypothetical protein |
| ORF02480 | 4959 & 4960 | DNA gyrase inhibitory protein |
| ORF02481 | 4961 & 4962 | Penicillin-binding protein 6B precursor (PBP) |
| ORF02482 | 4963 & 4964 | penicillin binding protein 6b |
| ORF02483 | 4965 & 4966 | Exodeoxyribonuclease I |
| ORF02484 | 4967 & 4968 | amino acid permease |
| ORF02485 | 4969 & 4970 | transcriptional regulator, LysR family |
| ORF02486 | 4971 & 4972 | Protein yeeZ precursor |
| ORF02487 | 4973 & 4974 | addiction module toxin, Txe-YoeB family |
| ORF02488 | 4975 & 4976 | yefM protein |
| ORF02489 | 4977 & 4978 | ATP phosphoribosyltransferase (hisG) [2.4.2.17] |
| ORF02490 | 4979 & 4980 | histidinol dehydrogenase (hisD) [1.1.1.23] |
| ORF02491 | 4981 & 4982 | histidinol-phosphate aminotransferase (hisC) [2.6.1.9] |
| ORF02492 | 4983 & 4984 | Histidine biosynthesis bifunctional protein hisB |
| ORF02493 | 4985 & 4986 | Imidazole glycerol phosphate synthase subunit hisH (IGPsynthase glutamine amidotransferase subunit) (IGP synthase subunithisH) (ImGP synthase subunit hisH) (IGPS subunit hisH) [2.4.2.—] |
| ORF02494 | 4987 & 4988 | imidazole glycerol phosphate synthase, glutamine amidotransferase subunit (hisH) [2.4.2.—] |
| ORF02495 | 4989 & 4990 | phosphoribosylformimino-5-aminoimidazole carboxamide ribotide isomerase (hisA) [5.3.1.16] |
| ORF02496 | 4991 & 4992 | imidazoleglycerol phosphate synthase, cyclase subunit (hisF) |
| ORF02497 | 4993 & 4994 | Histidine biosynthesis bifunctional protein hislE [Includes: Phosphoribosyl-AMP cyclohydrolase (PRA-CH); Phosphoribosyl-ATP pyrophosphatase (EC 3.6.1.31) (PRA-PH)] (PRA-PH) [3.5.4.19] |
| ORF02498 | 4995 & 4996 | Chain length determinant protein |
| ORF02499 | 4997 & 4998 | UDP-glucose 6-dehydrogenase (UDPGDH) [1.1.1.22] |
| ORF02500 | 4999 & 5000 | 6-phosphogluconate dehydrogenase, decarboxylating (gnd) [1.1.1.44] |
| ORF02501 | 5001 & 5002 | WbnE [2.4.1.—] |
| ORF02502 | 5003 & 5004 | putative glycosyltransferase [2.4.1.—] |
| ORF02503 | 5005 & 5006 | glycosyl transferase CpsO |
| ORF02504 | 5007 & 5008 | rhamnosyl transferase Cps6bS |
| ORF02505 | 5009 & 5010 | O-antigen modification protein |
| ORF02506 | 5011 & 5012 | rfbX protein |
| ORF02507 | 5013 & 5014 | dTDP-4-dehydrorhamnose 3,5-epimerase (rfbC) [5.1.3.13] |
| ORF02508 | 5015 & 5016 | glucose-1-phosphate thymidylyltransferase (rfbA) [2.7.7.24] |
| ORF02509 | 5017 & 5018 | dTDP-4-dehydrorhamnose reductase (rfbD) [1.1.1.133] |
| ORF02510 | 5019 & 5020 | dTDP-glucose 4,6-dehydratase (rfbB) [4.2.1.46] |
| ORF02511 | 5021 & 5022 | regulatory protein GalF (galF) |
| ORF02512 | 5023 & 5024 | Colanic acid biosynthesis protein wcaM |
| ORF02513 | 5025 & 5026 | Amylovoran biosynthesis glycosyl transferase amsK [2.—.—.—] |
| ORF02514 | 5027 & 5028 | Colanic acid biosynthesis protein wcaK [2.—.—.—] |
| ORF02515 | 5029 & 5030 | Lipopolysaccharide biosynthesis protein wzxC |
| ORF02516 | 5031 & 5032 | glycosyl transferase (WcaJ) [2.7.—.—] |
| ORF02517 | 5033 & 5034 | Phosphomannomutase |
| ORF02518 | 5035 & 5036 | mannose-1-phosphate guanylyltransferase-mannose-6-phosphate isomerase |
| ORF02519 | 5037 & 5038 | lipopolysaccharide biosynthesis protein, putative |
| ORF02520 | 5039 & 5040 | GDP-mannose mannosyl hydrolase [3.6.1.—] |
| ORF02521 | 5041 & 5042 | GDP-fucose synthetase chain A (GER1) [1.1.1.271] |
| ORF02522 | 5043 & 5044 | GDP-mannose 4,6-dehydratase (gmd) [4.2.1.47] |

TABLE 1-continued

Annotation of ORF00001 to ORF04995

| ORFnnnnn | SEQ ID NOs Annotation |
|---|---|
| ORF02523 | 5045 & 5046 acetyltransferase, CysE-LacA-LpxA-NodL family, putative [2.3.1.—] |
| ORF02524 | 5047 & 5048 glycosyl transferase, group 2 family protein, putative |
| ORF02525 | 5049 & 5050 Putative colanic acid polymerase |
| ORF02526 | 5051 & 5052 possible glycosyl transferase |
| ORF02527 | 5053 & 5054 serine acetyltransferase [2.3.1.—] |
| ORF02528 | 5055 & 5056 possible glycosyl transferase |
| ORF02529 | 5057 & 5058 Tyrosine-protein kinase wzc |
| ORF02530 | 5059 & 5060 Low molecular weight protein-tyrosine-phosphatase wzb [3.1.3.48] |
| ORF02531 | 5061 & 5062 membrane protein |
| ORF02532 | 5063 & 5064 putative transport protein |
| ORF02533 | 5065 & 5066 unnamed protein product |
| ORF02534 | 5067 & 5068 PHIKZ114 |
| ORF02535 | 5069 & 5070 Protein asmA precursor |
| ORF02536 | 5071 & 5072 deoxycytidine triphosphate deaminase (dcd) [3.5.4.13] |
| ORF02537 | 5073 & 5074 uridine kinase (udk) [2.7.1.48] |
| ORF02538 | 5075 & 5076 MASE1 domain family |
| ORF02539 | 5077 & 5078 Ada regulatory protein, putative [3.2.2.21] |
| ORF02540 | 5079 & 5080 hypothetical protein |
| ORF02541 | 5081 & 5082 Molecular chaperone |
| ORF02542 | 5083 & 5084 conserved hypothetical protein |
| ORF02543 | 5085 & 5086 conserved hypothetical protein |
| ORF02544 | 5087 & 5088 von Willebrand factor type A domain protein |
| ORF02545 | 5089 & 5090 putative membrane protein |
| ORF02546 | 5091 & 5092 AcrB-AcrD-AcrF (HAE1) |
| ORF02547 | 5093 & 5094 AcrB-AcrD-AcrF family membrane protein |
| ORF02548 | 5095 & 5096 MFS superfamily drug efflux pump |
| ORF02549 | 5097 & 5098 sensor histidine kinase SrrB, putative [2.7.3.—] |
| ORF02550 | 5099 & 5100 Transcriptional regulatory protein baeR (ResD) |
| ORF02551 | 5101 & 5102 Domain of unknown function (DUF1508) family |
| ORF02552 | 5103 & 5104 conserved hypothetical protein |
| ORF02553 | 5105 & 5106 conserved hypothetical protein |
| ORF02554 | 5107 & 5108 conserved hypothetical protein |
| ORF02555 | 5109 & 5110 conserved hypothetical protein |
| ORF02556 | 5111 & 5112 YegQ [3.4.—.—] |
| ORF02557 | 5113 & 5114 conserved hypothetical protein TIGR00147 |
| ORF02558 | 5115 & 5116 Galactitol utilization operon repressor (fragment) |
| ORF02559 | 5117 & 5118 hexitol dehydrogenase [1.1.1.251] |
| ORF02560 | 5119 & 5120 PTS system, sorbitol-specific IIC component (EIIC-GAT) |
| ORF02561 | 5121 & 5122 PTS system, galactitol-specific IIB component (EIIB-Gat) (Galacticol-permease IIB component) (Phosphotransferase enzyme II, B component)(EC 2.7.1.69) [2.7.1.69] |
| ORF02562 | 5123 & 5124 PTS system, galactitol-specific IIA component (EIIA-Gat) (Galacticol-permease IIA component) (Phosphotransferase enzyme II, A component)(EC 2.7.1.69) (EIIA-GAT) [2.7.1.69] |
| ORF02563 | 5125 & 5126 PUTATIVE TAGATOSE 6-PHOSPHATE KINASE PROTEIN [2.7.1.144] |
| ORF02564 | 5127 & 5128 class II aldolase, tagatose bisphosphate family [4.1.2.—] |
| ORF02565 | 5129 & 5130 dehydrin [4.1.2.13] |
| ORF02566 | 5131 & 5132 nucleoside permease NupG, putative |
| ORF02567 | 5133 & 5134 ADP-ribosylglycohydrolase, putative |
| ORF02568 | 5135 & 5136 transcriptional regulator, GntR family, putative |
| ORF02569 | 5137 & 5138 Ribokinase (EC 2.7.1.15). [2.7.1.15] |
| ORF02570 | 5139 & 5140 glycosyl hydrolase, family 25 [3.2.1.17] |
| ORF02571 | 5141 & 5142 phosphomethylpyrimidine kinase (thiD) [2.7.4.7] |
| ORF02572 | 5143 & 5144 hydroxyethylthiazole kinase (thiM) [2.7.1.50] |
| ORF02573 | 5145 & 5146 Uncharacterized BCR, COG1937 family |
| ORF02574 | 5147 & 5148 NirC |
| ORF02575 | 5149 & 5150 conserved hypothetical protein |
| ORF02576 | 5151 & 5152 conserved hypothetical protein |
| ORF02577 | 5153 & 5154 Hypothetical outer membrane usher protein yehB precursor |
| ORF02578 | 5155 & 5156 Hypothetical fimbrial chaperone yehC precursor |
| ORF02579 | 5157 & 5158 Fimbrial protein subfamily |
| ORF02580 | 5159 & 5160 Mrp protein (mrp) |
| ORF02581 | 5161 & 5162 Methionyl-tRNA synthetase (metG) [6.1.1.10] |
| ORF02582 | 5163 & 5164 molybdate metabolism regulator, second fragment 2 (fragment) |
| ORF02583 | 5165 & 5166 yehI (fragment) |
| ORF02584 | 5167 & 5168 yehI (fragment) |
| ORF02585 | 5169 & 5170 conserved hypothetical protein |
| ORF02586 | 5171 & 5172 conserved hypothetical protein |
| ORF02587 | 5173 & 5174 VWA domain containing CoxE-like protein family |
| ORF02588 | 5175 & 5176 yehQ gene product |
| ORF02589 | 5177 & 5178 Hypothetical lipoprotein yehR precursor |
| ORF02590 | 5179 & 5180 uncharacterized protein conserved in bacteria |
| ORF02591 | 5181 & 5182 unnamed protein product |
| ORF02592 | 5183 & 5184 putative 2-component sensor protein |
| ORF02593 | 5185 & 5186 MerR-like regulator A |
| ORF02594 | 5187 & 5188 glycine betaine-l-proline transport system permease protein prow (AE005444) |
| ORF02595 | 5189 & 5190 putative membrane protein |

TABLE 1-continued

Annotation of ORF00001 to ORF04995

| ORFnnnnn | SEQ ID NOs | Annotation |
|---|---|---|
| ORF02596 | 5191 & 5192 | amino acid ABC transporter, ATP-binding protein (AE005444) |
| ORF02597 | 5193 & 5194 | ABC transporter, permease protein (AE005444) |
| ORF02598 | 5195 & 5196 | glycine betaine-L-proline ABC transporter, periplasmic substrate-binding protein, putative |
| ORF02599 | 5197 & 5198 | yohA (STI) [3.2.1.21] |
| ORF02600 | 5199 & 5200 | D-lactate dehydrogenase |
| ORF02601 | 5201 & 5202 | beta-lactamase |
| ORF02602 | 5203 & 5204 | Protein of unknown function (DUF1282) superfamily |
| ORF02603 | 5205 & 5206 | DedA family protein |
| ORF02604 | 5207 & 5208 | yohF [1.—.—.—] |
| ORF02605 | 5209 & 5210 | Putative channel-filament proteins |
| ORF02606 | 5211 & 5212 | Dihydrouridine synthase (Dus) superfamily |
| ORF02607 | 5213 & 5214 | LrgA family subfamily, putative |
| ORF02608 | 5215 & 5216 | membrane protein, putative |
| ORF02609 | 5217 & 5218 | cytidine deaminase (cdd) [3.5.4.5] |
| ORF02610 | 5219 & 5220 | SanA protein |
| ORF02611 | 5221 & 5222 | conserved hypothetical protein |
| ORF02612 | 5223 & 5224 | glutamate synthase, small subunit (NADPH) |
| ORF02613 | 5225 & 5226 | dihydroorotase dehydrogenase (pyrD) |
| ORF02614 | 5227 & 5228 | conserved hypothetical protein |
| ORF02615 | 5229 & 5230 | ribose ABC transporter, permease protein (membrane) |
| ORF02616 | 5231 & 5232 | Galactoside transport ATP-binding protein mglA (atp_bind) |
| ORF02617 | 5233 & 5234 | D-galactose-binding periplasmic protein precursor (GBP) (D-galactose-D-glucose binding protein) (GGBP) |
| ORF02618 | 5235 & 5236 | Mgl repressor and galactose ultrainduction factor |
| ORF02619 | 5237 & 5238 | unnamed protein product |
| ORF02620 | 5239 & 5240 | conserved hypothetical protein |
| ORF02621 | 5241 & 5242 | GTP cyclohydrolase I (folE) [3.5.4.16] |
| ORF02622 | 5243 & 5244 | carboxylesterase [3.1.1.—] |
| ORF02623 | 5245 & 5246 | Colicin I receptor precursor |
| ORF02624 | 5247 & 5248 | lysine-specific permease |
| ORF02625 | 5249 & 5250 | transcriptional regulator, LysR family |
| ORF02626 | 5251 & 5252 | membrane protein, putative |
| ORF02627 | 5253 & 5254 | Endonuclease IV (Endodeoxyribonuclease IV) [3.1.21.2] |
| ORF02628 | 5255 & 5256 | yeiI |
| ORF02629 | 5257 & 5258 | inosine-uridine preferring nucleoside hydrolase (AL355920) |
| ORF02630 | 5259 & 5260 | Regulatory protein nsr |
| ORF02631 | 5261 & 5262 | nucleoside transporter |
| ORF02632 | 5263 & 5264 | uncharacterized enzyme involved in pigment biosynthesis |
| ORF02633 | 5265 & 5266 | yeiI |
| ORF02634 | 5267 & 5268 | PTS system, fructose-specific IIBC component [2.7.1.69] |
| ORF02635 | 5269 & 5270 | 1-phosphofructokinase (Fructose 1-phosphate kinase) (fruK) [2.7.1.56] |
| ORF02636 | 5271 & 5272 | PTS system, fructose-specific IIA-FPr component (EIIA-Fru) (Fructose-permease IIA-FPr component) (Phosphotransferase enzyme II, A-FPrcomponent) (Phosphotransferase FPr protein) (Pseudo-HPr)(EIII-Fru) (Fructose PTS diphosphoryl transfer protein) (EIII-FRU) [2.7.1.69] |
| ORF02637 | 5273 & 5274 | conserved hypothetical protein |
| ORF02638 | 5275 & 5276 | Sugar efflux transporter B (orf104) |
| ORF02639 | 5277 & 5278 | translation elongation factor EF-P (EF-P) |
| ORF02640 | 5279 & 5280 | D-MANNONATE OXIDOREDUCTASE |
| ORF02641 | 5281 & 5282 | CobW-P47K family protein domain protein |
| ORF02642 | 5283 & 5284 | PAP2 superfamily domain protein |
| ORF02643 | 5285 & 5286 | Lipoprotein spr precursor (spr) |
| ORF02644 | 5287 & 5288 | Rtn protein |
| ORF02645 | 5289 & 5290 | ABC transporter substrate-binding protein |
| ORF02646 | 5291 & 5292 | peptide ABC transporter, permease protein |
| ORF02647 | 5293 & 5294 | ABC transporter, permease protein |
| ORF02648 | 5295 & 5296 | ABC transporter, nucleotide binding-ATPase protein [peptide] |
| ORF02649 | 5297 & 5298 | unnamed protein product |
| ORF02650 | 5299 & 5300 | bicyclomycin resistance protein |
| ORF02651 | 5301 & 5302 | ribosomal small subunit pseudouridine synthase A |
| ORF02652 | 5303 & 5304 | yejH |
| ORF02653 | 5305 & 5306 | 50S ribosomal protein L25 |
| ORF02654 | 5307 & 5308 | nucleoid-associated protein |
| ORF02655 | 5309 & 5310 | hypothetical protein |
| ORF02656 | 5311 & 5312 | Protein of unknown function (DUF1414) superfamily |
| ORF02657 | 5313 & 5314 | Predicted hydrolase of alkaline phosphatase superfamily |
| ORF02658 | 5315 & 5316 | yejO |
| ORF02659 | 5317 & 5318 | Nitrate-nitrite response regulator protein narP |
| ORF02660 | 5319 & 5320 | Cytochrome c-type biogenesis protein ccmH precursor (nrfF) |
| ORF02661 | 5321 & 5322 | Thiol:disulfide interchange protein dsbE (Cytochrome c biogenesisprotein ccmG) (dsbE) |
| ORF02662 | 5323 & 5324 | cytochrome c-type biogenesis protein CcmF (ccmF) |
| ORF02663 | 5325 & 5326 | Cytochrome c-type biogenesis protein ccmE |
| ORF02664 | 5327 & 5328 | Heme exporter protein D (Cytochrome c-type biogenesis protein ccmD)-related protein |

TABLE 1-continued

Annotation of ORF00001 to ORF04995

| ORFnnnnn | SEQ ID NOs | Annotation |
|---|---|---|
| ORF02665 | 5329 & 5330 | heme exporter protein C |
| ORF02666 | 5331 & 5332 | heme exporter protein CcmB (ccmB) |
| ORF02667 | 5333 & 5334 | heme exporter protein CcmA (ccmA) |
| ORF02668 | 5335 & 5336 | Cytochrome c-type protein napC |
| ORF02669 | 5337 & 5338 | periplasmic nitrate reductase, diheme cytochrome c subunit (napB) |
| ORF02670 | 5339 & 5340 | Ferredoxin-type protein napH (napH) |
| ORF02671 | 5341 & 5342 | Ferredoxin-type protein napG (napG) |
| ORF02672 | 5343 & 5344 | periplasmic nitrate reductase, large subunit (napA) [1.7.99.4] |
| ORF02673 | 5345 & 5346 | NapD protein (napD) |
| ORF02674 | 5347 & 5348 | ferredoxin-type protein NapF (napF) |
| ORF02675 | 5349 & 5350 | Ecotin |
| ORF02676 | 5351 & 5352 | malate:quinone-oxidoreductase (mqo) [1.1.99.16] |
| ORF02677 | 5353 & 5354 | hypothetical protein |
| ORF02678 | 5355 & 5356 | MdlB protein |
| ORF02679 | 5357 & 5358 | Alkylated DNA repair protein alkB (alkB) |
| ORF02680 | 5359 & 5360 | O6-methylguanine-DNA methyltransferase; transcription activator-repressor [2.1.1.63] |
| ORF02681 | 5361 & 5362 | thiamine biosynthesis lipoprotein ApbE, putative |
| ORF02682 | 5363 & 5364 | Outer membrane protein C precursor (Porin ompC) (Outer membraneprotein 1B) (Ibc) |
| ORF02683 | 5365 & 5366 | YojQ [2.7.3.—] |
| ORF02684 | 5367 & 5368 | positive response regulator for colanic capsule biosynthesis |
| ORF02685 | 5369 & 5370 | Sensor protein rcsC |
| ORF02686 | 5371 & 5372 | Sensor protein atoS |
| ORF02687 | 5373 & 5374 | Acetoacetate metabolism Regulatory protein atoC (atoC) |
| ORF02688 | 5375 & 5376 | Acetate CoA-transferase alpha subunit [2.8.3.8] |
| ORF02689 | 5377 & 5378 | Acetate CoA-transferase beta subunit (atoA) [2.8.3.8] |
| ORF02690 | 5379 & 5380 | membrane protein, putative |
| ORF02691 | 5381 & 5382 | Acetyl-CoA acetyltransferase (atoB) [2.3.1.9] |
| ORF02692 | 5383 & 5384 | conserved hypothetical protein |
| ORF02693 | 5385 & 5386 | conserved hypothetical protein |
| ORF02694 | 5387 & 5388 | Alpha-2-macroglobulin family N-terminal region family |
| ORF02695 | 5389 & 5390 | Protein of unknown function (DUF1175) superfamily |
| ORF02696 | 5391 & 5392 | conserved hypothetical protein |
| ORF02697 | 5393 & 5394 | DNA gyrase, A subunit (gyrA) [5.99.1.3] |
| ORF02698 | 5395 & 5396 | ubiquinone biosynthesis O-methyltransferase (ubiG) [2.1.1.—] |
| ORF02699 | 5397 & 5398 | similar to [SwissProt Accession Number P45508] |
| ORF02700 | 5399 & 5400 | ribonucleoside diphosphate reductase 1, alpha subunit, B1 (nrdA) [1.17.4.1] |
| ORF02701 | 5401 & 5402 | ribonucleoside diphosphage reductase 1, beta subunit, B2 |
| ORF02702 | 5403 & 5404 | adrenodoxin family ferredoxin |
| ORF02703 | 5405 & 5406 | Protein inaA |
| ORF02704 | 5407 & 5408 | glycerophosphodiester phosphodiesterase, periplasmic |
| ORF02705 | 5409 & 5410 | glycerol-3-phosphate transporter (glpT) |
| ORF02706 | 5411 & 5412 | glpD2, putative [1.1.99.5] |
| ORF02707 | 5413 & 5414 | Anaerobic glycerol-3-phosphate dehydrogenase subunit B |
| ORF02708 | 5415 & 5416 | Anaerobic glycerol-3-phosphate dehydrogenase subunit C [1.1.99.5] |
| ORF02709 | 5417 & 5418 | conserved hypothetical protein |
| ORF02710 | 5419 & 5420 | transposase |
| ORF02711 | 5421 & 5422 | transposase |
| ORF02712 | 5423 & 5424 | similar to [SwissProt Accession Number P23522] |
| ORF02713 | 5425 & 5426 | major facilitator family transporter |
| ORF02714 | 5427 & 5428 | Mandelate racemase - muconate lactonizing enzyme, C-terminal domain protein |
| ORF02715 | 5429 & 5430 | transcriptional regulator, IclR family, putative |
| ORF02716 | 5431 & 5432 | CinA-like protein |
| ORF02717 | 5433 & 5434 | YfaZ precursor superfamily |
| ORF02718 | 5435 & 5436 | hydrolase, NUDIX family, putative |
| ORF02719 | 5437 & 5438 | protein induced by aluminum |
| ORF02720 | 5439 & 5440 | lipopolysaccharide biosynthesis protein |
| ORF02721 | 5441 & 5442 | Glycosyl transferase arnC (Ara4N transferase) (Polymixinresistance protein pmrF) [2.—.—.—] |
| ORF02722 | 5443 & 5444 | Formyl transferase, C-terminal domain protein |
| ORF02723 | 5445 & 5446 | PbgP4 protein |
| ORF02724 | 5447 & 5448 | melittin resistance protein PqaB |
| ORF02725 | 5449 & 5450 | sucrose-6 phosphate hydrolase |
| ORF02726 | 5451 & 5452 | conserved hypothetical protein |
| ORF02727 | 5453 & 5454 | Polymyxin B resistance protein pmrD |
| ORF02728 | 5455 & 5456 | O-succinylbenzoate-CoA ligase (menE) [6.2.1.26] |
| ORF02729 | 5457 & 5458 | o-succinylbenzoic acid (OSB) synthetase (menC) [4.2.1.—] |
| ORF02730 | 5459 & 5460 | naphthoate synthase (menB) [4.1.3.36] |
| ORF02731 | 5461 & 5462 | hydrolase, alpha-beta hydrolase fold family, putative |
| ORF02732 | 5463 & 5464 | 2-succinyl-6-hydroxy-2,4-cyclohexadiene-1-carboxylic acid synthase-2-oxoglutarate decarboxylase (menD) [4.1.1.71] |
| ORF02733 | 5465 & 5466 | Menaquinone-specific isochorismate synthase |
| ORF02734 | 5467 & 5468 | ElaB protein |
| ORF02735 | 5469 & 5470 | elaA protein VC2565 (putative) |
| ORF02736 | 5471 & 5472 | metallo-beta-lactamase superfamily protein [3.1.26.11] |

TABLE 1-continued

Annotation of ORF00001 to ORF04995

| ORFnnnnn | SEQ ID NOs | Annotation |
|---|---|---|
| ORF02737 | 5473 & 5474 | von Willebrand factor type A domain protein |
| ORF02738 | 5475 & 5476 | putative aminopeptidase |
| ORF02739 | 5477 & 5478 | conserved hypothetical protein |
| ORF02740 | 5479 & 5480 | NADH dehydrogenase I chain N (NUO14) [1.6.99.5] |
| ORF02741 | 5481 & 5482 | NADH dehydrogenase I chain M (NUO13) [1.6.99.5] |
| ORF02742 | 5483 & 5484 | NADH dehydrogenase I chain L ECs3162 (NUO12) [1.6.99.5] |
| ORF02743 | 5485 & 5486 | NADH dehydrogenase I chain L ECs3162 (NUO12) [1.6.99.5] |
| ORF02744 | 5487 & 5488 | NADH dehydrogenase I, K subunit (NUO11) [1.6.5.3] |
| ORF02745 | 5489 & 5490 | NADH-quinone oxidoreductase chain J (NADH dehydrogenaseI, chain J) (NDH-1, chain J) (NUO10) [1.6.99.5] |
| ORF02746 | 5491 & 5492 | NADH DEHYDROGENASE I CHAIN I (EC 1.6.5.3) (NADH-UBIQUINONE OXIDOREDUCTASE CHAIN 9) (NUO9) [1.6.5.3] |
| ORF02747 | 5493 & 5494 | NADH dehydrogenase I chain H (NUO8) [1.6.99.5] |
| ORF02748 | 5495 & 5496 | NADH DEHYDROGENASE I CHAIN G (EC 1.6.5.3) (NADH-UBIQUINONE OXIDOREDUCTASE CHAIN 7) (NUO7) (FRAGMENT) [1.6.5.3] |
| ORF02749 | 5497 & 5498 | NADH-quinone oxidoreductase, F subunit (nuoF) |
| ORF02750 | 5499 & 5500 | NADH-quinone oxidoreductase chain E (NADH dehydrogenaseI, chain E) (NDH-1, chain E) (NUO5) [1.6.99.5] |
| ORF02751 | 5501 & 5502 | NADH dehydrogenase I chain C-D (NUO4) [1.6.99.5] |
| ORF02752 | 5503 & 5504 | NADH-quinone oxidoreductase chain B (NADH dehydrogenaseI, chain B) (NDH-1, chain B) (NUO2) (NUO2) [1.6.99.5] |
| ORF02753 | 5505 & 5506 | NADH-quinone oxidoreductase chain A (NADH dehydrogenaseI, chain A) (NDH-1, chain A) (NUO1) [1.6.99.5] |
| ORF02754 | 5507 & 5508 | LysR family NADH dehydrogenase transcriptional regulator (RssB) |
| ORF02755 | 5509 & 5510 | hypothetical protein |
| ORF02756 | 5511 & 5512 | aminotransferase, classes I and II (ASPAT) [2.6.1.—] |
| ORF02757 | 5513 & 5514 | b2291 |
| ORF02758 | 5515 & 5516 | unnamed protein product |
| ORF02759 | 5517 & 5518 | hydrolase, haloacid dehalogenase-like family [3.1.3.—] |
| ORF02760 | 5519 & 5520 | Protein yfbU |
| ORF02761 | 5521 & 5522 | Hypothetical UPF0208 protein yfbV |
| ORF02762 | 5523 & 5524 | acetate kinase (ackA) [2.7.2.1] |
| ORF02763 | 5525 & 5526 | Phosphate acetyltransferase |
| ORF02764 | 5527 & 5528 | predicted membrane protein |
| ORF02765 | 5529 & 5530 | IPP isomerase type 1 family protein, putative [3.6.—.—] |
| ORF02766 | 5531 & 5532 | phosphoesterase, putative subfamily |
| ORF02767 | 5533 & 5534 | Glutathione S-transferase, N-terminal domain protein |
| ORF02768 | 5535 & 5536 | glutathione S-transferase, putative |
| ORF02769 | 5537 & 5538 | dihydroneopterin aldolase (folB) [4.1.2.25] |
| ORF02770 | 5539 & 5540 | conserved hypothetical protein TIGR01777 |
| ORF02771 | 5541 & 5542 | conserved hypothetical protein subfamily |
| ORF02772 | 5543 & 5544 | ATP-binding component of histidine transport ECs3190 |
| ORF02773 | 5545 & 5546 | histidine transport system membrane protein M (membrane) |
| ORF02774 | 5547 & 5548 | amino acid ABC transporter, permease protein |
| ORF02775 | 5549 & 5550 | Histidine-binding periplasmic protein precursor (HBP) |
| ORF02776 | 5551 & 5552 | Lysine-arginine-ornithine-binding periplasmic protein precursor (LAO-binding protein) |
| ORF02777 | 5553 & 5554 | 3-octaprenyl-4-hydroxybenzoate carboxy-lyase (Polyprenylp-hydroxybenzoate decarboxylase) [4.1.1.—] |
| ORF02778 | 5555 & 5556 | amidophosphoribosyltransferase (purF) [2.4.2.14] |
| ORF02779 | 5557 & 5558 | CvpA family protein (cvpA) |
| ORF02780 | 5559 & 5560 | DedD protein |
| ORF02781 | 5561 & 5562 | FolC bifunctional protein [6.3.2.17] |
| ORF02782 | 5563 & 5564 | acetyl-CoA carboxylase, carboxyl transferase, beta subunit (accD) [6.4.1.2] |
| ORF02783 | 5565 & 5566 | DedA protein |
| ORF02784 | 5567 & 5568 | tRNA pseudouridine synthase A (truA) [4.2.1.70] |
| ORF02785 | 5569 & 5570 | USG-1 protein [1.2.1.—] |
| ORF02786 | 5571 & 5572 | Erythronate-4-phosphate dehydrogenase [1.1.1.—] |
| ORF02787 | 5573 & 5574 | hypothetical protein |
| ORF02788 | 5575 & 5576 | Int |
| ORF02789 | 5577 & 5578 | Regulatory protein cox |
| ORF02790 | 5579 & 5580 | hypothetical protein |
| ORF02791 | 5581 & 5582 | unknown protein encoded by prophage CP-933T |
| ORF02792 | 5583 & 5584 | unknown protein encoded by prophage CP-933T |
| ORF02793 | 5585 & 5586 | unknown protein encoded by prophage CP-933T |
| ORF02794 | 5587 & 5588 | hypothetical protein |
| ORF02795 | 5589 & 5590 | conserved hypothetical protein |
| ORF02796 | 5591 & 5592 | unknown protein encoded by prophage CP-933T |
| ORF02797 | 5593 & 5594 | unknown protein encoded by prophage CP-933T-related protein |
| ORF02798 | 5595 & 5596 | conserved hypothetical protein |
| ORF02799 | 5597 & 5598 | Fels-2 prophage protein |
| ORF02800 | 5599 & 5600 | gpH |
| ORF02801 | 5601 & 5602 | gpU (gpG) |
| ORF02802 | 5603 & 5604 | gpU prime (gpG) |
| ORF02803 | 5605 & 5606 | DNA-invertase (pin) |
| ORF02804 | 5607 & 5608 | Fels-2 prophage protein (gpU) |

TABLE 1-continued

Annotation of ORF00001 to ORF04995

| ORFnnnnn | SEQ ID NOs | Annotation |
|---|---|---|
| ORF02805 | 5609 & 5610 | phage tail tape measure protein, TP901 family, putative |
| ORF02806 | 5611 & 5612 | probable phage tail protein-related protein |
| ORF02807 | 5613 & 5614 | probable tail protein (gpE) |
| ORF02808 | 5615 & 5616 | phage major tail tube protein |
| ORF02809 | 5617 & 5618 | Phage tail sheath protein |
| ORF02810 | 5619 & 5620 | hypothetical protein |
| ORF02811 | 5621 & 5622 | bacteriophage late gene control protein D |
| ORF02812 | 5623 & 5624 | hypothetical protein |
| ORF02813 | 5625 & 5626 | Phage transcriptional activator, Ogr-Delta |
| ORF02814 | 5627 & 5628 | conserved hypothetical protein |
| ORF02815 | 5629 & 5630 | hypothetical protein |
| ORF02816 | 5631 & 5632 | hypothetical protein |
| ORF02817 | 5633 & 5634 | DIV protein (FRAGMENT) |
| ORF02818 | 5635 & 5636 | Hypothetical UPF0226 protein yfcJ |
| ORF02819 | 5637 & 5638 | 3-oxoacyl-[acyl-carrier-protein] synthase I (Beta-ketoacyl-ACP synthase I) (KAS I) [2.3.1.41] |
| ORF02820 | 5639 & 5640 | Glycine-D-amino acid oxidases (deaminating) |
| ORF02821 | 5641 & 5642 | conserved hypothetical protein |
| ORF02822 | 5643 & 5644 | similar to [SwissProt Accession Number P44255] |
| ORF02823 | 5645 & 5646 | predicted permease (ORF9) |
| ORF02824 | 5647 & 5648 | Penicillin-insensitive murein endopeptidase precursor [3.4.99.—] |
| ORF02825 | 5649 & 5650 | chorismate synthase (aroC) [4.2.3.5] |
| ORF02826 | 5651 & 5652 | Predicted rRNA or tRNA methylase [2.1.1.72] |
| ORF02827 | 5653 & 5654 | Smr domain protein |
| ORF02828 | 5655 & 5656 | conserved hypothetical protein |
| ORF02829 | 5657 & 5658 | minor fimbrial subunit StfG |
| ORF02830 | 5659 & 5660 | minor fimbrial subunit StfF |
| ORF02831 | 5661 & 5662 | fimbrial subunit |
| ORF02832 | 5663 & 5664 | periplasmic fimbrial chaperone StfD |
| ORF02833 | 5665 & 5666 | outer membrane usher protein StfC |
| ORF02834 | 5667 & 5668 | major fimbrial subunit StfA |
| ORF02835 | 5669 & 5670 | hypothetical protein |
| ORF02836 | 5671 & 5672 | phosphohistidine phosphatase SixA (sixA) [3.1.3.—] |
| ORF02837 | 5673 & 5674 | fatty oxidation complex, alpha subunit FadJ (fadJ) [4.2.1.17 1.1.1.35 5.1.2.3] |
| ORF02838 | 5675 & 5676 | acetyl-CoA C-acyltransferase FadI (fadI) [2.3.1.16] |
| ORF02839 | 5677 & 5678 | conserved hypothetical protein superfamily |
| ORF02840 | 5679 & 5680 | Long-chain fatty acid transport protein precursor (Outer membrane fadL protein) (Outer membrane flp protein) |
| ORF02841 | 5681 & 5682 | VACJ LIPOPROTEIN PRECURSOR. (vacJ) |
| ORF02842 | 5683 & 5684 | probable transport yfdC |
| ORF02843 | 5685 & 5686 | putative prophage integrase |
| ORF02844 | 5687 & 5688 | hypothetical protein |
| ORF02845 | 5689 & 5690 | endo-alpha-sialidase [3.2.1.129] |
| ORF02846 | 5691 & 5692 | hypothetical protein |
| ORF02847 | 5693 & 5694 | endo-alpha-sialidase [3.2.1.129] |
| ORF02848 | 5695 & 5696 | Antirepressor protein ant |
| ORF02849 | 5697 & 5698 | unnamed protein product; pot. mnt-gene product (aa 1-83) |
| ORF02850 | 5699 & 5700 | DNA transfer protein |
| ORF02851 | 5701 & 5702 | hypothetical protein |
| ORF02852 | 5703 & 5704 | DNA transfer protein |
| ORF02853 | 5705 & 5706 | DNA transfer protein gp7 |
| ORF02854 | 5707 & 5708 | head assembly protein |
| ORF02855 | 5709 & 5710 | DNA stabilization protein |
| ORF02856 | 5711 & 5712 | DNA stabilization protein |
| ORF02857 | 5713 & 5714 | gene 7 protein |
| ORF02858 | 5715 & 5716 | hypothetical protein |
| ORF02859 | 5717 & 5718 | coat protein, putative |
| ORF02860 | 5719 & 5720 | P23, putative |
| ORF02861 | 5721 & 5722 | portal protein |
| ORF02862 | 5723 & 5724 | phage terminase, large subunit, PBSX family |
| ORF02863 | 5725 & 5726 | conserved hypothetical protein |
| ORF02864 | 5727 & 5728 | gene 67 protein |
| ORF02865 | 5729 & 5730 | alternate start at bp 59; ORF |
| ORF02866 | 5731 & 5732 | Bacteriophage lysis protein |
| ORF02867 | 5733 & 5734 | lysozyme [3.2.1.17] |
| ORF02868 | 5735 & 5736 | phage holin, lambda family |
| ORF02869 | 5737 & 5738 | gene 59 protein |
| ORF02870 | 5739 & 5740 | Phage NinH protein superfamily |
| ORF02871 | 5741 & 5742 | holiday-junction resolvase [3.1.22.—] |
| ORF02872 | 5743 & 5744 | Gp66 |
| ORF02873 | 5745 & 5746 | DNA-binding protein Roi (Ant1) |
| ORF02874 | 5747 & 5748 | NinF protein superfamily |
| ORF02875 | 5749 & 5750 | NinX |
| ORF02876 | 5751 & 5752 | Protein ninE-related protein |
| ORF02877 | 5753 & 5754 | Protein ninB |
| ORF02878 | 5755 & 5756 | DnaB analogue [3.6.1.—] |

TABLE 1-continued

Annotation of ORF00001 to ORF04995

| ORFnnnnn | SEQ ID NOs | Annotation |
|---|---|---|
| ORF02879 | 5757 & 5758 | Gp54 |
| ORF02880 | 5759 & 5760 | Regulatory protein Cll (cll) |
| ORF02881 | 5761 & 5762 | hypothetical protein |
| ORF02882 | 5763 & 5764 | gene 33 protein |
| ORF02883 | 5765 & 5766 | gene 33 protein |
| ORF02884 | 5767 & 5768 | Kil protein-related protein |
| ORF02885 | 5769 & 5770 | Gp42.1 |
| ORF02886 | 5771 & 5772 | Gp40 |
| ORF02887 | 5773 & 5774 | gene 25 protein |
| ORF02888 | 5775 & 5776 | hypothetical protein |
| ORF02889 | 5777 & 5778 | Gp37 |
| ORF02890 | 5779 & 5780 | Protein of unknown function (DUF551) family |
| ORF02891 | 5781 & 5782 | conserved hypothetical protein |
| ORF02892 | 5783 & 5784 | gene 18 protein-related protein |
| ORF02893 | 5785 & 5786 | D-serine deaminase transcriptional activator (dsdC) |
| ORF02894 | 5787 & 5788 | DsdX permease |
| ORF02895 | 5789 & 5790 | D-serine ammonia-lyase (dsdA) [4.3.1.18] |
| ORF02896 | 5791 & 5792 | Multidrug resistance protein Y |
| ORF02897 | 5793 & 5794 | Multidrug resistance protein K |
| ORF02898 | 5795 & 5796 | conserved hypothetical protein |
| ORF02899 | 5797 & 5798 | Positive transcription regulator evgA |
| ORF02900 | 5799 & 5800 | Sensor protein evgS precursor [2.7.3.—] |
| ORF02901 | 5801 & 5802 | CAIB-BAIF family protein |
| ORF02902 | 5803 & 5804 | similar to [SwissProt Accession Number P45869] |
| ORF02903 | 5805 & 5806 | oxcA [4.1.1.8] |
| ORF02904 | 5807 & 5808 | CAIB-BAIF family protein [2.8.3.16] |
| ORF02905 | 5809 & 5810 | YfdX protein precursor |
| ORF02906 | 5811 & 5812 | conserved hypothetical protein |
| ORF02907 | 5813 & 5814 | DDG protein |
| ORF02908 | 5815 & 5816 | transaminase [similarity] (ASPAT) [2.6.1.—] |
| ORF02909 | 5817 & 5818 | Histidine kinase family |
| ORF02910 | 5819 & 5820 | Autolysin response regulator |
| ORF02911 | 5821 & 5822 | transcription regulator VC1825 |
| ORF02912 | 5823 & 5824 | Phosphoenolpyruvate-protein phosphotransferase ptsA(Phosphotransferase system, enzyme I) (Enzyme I-Ani) [2.7.3.9] |
| ORF02913 | 5825 & 5826 | frv operon protein |
| ORF02914 | 5827 & 5828 | proline dipeptidase [3.4.—.—] |
| ORF02915 | 5829 & 5830 | PTS system, fructose specific IIABC components, putative [2.7.1.69] |
| ORF02916 | 5831 & 5832 | PTS system, fructose-like-2 IIB component 1 (phosphotransferase |
| ORF02917 | 5833 & 5834 | glucokinase (glk) [2.7.1.2] |
| ORF02918 | 5835 & 5836 | Putative ion-transport protein yfeO |
| ORF02919 | 5837 & 5838 | conserved hypothetical protein |
| ORF02920 | 5839 & 5840 | transport protein, NRAMP family |
| ORF02921 | 5841 & 5842 | Nucleoside permease nupC |
| ORF02922 | 5843 & 5844 | Nucleoside permease nupC |
| ORF02923 | 5845 & 5846 | similar to [SwissProt Accession Number P23842] start codon is not identified yet |
| ORF02924 | 5847 & 5848 | similar to [SwissProt Accession Number P27239] start codon is not identified yet |
| ORF02925 | 5849 & 5850 | similar to [SwissProt Accession Number P27239] start codon is not identified yet |
| ORF02926 | 5851 & 5852 | glutamyl-tRNA synthetase (gltX) [6.1.1.17] |
| ORF02927 | 5853 & 5854 | transcriptional regulator, LysR family, putative |
| ORF02928 | 5855 & 5856 | conserved hypothetical protein |
| ORF02929 | 5857 & 5858 | nucleoside permease NupG |
| ORF02930 | 5859 & 5860 | xanthosine phosphorylase (xapA) [2.4.2.1] |
| ORF02931 | 5861 & 5862 | hypothetical protein |
| ORF02932 | 5863 & 5864 | Protein of unknown function (DUF1384) superfamily |
| ORF02933 | 5865 & 5866 | OsmT protein |
| ORF02934 | 5867 & 5868 | similar to [SwissProt Accession Number P39836] start codon is not identified yet |
| ORF02935 | 5869 & 5870 | conserved hypothetical protein |
| ORF02936 | 5871 & 5872 | DNA ligase, NAD-dependent (ligA) [6.5.1.2] |
| ORF02937 | 5873 & 5874 | cell division protein ZipA (zipA) |
| ORF02938 | 5875 & 5876 | CysZ protein |
| ORF02939 | 5877 & 5878 | cysteine synthase A (cysK) [2.5.1.47] |
| ORF02940 | 5879 & 5880 | Phosphocarrier protein HPr (Histidine-containing protein) (ptsH) [2.7.1.69] |
| ORF02941 | 5881 & 5882 | phosphoenolpyruvate-protein phosphotransferase (ptsI) [2.7.3.9] |
| ORF02942 | 5883 & 5884 | phosphotransferase system enzyme II, glucose-specific, factor III (crr) [2.7.1.69] |
| ORF02943 | 5885 & 5886 | pyridoxal kinase [2.7.1.35] |
| ORF02944 | 5887 & 5888 | conserved hypothetical protein |
| ORF02945 | 5889 & 5890 | cysteine synthase B (cysM) [2.5.1.47] |
| ORF02946 | 5891 & 5892 | Sulfate-thiosulfate import ATP-binding protein cysA(Sulfate-transporting ATPase) (atp_bind) [3.6.3.25] |
| ORF02947 | 5893 & 5894 | sulfate ABC transporter, permease protein CysW (cysW) |
| ORF02948 | 5895 & 5896 | sulfate ABC transporter, permease protein CysT (cysT) |
| ORF02949 | 5897 & 5898 | thiosulfate binding protein |
| ORF02950 | 5899 & 5900 | 3-oxoacyl-(acyl-carrier-protein) reductase |
| ORF02951 | 5901 & 5902 | glucokinase regulator-related protein |

TABLE 1-continued

Annotation of ORF00001 to ORF04995

| ORFnnnnn | SEQ ID NOs | Annotation |
|---|---|---|
| ORF02952 | 5903 & 5904 | PTS system, sucrose-specific IIBC component (EIIBC-Scr) (Sucrose-permease IIBC component) (Phosphotransferase enzyme II, BC component)(EC 2.7.1.69) (EII-Scr) [2.7.1.69] |
| ORF02953 | 5905 & 5906 | tyrA protein VC2145 |
| ORF02954 | 5907 & 5908 | Protein of unknown function (DUF1131) superfamily |
| ORF02955 | 5909 & 5910 | conserved hypothetical protein |
| ORF02956 | 5911 & 5912 | acetyltransferase, GNAT family family |
| ORF02957 | 5913 & 5914 | N-acetylmuramoyl-l-alanine amidase I [3.5.1.28] |
| ORF02958 | 5915 & 5916 | coproporphyrinogen III oxidase, aerobic (hemF) [1.3.3.3] |
| ORF02959 | 5917 & 5918 | Ethanolamine operon Regulatory protein |
| ORF02960 | 5919 & 5920 | Ethanolamine utilization protein eutK precursor |
| ORF02961 | 5921 & 5922 | Ethanolamine utilization protein eutL (eutL) |
| ORF02962 | 5923 & 5924 | ethanolamine ammonia-lyase, light subunit, putative [4.3.1.7] |
| ORF02963 | 5925 & 5926 | ethanolamine ammonia-lyase, large subunit (eutB) [4.3.1.7] |
| ORF02964 | 5927 & 5928 | Ethanolamine utilization protein eutA |
| ORF02965 | 5929 & 5930 | Ethanolamine utilization protein eutH |
| ORF02966 | 5931 & 5932 | Ethanolamine utilization protein eutG |
| ORF02967 | 5933 & 5934 | Ethanolamine utilization protein eutJ (EutJ) |
| ORF02968 | 5935 & 5936 | aldehyde-alcohol dehydrogenase (EutE) |
| ORF02969 | 5937 & 5938 | carbon dioxide concentrating mechanism protein CcmL, putative |
| ORF02970 | 5939 & 5940 | detox protein (EutM) |
| ORF02971 | 5941 & 5942 | phosphate acetyltransferase (pta) [2.3.1.8] |
| ORF02972 | 5943 & 5944 | Ethanolamine utilization cobalamin adenosyltransferase [2.5.1.17] |
| ORF02973 | 5945 & 5946 | Ethanolamine utilization protein eutQ |
| ORF02974 | 5947 & 5948 | Ethanolamine utilization protein eutP |
| ORF02975 | 5949 & 5950 | ethanolamine utilization protein eutS |
| ORF02976 | 5951 & 5952 | NADP-dependent malic enzyme (NADP-ME) [1.1.1.40] |
| ORF02977 | 5953 & 5954 | transaldolase (tal) [2.2.1.2] |
| ORF02978 | 5955 & 5956 | transketolase (tkt) [2.2.1.1] |
| ORF02979 | 5957 & 5958 | Protein of unknown function (DUF1176) superfamily |
| ORF02980 | 5959 & 5960 | conserved hypothetical protein |
| ORF02981 | 5961 & 5962 | conserved hypothetical protein TIGR00052 |
| ORF02982 | 5963 & 5964 | similar to [SwissProt Accession Number P37127] start codon is not identified yet (GltD) [1.4.1.13] |
| ORF02983 | 5965 & 5966 | Nitrate-nitrite sensor protein narQ |
| ORF02984 | 5967 & 5968 | 1037 amino acids, 113 kDa protein |
| ORF02985 | 5969 & 5970 | Protein yffB [1.—.—.—] |
| ORF02986 | 5971 & 5972 | succinyl-diaminopimelate desuccinylase (dapE) [3.5.1.18] |
| ORF02987 | 5973 & 5974 | conserved hypothetical protein |
| ORF02988 | 5975 & 5976 | 3.1.—.—[3.1.—.—] |
| ORF02989 | 5977 & 5978 | similar to [SwissProt Accession Number P44140] |
| ORF02990 | 5979 & 5980 | metallopeptidase, zinc binding [3.4.—.—] |
| ORF02991 | 5981 & 5982 | phosphoribosylaminoimidazole-succinocarboxamide synthase (purC) [6.3.2.6] |
| ORF02992 | 5983 & 5984 | Lipoprotein-34 precursor |
| ORF02993 | 5985 & 5986 | dihydrodipicolinate synthase (dapA) [4.2.1.52] |
| ORF02994 | 5987 & 5988 | transcriptional regulation of gcv operon |
| ORF02995 | 5989 & 5990 | bcp [1.11.1.—] |
| ORF02996 | 5991 & 5992 | predicted permease |
| ORF02997 | 5993 & 5994 | Peptidase family M48 family [3.4.—.—.] |
| ORF02998 | 5995 & 5996 | arsenate reductase (arsC) [1.20.4.1] |
| ORF02999 | 5997 & 5998 | ATPase involved in DNA replication initiation |
| ORF03000 | 5999 & 6000 | Uracil permease |
| ORF03001 | 6001 & 6002 | uracil phosphoribosyltransferase (upp) [2.4.2.9] |
| ORF03002 | 6003 & 6004 | phosphoribosylformylglycinamidine cyclo-ligase (purM) [6.3.3.1] |
| ORF03003 | 6005 & 6006 | phosphoribosylglycinamide formyltransferase (purN) [2.1.2.2] |
| ORF03004 | 6007 & 6008 | polyphosphate kinase (ppk) [2.7.4.1] |
| ORF03005 | 6009 & 6010 | exopolyphosphatase [3.6.1.11] |
| ORF03006 | 6011 & 6012 | MASE1 domain family |
| ORF03007 | 6013 & 6014 | conserved hypothetical protein |
| ORF03008 | 6015 & 6016 | hypothetical protein |
| ORF03009 | 6017 & 6018 | putative outer membrane lipoprotein |
| ORF03010 | 6019 & 6020 | probable membrane protein Z3770 |
| ORF03011 | 6021 & 6022 | putative Rz-like protein |
| ORF03012 | 6023 & 6024 | endolysin |
| ORF03013 | 6025 & 6026 | holin |
| ORF03014 | 6027 & 6028 | endo-alpha-sialidase |
| ORF03015 | 6029 & 6030 | hypothetical protein |
| ORF03016 | 6031 & 6032 | endo-alpha-sialidase [3.2.1.129] |
| ORF03017 | 6033 & 6034 | hypothetical protein |
| ORF03018 | 6035 & 6036 | Gp27 |
| ORF03019 | 6037 & 6038 | hypothetical protein |
| ORF03020 | 6039 & 6040 | hypothetical protein |
| ORF03021 | 6041 & 6042 | hypothetical protein |
| ORF03022 | 6043 & 6044 | conserved hypothetical protein |
| ORF03023 | 6045 & 6046 | conserved hypothetical protein |
| ORF03024 | 6047 & 6048 | hypothetical protein |

TABLE 1-continued

Annotation of ORF00001 to ORF04995

| ORFnnnnn | SEQ ID NOs | Annotation |
|---|---|---|
| ORF03025 | 6049 & 6050 | Bbp13 |
| ORF03026 | 6051 & 6052 | gp11 |
| ORF03027 | 6053 & 6054 | Bbp20 |
| ORF03028 | 6055 & 6056 | conserved hypothetical protein |
| ORF03029 | 6057 & 6058 | Bbp16 |
| ORF03030 | 6059 & 6060 | gp08 |
| ORF03031 | 6061 & 6062 | Bbp18 |
| ORF03032 | 6063 & 6064 | hypothetical protein |
| ORF03033 | 6065 & 6066 | Bbp19 |
| ORF03034 | 6067 & 6068 | Bbp21 |
| ORF03035 | 6069 & 6070 | conserved hypothetical protein |
| ORF03036 | 6071 & 6072 | hypothetical protein |
| ORF03037 | 6073 & 6074 | hypothetical protein |
| ORF03038 | 6075 & 6076 | terminase large subunit |
| ORF03039 | 6077 & 6078 | conserved hypothetical protein |
| ORF03040 | 6079 & 6080 | putative repressor |
| ORF03041 | 6081 & 6082 | conserved hypothetical protein |
| ORF03042 | 6083 & 6084 | conserved hypothetical protein |
| ORF03043 | 6085 & 6086 | exonuclease VIII RecE [3.1.11.—] |
| ORF03044 | 6087 & 6088 | enterohemolysin 1 |
| ORF03045 | 6089 & 6090 | Prophage CP4-57 regulatory protein (AlpA) family |
| ORF03046 | 6091 & 6092 | conserved hypothetical protein |
| ORF03047 | 6093 & 6094 | adenine methylase |
| ORF03048 | 6095 & 6096 | adenine methylase |
| ORF03049 | 6097 & 6098 | integrase |
| ORF03050 | 6099 & 6100 | GMP synthase [glutamine-hydrolyzing] (Glutamineamidotransferase) (GMP synthetase) (glutamine-hydro) [6.3.5.2] |
| ORF03051 | 6101 & 6102 | inosine-5'-monophosphate dehydrogenase (guaB) [1.1.1.205] |
| ORF03052 | 6103 & 6104 | exodeoxyribonuclease VII, large subunit (xseA) [3.1.11.6] |
| ORF03053 | 6105 & 6106 | Aec4 precursor |
| ORF03054 | 6107 & 6108 | SinI homolog |
| ORF03055 | 6109 & 6110 | Aec1 precursor |
| ORF03056 | 6111 & 6112 | Protein of unknown function (DUF1407) superfamily |
| ORF03057 | 6113 & 6114 | predicted GTP-binding protein |
| ORF03058 | 6115 & 6116 | PQQ enzyme repeat domain protein [2.7.1.—] |
| ORF03059 | 6117 & 6118 | unnamed protein product |
| ORF03060 | 6119 & 6120 | histidyl-tRNA synthetase (hisS) [6.1.1.21] |
| ORF03061 | 6121 & 6122 | 4-hydroxy-3-methylbut-2-en-1-yl diphosphate synthase (ispG) [1.17.4.3] |
| ORF03062 | 6123 & 6124 | similar to [SwissProt Accession Number P27434] |
| ORF03063 | 6125 & 6126 | radical SAM enzyme, Cfr family |
| ORF03064 | 6127 & 6128 | Nucleoside diphosphate kinase (ndk) [2.7.4.6] |
| ORF03065 | 6129 & 6130 | penicillin-binding protein 1C (pbpC) |
| ORF03066 | 6131 & 6132 | Hypothetical lipoprotein yfhM precursor |
| ORF03067 | 6133 & 6134 | 3-mercaptopyruvate sulfurtransferase (AF109156) [2.8.1.1] |
| ORF03068 | 6135 & 6136 | enhanced serine sensitivity |
| ORF03069 | 6137 & 6138 | Cytosol aminopeptidase family, catalytic domain family |
| ORF03070 | 6139 & 6140 | Protein of unknown function (DUF528) superfamily |
| ORF03071 | 6141 & 6142 | ferredoxin, 2Fe—2S type, ISC system (fdx) |
| ORF03072 | 6143 & 6144 | Fe—S protein assembly chaperone HscA (hscA) |
| ORF03073 | 6145 & 6146 | Fe—S protein assembly co-chaperone HscB (hscB) |
| ORF03074 | 6147 & 6148 | iron-sulfur cluster assembly protein IscA (iscA) |
| ORF03075 | 6149 & 6150 | FeS cluster assembly scaffold IscU (iscU) |
| ORF03076 | 6151 & 6152 | cysteine desulfurase IscS (iscS) [4.4.1.—] |
| ORF03077 | 6153 & 6154 | iron-sulfur cluster assembly transcription factor IscR (iscR) |
| ORF03078 | 6155 & 6156 | RNA methyltransferase, TrmH family, group 1 |
| ORF03079 | 6157 & 6158 | Inositol-1-monophosphatase (IMPase) (Inositol-1-phosphatase) (I-1-Pase) (I-1-Pase) [3.1.3.25] |
| ORF03080 | 6159 & 6160 | conserved hypothetical protein |
| ORF03081 | 6161 & 6162 | MFS (major facilitator superfamily) transporter |
| ORF03082 | 6163 & 6164 | csiE |
| ORF03083 | 6165 & 6166 | DoxX subfamily, putative |
| ORF03084 | 6167 & 6168 | Aldose 1-epimerase superfamily |
| ORF03085 | 6169 & 6170 | oxidoreductase, zinc-binding dehydrogenase family superfamily [1.1.1.14] |
| ORF03086 | 6171 & 6172 | ribose ABC transporter, permease protein |
| ORF03087 | 6173 & 6174 | D-xylose ABC transporter, ATP-binding protein |
| ORF03088 | 6175 & 6176 | ribose ABC transporter, periplasmic ribose-binding protein, putative |
| ORF03089 | 6177 & 6178 | TPR Domain domain protein |
| ORF03090 | 6179 & 6180 | ROK family protein domain protein |
| ORF03091 | 6181 & 6182 | serine hydroxymethyltransferase (glyA) [2.1.2.1] |
| ORF03092 | 6183 & 6184 | dihydropteridine reductase (NOD) [1.5.1.34] |
| ORF03093 | 6185 & 6186 | Nitrogen regulatory protein P-II |
| ORF03094 | 6187 & 6188 | transcriptional regulatory protein |
| ORF03095 | 6189 & 6190 | unnamed protein product |
| ORF03096 | 6191 & 6192 | two-component system sensor kinase |
| ORF03097 | 6193 & 6194 | phosphoribosylformylglycinamidine synthase (purL) [6.3.5.3] |
| ORF03098 | 6195 & 6196 | transglycosylase, Slt family |

TABLE 1-continued

Annotation of ORF00001 to ORF04995

| ORFnnnnn | SEQ ID NOs | Annotation |
|---|---|---|
| ORF03099 | 6197 & 6198 | tRNA-specific adenosine deaminase [3.5.4.—] |
| ORF03100 | 6199 & 6200 | HAD superfamily (subfamily IF) hydrolase, YfhB (yfhb) |
| ORF03101 | 6201 & 6202 | Transcriptional regulator (membrane) |
| ORF03102 | 6203 & 6204 | NapF protein (fdx) |
| ORF03103 | 6205 & 6206 | holo-(acyl-carrier-protein) synthase (acpS) [2.7.8.7] |
| ORF03104 | 6207 & 6208 | pyridoxal phosphate biosynthetic protein PdxJ (pdxJ) |
| ORF03105 | 6209 & 6210 | DNA repair protein RecO (recO) |
| ORF03106 | 6211 & 6212 | GTP-binding protein Era (era) |
| ORF03107 | 6213 & 6214 | ribonuclease III (rnc) [3.1.26.3] |
| ORF03108 | 6215 & 6216 | signal peptidase I [similarity] (lep) [3.4.21.89] |
| ORF03109 | 6217 & 6218 | GTP-binding protein LepA (lepA) |
| ORF03110 | 6219 & 6220 | Sigma-E factor Regulatory protein rseC |
| ORF03111 | 6221 & 6222 | Sigma-E factor Regulatory protein rseB precursor (rseB) |
| ORF03112 | 6223 & 6224 | sigma-E factor, negative regulatory protein |
| ORF03113 | 6225 & 6226 | RNA polymerase sigma E (SIGMA) |
| ORF03114 | 6227 & 6228 | hypothetical protein |
| ORF03115 | 6229 & 6230 | unnamed protein product |
| ORF03116 | 6231 & 6232 | L-aspartate oxidase (nadB) [1.4.3.16] |
| ORF03117 | 6233 & 6234 | ATP-dependent RNA helicase (srmB) |
| ORF03118 | 6235 & 6236 | similar to [SwissProt Accession Number P33634] |
| ORF03119 | 6237 & 6238 | translocator protein, LysE family superfamily |
| ORF03120 | 6239 & 6240 | Protein yfiD |
| ORF03121 | 6241 & 6242 | uracil-DNA glycosylase (ung) [3.2.2.—] |
| ORF03122 | 6243 & 6244 | similar to [SwissProt Accession Number P33635] start codon is not identified yet |
| ORF03123 | 6245 & 6246 | hypothetical protein |
| ORF03124 | 6247 & 6248 | thioredoxin (trx) |
| ORF03125 | 6249 & 6250 | DTW domain protein |
| ORF03126 | 6251 & 6252 | Acyl-CoA synthetase (NDP forming) |
| ORF03127 | 6253 & 6254 | CDP-DIACYLGLYCEROL--SERINE O-PHOSPHATIDYLTRANSFERASE (EC 2.7.8.8) (PHOSPHATIDYLSERINE SYNTHASE). [2.7.8.8] |
| ORF03128 | 6255 & 6256 | lipoprotein, putative |
| ORF03129 | 6257 & 6258 | Alpha-ketoglutarate permease |
| ORF03130 | 6259 & 6260 | transposase |
| ORF03131 | 6261 & 6262 | transposase |
| ORF03132 | 6263 & 6264 | transposase |
| ORF03133 | 6265 & 6266 | hypothetical |
| ORF03134 | 6267 & 6268 | hypothetical protein |
| ORF03135 | 6269 & 6270 | heat shock protein [3.4.21.—] |
| ORF03136 | 6271 & 6272 | conserved hypothetical protein TIGR00726 |
| ORF03137 | 6273 & 6274 | ribosomal large subunit pseudouridine synthase D (sfhB) [4.2.1.70] |
| ORF03138 | 6275 & 6276 | unkown |
| ORF03139 | 6277 & 6278 | ribosomal subunit interface protein (yfiA) |
| ORF03140 | 6279 & 6280 | P-protein (PDT) [5.4.99.5] |
| ORF03141 | 6281 & 6282 | T-protein (PDH) [5.4.99.5] |
| ORF03142 | 6283 & 6284 | phospho-2-dehydro-3-deoxyheptonate aldolase [2.5.1.54] |
| ORF03143 | 6285 & 6286 | lipoprotein, putative |
| ORF03144 | 6287 & 6288 | conserved hypothetical protein |
| ORF03145 | 6289 & 6290 | similar to [SwissProt Accession Number P46139] |
| ORF03146 | 6291 & 6292 | unnamed protein product; unidentified reading frame (16K polypeptide) (aa 1-127) |
| ORF03147 | 6293 & 6294 | ribosomal protein L19 (rplS) |
| ORF03148 | 6295 & 6296 | tRNA (guanine-N1)-methyltransferase (trmD) [2.1.1.31] |
| ORF03149 | 6297 & 6298 | 16S rRNA processing protein RimM (rimM) |
| ORF03150 | 6299 & 6300 | 30S ribosomal protein S16 (rpS16) |
| ORF03151 | 6301 & 6302 | signal recognition particle protein (ffh) |
| ORF03152 | 6303 & 6304 | CorE |
| ORF03153 | 6305 & 6306 | unnamed protein product |
| ORF03154 | 6307 & 6308 | co-chaperone GrpE (grpE) |
| ORF03155 | 6309 & 6310 | NAD+ kinase [2.7.1.23] |
| ORF03156 | 6311 & 6312 | hypothetical protein |
| ORF03157 | 6313 & 6314 | DNA repair protein RecN (recN) |
| ORF03158 | 6315 & 6316 | Small protein A precursor |
| ORF03159 | 6317 & 6318 | Protein yfjF |
| ORF03160 | 6319 & 6320 | Streptomyces cyclase-dehydrase family |
| ORF03161 | 6321 & 6322 | SsrA-binding protein (smpB) |
| ORF03162 | 6323 & 6324 | hypothetical protein |
| ORF03163 | 6325 & 6326 | conserved hypothetical protein |
| ORF03164 | 6327 & 6328 | DinI-like protein Z3916-ECs3483 (AF175466) |
| ORF03165 | 6329 & 6330 | T4-exclusion protein stimulator gIBEGs |
| ORF03166 | 6331 & 6332 | ycfE protein (fragment) |
| ORF03167 | 6333 & 6334 | unnamed protein product; unidentified reading frame P-293 |
| ORF03168 | 6335 & 6336 | heat shock protein [3.4.21.—] |
| ORF03169 | 6337 & 6338 | heat shock protein [3.4.21.—] |
| ORF03170 | 6339 & 6340 | conserved hypothetical protein |
| ORF03171 | 6341 & 6342 | Sb36 |
| ORF03172 | 6343 & 6344 | conserved hypothetical protein |
| ORF03173 | 6345 & 6346 | hypothetical protein |

TABLE 1-continued

Annotation of ORF00001 to ORF04995

| ORFnnnnn | SEQ ID NOs | Annotation |
|---|---|---|
| ORF03174 | 6347 & 6348 | conserved hypothetical protein |
| ORF03175 | 6349 & 6350 | unnamed protein product |
| ORF03176 | 6351 & 6352 | hypothetical protein |
| ORF03177 | 6353 & 6354 | gab protein |
| ORF03178 | 6355 & 6356 | predicted dehydrogenase |
| ORF03179 | 6357 & 6358 | Succinate-semialdehyde dehydrogenase [NADP+] [1.2.1.16] |
| ORF03180 | 6359 & 6360 | 4-aminobutyrate transaminase (gabT) [2.6.1.19] |
| ORF03181 | 6361 & 6362 | GABA permease (gabP) |
| ORF03182 | 6363 & 6364 | transcriptional regulator, GntR family, putative |
| ORF03183 | 6365 & 6366 | Putative phospholipid-binding domain family |
| ORF03184 | 6367 & 6368 | Hypothetical UPF0057 protein yqaE-related protein |
| ORF03185 | 6369 & 6370 | transcriptional regulator, ArsR family (AJ001934) |
| ORF03186 | 6371 & 6372 | rhodanese family protein, putative |
| ORF03187 | 6373 & 6374 | DNA-binding protein stpA |
| ORF03188 | 6375 & 6376 | Protein of unknown function (DUF1144) superfamily |
| ORF03189 | 6377 & 6378 | similar to [SwissProt Accession Number P36931] start codon is not identified yet |
| ORF03190 | 6379 & 6380 | unnamed protein product; ORFA |
| ORF03191 | 6381 & 6382 | GntR-family transcriptional regulator (X78503) |
| ORF03192 | 6383 & 6384 | Uncharacterized ACR |
| ORF03193 | 6385 & 6386 | nrdH-related protein |
| ORF03194 | 6387 & 6388 | nrdI protein (nrdI) |
| ORF03195 | 6389 & 6390 | ribonucleoside-diphosphate reductase alpha chain |
| ORF03196 | 6391 & 6392 | ribonucleoside-diphosphate reductase, beta subunit [1.17.4.1] |
| ORF03197 | 6393 & 6394 | ATP-binding component of transport system for glycine, betaine and proline (atp_bind) |
| ORF03198 | 6395 & 6396 | Glycine betaine-L-proline transport system permease protein proW (membrane) |
| ORF03199 | 6397 & 6398 | high-affinity glycine betaine - proline transport system |
| ORF03200 | 6399 & 6400 | major facilitator family transporter (permease) |
| ORF03201 | 6401 & 6402 | AzlC family protein, putative |
| ORF03202 | 6403 & 6404 | YgaH protein |
| ORF03203 | 6405 & 6406 | Transcriptional repressor mprA (EmrR protein) |
| ORF03204 | 6407 & 6408 | Multidrug resistance protein A |
| ORF03205 | 6409 & 6410 | Multidrug resistance protein B |
| ORF03206 | 6411 & 6412 | conserved hypothetical protein |
| ORF03207 | 6413 & 6414 | conserved hypothetical protein |
| ORF03208 | 6415 & 6416 | autoinducer-2 production protein LuxS (luxS) |
| ORF03209 | 6417 & 6418 | glutamate--cysteine ligase (gshA) [6.3.2.2] |
| ORF03210 | 6419 & 6420 | gamma-glutamate-cysteine ligase (GCS) |
| ORF03211 | 6421 & 6422 | conserved hypothetical protein |
| ORF03212 | 6423 & 6424 | CbbY family protein VCA0662 (pgp) |
| ORF03213 | 6425 & 6426 | carbon storage regulator (csrA) |
| ORF03214 | 6427 & 6428 | alanyl-tRNA synthetase (alaS) [6.1.1.7] |
| ORF03215 | 6429 & 6430 | Regulatory protein recX (oraA protein) (recX) |
| ORF03216 | 6431 & 6432 | recA protein (recA) |
| ORF03217 | 6433 & 6434 | Protein ygaD |
| ORF03218 | 6435 & 6436 | Membrane-bound lytic murein transglycosylase B precursor |
| ORF03219 | 6437 & 6438 | PTS SYSTEM, GLUCITOL-SORBITOL-SPECIFIC IIBC COMPONENT (EIIBC-GUT) (GLUCITOL-SORBITOL-PERMEASE IIBC COMPONENT) (PHOSPHOTRANSFERASE ENZYME II, BC COMPONENT) (EC 2.7.1.69) (EII-GUT) [2.7.1.69] |
| ORF03220 | 6439 & 6440 | PTS SYSTEM, GLUCITOL-SORBITOL-SPECIFIC IIBC COMPONENT (EIIBC-GUT) (GLUCITOL-SORBITOL-PERMEASE IIBC COMPONENT) (PHOSPHOTRANSFERASE ENZYME II, BC COMPONENT) (EC 2.7.1.69) (EII-GUT) [2.7.1.69] |
| ORF03221 | 6441 & 6442 | PTS enzyme III glucitol [2.7.1.69] |
| ORF03222 | 6443 & 6444 | 3-oxoacyl-(acyl-carrier-protein) reductase (sorbitol) [1.1.1.140] |
| ORF03223 | 6445 & 6446 | Glucitol operon activator protein (gutM) |
| ORF03224 | 6447 & 6448 | Glucitol operon repressor (sri) |
| ORF03225 | 6449 & 6450 | GutQ protein |
| ORF03226 | 6451 & 6452 | ygaA protein (fhlA) |
| ORF03227 | 6453 & 6454 | Anaerobic nitric oxide reductase flavorubredoxin (FlRd) (FlavoRb) (fprA) [1.—.—.—] |
| ORF03228 | 6455 & 6456 | Nitric oxide reductase FlRd-NAD(+) reductase(Flavorubredoxin reductase) (FlRd-reductase) (FlavoRb reductase) (FAD) [1.18.1.—] |
| ORF03229 | 6457 & 6458 | [NiFe] hydrogenase maturation protein HypF (hypF) |
| ORF03230 | 6459 & 6460 | Electron transport protein hydN |
| ORF03231 | 6461 & 6462 | hypothetical protein |
| ORF03232 | 6463 & 6464 | ascBF operon repressor |
| ORF03233 | 6465 & 6466 | PTS system enzyme II ABC (asc) [2.7.1.69] |
| ORF03234 | 6467 & 6468 | 6-phospho-beta-glucosidase [3.2.1.86] |
| ORF03235 | 6469 & 6470 | unnamed protein product |
| ORF03236 | 6471 & 6472 | conserved hypothetical protein |
| ORF03237 | 6473 & 6474 | hydrogenase maturation protease HycI |
| ORF03238 | 6475 & 6476 | Formate hydrogenlyase maturation protein hycH (HycE) [1.—.—.—] |
| ORF03239 | 6477 & 6478 | Formate hydrogenlyase subunit 7 [1.18.99.1] |
| ORF03240 | 6479 & 6480 | Formate hydrogenlyase subunit 6 [1.18.99.1] |
| ORF03241 | 6481 & 6482 | hydrogenase 3 large subunit [1.18.99.1] |

TABLE 1-continued

Annotation of ORF00001 to ORF04995

| ORFnnnnn | SEQ ID NOs | Annotation |
|---|---|---|
| ORF03242 | 6483 & 6484 | Formate hydrogenlyase subunit 4 (hycD) [1.18.99.1] |
| ORF03243 | 6485 & 6486 | Formate hydrogenlyase subunit 3 (FHL subunit 3) (Hydrogenase-3component C) [1.18.99.1] |
| ORF03244 | 6487 & 6488 | formate hydrogenlyase subunit-7 component B (FHL) |
| ORF03245 | 6489 & 6490 | Formate hydrogenlyase regulatory protein hycA |
| ORF03246 | 6491 & 6492 | hydrogenase nickel insertion protein HypA (hypA) |
| ORF03247 | 6493 & 6494 | hydrogenase accessory protein HypB |
| ORF03248 | 6495 & 6496 | hydrogenase assembly chaperone HypC-HupF (hypC) |
| ORF03249 | 6497 & 6498 | hydrogenase expression-formation protein HypD (hypD) |
| ORF03250 | 6499 & 6500 | hydrogenase expression-formation protein HypE (hypE) |
| ORF03251 | 6501 & 6502 | Formate hydrogenlyase transcriptional activator |
| ORF03252 | 6503 & 6504 | Potential molybdenum-pterin-binding-protein |
| ORF03253 | 6505 & 6506 | conserved hypothetical protein |
| ORF03254 | 6507 & 6508 | DNA mismatch repair protein MutS (mutS) |
| ORF03255 | 6509 & 6510 | Serine-threonine protein phosphatase 2 [3.1.3.16] |
| ORF03256 | 6511 & 6512 | Transcriptional regulator of sugar metabolism |
| ORF03257 | 6513 & 6514 | 3-hydroxyisobutyrate dehydrogenase [1.1.—.—] |
| ORF03258 | 6515 & 6516 | tRNA synthase-like protein |
| ORF03259 | 6517 & 6518 | L-fuculose-1-phosphate aldolase-like protein (fucA) [4.1.2.17] |
| ORF03260 | 6519 & 6520 | Hfi protein [5.3.1.22] |
| ORF03261 | 6521 & 6522 | gluconate permease |
| ORF03262 | 6523 & 6524 | metallo-beta-lactamase superfamily domain protein |
| ORF03263 | 6525 & 6526 | tryptophan repressor binding protein |
| ORF03264 | 6527 & 6528 | sigma factor RpoS (sigma38) |
| ORF03265 | 6529 & 6530 | sigma factor RpoS (sigma38) |
| ORF03266 | 6531 & 6532 | Lipoprotein nlpD precursor |
| ORF03267 | 6533 & 6534 | protein-L-isoaspartate O-methyltransferase (pcm) [2.1.1.77] |
| ORF03268 | 6535 & 6536 | acid phosphatase SurE (surE) [3.1.3.2] |
| ORF03269 | 6537 & 6538 | conserved hypothetical protein TIGR00094 |
| ORF03270 | 6539 & 6540 | 2C-methyl-D-erythritol 2,4-cyclodiphosphate synthase (ispF) [4.6.1.12] |
| ORF03271 | 6541 & 6542 | 2-C-methyl-D-erythritol 4-phosphate cytidylyltransferase (ispD) [2.7.7.60] |
| ORF03272 | 6543 & 6544 | Cell division protein ftsB |
| ORF03273 | 6545 & 6546 | YgbE |
| ORF03274 | 6547 & 6548 | adenylylsulfate kinase (cysC) [2.7.1.25] |
| ORF03275 | 6549 & 6550 | Sulfate adenylyltransferase subunit 1 (Sulfate adenylatetransferase) (SAT) (ATP-sulfurylase large subunit) (SAT) [2.7.7.4] |
| ORF03276 | 6551 & 6552 | Sulfate adenylyltransferase subunit 2 (Sulfate adenylatetransferase) (SAT) (ATP-sulfurylase small subunit) (SAT) [2.7.7.4] |
| ORF03277 | 6553 & 6554 | hypothetical protein |
| ORF03278 | 6555 & 6556 | Alkaline phosphatase isozyme conversion protein precursor [3.4.11.—] |
| ORF03279 | 6557 & 6558 | Hok-gef family superfamily |
| ORF03280 | 6559 & 6560 | 3-phosphoadenosine 5-phosphosulfate reductase |
| ORF03281 | 6561 & 6562 | sulfite reductase (NADPH) hemoprotein, beta subunit (cysI) [1.8.1.2] |
| ORF03282 | 6563 & 6564 | sulfite reductase [NADPH] flavoprotein, alpha chain [1.8.1.2] |
| ORF03283 | 6565 & 6566 | 6-pyruvoyl-tetrahydropterin synthase |
| ORF03284 | 6567 & 6568 | Probable electron transfer flavoprotein-quinone oxidoreductase ygcN |
| ORF03285 | 6569 & 6570 | Ferredoxin-like protein ygcO |
| ORF03286 | 6571 & 6572 | glycerol uptake operon antiterminator regulatory protein, putative |
| ORF03287 | 6573 & 6574 | electron transfer flavoprotein, alpha subunit subfamily (etfA) |
| ORF03288 | 6575 & 6576 | putative transport protein |
| ORF03289 | 6577 & 6578 | sugar transporter, putative |
| ORF03290 | 6579 & 6580 | alkyl-dihydroxyacetonephosphate synthase, putative |
| ORF03291 | 6581 & 6582 | 1.—.—.—[1.1.1.—] |
| ORF03292 | 6583 & 6584 | Major Facilitator Superfamily subfamily |
| ORF03293 | 6585 & 6586 | sugar kinase, FGGY family, putative [2.7.1.17] |
| ORF03294 | 6587 & 6588 | radical activating enzyme |
| ORF03295 | 6589 & 6590 | radical activating enzyme |
| ORF03296 | 6591 & 6592 | LemA family superfamily |
| ORF03297 | 6593 & 6594 | glycine rich protein |
| ORF03298 | 6595 & 6596 | conserved hypothetical protein |
| ORF03299 | 6597 & 6598 | Domain of unknown function (DUF477) family |
| ORF03300 | 6599 & 6600 | glycine rich protein |
| ORF03301 | 6601 & 6602 | enolase (eno) [4.2.1.11] |
| ORF03302 | 6603 & 6604 | CTP synthase (pyrG) [6.3.4.2] |
| ORF03303 | 6605 & 6606 | MazG protein (mazG) |
| ORF03304 | 6607 & 6608 | PemK-like protein 1 (MazF protein) (AF027767) |
| ORF03305 | 6609 & 6610 | PemI-like protein 1 (MazE protein) |
| ORF03306 | 6611 & 6612 | GTP pyrophosphokinase (ATP: GTP 3'-pyrophosphotransferase)(ppGpp synthetase I) ((p)ppGpp synthetase) (relA) [2.7.6.5] |
| ORF03307 | 6613 & 6614 | 23S rRNA (uracil-5-)-methyltransferase RumA (rumA) [2.1.1.—] |
| ORF03308 | 6615 & 6616 | Sensor protein barA [2.7.3.—] |
| ORF03309 | 6617 & 6618 | hypothetical protein |
| ORF03310 | 6619 & 6620 | glucarate dehydratase [4.2.1.40] |
| ORF03311 | 6621 & 6622 | glucarate dehydratase [4.2.1.—] |
| ORF03312 | 6623 & 6624 | MFS transporter, phthalate permease family |
| ORF03313 | 6625 & 6626 | Exoenzyme regulation regulon (mioC) |

TABLE 1-continued

Annotation of ORF00001 to ORF04995

| ORFnnnnn | SEQ ID NOs | Annotation |
|---|---|---|
| ORF03314 | 6627 & 6628 | RNA pseudouridylate synthase family protein [4.2.1.70] |
| ORF03315 | 6629 & 6630 | tRNA pseudouridine synthase C (Pseudouridylate synthase)(Uracil hydrolyase) [4.2.1.70] |
| ORF03316 | 6631 & 6632 | interacts with secY |
| ORF03317 | 6633 & 6634 | hypothetical protein |
| ORF03318 | 6635 & 6636 | GTP cyclohydrolase I-like protein |
| ORF03319 | 6637 & 6638 | Predicted Rossmann fold nucleotide-binding protein |
| ORF03320 | 6639 & 6640 | Serine transporter |
| ORF03321 | 6641 & 6642 | L-serine ammonia-lyase (sdaA) [4.3.1.17] |
| ORF03322 | 6643 & 6644 | exodeoxyribonuclease IX |
| ORF03323 | 6645 & 6646 | Lactaldehyde reductase [1.1.1.77] |
| ORF03324 | 6647 & 6648 | L-fuculose phosphate aldolase (fucA) [4.1.2.17] |
| ORF03325 | 6649 & 6650 | conserved hypothetical protein |
| ORF03326 | 6651 & 6652 | L-fucose permease (fucP) |
| ORF03327 | 6653 & 6654 | L-fucose isomerase (fucI) [5.3.1.25] |
| ORF03328 | 6655 & 6656 | L-fuculokinase (L-fuculose kinase) (fucK) [2.7.1.51] |
| ORF03329 | 6657 & 6658 | Fucose operon fucU protein (fucU) |
| ORF03330 | 6659 & 6660 | hypothetical protein |
| ORF03331 | 6661 & 6662 | L-fucose operon activator |
| ORF03332 | 6663 & 6664 | SAM-dependent methyltransferase-like protein |
| ORF03333 | 6665 & 6666 | Uncharacterized small membrane protein |
| ORF03334 | 6667 & 6668 | transcriptional regulator, LysR family (gcvA) |
| ORF03335 | 6669 & 6670 | Bacterial protein of unknown function (DUF903) superfamily |
| ORF03336 | 6671 & 6672 | Cysteine sulfinate desulfinase |
| ORF03337 | 6673 & 6674 | Fe—S metabolism associated domain subfamily |
| ORF03338 | 6675 & 6676 | Dinucleotide-utilizing enzymes involved in molybdopterin and thiamine biosynthesis family 1 |
| ORF03339 | 6677 & 6678 | Membrane-bound lytic murein transglycosylase A precursor |
| ORF03340 | 6679 & 6680 | Protein of unknown function (DUF770) superfamily |
| ORF03341 | 6681 & 6682 | Aec18 |
| ORF03342 | 6683 & 6684 | Bacterial protein of unknown function (DUF876) superfamily |
| ORF03343 | 6685 & 6686 | Possibly conserved membrane protein |
| ORF03344 | 6687 & 6688 | unnamed protein product |
| ORF03345 | 6689 & 6690 | Secreted protein Hcp |
| ORF03346 | 6691 & 6692 | ClpB protein |
| ORF03347 | 6693 & 6694 | Rhs element Vgr protein subfamily, putative |
| ORF03348 | 6695 & 6696 | unnamed protein product; Similar to unknown protein |
| ORF03349 | 6697 & 6698 | unnamed protein product; Highly similar to unknown protein of Photorhabdus. Putative secreted protein, putative |
| ORF03350 | 6699 & 6700 | unnamed protein product |
| ORF03351 | 6701 & 6702 | unnamed protein product |
| ORF03352 | 6703 & 6704 | ImpA-related N-terminal family |
| ORF03353 | 6705 & 6706 | conserved hypothetical protein |
| ORF03354 | 6707 & 6708 | hypothetical protein |
| ORF03355 | 6709 & 6710 | Bacterial protein of unknown function (DUF879) superfamily |
| ORF03356 | 6711 & 6712 | Protein of unknown function (DUF1305) superfamily |
| ORF03357 | 6713 & 6714 | lipoprotein, putative |
| ORF03358 | 6715 & 6716 | Protein of unknown function (DUF1316) subfamily |
| ORF03359 | 6717 & 6718 | conserved hypothetical protein |
| ORF03360 | 6719 & 6720 | ImpA-related N-terminal family |
| ORF03361 | 6721 & 6722 | 2-hydroxyacid dehydrogenase (serA) |
| ORF03362 | 6723 & 6724 | Phosphosugar isomerase |
| ORF03363 | 6725 & 6726 | Beta-cystathionase |
| ORF03364 | 6727 & 6728 | PTS system, IIBC components, putative [2.7.1.69] |
| ORF03365 | 6729 & 6730 | Antiterminator |
| ORF03366 | 6731 & 6732 | N-acetylmuramoyl-L-alanine amidase amiC precursor [3.5.1.28] |
| ORF03367 | 6733 & 6734 | amino-acid N-acetyltransferase (argA) [2.3.1.1] |
| ORF03368 | 6735 & 6736 | exodeoxyribonuclease V, alpha subunit (recD) [3.1.11.5] |
| ORF03369 | 6737 & 6738 | exodeoxyribonuclease V, beta subunit (recB) [3.1.11.5] |
| ORF03370 | 6739 & 6740 | Protease III precursor (Pitrilysin) (Protease pi) (pitrilysin) [3.4.24.55] |
| ORF03371 | 6741 & 6742 | exodeoxyribonuclease V, gamma subunit (recC) [3.1.11.5] |
| ORF03372 | 6743 & 6744 | Prepilin peptidase dependent protein C precursor |
| ORF03373 | 6745 & 6746 | conserved hypothetical protein |
| ORF03374 | 6747 & 6748 | unnamed protein product; URF1 (aa 1-267) |
| ORF03375 | 6749 & 6750 | Prepilin peptidase dependent protein A precursor |
| ORF03376 | 6751 & 6752 | thymidylate synthase (thyA) [2.1.1.45] |
| ORF03377 | 6753 & 6754 | prolipoprotein diacylglyceryl transferase (lgt) [2.4.99.—] |
| ORF03378 | 6755 & 6756 | Phosphoenolpyruvate-protein phosphotransferase ptsP (Ntr) [2.7.3.9] |
| ORF03379 | 6757 & 6758 | NTP pyrophosphohydrolases including oxidative damage repair enzymes |
| ORF03380 | 6759 & 6760 | DNA mismatch repair endonuclease mutH (mutH) |
| ORF03381 | 6761 & 6762 | TerC protein |
| ORF03382 | 6763 & 6764 | lipoprotein |
| ORF03383 | 6765 & 6766 | Tas protein |
| ORF03384 | 6767 & 6768 | unnamed protein product |
| ORF03385 | 6769 & 6770 | AAS bifunctional protein |
| ORF03386 | 6771 & 6772 | Galactose operon repressor |

TABLE 1-continued

Annotation of ORF00001 to ORF04995

| ORFnnnnn | SEQ ID NOs | Annotation |
|---|---|---|
| ORF03387 | 6773 & 6774 | diaminopimelate decarboxylase (lysA) [4.1.1.20] |
| ORF03388 | 6775 & 6776 | aspartate racemase subfamily [5.1.1.13] |
| ORF03389 | 6777 & 6778 | Transcriptional activator protein lysR |
| ORF03390 | 6779 & 6780 | Arabinose-proton symporter |
| ORF03391 | 6781 & 6782 | 2-deoxy-D-gluconate 3-dehydrogenase (kduD) [1.1.1.125] |
| ORF03392 | 6783 & 6784 | 4-deoxy-L-threo-5-hexosulose-uronate ketol-isomerase |
| ORF03393 | 6785 & 6786 | Probable acetyl-CoA acetyltransferase |
| ORF03394 | 6787 & 6788 | serine transporter |
| ORF03395 | 6789 & 6790 | possible lipoprotein |
| ORF03396 | 6791 & 6792 | aldehyde oxidoreductase, putative [1.1.1.204] |
| ORF03397 | 6793 & 6794 | Xanthine dehydrogenase, FAD binding subunit (cutB) [1.1.1.204] |
| ORF03398 | 6795 & 6796 | small chain CO dehydrogenase (cutC) |
| ORF03399 | 6797 & 6798 | signal-transduction and transcriptional-control protein |
| ORF03400 | 6799 & 6800 | hypothetical protein |
| ORF03401 | 6801 & 6802 | Aspartate-ornithine carbamoyltransferase, Asp-Orn binding domain family |
| ORF03402 | 6803 & 6804 | threonine dehydratase biosynthetic [4.3.1.15] |
| ORF03403 | 6805 & 6806 | acetylornithine deacetylase, putative |
| ORF03404 | 6807 & 6808 | dihydropyrimidinase (hydA) [3.5.2.2] |
| ORF03405 | 6809 & 6810 | carbamate kinase (arcC) [2.7.2.2] |
| ORF03406 | 6811 & 6812 | xanthine dehydrogenase accessory factor, putative subfamily, putative |
| ORF03407 | 6813 & 6814 | conserved hypothetical protein |
| ORF03408 | 6815 & 6816 | hypotehtical ygfJ |
| ORF03409 | 6817 & 6818 | oxidoreductase, pyridine nucleotide-disulfide family |
| ORF03410 | 6819 & 6820 | chlorohydrolase family protein, putative |
| ORF03411 | 6821 & 6822 | FAD binding domain in molybdopterin dehydrogenase protein |
| ORF03412 | 6823 & 6824 | aldehyde oxidoreductase, putative [1.—.—.—] |
| ORF03413 | 6825 & 6826 | xanthine-urcil permease family protein |
| ORF03414 | 6827 & 6828 | Guanine deaminase |
| ORF03415 | 6829 & 6830 | xanthine-uracil permease family protein |
| ORF03416 | 6831 & 6832 | Electron transport protein hydN |
| ORF03417 | 6833 & 6834 | anaerobically expressed oxidoreductase (GltD) [1.4.1.13] |
| ORF03418 | 6835 & 6836 | xanthine permease |
| ORF03419 | 6837 & 6838 | isopentenyl-diphosphate delta-isomerase, type 1 (idi) [5.3.3.2] |
| ORF03420 | 6839 & 6840 | Iysyl-tRNA synthetase (IysS) [6.1.1.6] |
| ORF03421 | 6841 & 6842 | peptide chain release factor 2 (prfB) |
| ORF03422 | 6843 & 6844 | single-stranded-DNA-specific exonuclease RecJ (recJ) [3.1.—.—] |
| ORF03423 | 6845 & 6846 | Thiol:disulfide interchange protein dsbC precursor (DsbC) [5.3.4.1] |
| ORF03424 | 6847 & 6848 | tyrosine recombinase XerD (xerD) |
| ORF03425 | 6849 & 6850 | flavodoxin |
| ORF03426 | 6851 & 6852 | unnamed protein product |
| ORF03427 | 6853 & 6854 | Uncharacterized conserved protein |
| ORF03428 | 6855 & 6856 | Predicted aminomethyltransferase |
| ORF03429 | 6857 & 6858 | similar to hemolysin III homolog |
| ORF03430 | 6859 & 6860 | UPF0267 protein |
| ORF03431 | 6861 & 6862 | 6-phospho-beta-glucosidase |
| ORF03432 | 6863 & 6864 | glycine dehydrogenase (gcvP) [1.4.4.2] |
| ORF03433 | 6865 & 6866 | glycine cleavage system H protein (gcvH) |
| ORF03434 | 6867 & 6868 | glycine cleavage system T protein (gcvT) [2.1.2.10] |
| ORF03435 | 6869 & 6870 | Protein visC [1.—.—.—] |
| ORF03436 | 6871 & 6872 | 2-polyprenyl-6-methoxyphenol 4-hydroxylase (ubiH) [1.14.13.—] |
| ORF03437 | 6873 & 6874 | Xaa-Pro aminopeptidase (APP-II) [3.4.11.9] |
| ORF03438 | 6875 & 6876 | yecA family protein subfamily |
| ORF03439 | 6877 & 6878 | Family of unknown function (DUF710) superfamily |
| ORF03440 | 6879 & 6880 | 5-formyltetrahydrofolate cyclo-ligase family protein, putative |
| ORF03441 | 6881 & 6882 | D-3-phosphoglycerate dehydrogenase [1.1.1.95] |
| ORF03442 | 6883 & 6884 | ribose 5-phosphate isomerase A (rpiA) [5.3.1.6] |
| ORF03443 | 6885 & 6886 | conserved hypothetical protein |
| ORF03444 | 6887 & 6888 | Chromosome initiation inhibitor |
| ORF03445 | 6889 & 6890 | unnamed protein product; sbm orf (MCM) |
| ORF03446 | 6891 & 6892 | putative transcriptional regulator LYSR-type |
| ORF03447 | 6893 & 6894 | IpgG, putative |
| ORF03448 | 6895 & 6896 | possible membrane transport protein |
| ORF03449 | 6897 & 6898 | small-conductance mechanosensitive channel |
| ORF03450 | 6899 & 6900 | fructose-bisphosphate aldolase, class II (fbaA) [4.1.2.13] |
| ORF03451 | 6901 & 6902 | phosphoglycerate kinase (pgk) [2.7.2.3] |
| ORF03452 | 6903 & 6904 | D-erythrose-4-phosphate dehydrogenase (epd) [1.2.1.—] |
| ORF03453 | 6905 & 6906 | hypothetical protein |
| ORF03454 | 6907 & 6908 | Domain of unknown function (DUF296) family |
| ORF03455 | 6909 & 6910 | conserved hypothetical protein |
| ORF03456 | 6911 & 6912 | conserved hypothetical protein |
| ORF03457 | 6913 & 6914 | ABC transporter, ATP-binding protein |
| ORF03458 | 6915 & 6916 | kinase-related protein |
| ORF03459 | 6917 & 6918 | Cobalt transport ATP-binding protein cbiO |
| ORF03460 | 6919 & 6920 | unnamed protein product; ORF2 (AA 1-133) |
| ORF03461 | 6921 & 6922 | fructose-1,6-bisphosphatase, class II |
| ORF03462 | 6923 & 6924 | Putative oxidoreductase |

TABLE 1-continued

Annotation of ORF00001 to ORF04995

| ORFnnnnn | SEQ ID NOs | Annotation |
|---|---|---|
| ORF03463 | 6925 & 6926 | PTS system, mannitol (Cryptic) [2.7.1.69] |
| ORF03464 | 6927 & 6928 | PTS system, mannitol (Cryptic)-specific IIA component (EIIA-(C)Mtl)(Mannitol (Cryptic)-permease IIA component) (Phosphotranferase enzymeII, A component) (Cryptic) [2.7.1.69] |
| ORF03465 | 6929 & 6930 | putative serine protease |
| ORF03466 | 6931 & 6932 | transketolase (tkt) [2.2.1.1] |
| ORF03467 | 6933 & 6934 | Putative metalloprotease yggG |
| ORF03468 | 6935 & 6936 | agmatinase, putative [3.5.3.11] |
| ORF03469 | 6937 & 6938 | lipoprotein, putative |
| ORF03470 | 6939 & 6940 | arginine decarboxylase (speA) [4.1.1.19] |
| ORF03471 | 6941 & 6942 | conserved hypothetical protein |
| ORF03472 | 6943 & 6944 | conserved hypothetical protein |
| ORF03473 | 6945 & 6946 | S-adenosylmethionine synthetase (metK) [2.5.1.6] |
| ORF03474 | 6947 & 6948 | Galactose-proton symporter |
| ORF03475 | 6949 & 6950 | Protein sprT |
| ORF03476 | 6951 & 6952 | Endonuclease I precursor |
| ORF03477 | 6953 & 6954 | conserved hypothetical protein TIGR00046 |
| ORF03478 | 6955 & 6956 | glutathione synthase (gshB) [6.3.2.3] |
| ORF03479 | 6957 & 6958 | Uncharacterized ACR, COG1678 |
| ORF03480 | 6959 & 6960 | conserved hypothetical protein TIGR00250 |
| ORF03481 | 6961 & 6962 | Predicted ATPases involved in pili biogenesis, PilT homologs |
| ORF03482 | 6963 & 6964 | conserved hypothetical protein TIGR00044 |
| ORF03483 | 6965 & 6966 | Predicted integral membrane protein |
| ORF03484 | 6967 & 6968 | conserved hypothetical protein TIGR00251 |
| ORF03485 | 6969 & 6970 | non-canonical purine NTP pyrophosphatase, rdgB-HAM1 family (rdgB) |
| ORF03486 | 6971 & 6972 | oxygen-independent coproporphyrinogen III oxidase, putative |
| ORF03487 | 6973 & 6974 | Protein of unknown function (DUF1202) superfamily |
| ORF03488 | 6975 & 6976 | L-asparaginase II (ansB) [3.5.1.1] |
| ORF03489 | 6977 & 6978 | conserved hypothetical protein |
| ORF03490 | 6979 & 6980 | conserved hypothetical protein |
| ORF03491 | 6981 & 6982 | Protein |
| ORF03492 | 6983 & 6984 | tRNA (guanine-N(7)-)-methyltransferase (tRNA(m7G46)-methyltransferase) [2.1.1.33] |
| ORF03493 | 6985 & 6986 | A-G-specific adenine glycosylase |
| ORF03494 | 6987 & 6988 | Protein yggX |
| ORF03495 | 6989 & 6990 | yggZ protein (mltC) [3.2.1.—] |
| ORF03496 | 6991 & 6992 | nucleoside permease NupG |
| ORF03497 | 6993 & 6994 | ornithine decarboxylase isozyme (speC) [4.1.1.17] |
| ORF03498 | 6995 & 6996 | integral membrane protein |
| ORF03499 | 6997 & 6998 | transposase, truncated |
| ORF03500 | 6999 & 7000 | KpsF |
| ORF03501 | 7001 & 7002 | Capsule polysaccharide export inner-membrane protein kpsE |
| ORF03502 | 7003 & 7004 | polysaccharide biosynthesis protein, putative |
| ORF03503 | 7005 & 7006 | 3-deoxy-D-manno-octulosonate cytidylyltransferase (kdsB) [2.7.7.38] |
| ORF03504 | 7007 & 7008 | capsule polysaccharide export protein kpsC |
| ORF03505 | 7009 & 7010 | KpsS protein |
| ORF03506 | 7011 & 7012 | polysialic acid capsule biosynthesis protein SiaD, truncation; disrupted by foreign ermC, putative [2.4.—.—] |
| ORF03507 | 7013 & 7014 | NeuE protein |
| ORF03508 | 7015 & 7016 | UDP-N-acetylglucosamine 2-epimerase [5.1.3.14] |
| ORF03509 | 7017 & 7018 | acylneuraminate cytidylyltransferase, putative [2.7.7.43] |
| ORF03510 | 7019 & 7020 | neuB protein [4.1.3.—] |
| ORF03511 | 7021 & 7022 | Polysialic acid transport ATP-binding protein kpsT [3.6.3.38] |
| ORF03512 | 7023 & 7024 | Polysialic acid transport protein kpsM |
| ORF03513 | 7025 & 7026 | Putative general secretion pathway protein M-type yghD |
| ORF03514 | 7027 & 7028 | general secretion pathway protein L (gspL) |
| ORF03515 | 7029 & 7030 | General secretion pathway protein K (gspK) |
| ORF03516 | 7031 & 7032 | general secretion pathway protein J (gspJ) |
| ORF03517 | 7033 & 7034 | general secretion pathway protein I (gspI) |
| ORF03518 | 7035 & 7036 | GspH, hypothetical type II secretion protein |
| ORF03519 | 7037 & 7038 | general secretion pathway protein G (gspG) |
| ORF03520 | 7039 & 7040 | general secretion pathway protein F (gspF) |
| ORF03521 | 7041 & 7042 | general secretion pathway protein E (GSP) |
| ORF03522 | 7043 & 7044 | type II secretory pathway, component EpsD |
| ORF03523 | 7045 & 7046 | general secretion pathway protein C (gspC) |
| ORF03524 | 7047 & 7048 | YghG protein |
| ORF03525 | 7049 & 7050 | secretion protein b2972 [3.4.23.43] |
| ORF03526 | 7051 & 7052 | Accessory colonization factor AcfD precursor |
| ORF03527 | 7053 & 7054 | Glycolate permease glcA |
| ORF03528 | 7055 & 7056 | malate synthase G (glcB) [2.3.3.9] |
| ORF03529 | 7057 & 7058 | glcG protein |
| ORF03530 | 7059 & 7060 | glycolate oxidase subunits GlcE and GlcF (Fe—S) [1.1.3.15] |
| ORF03531 | 7061 & 7062 | glycolate oxidase subunits GlcE and GlcF |
| ORF03532 | 7063 & 7064 | glycolate oxidase, subunit GlcD (glcD) |
| ORF03533 | 7065 & 7066 | Glc operon transcriptional activator |
| ORF03534 | 7067 & 7068 | conserved hypothetical protein |

TABLE 1-continued

Annotation of ORF00001 to ORF04995

| ORFnnnnn | SEQ ID NOs | Annotation |
| --- | --- | --- |
| ORF03535 | 7069 & 7070 | acyl-CoA synthase |
| ORF03536 | 7071 & 7072 | conserved hypothetical protein |
| ORF03537 | 7073 & 7074 | Phosphopantetheine attachment site (ACP) |
| ORF03538 | 7075 & 7076 | 8-amino-7-oxononanoate synthase |
| ORF03539 | 7077 & 7078 | Predicted permease YjgP-YjgQ family superfamily |
| ORF03540 | 7079 & 7080 | Predicted permease YjgP-YjgQ family superfamily |
| ORF03541 | 7081 & 7082 | conserved hypothetical protein YtfJ-family, TIGR01626 |
| ORF03542 | 7083 & 7084 | conserved hypothetical protein |
| ORF03543 | 7085 & 7086 | Polysaccharide biosynthesis protein domain protein |
| ORF03544 | 7087 & 7088 | Hypothetical ATP-binding protein yghR |
| ORF03545 | 7089 & 7090 | Hypothetical ATP-binding protein yghS |
| ORF03546 | 7091 & 7092 | hypothetical protein |
| ORF03547 | 7093 & 7094 | Hypothetical ATP-binding protein yghT |
| ORF03548 | 7095 & 7096 | low-affinity phosphate transport protein |
| ORF03549 | 7097 & 7098 | Glutathionylspermidine synthase |
| ORF03550 | 7099 & 7100 | Hypothetical GST-like protein yghU |
| ORF03551 | 7101 & 7102 | hydrogenase assembly chaperone HypC-HupF (hypC) |
| ORF03552 | 7103 & 7104 | hydrogenase nickel insertion protein HypA (hypA) |
| ORF03553 | 7105 & 7106 | Hydrogenase-2 operon protein hybE |
| ORF03554 | 7107 & 7108 | hydrogenase expression-formation protein |
| ORF03555 | 7109 & 7110 | hydrogenase-2 large subunit HybC [1.18.99.1] |
| ORF03556 | 7111 & 7112 | cytochrome Ni—Fe component of hydrogenase-2 |
| ORF03557 | 7113 & 7114 | Hydrogenase-2 operon protein hybA precursor |
| ORF03558 | 7115 & 7116 | Hydrogenase-2 small chain precursor (NiFe hydrogenase)(Membrane-bound hydrogenase 2 small subunit) (HYD2) (hydA) [1.12.99.6] |
| ORF03559 | 7117 & 7118 | conserved hypothetical protein |
| ORF03560 | 7119 & 7120 | dienelactone hydrolase family protein |
| ORF03561 | 7121 & 7122 | oxidoreductase, aldo-keto reductase family |
| ORF03562 | 7123 & 7124 | conserved hypothetical protein TIGR00645 |
| ORF03563 | 7125 & 7126 | oxidoreductase, short chain dehydrogenase-reductase family [1.—.—.—] |
| ORF03564 | 7127 & 7128 | Biopolymer transport exbD protein |
| ORF03565 | 7129 & 7130 | biopolymer transport ExbB protein (uptake) |
| ORF03566 | 7131 & 7132 | cystathionine beta-lyase (metC) [4.4.1.8] |
| ORF03567 | 7133 & 7134 | unnamed protein product; Similar to DedA-family integral membrane protein YghB of Escherichia coli |
| ORF03568 | 7135 & 7136 | transcriptional regulator, AraC family |
| ORF03569 | 7137 & 7138 | uncharacterized oxidoreductase |
| ORF03570 | 7139 & 7140 | oxidoreductase, aldo-keto reductase family [1.1.1.274] |
| ORF03571 | 7141 & 7142 | conserved hypothetical protein |
| ORF03572 | 7143 & 7144 | major outer membrane lipoprotein |
| ORF03573 | 7145 & 7146 | radical SAM domain protein protein |
| ORF03574 | 7147 & 7148 | regulator for uxu operon |
| ORF03575 | 7149 & 7150 | Hypothetical oxidoreductase ydfI |
| ORF03576 | 7151 & 7152 | 2,3-butanediol dehydrogenase, putative [1.1.1.14] |
| ORF03577 | 7153 & 7154 | Ureidoglycolate dehydrogenase [1.1.1.—] |
| ORF03578 | 7155 & 7156 | TRAP-type C4-dicarboxylate transport system, periplasmic component (AP001509) |
| ORF03579 | 7157 & 7158 | unnamed protein product |
| ORF03580 | 7159 & 7160 | TRAP dicarboxylate transporter, DctM subunit |
| ORF03581 | 7161 & 7162 | suppressor of ftsI |
| ORF03582 | 7163 & 7164 | 1-acyl-sn-glycerol-3-phosphate acyltransferase (LPAAT) [2.3.1.51] |
| ORF03583 | 7165 & 7166 | DNA topoisomerase IV, A subunit (parC) [5.99.1.—] |
| ORF03584 | 7167 & 7168 | ABC superfamily (periplasm), oligopeptide transport protein with |
| ORF03585 | 7169 & 7170 | transcriptional regulator, AraC family |
| ORF03586 | 7171 & 7172 | conserved hypothetical protein TIGR00156 |
| ORF03587 | 7173 & 7174 | Transcriptional Regulatory protein qseB |
| ORF03588 | 7175 & 7176 | Sensor protein qseC [2.7.3.—] |
| ORF03589 | 7177 & 7178 | unnamed protein product; Similar to Hcp protein |
| ORF03590 | 7179 & 7180 | NAD(P)H quinone oxidoreductase, putative |
| ORF03591 | 7181 & 7182 | Protein ygiN |
| ORF03592 | 7183 & 7184 | SIS domain protein |
| ORF03593 | 7185 & 7186 | Putative iron compound-binding protein of ABC transporter |
| ORF03594 | 7187 & 7188 | iron compound ABC transporter, permease protein (III) |
| ORF03595 | 7189 & 7190 | ferric exochelin uptake (fxuC) |
| ORF03596 | 7191 & 7192 | ferric exochelin uptake (fxuB) |
| ORF03597 | 7193 & 7194 | Putative iron compound receptor |
| ORF03598 | 7195 & 7196 | DNA topoisomerase IV, B subunit (parE) [5.99.1.—] |
| ORF03599 | 7197 & 7198 | Predicted esterase |
| ORF03600 | 7199 & 7200 | Icc protein |
| ORF03601 | 7201 & 7202 | Protein of unknown function (DUF1249) superfamily |
| ORF03602 | 7203 & 7204 | conserved hypothetical protein TIGR00052 |
| ORF03603 | 7205 & 7206 | outer membrane channel specific tolerance to colicin |
| ORF03604 | 7207 & 7208 | conserved hypothetical protein |
| ORF03605 | 7209 & 7210 | glutathionylspermidine synthase (O386) |
| ORF03606 | 7211 & 7212 | arylsulfate sulfotransferase |
| ORF03607 | 7213 & 7214 | Thiol:disulfide interchange protein dsbA-like precursor [5.3.4.1] |
| ORF03608 | 7215 & 7216 | disulfide bond formation protein B (dsbB) [1.8.4.—] |

TABLE 1-continued

Annotation of ORF00001 to ORF04995

| ORFnnnnn | SEQ ID NOs | Annotation |
| --- | --- | --- |
| ORF03609 | 7217 & 7218 | Catalytic LigB subunit of aromatic ring-opening dioxygenase superfamily |
| ORF03610 | 7219 & 7220 | hypothetical protein |
| ORF03611 | 7221 & 7222 | Zinc transporter zupT |
| ORF03612 | 7223 & 7224 | conserved hypothetical protein |
| ORF03613 | 7225 & 7226 | fimbrial protein |
| ORF03614 | 7227 & 7228 | outer membrane fimbrial usher porin |
| ORF03615 | 7229 & 7230 | OUTER MEMBRANE USHER PROTEIN PMFC PRECURSOR. |
| ORF03616 | 7231 & 7232 | Hypothetical fimbrial chaperone yqiH precursor |
| ORF03617 | 7233 & 7234 | ybgO protein |
| ORF03618 | 7235 & 7236 | 3,4-dihydroxy-2-butanone 4-phosphate synthase (ribB) |
| ORF03619 | 7237 & 7238 | Protein of unknown function (DUF526) family |
| ORF03620 | 7239 & 7240 | glycogen biosynthesis, rpoS dependent-related protein |
| ORF03621 | 7241 & 7242 | YgiJ |
| ORF03622 | 7243 & 7244 | Uncharacterized BCR, putative |
| ORF03623 | 7245 & 7246 | ADP-heptose synthase [2.7.—.—] |
| ORF03624 | 7247 & 7248 | Glutamate-ammonia-ligase adenylyltransferase |
| ORF03625 | 7249 & 7250 | Adenylate cyclase, putative |
| ORF03626 | 7251 & 7252 | conserved hypothetical protein |
| ORF03627 | 7253 & 7254 | tRNA nucleotidyl transferase |
| ORF03628 | 7255 & 7256 | undecaprenol kinase, putative [2.7.1.66] |
| ORF03629 | 7257 & 7258 | dihydroneopterin aldolase (folB) [4.1.2.25] |
| ORF03630 | 7259 & 7260 | conserved hypothetical protein TIGR00023 |
| ORF03631 | 7261 & 7262 | LysR family regulatory protein |
| ORF03632 | 7263 & 7264 | hypothetical protein |
| ORF03633 | 7265 & 7266 | fumarase (fumarase) [4.2.1.32] |
| ORF03634 | 7267 & 7268 | fumarate hydratase, class I, putative [4.2.1.32] |
| ORF03635 | 7269 & 7270 | DASS family, citrate:succinate transport (antiport) |
| ORF03636 | 7271 & 7272 | O-sialoglycoprotein endopeptidase (gcp) [3.4.24.57] |
| ORF03637 | 7273 & 7274 | 30S ribosomal protein S21-related protein |
| ORF03638 | 7275 & 7276 | DNA primase [2.7.7.—] |
| ORF03639 | 7277 & 7278 | sigma D factor of RNA polymerase |
| ORF03640 | 7279 & 7280 | sigma D factor of RNA polymerase |
| ORF03641 | 7281 & 7282 | G-U mismatch-specific DNA glycosylase (Mismatch-specificuracil DNA-glycosylase) (UDG) [3.2.2.—] |
| ORF03642 | 7283 & 7284 | iron-chelator utilization protein |
| ORF03643 | 7285 & 7286 | transcriptional regulator, PadR family |
| ORF03644 | 7287 & 7288 | Aerotaxis receptor |
| ORF03645 | 7289 & 7290 | ornithine aminotransferase (rocD) [2.6.1.13] |
| ORF03646 | 7291 & 7292 | tRNA-binding protein ygjH (mets) [6.1.1.10] |
| ORF03647 | 7293 & 7294 | galactose operon repressor galR |
| ORF03648 | 7295 & 7296 | Evolved beta-galactosidase alpha-subunit |
| ORF03649 | 7297 & 7298 | EGB enzyme beta subunit [3.2.1.23] |
| ORF03650 | 7299 & 7300 | probable oxidoreductase ygjI |
| ORF03651 | 7301 & 7302 | conserved hypothetical protein |
| ORF03652 | 7303 & 7304 | conserved hypothetical protein |
| ORF03653 | 7305 & 7306 | 2,4-dienoyl-coA reductase [1.—.—.—] |
| ORF03654 | 7307 & 7308 | 2.1.1.52 [2.1.1.52] |
| ORF03655 | 7309 & 7310 | conserved hypothetical protein |
| ORF03656 | 7311 & 7312 | sanA protein |
| ORF03657 | 7313 & 7314 | oxidoreductase [1.—.—.—] |
| ORF03658 | 7315 & 7316 | Alx protein |
| ORF03659 | 7317 & 7318 | Sodium:dicarboxylate symporter family superfamily |
| ORF03660 | 7319 & 7320 | conserved hypothetical protein |
| ORF03661 | 7321 & 7322 | Altronate hydrolase [4.2.1.7] |
| ORF03662 | 7323 & 7324 | Glucuronate isomerase (uxaC) [5.3.1.12] |
| ORF03663 | 7325 & 7326 | major facilitator family transporter, putative |
| ORF03664 | 7327 & 7328 | Exu regulon transcriptional regulator |
| ORF03665 | 7329 & 7330 | unnamed protein product; Similar to DedA-family integral membrane protein YghB of *Escherichia coli* |
| ORF03666 | 7331 & 7332 | conserved hypothetical protein |
| ORF03667 | 7333 & 7334 | Protein ygjC precursor [3.4.24.13] |
| ORF03668 | 7335 & 7336 | Bacterial protein of unknown function (DUF883) superfamily |
| ORF03669 | 7337 & 7338 | conserved hypothetical protein |
| ORF03670 | 7339 & 7340 | conserved hypothetical protein |
| ORF03671 | 7341 & 7342 | predicted membrane protein |
| ORF03672 | 7343 & 7344 | Glutathione S-transferase C terminus (O328) |
| ORF03673 | 7345 & 7346 | Protein of unknown function (DUF805) superfamily |
| ORF03674 | 7347 & 7348 | lysR-family transcription regulatory protein YPO3545 |
| ORF03675 | 7349 & 7350 | Uncharacterized BCR, YhhW family COG1741 family |
| ORF03676 | 7351 & 7352 | conserved hypothetical protein |
| ORF03677 | 7353 & 7354 | Protein of unknown function (DUF1063) superfamily |
| ORF03678 | 7355 & 7356 | putative transport system permease protein |
| ORF03679 | 7357 & 7358 | L-serine ammonia-lyase (sdaA) [4.3.1.17] |
| ORF03680 | 7359 & 7360 | endoribonuclease L-PSP, putative |
| ORF03681 | 7361 & 7362 | formate acetyltransferase (pflB) [2.3.1.54] |
| ORF03682 | 7363 & 7364 | acetate kinase (ackA) [2.7.2.1] |

TABLE 1-continued

Annotation of ORF00001 to ORF04995

| ORFnnnnn | SEQ ID NOs | Annotation |
| --- | --- | --- |
| ORF03683 | 7365 & 7366 | Threonine-serine transporter |
| ORF03684 | 7367 & 7368 | Threonine dehydratase catabolic (Threonine deaminase) (tdcB) [4.3.1.19] |
| ORF03685 | 7369 & 7370 | transcriptional regulator, LysR family, putative [4.2.1.16] |
| ORF03686 | 7371 & 7372 | Glycerate kinase 2 |
| ORF03687 | 7373 & 7374 | 2-hydroxy-3-oxopropionate reductase [1.1.1.60] |
| ORF03688 | 7375 & 7376 | 2-dehydro-3-deoxyglucarate aldolase (ptpA) [4.1.2.20] |
| ORF03689 | 7377 & 7378 | MFS transporter, phthalate permease family |
| ORF03690 | 7379 & 7380 | D-galactarate dehydratase (GalcD) [4.2.1.42] |
| ORF03691 | 7381 & 7382 | DeoR-family regulatory protein (srl) |
| ORF03692 | 7383 & 7384 | PUTATIVE TAGATOSE 6-PHOSPHATE KINASE PROTEIN |
| ORF03693 | 7385 & 7386 | N-acetylgalactosamine-specific PTS system enzyme IIB component (EIIB-AGA) [2.7.1.69] |
| ORF03694 | 7387 & 7388 | N-acetylgalactosameine-specific IIC component 2 |
| ORF03695 | 7389 & 7390 | PTS system, N-acetylgalactosamine-specific IID component |
| ORF03696 | 7391 & 7392 | AgaF [2.7.1.69] |
| ORF03697 | 7393 & 7394 | N-acetylglucosamine-6-phosphate deacetylase (nagA) [3.5.1.25] |
| ORF03698 | 7395 & 7396 | sugar isomerase domain protein AgaS [5.—.—.—] |
| ORF03699 | 7397 & 7398 | class II aldolase, tagatose bisphosphate family [4.1.2.—] |
| ORF03700 | 7399 & 7400 | PTS system, N-acetylgalactosamine-specific IIB component 1 (EIIB-Aga)(N-acetylgalactosamine-permease IIB component 1) (Phosphotransferaseenzyme II, B component 1) (EIIB-AGA) [2.7.1.69] |
| ORF03701 | 7401 & 7402 | PTS system, N-acetylgalactosamine-specific IIC component 1 (EIIC-Aga)(N-acetylgalactosamine-permease IIC component 1) |
| ORF03702 | 7403 & 7404 | PTS system, N-acetylgalactosamine-specific IID component (EIID-AGA) |
| ORF03703 | 7405 & 7406 | glucosamine-6-phosphate isomerase, putative [5.3.1.—] |
| ORF03704 | 7407 & 7408 | conserved hypothetical protein TIGR00096 |
| ORF03705 | 7409 & 7410 | LppC |
| ORF03706 | 7411 & 7412 | conserved hypothetical protein TIGR00252 |
| ORF03707 | 7413 & 7414 | phosphoheptose isomerase (gmhA) |
| ORF03708 | 7415 & 7416 | Putative phospholipid-binding domain family |
| ORF03709 | 7417 & 7418 | Predicted permease superfamily |
| ORF03710 | 7419 & 7420 | conserved hypothetical protein |
| ORF03711 | 7421 & 7422 | unnamed protein product |
| ORF03712 | 7423 & 7424 | protease I |
| ORF03713 | 7425 & 7426 | ACETYLTRANSFERASE [2.3.1.—] |
| ORF03714 | 7427 & 7428 | predicted endonuclease |
| ORF03715 | 7429 & 7430 | SCP-2 sterol transfer family family |
| ORF03716 | 7431 & 7432 | collagenase |
| ORF03717 | 7433 & 7434 | peptidase, U32 family family [3.4.—.—] |
| ORF03718 | 7435 & 7436 | flavin dependant oxidoreductase |
| ORF03719 | 7437 & 7438 | Tryptophan-specific transport protein |
| ORF03720 | 7439 & 7440 | ATP-dependent RNA helicase DeaD |
| ORF03721 | 7441 & 7442 | Lipoprotein nlpI precursor |
| ORF03722 | 7443 & 7444 | Polyribonucleotide nucleotidyltransferase (CAP87K) |
| ORF03723 | 7445 & 7446 | ribosomal protein S15 (rpsO) |
| ORF03724 | 7447 & 7448 | tRNA pseudouridine synthase B [4.2.1.70] |
| ORF03725 | 7449 & 7450 | ribosome-binding factor A (rbfA) |
| ORF03726 | 7451 & 7452 | Translation initiation factor IF-2 |
| ORF03727 | 7453 & 7454 | Transcription elongation protein nusA (N utilization substance proteinA) (L factor) (nusA) |
| ORF03728 | 7455 & 7456 | YhbC-like protein |
| ORF03729 | 7457 & 7458 | argininosuccinate synthase (argG) [6.3.4.5] |
| ORF03730 | 7459 & 7460 | Outer-membrane protein yhbX precursor |
| ORF03731 | 7461 & 7462 | Protein-export membrane protein secG |
| ORF03732 | 7463 & 7464 | phosphoglucosamine mutase (glmM) [5.4.2.—] |
| ORF03733 | 7465 & 7466 | dihydropteroate synthase (folP) [2.5.1.15] |
| ORF03734 | 7467 & 7468 | ATP-binding protein [3.4.24.—] |
| ORF03735 | 7469 & 7470 | ribosomal RNA large subunit methyltransferase J (rrmJ) [2.1.1.—] |
| ORF03736 | 7471 & 7472 | conserved hypothetical protein TIGR00253 |
| ORF03737 | 7473 & 7474 | Transcription elongation factor greA (Transcript cleavage factorgreA) (greA) |
| ORF03738 | 7475 & 7476 | D-alanyl-D-alanine carboxypeptidase-D-alanyl-D-alanine-endopeptidase (dacB) [3.4.16.4] |
| ORF03739 | 7477 & 7478 | Obg protein (Obg) |
| ORF03740 | 7479 & 7480 | Obg protein (F390) |
| ORF03741 | 7481 & 7482 | RhaT protein |
| ORF03742 | 7483 & 7484 | RhaT protein |
| ORF03743 | 7485 & 7486 | ribosomal protein L27 (rpmA) |
| ORF03744 | 7487 & 7488 | 50S ribosomal protein L21 |
| ORF03745 | 7489 & 7490 | conserved hypothetical protein |
| ORF03746 | 7491 & 7492 | RhaT protein |
| ORF03747 | 7493 & 7494 | ribosomal protein L27 (rpmA) |
| ORF03748 | 7495 & 7496 | 50S ribosomal protein L21 |
| ORF03749 | 7497 & 7498 | ribosomal protein L21 (rplU) |
| ORF03750 | 7499 & 7500 | conserved hypothetical protein |
| ORF03751 | 7501 & 7502 | Octaprenyl-diphosphate synthase (Octaprenyl pyrophosphatesynthetase) (OPP synthetase) [2.5.1.—] |

TABLE 1-continued

Annotation of ORF00001 to ORF04995

| ORFnnnnn | SEQ ID NOs | Annotation |
|---|---|---|
| ORF03752 | 7503 & 7504 | Sugar fermentation stimulation protein B (Ner-like protein) |
| ORF03753 | 7505 & 7506 | UDP-N-acetylglucosamine 1-carboxyvinyltransferase (murA) [2.5.1.7] |
| ORF03754 | 7507 & 7508 | BolA-like protein |
| ORF03755 | 7509 & 7510 | conserved hypothetical protein |
| ORF03756 | 7511 & 7512 | Protein yrbC precursor (Ttg2D) |
| ORF03757 | 7513 & 7514 | conserved hypothetical protein |
| ORF03758 | 7515 & 7516 | VpsC |
| ORF03759 | 7517 & 7518 | unnamed protein product; Highly similar to ABC transporter, permease protein YrbE of *Escherichia coli* |
| ORF03760 | 7519 & 7520 | ABC transporter, ATP-binding protein (atp_bind) |
| ORF03761 | 7521 & 7522 | K+-dependent Na+-Ca+ exchanger related-protein |
| ORF03762 | 7523 & 7524 | hypothetical protein |
| ORF03763 | 7525 & 7526 | conserved hypothetical protein |
| ORF03764 | 7527 & 7528 | putative isomerase |
| ORF03765 | 7529 & 7530 | 3-deoxy-D-manno-octulosonate 8-phosphate phosphatase(KDO 8-P phosphatase) [3.1.3.45] |
| ORF03766 | 7531 & 7532 | unnamed protein product; Similar to YrbK precursor protein of *Escherichia coli* |
| ORF03767 | 7533 & 7534 | OstA-like protein family |
| ORF03768 | 7535 & 7536 | ABC transporter, ATP-binding component |
| ORF03769 | 7537 & 7538 | RNA polymerase sigma-54 factor (rpoN) |
| ORF03770 | 7539 & 7540 | ribosomal subunit interface protein (yfiA) |
| ORF03771 | 7541 & 7542 | PTS IIA-like nitrogen-regulatory protein PtsN (ptsN) |
| ORF03772 | 7543 & 7544 | unnamed protein product; ORF193 peptide fragment (AA 1-192) (1524 is 2nd base in codon) |
| ORF03773 | 7545 & 7546 | phosphocarrier protein (NPr) |
| ORF03774 | 7547 & 7548 | conserved hypothetical protein |
| ORF03775 | 7549 & 7550 | monofunctional biosynthetic peptidoglycan transglycosylase (mtgA) [2.4.2.—] |
| ORF03776 | 7551 & 7552 | sigma cross-reacting protein 27A (SCRP-27A) |
| ORF03777 | 7553 & 7554 | Aerobic respiration control sensor protein arcB [2.7.3.—] |
| ORF03778 | 7555 & 7556 | radical SAM protein, TIGR01212 family |
| ORF03779 | 7557 & 7558 | hypothetical protein |
| ORF03780 | 7559 & 7560 | Glutamate synthase [NADPH] large chain precursor [1.4.1.13] |
| ORF03781 | 7561 & 7562 | glutamate synthase (NADPH) small chain (NADPH) [1.4.1.13] |
| ORF03782 | 7563 & 7564 | conserved hypothetical protein subfamily |
| ORF03783 | 7565 & 7566 | ROK family protein domain protein, putative |
| ORF03784 | 7567 & 7568 | N-acetylmannosamine-6-phosphate 2-epimerase-N-acetylmannosamine kinase |
| ORF03785 | 7569 & 7570 | cis,cis-muconate transport protein MucK, putative |
| ORF03786 | 7571 & 7572 | N-acetylneuraminate lyase (nanA) [4.1.3.3] |
| ORF03787 | 7573 & 7574 | transcriptional regulator, GntR family, putative |
| ORF03788 | 7575 & 7576 | stringent starvation protein B (sspB) |
| ORF03789 | 7577 & 7578 | Stringent starvation protein A (Ssp) |
| ORF03790 | 7579 & 7580 | ribosomal protein S9 (rpsI) |
| ORF03791 | 7581 & 7582 | ribosomal protein L13 (rplM) |
| ORF03792 | 7583 & 7584 | Predicted ATPase |
| ORF03793 | 7585 & 7586 | Protein of unknown function (DUF1043) superfamily |
| ORF03794 | 7587 & 7588 | Protease degQ precursor |
| ORF03795 | 7589 & 7590 | periplasmic serine protease DegS (degS) [3.4.21.—] |
| ORF03796 | 7591 & 7592 | malate dehydrogenase, NAD-dependent (mdh) [1.1.1.37] |
| ORF03797 | 7593 & 7594 | arginine repressor (argR) |
| ORF03798 | 7595 & 7596 | Protein of unknown function (DUF1471) superfamily |
| ORF03799 | 7597 & 7598 | unnamed protein product; Similar to ribonuclease inhibitor (barstar) |
| ORF03800 | 7599 & 7600 | Fusaric acid resistance protein conserved region family |
| ORF03801 | 7601 & 7602 | fusaric acid resistance protein |
| ORF03802 | 7603 & 7604 | conserved hypothetical protein |
| ORF03803 | 7605 & 7606 | conserved hypothetical protein |
| ORF03804 | 7607 & 7608 | Transcriptional regulator |
| ORF03805 | 7609 & 7610 | TldD protein (CSRA) |
| ORF03806 | 7611 & 7612 | conserved hypothetical protein TIGR02099 |
| ORF03807 | 7613 & 7614 | bundles of cytoplasmic filaments |
| ORF03808 | 7615 & 7616 | maf protein (maf) |
| ORF03809 | 7617 & 7618 | rod shape-determining protein MreD (mreD) |
| ORF03810 | 7619 & 7620 | Rod shape-determining protein mreC (mreC) |
| ORF03811 | 7621 & 7622 | Rod shape-determining protein mreC (mreC) |
| ORF03812 | 7623 & 7624 | regulator of ftsI |
| ORF03813 | 7625 & 7626 | EAL domain protein |
| ORF03814 | 7627 & 7628 | Protein yhdH |
| ORF03815 | 7629 & 7630 | acetyl-CoA carboxylase, biotin carboxyl carrier protein (accB) |
| ORF03816 | 7631 & 7632 | acetyl-CoA carboxylase, biotin carboxylase (accC) [6.4.1.2] |
| ORF03817 | 7633 & 7634 | conserved hypothetical protein |
| ORF03818 | 7635 & 7636 | conserved hypothetical protein |
| ORF03819 | 7637 & 7638 | fructokinase (AB010074) [2.7.1.—] |
| ORF03820 | 7639 & 7640 | ribose ABC transporter, permease protein (permease) |
| ORF03821 | 7641 & 7642 | Ribose transport ATP-binding protein rbsA (aldose) |
| ORF03822 | 7643 & 7644 | periplasmic ribose-binding protein |
| ORF03823 | 7645 & 7646 | class II aldolase, tagatose bisphosphate family [4.1.2.—] |
| ORF03824 | 7647 & 7648 | conserved hypothetical protein |

TABLE 1-continued

Annotation of ORF00001 to ORF04995

| ORFnnnnn | SEQ ID NOs | Annotation |
|---|---|---|
| ORF03825 | 7649 & 7650 | aga operon transcriptional repressor (DeoR family) |
| ORF03826 | 7651 & 7652 | fructokinase (AB010074) [2.7.1.—] |
| ORF03827 | 7653 & 7654 | Protein of unknown function (DUF997) superfamily |
| ORF03828 | 7655 & 7656 | sodium-pantothenate symporter (panF) |
| ORF03829 | 7657 & 7658 | ribosomal protein L11 methyltransferase (prmA) [2.1.1.—] |
| ORF03830 | 7659 & 7660 | tRNA-dihydrouridine synthase B [1.—.—.—] |
| ORF03831 | 7661 & 7662 | DNA-binding protein fis (Factor-for-inversion stimulation protein)(HIN recombinational enhancer binding protein) (fis) |
| ORF03832 | 7663 & 7664 | ADENINE-SPECIFIC METHYLTRANSFERASE |
| ORF03833 | 7665 & 7666 | conserved hypothetical protein |
| ORF03834 | 7667 & 7668 | Potential acrEF-envCD operon repressor (acrEF) |
| ORF03835 | 7669 & 7670 | Acriflavine resistance protein E precursor |
| ORF03836 | 7671 & 7672 | Acriflavine resistance protein F |
| ORF03837 | 7673 & 7674 | lipoprotein, putative |
| ORF03838 | 7675 & 7676 | amino acid ABC transporter, periplasmic amino acid-binding protein |
| ORF03839 | 7677 & 7678 | L-amino acid ABC transporter permease protein |
| ORF03840 | 7679 & 7680 | L-amino acid ABC transporter permease protein |
| ORF03841 | 7681 & 7682 | L-amino acid ABC transporter ATP-binding protein |
| ORF03842 | 7683 & 7684 | glutamate decarboxylase [4.1.1.15] |
| ORF03843 | 7685 & 7686 | glutamate decarboxylase [4.1.1.15] |
| ORF03844 | 7687 & 7688 | unnamed protein product |
| ORF03845 | 7689 & 7690 | Protein yrdA |
| ORF03846 | 7691 & 7692 | shikimate 5-dehydrogenase (aroE) [1.1.1.25] |
| ORF03847 | 7693 & 7694 | Protein yrdC |
| ORF03848 | 7695 & 7696 | Protein smg |
| ORF03849 | 7697 & 7698 | Predicted Rossmann-fold nucleotide-binding protein involved in DNA |
| ORF03850 | 7699 & 7700 | peptide deformylase (def) [3.5.1.88] |
| ORF03851 | 7701 & 7702 | methionyl-tRNA formyltransferase (fmt) [2.1.2.9] |
| ORF03852 | 7703 & 7704 | sun protein (sun) [2.1.1.—] |
| ORF03853 | 7705 & 7706 | Trk system potassium uptake protein trkA (K(+)-uptake protein trkA) (trkA) |
| ORF03854 | 7707 & 7708 | large conductance mechanosensitive channel protein (mscL) |
| ORF03855 | 7709 & 7710 | Uncharacterized protein conserved in bacteria |
| ORF03856 | 7711 & 7712 | Zn(II)-responsive transcriptional regulator (zntR) |
| ORF03857 | 7713 & 7714 | conserved hypothetical protein |
| ORF03858 | 7715 & 7716 | ribosomal protein L17 (rplQ) |
| ORF03859 | 7717 & 7718 | DNA-directed RNA polymerase, alpha subunit (rpoA) [2.7.7.6] |
| ORF03860 | 7719 & 7720 | ribosomal protein S4 (rpsD) |
| ORF03861 | 7721 & 7722 | ribosomal protein S11 (rpsk) |
| ORF03862 | 7723 & 7724 | ribosomal protein S13p-S18e (rpsM) |
| ORF03863 | 7725 & 7726 | ribosomal protein L36 (rpmJ) |
| ORF03864 | 7727 & 7728 | preprotein translocase, SecY subunit |
| ORF03865 | 7729 & 7730 | Preprotein translocase secY subunit (secY) |
| ORF03866 | 7731 & 7732 | ribosomal protein L15 (rplO) |
| ORF03867 | 7733 & 7734 | ribosomal protein L30 (rpmD) |
| ORF03868 | 7735 & 7736 | ribosomal protein S5 (rpsE) |
| ORF03869 | 7737 & 7738 | ribosomal protein L18 (rplR) |
| ORF03870 | 7739 & 7740 | 50S ribosomal subunit protein L6 (rp1F) |
| ORF03871 | 7741 & 7742 | conserved hypothetical protein |
| ORF03872 | 7743 & 7744 | ribosomal protein S8 (rpsH) |
| ORF03873 | 7745 & 7746 | ribosomal protein S14p-S29e (rpsN) |
| ORF03874 | 7747 & 7748 | 50S ribosomal subunit protein L5 (rpL5) |
| ORF03875 | 7749 & 7750 | ribosomal protein L24 (rplX) |
| ORF03876 | 7751 & 7752 | ribosomal protein L14 (rplN) |
| ORF03877 | 7753 & 7754 | ribosomal protein S17 (rpsQ) |
| ORF03878 | 7755 & 7756 | ribosomal protein L29 (rpmC) |
| ORF03879 | 7757 & 7758 | ribosomal protein L16 (rplP) |
| ORF03880 | 7759 & 7760 | ribosomal protein S3 (rpsC) |
| ORF03881 | 7761 & 7762 | ribosomal protein L22 (rplV) |
| ORF03882 | 7763 & 7764 | ribosomal protein S19 (rpsS) |
| ORF03883 | 7765 & 7766 | ribosomal protein L2 (rplB) |
| ORF03884 | 7767 & 7768 | ribosomal protein L23 (rplW) |
| ORF03885 | 7769 & 7770 | ribosomal protein L4-L1 family (rplD) |
| ORF03886 | 7771 & 7772 | ribosomal protein L3 (rplC) |
| ORF03887 | 7773 & 7774 | ribosomal protein S10 (rpsJ) |
| ORF03888 | 7775 & 7776 | PioO protein (PinO protein) |
| ORF03889 | 7777 & 7778 | Probable general secretion pathway protein A (GSP) |
| ORF03890 | 7779 & 7780 | general secretion pathway protein C (gspC) |
| ORF03891 | 7781 & 7782 | General secretion pathway protein D precursor (Pullulanase secretionenvelope pulD) (GSP) |
| ORF03892 | 7783 & 7784 | General secretion pathway protein E (Type II traffic warden ATPase)(Cholera toxin secretion protein epsE) (GSP) |
| ORF03893 | 7785 & 7786 | general secretion pathway protein F (gspF) |
| ORF03894 | 7787 & 7788 | general secretion pathway protein G (gspG) |
| ORF03895 | 7789 & 7790 | General secretion pathway protein H precursor (Pullulanase secretionprotein pulH) (GSP) |
| ORF03896 | 7791 & 7792 | outer membrane secretion protein V (GSP) |

TABLE 1-continued

Annotation of ORF00001 to ORF04995

| ORFnnnnn | SEQ ID NOs | Annotation |
|---|---|---|
| ORF03897 | 7793 & 7794 | general secretion pathway protein J (gspJ) |
| ORF03898 | 7795 & 7796 | General secretion pathway protein K (gspK) |
| ORF03899 | 7797 & 7798 | general secretion pathway protein L (gspL) |
| ORF03900 | 7799 & 7800 | Putative general secretion pathway protein M (GSP) |
| ORF03901 | 7801 & 7802 | Type 4 prepilin-like proteins leader peptide processing enzyme (GSP) [3.4.23.43] |
| ORF03902 | 7803 & 7804 | bacterioferritin (bfr) |
| ORF03903 | 7805 & 7806 | Bacterioferritin-associated ferredoxin-related protein |
| ORF03904 | 7807 & 7808 | chitinase [3.2.1.14] |
| ORF03905 | 7809 & 7810 | translation elongation factor Tu (tuf) |
| ORF03906 | 7811 & 7812 | translation elongation factor G (fusA) |
| ORF03907 | 7813 & 7814 | ribosomal protein S7 (rpsG) |
| ORF03908 | 7815 & 7816 | ribosomal protein S12 (rpsL) |
| ORF03909 | 7817 & 7818 | DsrH protein |
| ORF03910 | 7819 & 7820 | Uncharacterized protein involved in the oxidation of |
| ORF03911 | 7821 & 7822 | Uncharacterized conserved protein involved in intracellular sulfur |
| ORF03912 | 7823 & 7824 | conserved hypothetical protein |
| ORF03913 | 7825 & 7826 | FKBP-type peptidyl-prolyl cis-trans isomerase fkpA precursor(EC 5.2.1.8) (PPIase) (Rotamase) (rotamase) [5.2.1.8] |
| ORF03914 | 7827 & 7828 | SlyX protein (slyX) |
| ORF03915 | 7829 & 7830 | FKBP-type peptidyl-prolyl cis-trans isomerase slyD(PPIase) (Rotamase) (Histidine-rich protein) (WHP) (rotamase) [5.2.1.8] |
| ORF03916 | 7831 & 7832 | conserved hypothetical protein |
| ORF03917 | 7833 & 7834 | Glutathione-regulated potassium-efflux system protein kefB (K(+)-H(+)antiporter) (NEM-activatable K(+)-H(+) antiporter) |
| ORF03918 | 7835 & 7836 | Glutathione-regulated potassium-efflux system ancillary protein kefG [1.6.99.2] |
| ORF03919 | 7837 & 7838 | ABC transporter ATP-binding protein |
| ORF03920 | 7839 & 7840 | Predicted hydrolase of the alpha-beta-hydrolase fold |
| ORF03921 | 7841 & 7842 | Hypothetical UPF0270 protein yheU-related protein |
| ORF03922 | 7843 & 7844 | phosphoribulokinase [2.7.1.19] |
| ORF03923 | 7845 & 7846 | no known function |
| ORF03924 | 7847 & 7848 | Catabolite gene activator (cAMP receptor protein) (cAMP-regulatoryprotein) (crp) |
| ORF03925 | 7849 & 7850 | integral membrane protein, YccS-YhfK family subfamily |
| ORF03926 | 7851 & 7852 | Acetylornithine aminotransferase (argD) [2.6.1.11] |
| ORF03927 | 7853 & 7854 | Para-aminobenzoate synthase glutamine amidotransferase component II [6.3.5.8] |
| ORF03928 | 7855 & 7856 | fic, putative |
| ORF03929 | 7857 & 7858 | Peptidyl-prolyl cis-trans isomerase A precursor (PPIaseA) (Rotamase A) (Cyclophilin A) (utu) [5.2.1.8] |
| ORF03930 | 7859 & 7860 | hypothetical protein |
| ORF03931 | 7861 & 7862 | TsgA protein |
| ORF03932 | 7863 & 7864 | nitrite reductase [NAD(P)H], large subunit (nirB) [1.7.1.4] |
| ORF03933 | 7865 & 7866 | nitrite reductase [NAD(P)H], small subunit (nirD) [1.7.1.4] |
| ORF03934 | 7867 & 7868 | Potential nitrite transporter (formate) |
| ORF03935 | 7869 & 7870 | Siroheme synthase |
| ORF03936 | 7871 & 7872 | lipoprotein, putative |
| ORF03937 | 7873 & 7874 | unnamed protein product |
| ORF03938 | 7875 & 7876 | membrane protein, putative |
| ORF03939 | 7877 & 7878 | conserved hypothetical protein |
| ORF03940 | 7879 & 7880 | parathion hydrolase, putative |
| ORF03941 | 7881 & 7882 | phosphopentomutase |
| ORF03942 | 7883 & 7884 | Alanine racemase, N-terminal domain family |
| ORF03943 | 7885 & 7886 | unnamed protein product |
| ORF03944 | 7887 & 7888 | conserved hypothetical protein |
| ORF03945 | 7889 & 7890 | tryptophanyl-tRNA synthetase (trpS) [6.1.1.2] |
| ORF03946 | 7891 & 7892 | phosphoglycolate phosphatase, bacterial (gph) [3.1.3.18] |
| ORF03947 | 7893 & 7894 | hypothetical protein |
| ORF03948 | 7895 & 7896 | Phosphoglycolate phosphatase (PGP) [3.1.3.18] |
| ORF03949 | 7897 & 7898 | ribulose-phosphate 3-epimerase (rpe) [5.1.3.1] |
| ORF03950 | 7899 & 7900 | DNA adenine methylase (dam) [2.1.1.72] |
| ORF03951 | 7901 & 7902 | DamX protein (1989) |
| ORF03952 | 7903 & 7904 | 3-dehydroquinate synthase (aroB) [4.2.3.4] |
| ORF03953 | 7905 & 7906 | shikimate kinase I |
| ORF03954 | 7907 & 7908 | Protein transport protein hofQ precursor (Tfp) |
| ORF03955 | 7909 & 7910 | conserved hypothetical protein |
| ORF03956 | 7911 & 7912 | conserved hypothetical protein |
| ORF03957 | 7913 & 7914 | Fimbrial assembly protein (PilN) superfamily |
| ORF03958 | 7915 & 7916 | conserved hypothetical protein |
| ORF03959 | 7917 & 7918 | Penicillin-binding protein 1A (PBP1a) [2.4.2.—] |
| ORF03960 | 7919 & 7920 | ADP compounds hydrolase nudE [3.6.1.—] |
| ORF03961 | 7921 & 7922 | Intracellular growth attenuator protein igaA |
| ORF03962 | 7923 & 7924 | HAD-superfamily hydrolase, subfamily IA, variant 3 protein family |
| ORF03963 | 7925 & 7926 | Heat shock protein 15 (HSP15) (HSP15) |
| ORF03964 | 7927 & 7928 | 33 kDa chaperonin (Heat shock protein 33) (HSP33) (HSP33) |
| ORF03965 | 7929 & 7930 | membrane protein, putative |
| ORF03966 | 7931 & 7932 | phosphoenolpyruvate carboxykinase (ATP) (pckA) [4.1.1.49] |
| ORF03967 | 7933 & 7934 | Osmolarity sensor protein envZ [2.7.3.—] |

TABLE 1-continued

Annotation of ORF00001 to ORF04995

| ORFnnnnn | SEQ ID NOs | Annotation |
|---|---|---|
| ORF03968 | 7935 & 7936 | response regulator (sensor, EnvZ) affecting transcription of ompC and ompF: outer membrane protein synthesis |
| ORF03969 | 7937 & 7938 | transcription elongation factor GreB (greB) |
| ORF03970 | 7939 & 7940 | Protein yhgF |
| ORF03971 | 7941 & 7942 | ferrous iron transport protein B |
| ORF03972 | 7943 & 7944 | ferrous iron transport protein B (feoB) |
| ORF03973 | 7945 & 7946 | conserved hypothetical protein |
| ORF03974 | 7947 & 7948 | transposase |
| ORF03975 | 7949 & 7950 | hypothetical protein |
| ORF03976 | 7951 & 7952 | bioH protein (bioH) |
| ORF03977 | 7953 & 7954 | hypothetical protein |
| ORF03978 | 7955 & 7956 | predicted amidophosphoribosyltransferase |
| ORF03979 | 7957 & 7958 | Protein yhgI |
| ORF03980 | 7959 & 7960 | High-affinity gluconate transporter (Gluconate permease) (Gnt-Isystem) |
| ORF03981 | 7961 & 7962 | 4-alpha-glucanotransferase (malQ) [2.4.1.25] |
| ORF03982 | 7963 & 7964 | Maltodextrin phosphorylase [2.4.1.1] |
| ORF03983 | 7965 & 7966 | transcriptional regulator, LuxR family, putative |
| ORF03984 | 7967 & 7968 | RNA 3'-terminal phosphate cyclase (rtcA) [6.5.1.4] |
| ORF03985 | 7969 & 7970 | Protein rtcB |
| ORF03986 | 7971 & 7972 | Glycerol-3-phosphate regulon repressor |
| ORF03987 | 7973 & 7974 | Transcriptional Regulatory protein rtcR |
| ORF03988 | 7975 & 7976 | Rhomboid family protein, putative |
| ORF03989 | 7977 & 7978 | unnamed protein product; glpE polypeptide (AA 1-131) |
| ORF03990 | 7979 & 7980 | Aerobic glycerol-3-phosphate dehydrogenase (aerobic) |
| ORF03991 | 7981 & 7982 | conserved hypothetical protein |
| ORF03992 | 7983 & 7984 | conserved hypothetical protein |
| ORF03993 | 7985 & 7986 | conserved hypothetical protein |
| ORF03994 | 7987 & 7988 | mannose binding protein FimH precursor |
| ORF03995 | 7989 & 7990 | fimbrial chaperone |
| ORF03996 | 7991 & 7992 | Putative minor fimbrial subunit precursor |
| ORF03997 | 7993 & 7994 | Putative minor fimbrial subunit precursor |
| ORF03998 | 7995 & 7996 | F1C fimbrial usher |
| ORF03999 | 7997 & 7998 | Chaperone protein fimC precursor |
| ORF04000 | 7999 & 8000 | Long polar fimbria protein A precursor (pilin) |
| ORF04001 | 8001 & 8002 | Glycogen phosphorylase [2.4.1.1] |
| ORF04002 | 8003 & 8004 | Glycogen synthase (Starch [bacterial glycogen]synthase) [2.4.1.21] |
| ORF04003 | 8005 & 8006 | glucose-1-phosphate adenylyltransferase (glgC) [2.7.7.27] |
| ORF04004 | 8007 & 8008 | glycogen debranching enzyme GlgX (glgX) [3.2.1.—] |
| ORF04005 | 8009 & 8010 | 1,4-alpha-glucan branching enzyme (glgB) [2.4.1.18] |
| ORF04006 | 8011 & 8012 | aspartate-semialdehyde dehydrogenase (asd) [1.2.1.11] |
| ORF04007 | 8013 & 8014 | membrane protein, putative |
| ORF04008 | 8015 & 8016 | gluconate permease, putative |
| ORF04009 | 8017 & 8018 | thermoresistant gluconokinase (gluconate kinase 2) |
| ORF04010 | 8019 & 8020 | HTH-type transcriptional regulator gntR (Gluconate utilization systemGNT-I transcriptional repressor) (gnt) |
| ORF04011 | 8021 & 8022 | Protein yhhW |
| ORF04012 | 8023 & 8024 | Putative oxidoreductase yhhX [1.—.—.—] |
| ORF04013 | 8025 & 8026 | conserved hypothetical protein |
| ORF04014 | 8027 & 8028 | acetyltransferase, GNAT family, putative [2.3.1.—] |
| ORF04015 | 8029 & 8030 | unnamed protein product; Similar to Hcp protein |
| ORF04016 | 8031 & 8032 | conserved hypothetical protein |
| ORF04017 | 8033 & 8034 | gamma-glutamyltransferase (ggt) [2.3.2.2] |
| ORF04018 | 8035 & 8036 | glycerophosphodiester phosphodiesterase [3.1.4.46] |
| ORF04019 | 8037 & 8038 | CG9973-PA |
| ORF04020 | 8039 & 8040 | SN-glycerol-3-phosphate transport ATP-binding protein ugpC |
| ORF04021 | 8041 & 8042 | SN-glycerol-3-phosphate transport system permease protein ugpE (membrane) |
| ORF04022 | 8043 & 8044 | glycerol-3-phosphate ABC transporter, permease protein (membrane) |
| ORF04023 | 8045 & 8046 | Glycerol-3-phosphate-binding periplasmic protein precursor |
| ORF04024 | 8047 & 8048 | ABC transporter domain protein |
| ORF04025 | 8049 & 8050 | High-affinity branched-chain amino acid transport ATP-binding proteinlivG (LIV-I protein G) (AJ272047) |
| ORF04026 | 8051 & 8052 | High-affinity branched-chain amino acid transport system permeaseprotein livM (LIV-I protein M) |
| ORF04027 | 8053 & 8054 | High-affinity branched-chain amino acid transport system permease protein livH |
| ORF04028 | 8055 & 8056 | Leucine-specific binding protein precursor |
| ORF04029 | 8057 & 8058 | acetyltransferase, GNAT family family |
| ORF04030 | 8059 & 8060 | Leu-Ile-Val-binding protein precursor |
| ORF04031 | 8061 & 8062 | PTS system, mannose-specific enzyme II, AB component (EIII-MAN) [2.7.1.69] |
| ORF04032 | 8063 & 8064 | PTS system, mannose-specific IIAB components, putative [2.7.1.69] |
| ORF04033 | 8065 & 8066 | PTS system, IIC component (PTS) |
| ORF04034 | 8067 & 8068 | mannose-specific PTS enzyme IID |
| ORF04035 | 8069 & 8070 | D-3-phosphoglycerate dehydrogenase (serA) [1.1.1.95] |
| ORF04036 | 8071 & 8072 | dihydrodipicolinate synthase (dapA) [4.2.1.52] |
| ORF04037 | 8073 & 8074 | alternative sigma factor RpoH (rpoH) |
| ORF04038 | 8075 & 8076 | putative protein insertion permease FtsX (ftsX) |
| ORF04039 | 8077 & 8078 | Cell division ATP-binding protein ftsE |

TABLE 1-continued

Annotation of ORF00001 to ORF04995

| ORFnnnnn | SEQ ID NOs | Annotation |
|---|---|---|
| ORF04040 | 8079 & 8080 | Cell division protein ftsY |
| ORF04041 | 8081 & 8082 | methyltransferase, putative |
| ORF04042 | 8083 & 8084 | overlaps previous ORF, probably uses downstream start |
| ORF04043 | 8085 & 8086 | conserved hypothetical protein |
| ORF04044 | 8087 & 8088 | membrane protein, putative |
| ORF04045 | 8089 & 8090 | Lead, cadmium, zinc and mercury transporting ATPase [3.6.3.3] |
| ORF04046 | 8091 & 8092 | SirA protein |
| ORF04047 | 8093 & 8094 | membrane protein (o221) |
| ORF04048 | 8095 & 8096 | DcrB protein precursor |
| ORF04049 | 8097 & 8098 | Hypothetical UPF0226 protein yhhS |
| ORF04050 | 8099 & 8100 | Domain of unknown function, putative |
| ORF04051 | 8101 & 8102 | 4'-phosphopantetheinyl transferase acpT [2.7.8.—] |
| ORF04052 | 8103 & 8104 | nickel ABC transporter, periplasmic nickel-binding protein (nikA) |
| ORF04053 | 8105 & 8106 | Nickel transport system permease protein nikB (permease) |
| ORF04054 | 8107 & 8108 | dipeptide ABC transporter, permease protein, putative |
| ORF04055 | 8109 & 8110 | Nickel transport ATP-binding protein nikD |
| ORF04056 | 8111 & 8112 | Nickel transport ATP-binding protein nikE |
| ORF04057 | 8113 & 8114 | Nickel responsive regulator |
| ORF04058 | 8115 & 8116 | transcriptional regulator, GntR family, putative |
| ORF04059 | 8117 & 8118 | PTS system IIA component, probable, putative |
| ORF04060 | 8119 & 8120 | PTS system, galactitol-specific enzyme II, B component [2.7.1.69] |
| ORF04061 | 8121 & 8122 | PTS system, sorbitol-specific IIC component |
| ORF04062 | 8123 & 8124 | probable xylulose kinase Z4878 [2.7.1.30] |
| ORF04063 | 8125 & 8126 | phosphotransferase system HPr enzyme (PTS) |
| ORF04064 | 8127 & 8128 | Tagatose-bisphosphate aldolase GatY [4.1.2.—] |
| ORF04065 | 8129 & 8130 | ABC-2 type transporter family |
| ORF04066 | 8131 & 8132 | ribosome-associated ATPase, ATP-binding domain (N-terminal) |
| ORF04067 | 8133 & 8134 | Type I antifreeze protein:HlyD family secretion protein |
| ORF04068 | 8135 & 8136 | membrane protein, putative |
| ORF04069 | 8137 & 8138 | conserved hypothetical protein TIGR00275 |
| ORF04070 | 8139 & 8140 | Low-affinity inorganic phosphate transporter 1 |
| ORF04071 | 8141 & 8142 | Universal stress protein B |
| ORF04072 | 8143 & 8144 | universal stress protein A (UspA) |
| ORF04073 | 8145 & 8146 | hypothetical protein |
| ORF04074 | 8147 & 8148 | Hypothetical transporter yhiP |
| ORF04075 | 8149 & 8150 | gtg start, alternate starts possible |
| ORF04076 | 8151 & 8152 | Oligopeptidase A |
| ORF04077 | 8153 & 8154 | Protein of unknown function (DUF519) superfamily |
| ORF04078 | 8155 & 8156 | glutathione-disulfide reductase (gor) [1.8.1.7] |
| ORF04079 | 8157 & 8158 | conserved hypothetical protein |
| ORF04080 | 8159 & 8160 | Arsenate reductase [1.20.4.1] |
| ORF04081 | 8161 & 8162 | outer membrane protein induced after carbon starvation |
| ORF04082 | 8163 & 8164 | Hypothetical transcriptional regulator yhiF |
| ORF04083 | 8165 & 8166 | Hemin transport protein hmuS |
| ORF04084 | 8167 & 8168 | outer membrane hemin receptor ChuA |
| ORF04085 | 8169 & 8170 | conserved hypothetical protein |
| ORF04086 | 8171 & 8172 | Putative Periplasmic binding protein |
| ORF04087 | 8173 & 8174 | HugW |
| ORF04088 | 8175 & 8176 | HuvX protein (fragment) |
| ORF04089 | 8177 & 8178 | conserved hypothetical protein |
| ORF04090 | 8179 & 8180 | hemin ABC transporter permease protein |
| ORF04091 | 8181 & 8182 | hemin transport system ATP-binding protein |
| ORF04092 | 8183 & 8184 | cation transport ATPase yqgG |
| ORF04093 | 8185 & 8186 | protein hdeB precursor |
| ORF04094 | 8187 & 8188 | Protein hdeA precursor, putative |
| ORF04095 | 8189 & 8190 | HdeD protein |
| ORF04096 | 8191 & 8192 | conserved hypothetical protein |
| ORF04097 | 8193 & 8194 | multidrug efflux pump SdeX |
| ORF04098 | 8195 & 8196 | RND family, acridine-multidrug efflux pump |
| ORF04099 | 8197 & 8198 | HTH-type transcriptional regulator appY (M5 polypeptide) |
| ORF04100 | 8199 & 8200 | Transcriptional regulator gadX |
| ORF04101 | 8201 & 8202 | glutamate decarboxylase [4.1.1.15] |
| ORF04102 | 8203 & 8204 | cytochrome c551 peroxidase |
| ORF04103 | 8205 & 8206 | Trehalase [3.2.1.28] |
| ORF04104 | 8207 & 8208 | virulence regulator |
| ORF04105 | 8209 & 8210 | transcriptional regulator |
| ORF04106 | 8211 & 8212 | ribonuclease, putative |
| ORF04107 | 8213 & 8214 | metabolite-proton symporter |
| ORF04108 | 8215 & 8216 | Uncharacterized protein involved in outer membrane biogenesis |
| ORF04109 | 8217 & 8218 | EAL domain, putative |
| ORF04110 | 8219 & 8220 | 2-dehydro-3-deoxygluconokinase |
| ORF04111 | 8221 & 8222 | Protein yhjJ precursor [3.4.99.—] |
| ORF04112 | 8223 & 8224 | Aerobic C4-dicarboxylate transport protein |
| ORF04113 | 8225 & 8226 | Protein yhjK |
| ORF04114 | 8227 & 8228 | Cellulose synthase operon protein C |
| ORF04115 | 8229 & 8230 | Endoglucanase precursor |

TABLE 1-continued

Annotation of ORF00001 to ORF04995

| ORFnnnnn | SEQ ID NOs | Annotation |
|---|---|---|
| ORF04116 | 8231 & 8232 | Cyclic di-GMP binding protein precursor |
| ORF04117 | 8233 & 8234 | Cellulose synthase catalytic subunit [UDP-forming] |
| ORF04118 | 8235 & 8236 | YhjQ protein family |
| ORF04119 | 8237 & 8238 | conserved hypothetical protein |
| ORF04120 | 8239 & 8240 | conserved hypothetical protein |
| ORF04121 | 8241 & 8242 | conserved hypothetical protein |
| ORF04122 | 8243 & 8244 | conserved hypothetical protein |
| ORF04123 | 8245 & 8246 | conserved hypothetical protein |
| ORF04124 | 8247 & 8248 | Hypothetical transport protein yhjV |
| ORF04125 | 8249 & 8250 | peptide ABC transporter, ATP-binding protein (atp_bind) |
| ORF04126 | 8251 & 8252 | Dipeptide transport ATP-binding protein dppD (atp_bind) |
| ORF04127 | 8253 & 8254 | Dipeptide transport system permease protein dppC (membrane) |
| ORF04128 | 8255 & 8256 | Dipeptide transport system permease protein dppB (permease) |
| ORF04129 | 8257 & 8258 | Periplasmic dipeptide transport protein precursor (DBP) |
| ORF04130 | 8259 & 8260 | conserved hypothetical protein |
| ORF04131 | 8261 & 8262 | Membrane-protein yhjW |
| ORF04132 | 8263 & 8264 | putative resistance protein |
| ORF04133 | 8265 & 8266 | conserved hypothetical protein |
| ORF04134 | 8267 & 8268 | DNA-3-methyladenine glycosylase I [3.2.2.20] |
| ORF04135 | 8269 & 8270 | Biotin sulfoxide reductase |
| ORF04136 | 8271 & 8272 | Hypothetical acetyltransferase yiaC (GNAT) [2.3.1.—] |
| ORF04137 | 8273 & 8274 | probable outer membrane protein yiaD |
| ORF04138 | 8275 & 8276 | 2-ketogluconate reductase [1.1.1.215] |
| ORF04139 | 8277 & 8278 | lipoprotein, putative |
| ORF04140 | 8279 & 8280 | Putative HTH-type transcriptional regulator yiaG |
| ORF04141 | 8281 & 8282 | cold shock-like protein |
| ORF04142 | 8283 & 8284 | probable membrane permeability altering protein Z4982-related protein |
| ORF04143 | 8285 & 8286 | glycyl-tRNA synthetase, beta subunit (glyS) [6.1.1.14] |
| ORF04144 | 8287 & 8288 | glycyl-tRNA synthetase, alpha subunit (glyQ) [6.1.1.14] |
| ORF04145 | 8289 & 8290 | conserved hypothetical protein |
| ORF04146 | 8291 & 8292 | Acyltransferase family, putative |
| ORF04147 | 8293 & 8294 | yiaA-B two helix domain family |
| ORF04148 | 8295 & 8296 | yiaA-B two helix domain family |
| ORF04149 | 8297 & 8298 | xylulokinase (xylB) [2.7.1.17] |
| ORF04150 | 8299 & 8300 | xylose isomerase (xylA) [5.3.1.5] |
| ORF04151 | 8301 & 8302 | D-xylose ABC transporter, periplasmic-D xylose binding protein |
| ORF04152 | 8303 & 8304 | sugar ABC transporter, ATP-binding protein (xylG) |
| ORF04153 | 8305 & 8306 | sugar ABC transporter, permease protein |
| ORF04154 | 8307 & 8308 | Xylose operon regulatory protein (xylR) |
| ORF04155 | 8309 & 8310 | BAX protein |
| ORF04156 | 8311 & 8312 | Alpha-amylase precursor [3.2.1.1] |
| ORF04157 | 8313 & 8314 | Valine--pyruvate aminotransferase |
| ORF04158 | 8315 & 8316 | Electron transport protein hydN |
| ORF04159 | 8317 & 8318 | lclR family transcriptional repressor |
| ORF04160 | 8319 & 8320 | 2-keto reductase [1.1.1.—] |
| ORF04161 | 8321 & 8322 | YiaL |
| ORF04162 | 8323 & 8324 | YiaX1 |
| ORF04163 | 8325 & 8326 | TRAP transporter, DctQ-like membrane protein superfamily |
| ORF04164 | 8327 & 8328 | C4-dicarboxylate transport system permease large protein (DctM) |
| ORF04165 | 8329 & 8330 | DctP protein (AP001509) |
| ORF04166 | 8331 & 8332 | sugar kinase, FGGY family, putative [2.7.1.53] |
| ORF04167 | 8333 & 8334 | hexulose-6-phosphate synthase (humps) [4.1.2.—] |
| ORF04168 | 8335 & 8336 | hexulose-6-phosphate isomerase, putative |
| ORF04169 | 8337 & 8338 | L-ribulose-5-phosphate 4-epimerase (araD) [5.1.3.4] |
| ORF04170 | 8339 & 8340 | aldehyde dehydrogenase family protein (AF029733) |
| ORF04171 | 8341 & 8342 | Fic protein family family |
| ORF04172 | 8343 & 8344 | alcohol dehydrogenase, class IV [1.1.1.1] |
| ORF04173 | 8345 & 8346 | selenocysteine-specific translation elongation factor (selB) |
| ORF04174 | 8347 & 8348 | L-seryl-tRNA selenium transferase (selA) [2.9.1.1] |
| ORF04175 | 8349 & 8350 | Hypothetical GST-like protein yibF |
| ORF04176 | 8351 & 8352 | multidrug resistance efflux pump |
| ORF04177 | 8353 & 8354 | GTPase |
| ORF04178 | 8355 & 8356 | PTS system, mannitol-specific enzyme IIABC components [2.7.1.69] |
| ORF04179 | 8357 & 8358 | Mannitol-1-phosphate 5-dehydrogenase [1.1.1.17] |
| ORF04180 | 8359 & 8360 | Mannitol operon repressor (Mannitol repressor protein) |
| ORF04181 | 8361 & 8362 | conserved hypothetical protein |
| ORF04182 | 8363 & 8364 | conserved hypothetical protein |
| ORF04183 | 8365 & 8366 | conserved hypothetical protein |
| ORF04184 | 8367 & 8368 | surface protein (partial) |
| ORF04185 | 8369 & 8370 | L-lactate permease |
| ORF04186 | 8371 & 8372 | transcriptional regulator |
| ORF04187 | 8373 & 8374 | L-lactate dehydrogenase (lctD) [1.1.2.3] |
| ORF04188 | 8375 & 8376 | RNA methyltransferase, TrmH family, group 2 |
| ORF04189 | 8377 & 8378 | Serine acetyltransferase (SAT) (SAT) [2.3.1.30] |
| ORF04190 | 8379 & 8380 | Glycerol-3-phosphate dehydrogenase [NAD(P)+] (NAD(P)H-dependent glycerol-3-phosphate dehydrogenase) (gpsA) [1.1.1.94] |

TABLE 1-continued

Annotation of ORF00001 to ORF04995

| ORFnnnnn | SEQ ID NOs | Annotation |
|---|---|---|
| ORF04191 | 8381 & 8382 | protein-export protein SecB (secB) |
| ORF04192 | 8383 & 8384 | glutaredoxin 3 (grxC) |
| ORF04193 | 8385 & 8386 | Rhodanese-like domain protein |
| ORF04194 | 8387 & 8388 | 2,3-bisphosphoglycerate-independent phosphoglycerate mutase (gpmI) [5.4.2.1] |
| ORF04195 | 8389 & 8390 | Membrane-bound metallopeptidase |
| ORF04196 | 8391 & 8392 | glycosyl transferase, group 2 family protein, putative [2.—.—.—] |
| ORF04197 | 8393 & 8394 | yibQ gene product |
| ORF04198 | 8395 & 8396 | L-threonine 3-dehydrogenase (tdh) [1.1.1.103] |
| ORF04199 | 8397 & 8398 | 2-amino-3-ketobutyrate coenzyme A ligase (kbl) [2.3.1.29] |
| ORF04200 | 8399 & 8400 | ADP-L-glycero-D-manno-heptose-6-epimerase (rfaD) [5.1.3.20] |
| ORF04201 | 8401 & 8402 | lipopolysaccharide heptosyltransferase II (rfaF) |
| ORF04202 | 8403 & 8404 | lipopolysaccharide heptosyltransferase I (rfaC) [2.—.—.—] |
| ORF04203 | 8405 & 8406 | Lipid A-core, surface polymer ligase |
| ORF04204 | 8407 & 8408 | beta-1,3-glucosyltransferase [2.4.1.166] |
| ORF04205 | 8409 & 8410 | UDP-galactose:(galactosyl)LPS alpha-1,2-galactosyltransferase (glucosyl) [2.4.1.58] |
| ORF04206 | 8411 & 8412 | heptosyl-II-kinase |
| ORF04207 | 8413 & 8414 | UDP-galactose: (glucosyl) [2.4.1.58] |
| ORF04208 | 8415 & 8416 | UDP-glucose: (glucosyl) [2.4.1.44] |
| ORF04209 | 8417 & 8418 | Lipopolysaccharide core biosynthesis protein rfaP |
| ORF04210 | 8419 & 8420 | UDP-glucose: (heptosyl) [2.4.1.—] |
| ORF04211 | 8421 & 8422 | lipopolysaccharide heptosyltransferase III, putative |
| ORF04212 | 8423 & 8424 | 3-deoxy-D-manno-octulosonic-acid transferase (KDOtransferase) (KDO) [2.—.—.—] |
| ORF04213 | 8425 & 8426 | pantetheine-phosphate adenylyltransferase (coaD) [2.7.7.3] |
| ORF04214 | 8427 & 8428 | formamidopyrimidine-DNA glycosylase (mutM) [3.2.2.23] |
| ORF04215 | 8429 & 8430 | ribosomal protein L33 (rpmG) |
| ORF04216 | 8431 & 8432 | RpmB protein (rpL28) |
| ORF04217 | 8433 & 8434 | DNA repair protein |
| ORF04218 | 8435 & 8436 | phosphopantothenoylcysteine decarboxylase-phosphopantothenate--cysteine ligase (coaBC) [4.1.1.36 6.3.2.5] |
| ORF04219 | 8437 & 8438 | Deoxyuridine 5'-triphosphate nucleotidohydrolase (dut) [3.6.1.23] |
| ORF04220 | 8439 & 8440 | Ttk protein |
| ORF04221 | 8441 & 8442 | orotate phosphoribosyltransferase (pyrE) [2.4.2.10] |
| ORF04222 | 8443 & 8444 | ribonuclease PH (rph) [2.7.7.56] |
| ORF04223 | 8445 & 8446 | conserved hypothetical protein TIGR00255 |
| ORF04224 | 8447 & 8448 | hypothetical protein |
| ORF04225 | 8449 & 8450 | DNA-damage-inducible protein D |
| ORF04226 | 8451 & 8452 | predicted membrane protein |
| ORF04227 | 8453 & 8454 | Hypothetical DNA ligase-like protein yicF |
| ORF04228 | 8455 & 8456 | conserved hypothetical protein |
| ORF04229 | 8457 & 8458 | guanylate kinase |
| ORF04230 | 8459 & 8460 | DNA-directed RNA polymerase omega chain (RNAP omegasubunit) (Transcriptase omega chain) (RNA polymerase omega subunit) (rpoZ) [2.7.7.6] |
| ORF04231 | 8461 & 8462 | Guanosine-3,5-bis(Diphosphate) 3-pyrophosphohydrolase (ppGpp) |
| ORF04232 | 8463 & 8464 | tRNA (Guanosine-2'-O-)-methyltransferase (Gm18) [2.1.1.34] |
| ORF04233 | 8465 & 8466 | ATP-dependent DNA helicase RecG (recG) [3.6.1.—] |
| ORF04234 | 8467 & 8468 | sodium-glutamate symporter (gltS) |
| ORF04235 | 8469 & 8470 | xanthine-uracil permease family protein |
| ORF04236 | 8471 & 8472 | possible exported protein |
| ORF04237 | 8473 & 8474 | Protein of unknown function (DUF1498) superfamily |
| ORF04238 | 8475 & 8476 | possible NAGC-like transcriptional regulator |
| ORF04239 | 8477 & 8478 | fructose-bisphosphate aldolase, class II family [4.1.2.13] |
| ORF04240 | 8479 & 8480 | fructose-bisphosphate aldolase, class II family [4.1.2.—] |
| ORF04241 | 8481 & 8482 | PTS system, IIbc component (PTS) [2.7.1.69] |
| ORF04242 | 8483 & 8484 | PTS system, fructose-like-2 IIB component 1 |
| ORF04243 | 8485 & 8486 | PTS system, EIIa component (PTS) [2.7.1.69] |
| ORF04244 | 8487 & 8488 | transcription antiterminator BglG family protein,, putative |
| ORF04245 | 8489 & 8490 | f772 [3.2.1.20] |
| ORF04246 | 8491 & 8492 | similar to melibiose carrier protein |
| ORF04247 | 8493 & 8494 | RhuM (partial) |
| ORF04248 | 8495 & 8496 | membrane protein |
| ORF04249 | 8497 & 8498 | Lipoprotein-28 precursor (hlpA) |
| ORF04250 | 8499 & 8500 | conserved hypothetical protein |
| ORF04251 | 8501 & 8502 | putative transport protein |
| ORF04252 | 8503 & 8504 | Protein of unknown function (DUF1198) superfamily |
| ORF04253 | 8505 & 8506 | xanthine-uracil permease family protein subfamily |
| ORF04254 | 8507 & 8508 | adenine deaminase (ade) [3.5.4.2] |
| ORF04255 | 8509 & 8510 | Hexose phosphate transport protein |
| ORF04256 | 8511 & 8512 | Regulatory protein uhpC |
| ORF04257 | 8513 & 8514 | Sensor protein uhpB |
| ORF04258 | 8515 & 8516 | hypothetical protein |
| ORF04259 | 8517 & 8518 | response regulator, positive activator of uhpT transcription |
| ORF04260 | 8519 & 8520 | acetolactate synthase, small subunit, putative [2.2.1.6] |
| ORF04261 | 8521 & 8522 | acetolactate synthase, large subunit, biosynthetic type (ilvB) [2.2.1.6] |
| ORF04262 | 8523 & 8524 | Multidrug resistance protein D |
| ORF04263 | 8525 & 8526 | f165 [1.—.—.—] |

TABLE 1-continued

Annotation of ORF00001 to ORF04995

| ORFnnnnn | SEQ ID NOs | Annotation |
|---|---|---|
| ORF04264 | 8527 & 8528 | conserved hypothetical protein |
| ORF04265 | 8529 & 8530 | Predicted membrane protein |
| ORF04266 | 8531 & 8532 | probable sulfatase yidJ [3.1.6.—] |
| ORF04267 | 8533 & 8534 | Putative sulfatase yidJ [3.1.6.—] |
| ORF04268 | 8535 & 8536 | Na+-myo-inositol cotransporter |
| ORF04269 | 8537 & 8538 | msm operon regulatory protein, putative |
| ORF04270 | 8539 & 8540 | potassium uptake protein TrkA, putative |
| ORF04271 | 8541 & 8542 | heat shock protein |
| ORF04272 | 8543 & 8544 | heat shock protein |
| ORF04273 | 8545 & 8546 | hypothetical protein |
| ORF04274 | 8547 & 8548 | o135 protein |
| ORF04275 | 8549 & 8550 | f416 |
| ORF04276 | 8551 & 8552 | MFS transporter, phthalate permease family |
| ORF04277 | 8553 & 8554 | conserved hypothetical protein |
| ORF04278 | 8555 & 8556 | mandelate racemase-muconate lactonizing enzyme family protein (partial) [4.2.1.6] |
| ORF04279 | 8557 & 8558 | 4-hydroxy-2-oxoglutarate aldolase-2-dehydro-3-deoxyphosphogluconate [4.1.2.21] |
| ORF04280 | 8559 & 8560 | 2-dehydro-3-deoxygalactonate kinase [2.7.1.58] |
| ORF04281 | 8561 & 8562 | transcriptional repressor for galactonate utilization (GntR family) (AF096293) |
| ORF04282 | 8563 & 8564 | probable replicase Z5187 |
| ORF04283 | 8565 & 8566 | Cof family protein |
| ORF04284 | 8567 & 8568 | Bacterial protein of unknown function (DUF937) family |
| ORF04285 | 8569 & 8570 | DNA gyrase, B subunit (gyrB) [5.99.1.3] |
| ORF04286 | 8571 & 8572 | DNA replication and repair protein recF [similarity] |
| ORF04287 | 8573 & 8574 | DNA polymerase III, beta subunit (dnaN) [2.7.7.7] |
| ORF04288 | 8575 & 8576 | chromosomal replication initiator protein DnaA (dnaA) |
| ORF04289 | 8577 & 8578 | ribosomal protein L34 (rpmH) |
| ORF04290 | 8579 & 8580 | ribonuclease P protein component (rnpA) [3.1.26.5] |
| ORF04291 | 8581 & 8582 | conserved hypothetical protein TIGR00278 |
| ORF04292 | 8583 & 8584 | Inner membrane protein oxaA (IMP) |
| ORF04293 | 8585 & 8586 | tRNA modification GTPase TrmE (trmE) |
| ORF04294 | 8587 & 8588 | tryptophanase (TNase) [4.1.99.1] |
| ORF04295 | 8589 & 8590 | Low affinity tryptophan permease |
| ORF04296 | 8591 & 8592 | similar to drug resistance translocases |
| ORF04297 | 8593 & 8594 | transcriptional regulator, LysR family |
| ORF04298 | 8595 & 8596 | hypothetical protein |
| ORF04299 | 8597 & 8598 | o252 |
| ORF04300 | 8599 & 8600 | YieF (putative) |
| ORF04301 | 8601 & 8602 | f445 |
| ORF04302 | 8603 & 8604 | haloacid dehalogenase-like hydrolase, putative |
| ORF04303 | 8605 & 8606 | conserved hypothetical protein |
| ORF04304 | 8607 & 8608 | pyrimidine-specific nucleoside hydrolase [3.5.99.6] |
| ORF04305 | 8609 & 8610 | Putative esterase family, putative |
| ORF04306 | 8611 & 8612 | putative xylanase |
| ORF04307 | 8613 & 8614 | f538 |
| ORF04308 | 8615 & 8616 | 6-phospho-beta-glucosidase bglB [3.2.1.86] |
| ORF04309 | 8617 & 8618 | PTS system, beta-glucoside-specific IIABC component |
| ORF04310 | 8619 & 8620 | Cryptic beta-glucoside bgl operon Antiterminator |
| ORF04311 | 8621 & 8622 | phosphate transport system regulatory protein PhoU (phoU) |
| ORF04312 | 8623 & 8624 | phosphate ABC transporter, ATP-binding protein (pstB) [3.6.3.27] |
| ORF04313 | 8625 & 8626 | phosphate ABC transporter, permease protein PstA (pstA) |
| ORF04314 | 8627 & 8628 | phosphate ABC transporter, permease protein PstC (pstC) |
| ORF04315 | 8629 & 8630 | phosphate ABC transporter, phosphate-binding protein (pstS) |
| ORF04316 | 8631 & 8632 | glucosamine--fructose-6-phosphate aminotransferase, isomerizing (glmS) [2.6.1.16] |
| ORF04317 | 8633 & 8634 | UDP-N-acetylglucosamine pyrophosphorylase (glmU) [2.7.7.23] |
| ORF04318 | 8635 & 8636 | ATP synthase F1, epsilon subunit (atpC) [3.6.3.14] |
| ORF04319 | 8637 & 8638 | ATP synthase F1, beta subunit (atpD) [3.6.3.14] |
| ORF04320 | 8639 & 8640 | ATP synthase F1, gamma subunit (atpG) [3.6.3.14] |
| ORF04321 | 8641 & 8642 | ATP synthase F1, alpha subunit (atpA) [3.6.3.14] |
| ORF04322 | 8643 & 8644 | ATP synthase F1, delta subunit (atpH) [3.6.3.14] |
| ORF04323 | 8645 & 8646 | ATP synthase F0, B subunit (atpF) [3.6.3.14] |
| ORF04324 | 8647 & 8648 | conserved hypothetical protein |
| ORF04325 | 8649 & 8650 | ATP synthase F0, C subunit [3.6.3.14] |
| ORF04326 | 8651 & 8652 | ATP synthase F0, A subunit (atpB) [3.6.3.14] |
| ORF04327 | 8653 & 8654 | ATP synthase F0, I subunit (atpI) [3.6.3.14] |
| ORF04328 | 8655 & 8656 | methyltransferase GidB (gidB) [2.1.—.—] |
| ORF04329 | 8657 & 8658 | glucose-inhibited division protein A (gidA) |
| ORF04330 | 8659 & 8660 | Protein mioC (mioC) |
| ORF04331 | 8661 & 8662 | transcriptional regulator, AsnC Family (asnC) |
| ORF04332 | 8663 & 8664 | aspartate--ammonia ligase (asnA) [6.3.1.1] |
| ORF04333 | 8665 & 8666 | conserved hypothetical protein |
| ORF04334 | 8667 & 8668 | unnamed protein product |
| ORF04335 | 8669 & 8670 | potassium uptake protein (kup) |
| ORF04336 | 8671 & 8672 | high affinity ribose transport protein rbsD |
| ORF04337 | 8673 & 8674 | ribose ABC transporter, ATP-binding protein (atp_bind) |
| ORF04338 | 8675 & 8676 | ribose ABC transporter, permease protein (rbsC) |
| ORF04339 | 8677 & 8678 | ribose ABC transporter, periplasmic D-ribose-binding protein |

TABLE 1-continued

Annotation of ORF00001 to ORF04995

| ORFnnnnn | SEQ ID NOs | Annotation |
|---|---|---|
| ORF04340 | 8679 & 8680 | ribokinase (rbsK) [2.7.1.15] |
| ORF04341 | 8681 & 8682 | drug resistance transporter, EmrB-QacA family |
| ORF04342 | 8683 & 8684 | regulator for rbs operon |
| ORF04343 | 8685 & 8686 | ProP protein |
| ORF04344 | 8687 & 8688 | yieP gene product (AF096293) |
| ORF04345 | 8689 & 8690 | hypothetical protein |
| ORF04346 | 8691 & 8692 | Transcription regulator |
| ORF04347 | 8693 & 8694 | o137 (YIFE) |
| ORF04348 | 8695 & 8696 | Mg chelatase-related protein |
| ORF04349 | 8697 & 8698 | hypothetical protein |
| ORF04350 | 8699 & 8700 | acetolactate synthase, large subunit, biosynthetic type (ilvB) [2.2.1.6] |
| ORF04351 | 8701 & 8702 | acetolactate synthase II small chain (ALS-II) [4.1.3.18] |
| ORF04352 | 8703 & 8704 | branched-chain amino acid aminotransferase (ilvE) [2.6.1.42] |
| ORF04353 | 8705 & 8706 | dihydroxy-acid dehydratase (ilvD) [4.2.1.9] |
| ORF04354 | 8707 & 8708 | threonine ammonia-lyase, biosynthetic (ilvA) [4.3.1.19] |
| ORF04355 | 8709 & 8710 | transcriptional regulator, LysR family, putative |
| ORF04356 | 8711 & 8712 | Ketol-acid reductoisomerase (ILVC) [1.1.1.86] |
| ORF04357 | 8713 & 8714 | peptidylprolyl isomerase (SPP39159) [5.2.1.8] |
| ORF04358 | 8715 & 8716 | ATP-dependent DNA helicase Rep (rep) [3.6.1.—] |
| ORF04359 | 8717 & 8718 | Guanosine-5'-triphosphate,3'-diphosphate pyrophosphatase [3.6.1.40] |
| ORF04360 | 8719 & 8720 | rhlB protein (RHLB) [3.6.1.—] |
| ORF04361 | 8721 & 8722 | thioredoxin 1 |
| ORF04362 | 8723 & 8724 | transcription termination factor Rho (rho) |
| ORF04363 | 8725 & 8726 | conserved hypothetical protein |
| ORF04364 | 8727 & 8728 | undecaprenyl-phosphate alpha-N-acetylglucosaminyl 1-phosphatetransferase (wecA) [2.7.8.—] |
| ORF04365 | 8729 & 8730 | Lipopolysaccharide biosynthesis protein wzzE |
| ORF04366 | 8731 & 8732 | UDP-N-acetylglucosamine 2-epimerase [5.1.3.14] |
| ORF04367 | 8733 & 8734 | UDP-N-acetyl-D-mannosamine dehydrogenase (ECA) [1.1.1.—] |
| ORF04368 | 8735 & 8736 | dTDP-glucose 4,6-dehydratase (rfbB) [4.2.1.46] |
| ORF04369 | 8737 & 8738 | glucose-1-phosphate thymidylyltransferase (rfbA) [2.7.7.24] |
| ORF04370 | 8739 & 8740 | TDP-D-fucosamine acetyltransferase (wecD) |
| ORF04371 | 8741 & 8742 | Lipopolysaccharide biosynthesis protein rffA (WECE) [4.2.1.—] |
| ORF04372 | 8743 & 8744 | WzxE protein (WZXE) |
| ORF04373 | 8745 & 8746 | TDP-Fuc4NAc:lipid II Fuc4Nac transferase (wecF) [2.4.1.—] |
| ORF04374 | 8747 & 8748 | ECA biosynthesis protein WzyE (wzyE) |
| ORF04375 | 8749 & 8750 | possibly rffM (ECA) [2.4.1.—] |
| ORF04376 | 8751 & 8752 | hypothetical protein |
| ORF04377 | 8753 & 8754 | similar to several amino acid transport proteins (o461) |
| ORF04378 | 8755 & 8756 | tyrosine recombinase XerC (xerC) |
| ORF04379 | 8757 & 8758 | o238 (YIGB) |
| ORF04380 | 8759 & 8760 | tyrosine recombinase XerC (xerC) |
| ORF04381 | 8761 & 8762 | o238 (YIGB) |
| ORF04382 | 8763 & 8764 | arylsulfatase regulator |
| ORF04383 | 8765 & 8766 | Arylsulfatase [3.1.6.1] |
| ORF04384 | 8767 & 8768 | hemY protein (hemY) |
| ORF04385 | 8769 & 8770 | uroporphyrinogen III methylase (HEMX) [2.1.1.107] |
| ORF04386 | 8771 & 8772 | uroporphyrinogen-III synthase (hemD) [4.2.1.75] |
| ORF04387 | 8773 & 8774 | porphobilinogen deaminase (hemC) [2.5.1.61] |
| ORF04388 | 8775 & 8776 | adenylate cyclase, class-I (cyaA) [4.6.1.1] |
| ORF04389 | 8777 & 8778 | CyaY protein (CYAY) |
| ORF04390 | 8779 & 8780 | possible exported protein |
| ORF04391 | 8781 & 8782 | lipoprotein, putative |
| ORF04392 | 8783 & 8784 | Hypothetical lipoprotein yifL precursor-related protein |
| ORF04393 | 8785 & 8786 | diaminopimelate epimerase (dapF) [5.1.1.7] |
| ORF04394 | 8787 & 8788 | Protein of unknown function, DUF484 superfamily |
| ORF04395 | 8789 & 8790 | tyrosine recombinase XerC (xerC) |
| ORF04396 | 8791 & 8792 | o238 (YIGB) |
| ORF04397 | 8793 & 8794 | DNA helicase II (uvrD) [3.6.1.—] |
| ORF04398 | 8795 & 8796 | Protein of unknown function superfamily |
| ORF04399 | 8797 & 8798 | yigE protein |
| ORF04400 | 8799 & 8800 | hypothetical protein |
| ORF04401 | 8801 & 8802 | magnesium and cobalt transport protein CorA (corA) |
| ORF04402 | 8803 & 8804 | Enterobacterial putative membrane protein (DUF943) superfamily |
| ORF04403 | 8805 & 8806 | conserved hypothetical protein |
| ORF04404 | 8807 & 8808 | hypothetical protein |
| ORF04405 | 8809 & 8810 | rarD protein (rarD) |
| ORF04406 | 8811 & 8812 | f161 (YIGI) |
| ORF04407 | 8813 & 8814 | phospholipase A1 family protein, interruption [3.1.1.32] |
| ORF04408 | 8815 & 8816 | ATP-dependent DNA helicase RecQ (recQ) [3.6.1.—] |
| ORF04409 | 8817 & 8818 | threonine efflux protein |
| ORF04410 | 8819 & 8820 | transporter, LysE family |
| ORF04411 | 8821 & 8822 | Lysophospholipase L2 (Lecithinase B) (PLDB) [3.1.1.5] |
| ORF04412 | 8823 & 8824 | Cof protein |
| ORF04413 | 8825 & 8826 | HTH-type transcriptional regulator metR (METR) |
| ORF04414 | 8827 & 8828 | Hypothetical membrane protein yigM |

TABLE 1-continued

Annotation of ORF00001 to ORF04995

| ORFnnnnn | SEQ ID NOs | Annotation |
|---|---|---|
| ORF04415 | 8829 & 8830 | 5-methyltetrahydropteroyltriglutamate--homocysteine S-methyltransferase (metE) [2.1.1.14] |
| ORF04416 | 8831 & 8832 | conserved hypothetical protein |
| ORF04417 | 8833 & 8834 | conserved hypothetical protein |
| ORF04418 | 8835 & 8836 | 6-phospho-3-hexuloisomerase (PHI) |
| ORF04419 | 8837 & 8838 | PTS system, glucose-specific IIBC component (ptsG) [2.7.1.69] |
| ORF04420 | 8839 & 8840 | transketolase (tkt) [2.2.1.1] |
| ORF04421 | 8841 & 8842 | transcriptional regulator, rpiR family domain protein |
| ORF04422 | 8843 & 8844 | transcriptional regulator, LysR family |
| ORF04423 | 8845 & 8846 | cytosine transporter, putative |
| ORF04424 | 8847 & 8848 | amidase family protein, putative |
| ORF04425 | 8849 & 8850 | Carbamate kinase-like protein yahI [2.7.2.2] |
| ORF04426 | 8851 & 8852 | YahG-YlbE-like protein |
| ORF04427 | 8853 & 8854 | YahF-FdrA-like protein |
| ORF04428 | 8855 & 8856 | conserved hypothetical protein |
| ORF04429 | 8857 & 8858 | isochorismatase family protein |
| ORF04430 | 8859 & 8860 | hypothetical protein |
| ORF04431 | 8861 & 8862 | Putative carboxymethylenebutenolidase |
| ORF04432 | 8863 & 8864 | conserved hypothetical protein |
| ORF04433 | 8865 & 8866 | uridine phosphorylase (udp) [2.4.2.3] |
| ORF04434 | 8867 & 8868 | tricarboxylate transport protein TctA, putative |
| ORF04435 | 8869 & 8870 | conserved hypothetical protein |
| ORF04436 | 8871 & 8872 | Bordetella uptake gene (bug) product superfamily |
| ORF04437 | 8873 & 8874 | 4-hydroxy-2-oxoglutarate aldolase-2-dehydro-3-deoxyphosphogluconate |
| ORF04438 | 8875 & 8876 | 2-dehydro-3-deoxygalactonate kinase |
| ORF04439 | 8877 & 8878 | transcriptional regulator, IclR family |
| ORF04440 | 8879 & 8880 | DNA recombination protein rmuC |
| ORF04441 | 8881 & 8882 | Ubiquinone-menaquinone biosynthesis methyltransferase ubiE(EC 2.1.1.—) (UBIE) [2.1.1.—] |
| ORF04442 | 8883 & 8884 | unnamed protein product |
| ORF04443 | 8885 & 8886 | 2-polyprenylphenol 6-hydroxylase (ubiB) [1.14.13.—] |
| ORF04444 | 8887 & 8888 | o261 (YIGT) |
| ORF04445 | 8889 & 8890 | o261 |
| ORF04446 | 8891 & 8892 | Sec-independent protein translocase TatC (tatC) |
| ORF04447 | 8893 & 8894 | tatD gene product (YIGW) [3.1.21.—] |
| ORF04448 | 8895 & 8896 | transcriptional activator RfaH (rfaH) |
| ORF04449 | 8897 & 8898 | 3-octaprenyl-4-hydroxybenzoate carboxy-lyase (Polyprenylp-hydroxybenzoate decarboxylase) (YIGC) [4.1.1.—] |
| ORF04450 | 8899 & 8900 | NAD(P)H-flavin reductase |
| ORF04451 | 8901 & 8902 | conserved hypothetical protein |
| ORF04452 | 8903 & 8904 | acetyl-CoA C-acyltransferase FadA (fadA) [2.3.1.16] |
| ORF04453 | 8905 & 8906 | fatty oxidation complex, alpha subunit FadB (fadB) [4.2.1.17 5.3.3.8 1.1.1.35 5.1.2.3] |
| ORF04454 | 8907 & 8908 | unnamed protein product; pepQ product, proline dipeptidase (PEPQ) [3.4.13.9] |
| ORF04455 | 8909 & 8910 | conserved hypothetical protein TIGR00257 |
| ORF04456 | 8911 & 8912 | bis(5'-nucleosyl)-tetraphosphatase, symmetrical-Trk system potassium uptake protein TrkG, fusion |
| ORF04457 | 8913 & 8914 | protoporphyrin oxidase |
| ORF04458 | 8915 & 8916 | hypothetical protein |
| ORF04459 | 8917 & 8918 | molybdopterin-guanine dinucleotide biosynthesis protein B (mobB) |
| ORF04460 | 8919 & 8920 | Molybdopterin-guanine dinucleotide biosynthesis protein A |
| ORF04461 | 8921 & 8922 | Protein yihD |
| ORF04462 | 8923 & 8924 | YihE |
| ORF04463 | 8925 & 8926 | Thiol:disulfide interchange protein dsbA precursor (por) [5.3.4.1] |
| ORF04464 | 8927 & 8928 | Bacterial protein of unknown function (DUF945) superfamily |
| ORF04465 | 8929 & 8930 | Acyltransferase domain protein |
| ORF04466 | 8931 & 8932 | DNA polymerase I (POL I) (polA) [2.7.7.7] |
| ORF04467 | 8933 & 8934 | essential GTPase for cell cycle |
| ORF04468 | 8935 & 8936 | neutrophil protein |
| ORF04469 | 8937 & 8938 | hypothetical protein |
| ORF04470 | 8939 & 8940 | oxygen-independent coproporphyrinogen III oxidase (hemN) |
| ORF04471 | 8941 & 8942 | hypothetical protein |
| ORF04472 | 8943 & 8944 | nitrogen regulation protein NR(I) (ntrC) |
| ORF04473 | 8945 & 8946 | Nitrogen regulation protein NR(II) [2.7.3.—] |
| ORF04474 | 8947 & 8948 | glutamine synthetase, type I (glnA) [6.3.1.2] |
| ORF04475 | 8949 & 8950 | GTP-binding protein TypA (typA) |
| ORF04476 | 8951 & 8952 | hypothetical protein |
| ORF04477 | 8953 & 8954 | Glycerol-3-phosphate regulon repressor |
| ORF04478 | 8955 & 8956 | Hypothetical sugar kinase yihV |
| ORF04479 | 8957 & 8958 | 3-hydroxyisobutyrate dehydrogenase |
| ORF04480 | 8959 & 8960 | Tagatose 1,6-diphosphate aldolase 2 (Tagatose-bisphosphate aldolase 2) (D-tagotase-1,6-bisphophate aldolase 2) [4.1.—.—.] |
| ORF04481 | 8961 & 8962 | 2,3-butanediol dehydrogenase, putative |
| ORF04482 | 8963 & 8964 | major facilitator family transporter, truncation, putative |
| ORF04483 | 8965 & 8966 | major facilitator family transporter |
| ORF04484 | 8967 & 8968 | Aldose 1-epimerase superfamily |

TABLE 1-continued

Annotation of ORF00001 to ORF04995

| ORFnnnnn | SEQ ID NOs | Annotation |
|---|---|---|
| ORF04485 | 8969 & 8970 | haloacid dehalogenase-like hydrolase, putative |
| ORF04486 | 8971 & 8972 | ribonuclease BN, putative [3.1.—.—] |
| ORF04487 | 8973 & 8974 | D-tyrosyl-tRNA(Tyr) deacylase (dtd) [3.1.—.—] |
| ORF04488 | 8975 & 8976 | conserved membrane protein [2.3.1.18] |
| ORF04489 | 8977 & 8978 | lipase, GDXG family VCA0490 |
| ORF04490 | 8979 & 8980 | transcriptional regulator, Cro-Cl family |
| ORF04491 | 8981 & 8982 | Ribbon-helix-helix protein, copG family domain protein |
| ORF04492 | 8983 & 8984 | formate dehydrogenase accessory protein FdhE (fdhE) |
| ORF04493 | 8985 & 8986 | formate dehydrogenase, gamma subunit [1.2.1.2] |
| ORF04494 | 8987 & 8988 | formate dehydrogenase, beta subunit (FdxH) [1.2.1.2] |
| ORF04495 | 8989 & 8990 | formate dehydrogenase, alpha subunit [1.2.1.2] |
| ORF04496 | 8991 & 8992 | formate dehydrogenase, alpha subunit, selenocysteine-containing [1.2.1.2] |
| ORF04497 | 8993 & 8994 | formate dehydrogenase family accessory protein FdhD (fdhD) |
| ORF04498 | 8995 & 8996 | conserved hypothetical protein |
| ORF04499 | 8997 & 8998 | conserved hypothetical protein |
| ORF04500 | 8999 & 9000 | Putative glycoporin |
| ORF04501 | 9001 & 9002 | B. subtilis YulD protein homolog lin2978, putative |
| ORF04502 | 9003 & 9004 | Rhamnulose-1-phosphate aldolase |
| ORF04503 | 9005 & 9006 | L-rhamnose isomerase (rhaA) [5.3.1.14] |
| ORF04504 | 9007 & 9008 | sugar kinase [2.7.1.5] |
| ORF04505 | 9009 & 9010 | hypothetical protein |
| ORF04506 | 9011 & 9012 | L-rhamnose operon Regulatory protein rhaS |
| ORF04507 | 9013 & 9014 | positive regulator for rhaRS operon |
| ORF04508 | 9015 & 9016 | L-rhamnose-proton symport |
| ORF04509 | 9017 & 9018 | Superoxide dismutase [Mn] (sodA) [1.15.1.1] |
| ORF04510 | 9019 & 9020 | conserved hypothetical protein |
| ORF04511 | 9021 & 9022 | 2-keto-3-deoxygluconate transporter (kdgT) |
| ORF04512 | 9023 & 9024 | MOSC domain protein |
| ORF04513 | 9025 & 9026 | Sensor protein cpxA [2.7.3.—] |
| ORF04514 | 9027 & 9028 | Transcriptional Regulatory protein cpxR |
| ORF04515 | 9029 & 9030 | Periplasmic protein cpxP precursor |
| ORF04516 | 9031 & 9032 | protein p34 |
| ORF04517 | 9033 & 9034 | 6-phosphofructokinase I |
| ORF04518 | 9035 & 9036 | Sulfate-binding protein precursor |
| ORF04519 | 9037 & 9038 | CDP-diacylglycerol pyrophosphatase |
| ORF04520 | 9039 & 9040 | triosephosphate isomerase (tpiA) [5.3.1.1] |
| ORF04521 | 9041 & 9042 | Protein of unknown function (DUF1454) superfamily |
| ORF04522 | 9043 & 9044 | conserved membrane protein |
| ORF04523 | 9045 & 9046 | conserved hypothetical protein superfamily |
| ORF04524 | 9047 & 9048 | Universal stress protein D (UspA) |
| ORF04525 | 9049 & 9050 | Ferredoxin--NADP reductase (DA1) [1.18.1.2] |
| ORF04526 | 9051 & 9052 | fructose-1,6-bisphosphatase, class II (glpX) [3.1.3.11] |
| ORF04527 | 9053 & 9054 | glycerol kinase (glpk) [2.7.1.30] |
| ORF04528 | 9055 & 9056 | Glycerol uptake facilitator protein (Aquaglyceroporin) (glpF) |
| ORF04529 | 9057 & 9058 | Protein of unknown function (DUF904) superfamily |
| ORF04530 | 9059 & 9060 | regulator of ribonuclease activity A (rraA) |
| ORF04531 | 9061 & 9062 | 1,4-dihydroxy-2-naphthoate octaprenyltransferase (menA) [2.5.—.—] |
| ORF04532 | 9063 & 9064 | heat shock protein HsIVU, ATPase subunit HsIU (hsIU) |
| ORF04533 | 9065 & 9066 | peptidase component of the HsIUV protease |
| ORF04534 | 9067 & 9068 | cell division protein FtsN (ftsN) |
| ORF04535 | 9069 & 9070 | regulator for deo operon, udp, cdd, tsx |
| ORF04536 | 9071 & 9072 | Primosomal protein N' |
| ORF04537 | 9073 & 9074 | ribosomal protein L31 (rpmE) |
| ORF04538 | 9075 & 9076 | Protein of unknown function (DUF1105) superfamily |
| ORF04539 | 9077 & 9078 | Met repressor |
| ORF04540 | 9079 & 9080 | O-succinylhomoserine (thiol)-lyase (metB) [2.5.1.48] |
| ORF04541 | 9081 & 9082 | AKII-HDII protein [2.7.2.4] |
| ORF04542 | 9083 & 9084 | Nucleoside-specific channel-forming protein tsx precursor |
| ORF04543 | 9085 & 9086 | 5-nucleotidase family protein, putative |
| ORF04544 | 9087 & 9088 | 5'-nucleotidase, C-terminal domain protein |
| ORF04545 | 9089 & 9090 | 5-nucleotidase, putative |
| ORF04546 | 9091 & 9092 | conserved hypothetical protein |
| ORF04547 | 9093 & 9094 | 5-nucleotidase family protein, putative |
| ORF04548 | 9095 & 9096 | 5,10-methylenetetrahydrofolate reductase (metF) [1.7.99.5] |
| ORF04549 | 9097 & 9098 | catalase-peroxidase HPI (katG) [1.11.1.6] |
| ORF04550 | 9099 & 9100 | Hypothetical transport protein yijE |
| ORF04551 | 9101 & 9102 | Protein of unknown function (DUF1287) superfamily |
| ORF04552 | 9103 & 9104 | conserved hypothetical protein |
| ORF04553 | 9105 & 9106 | Glycerol dehydrogenase (NAD) [1.1.1.6] |
| ORF04554 | 9107 & 9108 | transaldolase, putative |
| ORF04555 | 9109 & 9110 | Phosphoenolpyruvate-protein phosphotransferase ptsA [2.7.3.9] |
| ORF04556 | 9111 & 9112 | PTS system, fructose-specific IIABC components |
| ORF04557 | 9113 & 9114 | PTS system, fructose-like-2 IIB component 1 (Phosphotransferase enzymeII, B component) [2.7.1.69] |
| ORF04558 | 9115 & 9116 | pyruvate formate-lyase [2.3.1.54] |
| ORF04559 | 9117 & 9118 | similar to E. coli pyruvate formate-lyase activating enzyme |

TABLE 1-continued

Annotation of ORF00001 to ORF04995

| ORFnnnnn | SEQ ID NOs | Annotation |
|---|---|---|
| ORF04560 | 9119 & 9120 | AraC-type DNA-binding domain-containing protein |
| ORF04561 | 9121 & 9122 | PTS system fructose-like IIB component 2 (phosphotransfer) [2.7.1.69] |
| ORF04562 | 9123 & 9124 | integral membrane protein, putative |
| ORF04563 | 9125 & 9126 | phosphoenolpyruvate carboxylase (ppc) [4.1.1.31] |
| ORF04564 | 9127 & 9128 | acetylornithine deacetylase (ArgE) (argE) [3.5.1.16] |
| ORF04565 | 9129 & 9130 | N-acetyl-gamma-glutamyl-phosphate reductase (argC) [1.2.1.38] |
| ORF04566 | 9131 & 9132 | acetylglutamate kinase (argB) [2.7.2.8] |
| ORF04567 | 9133 & 9134 | argininosuccinate lyase (argH) [4.3.2.1] |
| ORF04568 | 9135 & 9136 | Starvation sensing protein rspA |
| ORF04569 | 9137 & 9138 | major facilitator family transporter |
| ORF04570 | 9139 & 9140 | soluble pyridine nucleotide transhydrogenase (STH) [1.6.1.1] |
| ORF04571 | 9141 & 9142 | Hydrogen peroxide-inducible genes activator (oxyR) |
| ORF04572 | 9143 & 9144 | hippurate hydolase |
| ORF04573 | 9145 & 9146 | major facilitator family transporter |
| ORF04574 | 9147 & 9148 | transcriptional regulator, TetR family |
| ORF04575 | 9149 & 9150 | ATPase of the AAA+ class |
| ORF04576 | 9151 & 9152 | tRNA (uracil-5-)-methyltransferase (trmA) [2.1.1.35] |
| ORF04577 | 9153 & 9154 | TonB-dependent vitamin B12 receptor (btuB) |
| ORF04578 | 9155 & 9156 | glutamate racemase (murI) [5.1.1.3] |
| ORF04579 | 9157 & 9158 | hypothetical protein |
| ORF04580 | 9159 & 9160 | UDP-N-acetylenolpyruvoylglucosamine reductase (murB) [1.1.1.158] |
| ORF04581 | 9161 & 9162 | BirA bifunctional protein (BIRA) [6.3.4.15] |
| ORF04582 | 9163 & 9164 | pantothenate kinase (coaA) [2.7.1.33] |
| ORF04583 | 9165 & 9166 | translation elongation factor EF-Tu.B |
| ORF04584 | 9167 & 9168 | translation elongation factor EF-Tu.B |
| ORF04585 | 9169 & 9170 | protein chain elongation factor EF-Tu |
| ORF04586 | 9171 & 9172 | preprotein translocase SecE subunit (SecE) |
| ORF04587 | 9173 & 9174 | transcription termination-antitermination factor NusG (nusG) |
| ORF04588 | 9175 & 9176 | ribosomal protein L11 (rplK) |
| ORF04589 | 9177 & 9178 | ribosomal protein L1 (rplA) |
| ORF04590 | 9179 & 9180 | 50S ribosomal subunit protein L10 (RPLJ) |
| ORF04591 | 9181 & 9182 | ribosomal protein L7-L12 (rplL) |
| ORF04592 | 9183 & 9184 | DNA-directed RNA polymerase, beta subunit (rpoB) [2.7.7.6] |
| ORF04593 | 9185 & 9186 | DNA-directed RNA polymerase, beta' subunit (rpoC) [2.7.7.6] |
| ORF04594 | 9187 & 9188 | thiazole biosynthesis protein ThiH (thiH) |
| ORF04595 | 9189 & 9190 | 4-methyl-5-(beta-hydroxyethyl)thiazole monophosphate synthesis protein ThiG |
| ORF04596 | 9191 & 9192 | thiamine biosynthesis protein ThiS (thiS) |
| ORF04597 | 9193 & 9194 | thiazole biosynthesis adenylyltransferase ThiF (thiF) |
| ORF04598 | 9195 & 9196 | thiamine-phosphate pyrophosphorylase (thiE) [2.5.1.3] |
| ORF04599 | 9197 & 9198 | Thiamine biosynthesis protein thiC |
| ORF04600 | 9199 & 9200 | Regulator of sigma D |
| ORF04601 | 9201 & 9202 | MutT-nudix family protein [3.6.1.—] |
| ORF04602 | 9203 & 9204 | uroporphyrinogen decarboxylase (hemE) [4.1.1.37] |
| ORF04603 | 9205 & 9206 | endonuclease V (deoxyinosine 3endoduclease) |
| ORF04604 | 9207 & 9208 | Protein of unknown function, DUF superfamily |
| ORF04605 | 9209 & 9210 | DNA-binding protein HU-alpha (NS2) (HU-2) (HU) |
| ORF04606 | 9211 & 9212 | unnamed protein product |
| ORF04607 | 9213 & 9214 | Zinc resistance-associated protein precursor |
| ORF04608 | 9215 & 9216 | sensor kinase for HydG, hydrogenase 3 activity [2.7.3.—] |
| ORF04609 | 9217 & 9218 | Transcriptional Regulatory protein zraR (sigma54) |
| ORF04610 | 9219 & 9220 | phosphoribosylamine--glycine ligase (purD) [6.3.4.13] |
| ORF04611 | 9221 & 9222 | bifunctional purine biosynthesis protein PurH (purH) |
| ORF04612 | 9223 & 9224 | conserved hypothetical protein |
| ORF04613 | 9225 & 9226 | hypothetical protein |
| ORF04614 | 9227 & 9228 | conserved hypothetical protein |
| ORF04615 | 9229 & 9230 | acetyltransferase, GNAT family (putative) [2.3.1.—] |
| ORF04616 | 9231 & 9232 | homoserine O-succinyltransferase (metA) [2.3.1.46] |
| ORF04617 | 9233 & 9234 | malate synthase A (aceB) [2.3.3.9] |
| ORF04618 | 9235 & 9236 | isocitrate lyase (aceA) [4.1.3.1] |
| ORF04619 | 9237 & 9238 | Isocitrate dehydrogenase kinase-phosphatase(EC 3.1.3.—) (IDH kinase-phosphatase) (IDHK-P) [2.7.1.116] |
| ORF04620 | 9239 & 9240 | transcriptional regulator, putative |
| ORF04621 | 9241 & 9242 | hypothetical protein |
| ORF04622 | 9243 & 9244 | 5-methyltetrahydrofolate--homocysteine methyltransferase (metH) [2.1.1.13] |
| ORF04623 | 9245 & 9246 | conserved hypothetical protein |
| ORF04624 | 9247 & 9248 | Na-Pi-cotransporter II-related protein, putative |
| ORF04625 | 9249 & 9250 | Peptidase E (Alpha-aspartyl dipeptidase) (Asp-specificdipeptidase) (Dipeptidase E) (alpha) [3.4.13.21] |
| ORF04626 | 9251 & 9252 | L-sorbose 1-phosphate reductase [1.1.1.—] |
| ORF04627 | 9253 & 9254 | PTS system, mannose-specific IID component |
| ORF04628 | 9255 & 9256 | PTS system, mannose-specific IIC component [2.7.1.69] |
| ORF04629 | 9257 & 9258 | sorbose-permease PTS system IIB component (EIII-MAN) [2.7.1.69] |
| ORF04630 | 9259 & 9260 | PTS system, sorbose-specific IIA component (EIIA-Sor) (Sorbose-permease IIA component) (Phosphotransferase enzyme II, A component)(EC 2.7.1.69) (EIII-F-Sor) [2.7.1.69] |
| ORF04631 | 9261 & 9262 | D-glucitol-6-phosphate dehydrogenase [1.1.1.140] |

TABLE 1-continued

Annotation of ORF00001 to ORF04995

| ORFnnnnn | SEQ ID NOs | Annotation |
|---|---|---|
| ORF04632 | 9263 & 9264 | Putative transcriptional regulator of sorbose uptake and |
| ORF04633 | 9265 & 9266 | RNA pseudouridylate synthase family protein [4.2.1.70] |
| ORF04634 | 9267 & 9268 | conserved hypothetical protein |
| ORF04635 | 9269 & 9270 | asparate kinase, monofunctional class [2.7.2.4] |
| ORF04636 | 9271 & 9272 | glucose-6-phosphate isomerase (pgi) [5.3.1.9] |
| ORF04637 | 9273 & 9274 | conserved hypothetical protein |
| ORF04638 | 9275 & 9276 | lipoprotein, putative |
| ORF04639 | 9277 & 9278 | Protein of unknown function (DUF1017) superfamily |
| ORF04640 | 9279 & 9280 | otnG protein (o698) |
| ORF04641 | 9281 & 9282 | conserved hypothetical protein |
| ORF04642 | 9283 & 9284 | PsiE protein homolog |
| ORF04643 | 9285 & 9286 | Maltose transport system permease protein malG (malG) |
| ORF04644 | 9287 & 9288 | Maltose transport system permease protein malF (membrane) |
| ORF04645 | 9289 & 9290 | Maltose-binding periplasmic protein precursor |
| ORF04646 | 9291 & 9292 | Maltose-maltodextrin transport ATP-binding protein malK |
| ORF04647 | 9293 & 9294 | Maltoporin precursor (Maltose-inducible porin) (malL) |
| ORF04648 | 9295 & 9296 | Maltose operon periplasmic protein precursor (MalM) superfamily |
| ORF04649 | 9297 & 9298 | conserved hypothetical protein |
| ORF04650 | 9299 & 9300 | chorismate lyase [4.—.—.—] |
| ORF04651 | 9301 & 9302 | 4-hydroxybenzoate polyprenyl transferase (ubiA) [2.5.1.—] |
| ORF04652 | 9303 & 9304 | glycerol-3-phosphate O-acyltransferase [2.3.1.15] |
| ORF04653 | 9305 & 9306 | diacylglycerol kinase (DGK) [2.7.1.107] |
| ORF04654 | 9307 & 9308 | LexA repressor (lexA) [3.4.21.88] |
| ORF04655 | 9309 & 9310 | DNA-damage-inducible protein F, truncation |
| ORF04656 | 9311 & 9312 | Protein yjbJ-related protein |
| ORF04657 | 9313 & 9314 | Zinc uptake regulation protein |
| ORF04658 | 9315 & 9316 | tRNA-dihydrouridine synthase A [1.—.—.—] |
| ORF04659 | 9317 & 9318 | conserved hypothetical protein |
| ORF04660 | 9319 & 9320 | quinone oxidoreductase |
| ORF04661 | 9321 & 9322 | Putative oxidoreductase |
| ORF04662 | 9323 & 9324 | metabolite-proton symporter |
| ORF04663 | 9325 & 9326 | enoyl-CoA hydratase-isomerase family protein |
| ORF04664 | 9327 & 9328 | acetyl-CoA-transferase subunit, putative [2.8.3.—] |
| ORF04665 | 9329 & 9330 | LACI-FAMILY TRANSCRIPTION REGULATOR |
| ORF04666 | 9331 & 9332 | replicative DNA helicase (dnaB) [3.6.1.—] |
| ORF04667 | 9333 & 9334 | alanine racemase (alr) [5.1.1.1] |
| ORF04668 | 9335 & 9336 | transporter, putative |
| ORF04669 | 9337 & 9338 | NadR homolog |
| ORF04670 | 9339 & 9340 | Aromatic-amino-acid aminotransferase |
| ORF04671 | 9341 & 9342 | 2-oxoglutarate dehydrogenase, E1 component (sucA) [1.2.4.2] |
| ORF04672 | 9343 & 9344 | 2-oxoglutarate dehydrogenase, E2 component, dihydrolipoamide succinyltransferase (sucB) [2.3.1.61] |
| ORF04673 | 9345 & 9346 | dihydrolipoamide dehydrogenase (lpdA) [1.8.1.4] |
| ORF04674 | 9347 & 9348 | Succinyl-CoA synthetase beta chain (AF326913) [6.2.1.5] |
| ORF04675 | 9349 & 9350 | Succinyl-CoA synthetase alpha chain [6.2.1.5] |
| ORF04676 | 9351 & 9352 | anion transporter family protein |
| ORF04677 | 9353 & 9354 | two-component response regulator |
| ORF04678 | 9355 & 9356 | Putative lactate dehydrogenase |
| ORF04679 | 9357 & 9358 | Putative transport sensor protein |
| ORF04680 | 9359 & 9360 | HAD superfamily (subfamily IIIB) phosphatase, TIGR01672 (AphA) [3.1.3.—] |
| ORF04681 | 9361 & 9362 | conserved hypothetical protein TIGR00149 |
| ORF04682 | 9363 & 9364 | Protein yjbR |
| ORF04683 | 9365 & 9366 | excinuclease ABC, A subunit (uvrA) |
| ORF04684 | 9367 & 9368 | ssDNA-binding protein |
| ORF04685 | 9369 & 9370 | conserved hypothetical protein |
| ORF04686 | 9371 & 9372 | EAL domain protein |
| ORF04687 | 9373 & 9374 | regulatory protein soxS |
| ORF04688 | 9375 & 9376 | redox-sensitive transcriptional activator SoxR (soxR) |
| ORF04689 | 9377 & 9378 | xanthine-uracil permease family protein |
| ORF04690 | 9379 & 9380 | Na+-H+ antiporter |
| ORF04691 | 9381 & 9382 | transcriptional regulator, LysR family, putative |
| ORF04692 | 9383 & 9384 | conserved hypothetical protein |
| ORF04693 | 9385 & 9386 | murein hydrolase exporter |
| ORF04694 | 9387 & 9388 | LrgB-like family superfamily |
| ORF04695 | 9389 & 9390 | Sodium, solute symporter family protein (PutP) |
| ORF04696 | 9391 & 9392 | Protein of unknown function, DUF485 superfamily |
| ORF04697 | 9393 & 9394 | acetate--CoA ligase (acsA) [6.2.1.1] |
| ORF04698 | 9395 & 9396 | nitrite reductase (cytochrome; ammonia-forming (nrfA) [1.7.2.2] |
| ORF04699 | 9397 & 9398 | formate-dependent nitrite reductase NrfB |
| ORF04700 | 9399 & 9400 | NrfC protein (NrfC) [1.—.—.—] |
| ORF04701 | 9401 & 9402 | NrfD protein (NrfD) [1.—.—.—] |
| ORF04702 | 9403 & 9404 | cytochrome c-type biogenesis protein CcmF (ccmF) |
| ORF04703 | 9405 & 9406 | formate-dependent nitrite reductase |
| ORF04704 | 9407 & 9408 | Formate-dependent nitrite reductase complex nrfG subunit (nrfF) |
| ORF04705 | 9409 & 9410 | conserved hypothetical protein |
| ORF04706 | 9411 & 9412 | glutamate-aspartate symport protein (gltP) |

TABLE 1-continued

Annotation of ORF00001 to ORF04995

| ORFnnnnn | SEQ ID NOs | Annotation |
| --- | --- | --- |
| ORF04707 | 9413 & 9414 | conserved hypothetical protein |
| ORF04708 | 9415 & 9416 | ABC transporter, ATP-binding protein |
| ORF04709 | 9417 & 9418 | ABC transporter, nucleotide binding-ATPase protein [dipeptide] |
| ORF04710 | 9419 & 9420 | ABC transporter, permease protein (AE006058) |
| ORF04711 | 9421 & 9422 | ABC transporter permease protein (AE005357) |
| ORF04712 | 9423 & 9424 | ABC transporter, periplasmic oligo-dipeptide-nickel binding protein (AE005357) |
| ORF04713 | 9425 & 9426 | formate dehydrogenase, alpha subunit [1.2.1.2] |
| ORF04714 | 9427 & 9428 | formate dehydrogenase, alpha subunit, putative [1.2.1.2] |
| ORF04715 | 9429 & 9430 | matches PS00443: Glutamine amidotransferases class-II active site; similar to Pseudomonas cepacia fusaric acid resistance protein FusA |
| ORF04716 | 9431 & 9432 | Fusaric acid resistance protein conserved region family |
| ORF04717 | 9433 & 9434 | HlyD family secretion protein, putative |
| ORF04718 | 9435 & 9436 | conserved hypothetical protein |
| ORF04719 | 9437 & 9438 | metallo-beta-lactamase superfamily protein |
| ORF04720 | 9439 & 9440 | glucokinase (EC 2.7.1.2), putative [2.7.1.2] |
| ORF04721 | 9441 & 9442 | ribulose-phosphate 3-epimerase (rpe) [5.1.3.1] |
| ORF04722 | 9443 & 9444 | ribose ABC transporter, permease protein (permease) |
| ORF04723 | 9445 & 9446 | ribose ABC transporter, permease protein (ECOWU89) |
| ORF04724 | 9447 & 9448 | D-allose transport ATP-binding protein alsA (aldose) |
| ORF04725 | 9449 & 9450 | hypothetical protein |
| ORF04726 | 9451 & 9452 | D-allose-binding periplasmic protein precursor (ALBP) |
| ORF04727 | 9453 & 9454 | Transcriptional regulator, putative |
| ORF04728 | 9455 & 9456 | hypothetical protein |
| ORF04729 | 9457 & 9458 | ribose 5-phosphate isomerase B (rpiB) [5.3.1.6] |
| ORF04730 | 9459 & 9460 | conserved hypothetical protein |
| ORF04731 | 9461 & 9462 | PhnP protein (phnp) |
| ORF04732 | 9463 & 9464 | PhnO protein |
| ORF04733 | 9465 & 9466 | phosphonate metabolism protein-1,5-bisphosphokinase (PRPP-forming) PhnN (phnN) |
| ORF04734 | 9467 & 9468 | phosphonate metabolism protein PhnM (phnM) |
| ORF04735 | 9469 & 9470 | phosphonate C-P lyase system protein PhnL (phnL) |
| ORF04736 | 9471 & 9472 | phosphonate C-P lyase system protein PhnK (phnK) |
| ORF04737 | 9473 & 9474 | Phosphonate metabolism protein PhnJ |
| ORF04738 | 9475 & 9476 | Bacterial phosphonate metabolism protein (PhnI) |
| ORF04739 | 9477 & 9478 | Bacterial phosphonate metabolism protein (PhnH) |
| ORF04740 | 9479 & 9480 | PhnG protein |
| ORF04741 | 9481 & 9482 | phosphonates metabolism transcriptional regulator PhnF (phnF) |
| ORF04742 | 9483 & 9484 | membrane channel protein component of Pn transporter |
| ORF04743 | 9485 & 9486 | phosphonate ABC transporter, substrate-binding protein, putative |
| ORF04744 | 9487 & 9488 | phosphonate ABC transporter, ATP-binding protein (phnC) |
| ORF04745 | 9489 & 9490 | PhnB protein |
| ORF04746 | 9491 & 9492 | alkylphosphonate utilization operon protein PhnA |
| ORF04747 | 9493 & 9494 | conserved hypothetical protein |
| ORF04748 | 9495 & 9496 | conserved hypothetical protein |
| ORF04749 | 9497 & 9498 | amino acid MFS transporter (PPII) |
| ORF04750 | 9499 & 9500 | Sensor protein basS-pmrB |
| ORF04751 | 9501 & 9502 | Transcriptional Regulatory protein basR-pmrA |
| ORF04752 | 9503 & 9504 | predicted membrane-associated, metal-dependent hydrolase |
| ORF04753 | 9505 & 9506 | Arginine-agmatine antiporter |
| ORF04754 | 9507 & 9508 | HTH-type transcriptional regulator adiY |
| ORF04755 | 9509 & 9510 | arginine decarboxylase [4.1.1.19] |
| ORF04756 | 9511 & 9512 | arginine decarboxylase adi, biodegradative (ldc) [4.1.1.19] |
| ORF04757 | 9513 & 9514 | Melibiose operon regulatory protein (AF049243) |
| ORF04758 | 9515 & 9516 | glycosyl hydrolase, family 4, putative [3.2.1.22] |
| ORF04759 | 9517 & 9518 | membrane protein, putative |
| ORF04760 | 9519 & 9520 | fumarate hydratase class I, anaerobic [4.2.1.2] |
| ORF04761 | 9521 & 9522 | anaerobic C4-dicarboxylate membrane transporter |
| ORF04762 | 9523 & 9524 | conserved hypothetical protein |
| ORF04763 | 9525 & 9526 | response regulator VC1604 (partial) |
| ORF04764 | 9527 & 9528 | Sensor protein dcuS [2.7.3.—] |
| ORF04765 | 9529 & 9530 | hypothetical protein |
| ORF04766 | 9531 & 9532 | YjdL-like protein |
| ORF04767 | 9533 & 9534 | acetyltransferase, GNAT family (GNAT) |
| ORF04768 | 9535 & 9536 | lysyl-tRNA synthetase (lysS) [6.1.1.6] |
| ORF04769 | 9537 & 9538 | PTR2-family transport protein STY0750 (POT) |
| ORF04770 | 9539 & 9540 | CadA (ldc) [4.1.1.18] |
| ORF04771 | 9541 & 9542 | transport of lysine-cadaverine |
| ORF04772 | 9543 & 9544 | transcriptional activator |
| ORF04773 | 9545 & 9546 | hypothetical protein |
| ORF04774 | 9547 & 9548 | transcriptional regulator, TetR family domain protein, putative |
| ORF04775 | 9549 & 9550 | Thiol: disulfide interchange protein dsbD precursor (dsbD) [1.8.1.8] |
| ORF04776 | 9551 & 9552 | divalent cation tolerance protein cytochrome c biogenesis |
| ORF04777 | 9553 & 9554 | Anaerobic C4-dicarboxylate transporter dcuA (DcuA) |
| ORF04778 | 9555 & 9556 | aspartate ammonia-lyase (aspA) [4.3.1.1] |
| ORF04779 | 9557 & 9558 | suppressor of F exclusion of bacteriophage T7 |
| ORF04780 | 9559 & 9560 | Amino acid permease superfamily |

TABLE 1-continued

Annotation of ORF00001 to ORF04995

| ORFnnnnn | SEQ ID NOs | Annotation |
|---|---|---|
| ORF04781 | 9561 & 9562 | chaperonin, 10 kDa (groES) |
| ORF04782 | 9563 & 9564 | chaperonin GroEL (groL) |
| ORF04783 | 9565 & 9566 | conserved hypothetical protein |
| ORF04784 | 9567 & 9568 | conserved hypothetical protein |
| ORF04785 | 9569 & 9570 | lysine 2; 3-aminomutase |
| ORF04786 | 9571 & 9572 | translation elongation factor P (efp) |
| ORF04787 | 9573 & 9574 | Entericidin B precursor-related protein |
| ORF04788 | 9575 & 9576 | Entericidin B precursor-related protein |
| ORF04789 | 9577 & 9578 | SugEL |
| ORF04790 | 9579 & 9580 | Outer membrane lipoprotein blc precursor |
| ORF04791 | 9581 & 9582 | beta-lactamase |
| ORF04792 | 9583 & 9584 | fumarate reductase, anaerobic, membrane anchor polypeptide |
| ORF04793 | 9585 & 9586 | Fumarate reductase subunit C (Fumarate reductase 15 kDa hydrophobicprotein) (frdC) [1.3.99.1] |
| ORF04794 | 9587 & 9588 | fumarate reductase, anaerobic, iron-sulfur protein subunit |
| ORF04795 | 9589 & 9590 | fumarate reductase, flavoprotein subunit (frdA) [1.3.99.1] |
| ORF04796 | 9591 & 9592 | Iysyl-tRNA synthetase-related protein GenX |
| ORF04797 | 9593 & 9594 | amino acid permease |
| ORF04798 | 9595 & 9596 | conserved hypothetical protein |
| ORF04799 | 9597 & 9598 | conserved hypothetical protein |
| ORF04800 | 9599 & 9600 | unnamed protein product |
| ORF04801 | 9601 & 9602 | phosphatidylserine decarboxylase phospholipid synthesis |
| ORF04802 | 9603 & 9604 | Predicted GTPases |
| ORF04803 | 9605 & 9606 | Oligoribonuclease |
| ORF04804 | 9607 & 9608 | unnamed protein product |
| ORF04805 | 9609 & 9610 | predicted sugar kinase |
| ORF04806 | 9611 & 9612 | conserved hypothetical protein TIGR00150 |
| ORF04807 | 9613 & 9614 | N-acetylmuramoyl-l-alanine amidase II a murein hydrolase |
| ORF04808 | 9615 & 9616 | DNA mismatch repair protein mutL |
| ORF04809 | 9617 & 9618 | tRNA delta(2)-isopentenylpyrophosphate transferase (miaA) [2.5.1.8] |
| ORF04810 | 9619 & 9620 | host factor I (HF-I) |
| ORF04811 | 9621 & 9622 | GTP-binding protein hflX |
| ORF04812 | 9623 & 9624 | HflK protein (hflK) [3.4.—.—] |
| ORF04813 | 9625 & 9626 | HflC protein (hflC) |
| ORF04814 | 9627 & 9628 | hypothetical protein |
| ORF04815 | 9629 & 9630 | conserved hypothetical protein |
| ORF04816 | 9631 & 9632 | hypothetical protein |
| ORF04817 | 9633 & 9634 | adenylosuccinate synthetase (purA) [6.3.4.4] |
| ORF04818 | 9635 & 9636 | Predicted transcriptional regulator |
| ORF04819 | 9637 & 9638 | ribonuclease R (rnr) [3.1.—.—] |
| ORF04820 | 9639 & 9640 | RNA methyltransferase, TrmH family, group 3 |
| ORF04821 | 9641 & 9642 | conserved hypothetical protein |
| ORF04822 | 9643 & 9644 | PspA-IM30 family protein |
| ORF04823 | 9645 & 9646 | conserved hypothetical protein |
| ORF04824 | 9647 & 9648 | predicted membrane protein (o132) |
| ORF04825 | 9649 & 9650 | Protein of unknown function (DUF1190) superfamily |
| ORF04826 | 9651 & 9652 | glutathionylspermidine synthase (O386) |
| ORF04827 | 9653 & 9654 | fadE8 |
| ORF04828 | 9655 & 9656 | Protein of unknown function (DUF1471) superfamily |
| ORF04829 | 9657 & 9658 | Protein of unknown function (DUF1471) family |
| ORF04830 | 9659 & 9660 | Hydrolases of the alpha-beta superfamily (putative) |
| ORF04831 | 9661 & 9662 | transcriptional regulator, DeoR family, putative |
| ORF04832 | 9663 & 9664 | Predicted Zn-dependent hydrolase of the beta-lactamase fold |
| ORF04833 | 9665 & 9666 | Putative sugar-specific permease, SgaT-UlaA superfamily, putative |
| ORF04834 | 9667 & 9668 | putative IIB protein of PTS system |
| ORF04835 | 9669 & 9670 | protein-Npi-phosphohistidine-sugar phosphotransferase (Ntr-type) [2.7.1.69] |
| ORF04836 | 9671 & 9672 | hexulose-6-phosphate synthase (humps) |
| ORF04837 | 9673 & 9674 | hexulose-6-phosphate isomerase, putative |
| ORF04838 | 9675 & 9676 | AraD |
| ORF04839 | 9677 & 9678 | Protein of unknown function (DUF1471) superfamily |
| ORF04840 | 9679 & 9680 | 30S ribosomal protein (rpS6) |
| ORF04841 | 9681 & 9682 | Single-strand binding protein family |
| ORF04842 | 9683 & 9684 | ribosomal protein S18 (rpsR) |
| ORF04843 | 9685 & 9686 | ribosomal protein L9 (rpll) |
| ORF04844 | 9687 & 9688 | conserved hypothetical protein |
| ORF04845 | 9689 & 9690 | MFS transporter, phthalate permease family, putative |
| ORF04846 | 9691 & 9692 | Putative oxidoreductase |
| ORF04847 | 9693 & 9694 | acetyl-CoA-transferase subunit, putative |
| ORF04848 | 9695 & 9696 | enoyl-CoA hydratase-isomerase FadB1x, putative [4.2.1.55] |
| ORF04849 | 9697 & 9698 | 3-dehydroshikimate dehydratase |
| ORF04850 | 9699 & 9700 | conserved hypothetical protein |
| ORF04851 | 9701 & 9702 | 3-oxoacyl-(acyl-carrier-protein) reductase |
| ORF04852 | 9703 & 9704 | Opacity-associated protein A superfamily |
| ORF04853 | 9705 & 9706 | Putative conserved protein |
| ORF04854 | 9707 & 9708 | FKBP-type 22 kDa peptidyl-prolyl cis-trans isomerase (rotamase) [5.2.1.8] |
| ORF04855 | 9709 & 9710 | D-serine-D-alanine-glycine transporter |

TABLE 1-continued

Annotation of ORF00001 to ORF04995

| ORFnnnnn | SEQ ID NOs | Annotation |
|---|---|---|
| ORF04856 | 9711 & 9712 | ScdA protein, putative |
| ORF04857 | 9713 & 9714 | integral membrane protein (f324) |
| ORF04858 | 9715 & 9716 | conserved hypothetical protein |
| ORF04859 | 9717 & 9718 | Predicted transcriptional regulators |
| ORF04860 | 9719 & 9720 | 2',3'-cyclic-nucleotide 2'-phosphodiesterase (cpdB) [3.1.4.16] |
| ORF04861 | 9721 & 9722 | conserved hypothetical protein YtfJ-family, TIGR01626 |
| ORF04862 | 9723 & 9724 | 3'(2'),5'-bisphosphate nucleotidase (cysQ) [3.1.3.7] |
| ORF04863 | 9725 & 9726 | Protein of unknown function (DUF1107) superfamily |
| ORF04864 | 9727 & 9728 | Hypothetical UPF0053 protein ytfL |
| ORF04865 | 9729 & 9730 | peptide methionine sulfoxide reductase |
| ORF04866 | 9731 & 9732 | unnamed protein product |
| ORF04867 | 9733 & 9734 | Family of unknown function (DUF490) family |
| ORF04868 | 9735 & 9736 | Hypothetical UPF0131 protein ytfP |
| ORF04869 | 9737 & 9738 | inorganic pyrophosphatase (ppa) [3.6.1.1] |
| ORF04870 | 9739 & 9740 | periplasmic ribose-binding protein |
| ORF04871 | 9741 & 9742 | ATP binding protein of ABC transporter |
| ORF04872 | 9743 & 9744 | ribose ABC transporter, permease protein VCA0129 |
| ORF04873 | 9745 & 9746 | ribose ABC transporter, permease protein |
| ORF04874 | 9747 & 9748 | fructose-1,6-bisphosphatase (fbp) [3.1.3.11] |
| ORF04875 | 9749 & 9750 | conserved hypothetical protein |
| ORF04876 | 9751 & 9752 | UDP-N-acetylmuramate: L-alanyl-gamma-D-glutamyl-meso-diaminopimelate ligase (mpl) |
| ORF04877 | 9753 & 9754 | Hypothetical UPF0307 protein yjgA (x96 protein) |
| ORF04878 | 9755 & 9756 | PmbA protein (pmbA) |
| ORF04879 | 9757 & 9758 | Soluble cytochrome b562 precursor (562) |
| ORF04880 | 9759 & 9760 | Anaerobic ribonucleoside-triphosphate reductase activating protein(EC 1.97.1.4) (Class III anaerobic ribonucleotide reductase smallcomponent) [1.97.1.4] |
| ORF04881 | 9761 & 9762 | anaerobic ribonucleoside-triphosphate reductase [1.17.4.2] |
| ORF04882 | 9763 & 9764 | hypothetical protein |
| ORF04883 | 9765 & 9766 | alpha, alpha-phosphotrehalase (treC) [3.2.1.93] |
| ORF04884 | 9767 & 9768 | PTS system, trehalose-specific IIBC component (treP) [2.7.1.69] |
| ORF04885 | 9769 & 9770 | trehalose operon repressor (treR) |
| ORF04886 | 9771 & 9772 | magnesium-translocating P-type ATPase (mgtA) [3.6.3.2] |
| ORF04887 | 9773 & 9774 | endoribonuclease L-PSP, putative |
| ORF04888 | 9775 & 9776 | aspartate carbamoyltransferase, regulatory subunit (pyrI) |
| ORF04889 | 9777 & 9778 | aspartate carbamoyltransferase (pyrB) [2.1.3.2] |
| ORF04890 | 9779 & 9780 | arginine repressor |
| ORF04891 | 9781 & 9782 | membrane protein, putative |
| ORF04892 | 9783 & 9784 | ornithine carbamoyltransferase (argF) [2.1.3.3] |
| ORF04893 | 9785 & 9786 | carbamate kinase (arcC) [2.7.2.2] |
| ORF04894 | 9787 & 9788 | arginine deiminase (arcA) [3.5.3.6] |
| ORF04895 | 9789 & 9790 | Protein yjgK |
| ORF04896 | 9791 & 9792 | ornithine carbamoyltransferase (argF) [2.1.3.3] |
| ORF04897 | 9793 & 9794 | Protein |
| ORF04898 | 9795 & 9796 | hypothetical protein |
| ORF04899 | 9797 & 9798 | acetyltransferase, GNAT family family |
| ORF04900 | 9799 & 9800 | probable innner membrane protein STY4813 |
| ORF04901 | 9801 & 9802 | valyl-tRNA synthetase (valS) [6.1.1.9] |
| ORF04902 | 9803 & 9804 | DNA polymerase III, chi subunit [2.7.7.7] |
| ORF04903 | 9805 & 9806 | Cytosol aminopeptidase (Leucine aminopeptidase) (LAP)(Leucyl aminopeptidase) (Aminopeptidase A-I) (LAP) [3.4.11.1] |
| ORF04904 | 9807 & 9808 | conserved hypothetical protein |
| ORF04905 | 9809 & 9810 | unnamed protein product |
| ORF04906 | 9811 & 9812 | hypothetical protein |
| ORF04907 | 9813 & 9814 | predicted permease |
| ORF04908 | 9815 & 9816 | conserved ATP-binding protein |
| ORF04909 | 9817 & 9818 | L-idonate Regulatory protein (gnt) |
| ORF04910 | 9819 & 9820 | Gnt-II system L-idonate transporter |
| ORF04911 | 9821 & 9822 | PROBABLE GLUCONATE 5-DEHYDROGENASE OXIDOREDUCTASE PROTEIN [1.1.1.69] |
| ORF04912 | 9823 & 9824 | 2,3-butanediol dehydrogenase [1.1.1.264] |
| ORF04913 | 9825 & 9826 | thermoresistant gluconokinase [2.7.1.12] |
| ORF04914 | 9827 & 9828 | NADP-dependent alcohol dehydrogenase [1.1.1.—] |
| ORF04915 | 9829 & 9830 | Integrase |
| ORF04916 | 9831 & 9832 | CII protein |
| ORF04917 | 9833 & 9834 | Beta protein |
| ORF04918 | 9835 & 9836 | Polarity suppression protein (Amber mutation-suppressing protein) |
| ORF04919 | 9837 & 9838 | Transactivation protein |
| ORF04920 | 9839 & 9840 | Glycoprotein 3 (Capsid size determination protein) |
| ORF04921 | 9841 & 9842 | phage DNA binding protein |
| ORF04922 | 9843 & 9844 | unnamed protein product; cI gene product (AA 1-137) |
| ORF04923 | 9845 & 9846 | conserved hypothetical protein |
| ORF04924 | 9847 & 9848 | conserved hypothetical protein |
| ORF04925 | 9849 & 9850 | Bacteriophage P4 DNA primase [2.7.7.—] |
| ORF04926 | 9851 & 9852 | hypothetical protein |
| ORF04927 | 9853 & 9854 | hypothetical protein |

TABLE 1-continued

Annotation of ORF00001 to ORF04995

| ORFnnnnn | SEQ ID NOs | Annotation |
| --- | --- | --- |
| ORF04928 | 9855 & 9856 | ATP-dependent protease La |
| ORF04929 | 9857 & 9858 | conserved hypothetical protein |
| ORF04930 | 9859 & 9860 | conserved hypothetical protein |
| ORF04931 | 9861 & 9862 | unnamed protein product; ORF616 |
| ORF04932 | 9863 & 9864 | Kelch motif domain protein |
| ORF04933 | 9865 & 9866 | Oligogalacturonate-specific porin protein (KdgM) superfamily |
| ORF04934 | 9867 & 9868 | FimB protein |
| ORF04935 | 9869 & 9870 | recombinase involved in phase variation regulator for |
| ORF04936 | 9871 & 9872 | type 1 fimbrial protein fimA precursor |
| ORF04937 | 9873 & 9874 | fimbrial protein |
| ORF04938 | 9875 & 9876 | Chaperone protein fimC precursor |
| ORF04939 | 9877 & 9878 | Outer membrane usher protein fimD precursor |
| ORF04940 | 9879 & 9880 | FimF protein precursor |
| ORF04941 | 9881 & 9882 | fimbrial morphology |
| ORF04942 | 9883 & 9884 | FimH |
| ORF04943 | 9885 & 9886 | mannonate dehydratase (uxuA) [4.2.1.8] |
| ORF04944 | 9887 & 9888 | D-mannonate oxidoreductase [1.1.1.57[ |
| ORF04945 | 9889 & 9890 | regulator of uxu operon |
| ORF04946 | 9891 & 9892 | Protein of unknown function (DUF1316) subfamily |
| ORF04947 | 9893 & 9894 | phosphoenolpyruvate-protein phosphotransferase, EI-HPr-EIIA components |
| ORF04948 | 9895 & 9896 | dihydroxyacetone kinase, L subunit [2.7.1.—] |
| ORF04949 | 9897 & 9898 | dihydroxyacetone kinase, DhaK subunit (dhaK) [2.7.1.—] |
| ORF04950 | 9899 & 9900 | hypothetical protein |
| ORF04951 | 9901 & 9902 | glycerol dehydrogenase CgrD (NAD) [1.1.1.6] |
| ORF04952 | 9903 & 9904 | putative transporter CgxT |
| ORF04953 | 9905 & 9906 | invasion protein IbeA |
| ORF04954 | 9907 & 9908 | choline-glycine betaine transporter |
| ORF04955 | 9909 & 9910 | Glycerate kinase [2.7.1.31] |
| ORF04956 | 9911 & 9912 | 2-hydroxy-3-oxopropionate reductase [1.1.1.60] |
| ORF04957 | 9913 & 9914 | hydroxypyruvate isomerase [5.3.1.22] |
| ORF04958 | 9915 & 9916 | hypothetical protein |
| ORF04959 | 9917 & 9918 | glyoxylate carboligase [4.1.1.47] |
| ORF04960 | 9919 & 9920 | glyoxylate carboligase [4.1.1.47] |
| ORF04961 | 9921 & 9922 | NtrC family Transcriptional regulator, ATPase domain |
| ORF04962 | 9923 & 9924 | invasion protein IbeA |
| ORF04963 | 9925 & 9926 | hypothetical protein |
| ORF04964 | 9927 & 9928 | Na+-H+ antiporter NhaC (nhaC) |
| ORF04965 | 9929 & 9930 | Hypothetical transcriptional regulator yjiE |
| ORF04966 | 9931 & 9932 | hypothetical protein |
| ORF04967 | 9933 & 9934 | isoaspartyl dipeptidase (iadA) [3.4.19.—] |
| ORF04968 | 9935 & 9936 | uncharacterized membrane protein |
| ORF04969 | 9937 & 9938 | Nucleoside recognition domain protein |
| ORF04970 | 9939 & 9940 | RNA 2'-phosphotransferase, Tpt1 - KptA family domain protein |
| ORF04971 | 9941 & 9942 | conserved hypothetical protein |
| ORF04972 | 9943 & 9944 | membrane protein, putative |
| ORF04973 | 9945 & 9946 | SrgB |
| ORF04974 | 9947 & 9948 | conserved hypothetical protein |
| ORF04975 | 9949 & 9950 | Activator of 2-hydroxyglutaryl-CoA dehydratase (HSP70-class ATPase domain) |
| ORF04976 | 9951 & 9952 | 2-hydroxyglutaryl-CoA dehydratase subunit beta homolog |
| ORF04977 | 9953 & 9954 | Protein of unknown function (DUF445) superfamily |
| ORF04978 | 9955 & 9956 | transposase |
| ORF04979 | 9957 & 9958 | conserved protein |
| ORF04980 | 9959 & 9960 | conserved hypothetical protein |
| ORF04981 | 9961 & 9962 | Type I restriction enzyme EcokI specificity protein (S protein)(S.EcoKI) [3.1.21.3] |
| ORF04982 | 9963 & 9964 | Type I restriction enzyme EcokI M protein (M.EcoKI) [2.1.1.72] |
| ORF04983 | 9965 & 9966 | Type I restriction enzyme EcokI R protein (R.EcoKI) [3.1.21.3] |
| ORF04984 | 9967 & 9968 | Mrr restriction system protein (EcoKMrr) |
| ORF04985 | 9969 & 9970 | CobW-P47K family protein domain protein |
| ORF04986 | 9971 & 9972 | Uncharacterized small protein |
| ORF04987 | 9973 & 9974 | YjiY |
| ORF04988 | 9975 & 9976 | Methyl-accepting chemotaxis protein I (MCP-I) (Serine chemoreceptorprotein) (MCP-I) |
| ORF04989 | 9977 & 9978 | C4-dicarboxylate transporter large subunit (DctM) |
| ORF04990 | 9979 & 9980 | TRAP transporter, DctQ-like membrane protein superfamily |
| ORF04991 | 9981 & 9982 | DctP protein |
| ORF04992 | 9983 & 9984 | Na+-H+ antiporter |
| ORF04993 | 9985 & 9986 | yjjM gene product |
| ORF04994 | 9987 & 9988 | sorbitol dehydrogenase, putative [1.1.1.14] |
| ORF04995 | 9989 & 9990 | hypothetical protein |

TABLE 2

142 preferred antigens

| | | | | |
|---|---|---|---|---|
| ORF00010 | ORF00017 | ORF00029 | ORF00041 | ORF00130 |
| ORF00250 | ORF00251 | ORF00252 | ORF00332 | ORF00333 |
| ORF00342 | ORF00353 | ORF00394 | ORF00405 | ORF00469 |
| ORF00631 | ORF00773 | ORF00905 | ORF00908 | ORF01034 |
| ORF01037 | ORF01056 | ORF01090 | ORF01103 | ORF01104 |
| ORF01108 | ORF01115 | ORF01118 | ORF01119 | ORF01194 |
| ORF01202 | ORF01207 | ORF01208 | ORF01214 | ORF01228 |
| ORF01236 | ORF01337 | ORF01338 | ORF01339 | ORF01340 |
| ORF01341 | ORF01342 | ORF01344 | ORF01348 | ORF01349 |
| ORF01350 | ORF01351 | ORF01365 | ORF01371 | ORF01462 |
| ORF01477 | ORF01491 | ORF01503 | ORF01506 | ORF01589 |
| ORF01590 | ORF01592 | ORF01656 | ORF01660 | ORF01705 |
| ORF01722 | ORF01723 | ORF01855 | ORF01932 | ORF02307 |
| ORF02314 | ORF02392 | ORF02412 | ORF02424 | ORF02470 |
| ORF02554 | ORF02735 | ORF02816 | ORF02828 | ORF02829 |
| ORF02830 | ORF02831 | ORF02832 | ORF02833 | ORF02834 |
| ORF02847 | ORF02866 | ORF02868 | ORF02878 | ORF02888 |
| ORF03011 | ORF03020 | ORF03021 | ORF03025 | ORF03044 |
| ORF03166 | ORF03174 | ORF03176 | ORF03235 | ORF03252 |
| ORF03262 | ORF03300 | ORF03348 | ORF03349 | ORF03364 |
| ORF03459 | ORF03501 | ORF03504 | ORF03507 | ORF03512 |
| ORF03515 | ORF03516 | ORF03517 | ORF03518 | ORF03519 |
| ORF03520 | ORF03522 | ORF03535 | ORF03539 | ORF03540 |
| ORF03541 | ORF03542 | ORF03575 | ORF03576 | ORF03579 |
| ORF03580 | ORF03613 | ORF04162 | ORF04163 | ORF04184 |
| ORF04203 | ORF04204 | ORF04282 | ORF04390 | ORF04391 |
| ORF04402 | ORF04477 | ORF04608 | ORF04693 | ORF04694 |
| ORF04844 | ORF04845 | ORF04849 | ORF04851 | ORF04922 |
| ORF04924 | ORF04925 | | | |

Cytoplasmic location: ORF00252, ORF01056, ORF01337, ORF01341, ORF01344, ORF01348, ORF01371, ORF01477, ORF02424, ORF02833, ORF03348, ORF03504, ORF03542, ORF04162, ORF04844.
Inner membrane location: ORF00010, ORF00017, ORF00029, ORF00041, ORF00130, ORF00332, ORF00333, ORF00342, ORF00353, ORF00394, ORF00405, ORF00631, ORF00773, ORF00905, ORF01034, ORF01037, ORF01090, ORF01103, ORF01104, ORF01108, ORF01115, ORF01118, ORF01119, ORF01194, ORF01202, ORF01207, ORF01208, ORF01214, ORF01338, ORF01339, ORF01349, ORF01350, ORF01365, ORF01462, ORF01491, ORF01503, ORF01506, ORF01590, ORF01705, ORF01722, ORF01723, ORF01855, ORF01932, ORF02314, ORF02392, ORF02412, ORF02470, ORF02554, ORF02735, ORF02847, ORF02868, ORF02878, ORF02888, ORF03020, ORF03021, ORF03025, ORF03044, ORF03174, ORF03176, ORF03235, ORF03300, ORF03349, ORF03364, ORF03459, ORF03501, ORF03507, ORF03512, ORF03519, ORF03520, ORF03535, ORF03539, ORF03540, ORF03575, ORF03576, ORF03579, ORF03580, ORF04163, ORF04184, ORF04203, ORF04204, ORF04402, ORF04477, ORF04608, ORF04693, ORF04694, ORF04845, ORF04849, ORF04851, ORF04922, ORF04924, ORF04925.
Outer membrane location: ORF00250, ORF00251, ORF00469, ORF01228, ORF01236, ORF01340, ORF01342, ORF01351, ORF01592, ORF01656, ORF02829, ORF02831, ORF02834, ORF03166, ORF03517, ORF03613, ORF04282.
Periplasmic location: ORF00908, ORF01589, ORF01660, ORF02307, ORF02816, ORF02828, ORF02830, ORF02832, ORF02866, ORF03011, ORF03252, ORF03262, ORF03515, ORF03516, ORF03518, ORF03522, ORF03541, ORF04390, ORF04391

TABLE 3 low homology with commensal strains

ORF00010, ORF00016, ORF00017, ORF00018, ORF00019, ORF00020, ORF00025, ORF00028, ORF00029, ORF00030, ORF00031, ORF00032, ORF00034, ORF00035, ORF00036, ORF00037, ORF00041, ORF00042, ORF00043, ORF00044, ORF00045, ORF00046, ORF00047, ORF00048, ORF00049, ORF00050, ORF00051, ORF00052, ORF00053, ORF00054, ORF00055, ORF00056, ORF00057, ORF00058, ORF00059, ORF00060, ORF00061, ORF00062, ORF00064, ORF00065, ORF00067, ORF00068, ORF00069, ORF00070, ORF00089, ORF00090, ORF00106, ORF00107, ORF00119, ORF00120, ORF00121, ORF00130, ORF00134, ORF00150, ORF00151, ORF00152, ORF00163, ORF00169, ORF00198, ORF00222, ORF00223, ORF00224, ORF00225, ORF00226, ORF00231, ORF00232, ORF00233, ORF00250, ORF00251, ORF00252, ORF00253, ORF00254, ORF00255, ORF00256, ORF00257, ORF00330, ORF00331, ORF00332, ORF00333, ORF00334, ORF00335, ORF00336, ORF00337, ORF00338, ORF00339, ORF00340, ORF00341, ORF00342, ORF00343, ORF00344, ORF00345, ORF00346, ORF00347, ORF00348, ORF00349, ORF00350, ORF00351, ORF00352, ORF00353, ORF00361, ORF00379, ORF00380, ORF00381, ORF00382, ORF00383, ORF00394, ORF00395, ORF00396, ORF00397, ORF00399, ORF00400, ORF00401, ORF00402, ORF00403, ORF00404, ORF00407, ORF00415, ORF00416, ORF00417, ORF00418, ORF00419, ORF00433, ORF00434, ORF00435, ORF00436, ORF00437, ORF00442, ORF00444, ORF00455, ORF00587, ORF00588, ORF00591, ORF00597, ORF00598, ORF00599, ORF00600, ORF00631, ORF00644, ORF00646, ORF00647, ORF00648, ORF00649, ORF00650, ORF00655, ORF00656, ORF00657, ORF00659, ORF00660, ORF00661, ORF00662, ORF00663, ORF00664, ORF00665, ORF00666, ORF00667, ORF00668, ORF00669, ORF00670, ORF00671, ORF00672, ORF00673, ORF00674, ORF00675, ORF00676, ORF00677, ORF00678, ORF00680, ORF00681, ORF00682, ORF00683, ORF00685, ORF00687, ORF00773, ORF00786, ORF00787, ORF00788, ORF00789, ORF00790, ORF00791, ORF00792, ORF00793, ORF00794, ORF00795, ORF00796, ORF00798, ORF00803, ORF00804, ORF00809, ORF00810, ORF00838, ORF00839, ORF00857, ORF00864, ORF00883, ORF00884, ORF00885, ORF00886, ORF00887, ORF00888, ORF00889, ORF00890, ORF00891, ORF00892, ORF00893, ORF00894, ORF00895, ORF00896, ORF00897, ORF00898, ORF00899, ORF00900, ORF00901, ORF00902, ORF00903, ORF00904, ORF00905, ORF00906, ORF00907, ORF00908, ORF00909, ORF00910, ORF00924, ORF00925, ORF00926, ORF00948, ORF00956, ORF01031, ORF01032, ORF01033, ORF01034, ORF01035, ORF01036, ORF01037, ORF01038, ORF01039, ORF01040, ORF01041, ORF01042, ORF01043, ORF01044, ORF01045, ORF01046, ORF01047, ORF01048, ORF01052, ORF01053, ORF01054, ORF01055, ORF01056, ORF01057, ORF01058, ORF01063, ORF01078, ORF01079, ORF01080, ORF01081, ORF01084, ORF01085, ORF01086, ORF01087, ORF01088, ORF01089, ORF01090, ORF01091, ORF01092, ORF01093, ORF01094, ORF01095, ORF01096, ORF01097, ORF01098, ORF01099, ORF01100, ORF01101, ORF01102, ORF01103, ORF01104, ORF01105, ORF01106, ORF01107, ORF01108, ORF01109, ORF01110, ORF01111, ORF01112, ORF01113, ORF01114, ORF01115, ORF01116, ORF01117, ORF01118, ORF01119, ORF01156, ORF01186, ORF01187, ORF01188, ORF01190, ORF01191, ORF01192, ORF01193, ORF01194, ORF01195, ORF01196, ORF01199, ORF01200, ORF01201, ORF01202, ORF01203, ORF01204, ORF01205, ORF01206, ORF01207, ORF01208, ORF01209, ORF01210, ORF01211, ORF01212, ORF01213, ORF01214, ORF01215, ORF01216, ORF01217, ORF01218, ORF01219, ORF01220, ORF01222, ORF01223, ORF01224, ORF01225, ORF01226, ORF01227, ORF01228, ORF01236, ORF01252, ORF01253, ORF01254, ORF01255, ORF01256, ORF01257, ORF01258, ORF01259, ORF01260, ORF01261, ORF01283, ORF01313, ORF01314, ORF01315, ORF01316, ORF01317, ORF01318, ORF01319, ORF01320, ORF01321, ORF01322, ORF01323, ORF01325, ORF01330, ORF01331, ORF01332, ORF01333, ORF01334, ORF01335, ORF01336, ORF01337, ORF01338, ORF01339, ORF01340, ORF01341, ORF01342, ORF01343, ORF01344, ORF01345, ORF01346, ORF01347, ORF01348, ORF01349, ORF01350,

TABLE 3-continued low homology with commensal strains

ORF01351, ORF01352, ORF01353, ORF01354, ORF01355, ORF01356, ORF01357, ORF01359, ORF01360,
ORF01361, ORF01365, ORF01366, ORF01367, ORF01368, ORF01371, ORF01373, ORF01374, ORF01375,
ORF01376, ORF01394, ORF01456, ORF01462, ORF01477, ORF01479, ORF01480, ORF01483, ORF01484,
ORF01485, ORF01486, ORF01487, ORF01488, ORF01490, ORF01491, ORF01492, ORF01493, ORF01494,
ORF01498, ORF01499, ORF01500, ORF01501, ORF01502, ORF01503, ORF01504, ORF01505, ORF01506,
ORF01507, ORF01508, ORF01509, ORF01510, ORF01511, ORF01512, ORF01513, ORF01514, ORF01518,
ORF01523, ORF01524, ORF01525, ORF01526, ORF01527, ORF01528, ORF01529, ORF01530, ORF01531,
ORF01532, ORF01533, ORF01534, ORF01535, ORF01536, ORF01537, ORF01538, ORF01539, ORF01540,
ORF01541, ORF01542, ORF01543, ORF01550, ORF01551, ORF01552, ORF01553, ORF01554, ORF01555,
ORF01556, ORF01557, ORF01558, ORF01559, ORF01560, ORF01561, ORF01562, ORF01563, ORF01564,
ORF01565, ORF01566, ORF01567, ORF01568, ORF01569, ORF01570, ORF01571, ORF01572, ORF01573,
ORF01574, ORF01575, ORF01576, ORF01577, ORF01578, ORF01583, ORF01588, ORF01589, ORF01590,
ORF01591, ORF01592, ORF01593, ORF01609, ORF01610, ORF01611, ORF01612, ORF01613, ORF01630,
ORF01631, ORF01637, ORF01651, ORF01655, ORF01656, ORF01657, ORF01658, ORF01659, ORF01660,
ORF01665, ORF01705, ORF01722, ORF01723, ORF01724, ORF01725, ORF01766, ORF01767, ORF01768,
ORF01769, ORF01770, ORF01790, ORF01810, ORF01812, ORF01813, ORF01815, ORF01816, ORF01817,
ORF01818, ORF01819, ORF01820, ORF01821, ORF01822, ORF01823, ORF01824, ORF01825, ORF01826,
ORF01827, ORF01828, ORF01829, ORF01830, ORF01831, ORF01832, ORF01833, ORF01834, ORF01835,
ORF01836, ORF01837, ORF01838, ORF01840, ORF01842, ORF01843, ORF01844, ORF01845, ORF01846,
ORF01847, ORF01848, ORF01849, ORF01850, ORF01852, ORF01853, ORF01854, ORF01855, ORF01856,
ORF01857, ORF01861, ORF01862, ORF01865, ORF01891, ORF01923, ORF01926, ORF01927, ORF01928,
ORF01929, ORF01930, ORF01931, ORF01932, ORF01946, ORF01953, ORF01955, ORF01956, ORF01987,
ORF02112, ORF02266, ORF02289, ORF02295, ORF02296, ORF02297, ORF02298, ORF02299, ORF02300,
ORF02301, ORF02302, ORF02303, ORF02304, ORF02305, ORF02306, ORF02307, ORF02308, ORF02309,
ORF02310, ORF02311, ORF02312, ORF02313, ORF02314, ORF02315, ORF02327, ORF02338, ORF02351,
ORF02352, ORF02353, ORF02354, ORF02355, ORF02356, ORF02358, ORF02359, ORF02361, ORF02362,
ORF02363, ORF02364, ORF02365, ORF02366, ORF02367, ORF02368, ORF02369, ORF02370, ORF02371,
ORF02372, ORF02373, ORF02374, ORF02375, ORF02382, ORF02383, ORF02384, ORF02385, ORF02386,
ORF02387, ORF02388, ORF02389, ORF02390, ORF02392, ORF02393, ORF02394, ORF02395, ORF02396,
ORF02397, ORF02398, ORF02399, ORF02400, ORF02401, ORF02402, ORF02403, ORF02404, ORF02405,
ORF02413, ORF02414, ORF02415, ORF02419, ORF02420, ORF02421, ORF02422, ORF02423, ORF02424,
ORF02425, ORF02429, ORF02432, ORF02436, ORF02437, ORF02438, ORF02439, ORF02440, ORF02441,
ORF02442, ORF02443, ORF02444, ORF02445, ORF02446, ORF02447, ORF02448, ORF02449, ORF02450,
ORF02451, ORF02452, ORF02453, ORF02454, ORF02455, ORF02456, ORF02457, ORF02458, ORF02459,
ORF02460, ORF02461, ORF02462, ORF02464, ORF02465, ORF02466, ORF02467, ORF02468, ORF02469,
ORF02470, ORF02471, ORF02472, ORF02501, ORF02502, ORF02503, ORF02504, ORF02505, ORF02506,
ORF02507, ORF02533, ORF02534, ORF02552, ORF02553, ORF02554, ORF02555, ORF02582, ORF02583,
ORF02595, ORF02614, ORF02628, ORF02633, ORF02699, ORF02735, ORF02788, ORF02789, ORF02790,
ORF02791, ORF02792, ORF02793, ORF02794, ORF02795, ORF02796, ORF02797, ORF02798, ORF02799,
ORF02800, ORF02801, ORF02802, ORF02803, ORF02804, ORF02805, ORF02806, ORF02807, ORF02808,
ORF02809, ORF02810, ORF02811, ORF02812, ORF02813, ORF02814, ORF02815, ORF02816, ORF02828,
ORF02829, ORF02830, ORF02831, ORF02832, ORF02833, ORF02834, ORF02835, ORF02844, ORF02845,
ORF02846, ORF02847, ORF02848, ORF02849, ORF02850, ORF02851, ORF02852, ORF02853, ORF02854,
ORF02855, ORF02856, ORF02857, ORF02858, ORF02859, ORF02860, ORF02861, ORF02862, ORF02863,
ORF02864, ORF02865, ORF02866, ORF02867, ORF02868, ORF02869, ORF02870, ORF02871, ORF02872,
ORF02873, ORF02874, ORF02875, ORF02876, ORF02877, ORF02878, ORF02879, ORF02880, ORF02881,
ORF02882, ORF02883, ORF02884, ORF02885, ORF02886, ORF02887, ORF02888, ORF02889, ORF02890,
ORF02891, ORF02931, ORF03011, ORF03012, ORF03013, ORF03014, ORF03015, ORF03016, ORF03017,
ORF03018, ORF03019, ORF03020, ORF03021, ORF03022, ORF03023, ORF03024, ORF03025, ORF03026,
ORF03027, ORF03028, ORF03029, ORF03030, ORF03031, ORF03032, ORF03033, ORF03034, ORF03035,
ORF03036, ORF03037, ORF03038, ORF03039, ORF03040, ORF03041, ORF03042, ORF03043, ORF03044,
ORF03045, ORF03046, ORF03047, ORF03048, ORF03049, ORF03053, ORF03054, ORF03055, ORF03056,
ORF03114, ORF03130, ORF03131, ORF03132, ORF03133, ORF03162, ORF03163, ORF03164, ORF03165,
ORF03166, ORF03167, ORF03173, ORF03174, ORF03175, ORF03176, ORF03191, ORF03192, ORF03206,
ORF03207, ORF03235, ORF03236, ORF03252, ORF03262, ORF03263, ORF03279, ORF03296, ORF03297,
ORF03298, ORF03299, ORF03300, ORF03325, ORF03340, ORF03341, ORF03342, ORF03343, ORF03344,
ORF03345, ORF03346, ORF03347, ORF03348, ORF03349, ORF03350, ORF03351, ORF03352, ORF03353,
ORF03354, ORF03355, ORF03356, ORF03357, ORF03358, ORF03359, ORF03360, ORF03361, ORF03362,
ORF03363, ORF03364, ORF03365, ORF03400, ORF03415, ORF03453, ORF03454, ORF03455, ORF03456,
ORF03457, ORF03458, ORF03459, ORF03465, ORF03469, ORF03499, ORF03500, ORF03501, ORF03502,
ORF03503, ORF03504, ORF03505, ORF03506, ORF03507, ORF03508, ORF03509, ORF03510, ORF03511,
ORF03512, ORF03515, ORF03516, ORF03517, ORF03518, ORF03519, ORF03520, ORF03521, ORF03522,
ORF03526, ORF03535, ORF03536, ORF03537, ORF03538, ORF03539, ORF03540, ORF03541, ORF03542,
ORF03574, ORF03575, ORF03576, ORF03577, ORF03578, ORF03579, ORF03580, ORF03589, ORF03592,
ORF03593, ORF03594, ORF03595, ORF03596, ORF03597, ORF03606, ORF03607, ORF03608, ORF03610,
ORF03612, ORF03613, ORF03614, ORF03615, ORF03616, ORF03617, ORF03619, ORF03695, ORF03696,
ORF03817, ORF03818, ORF03819, ORF03820, ORF03821, ORF03822, ORF03823, ORF03824, ORF03825,
ORF03826, ORF03975, ORF03991, ORF03992, ORF03993, ORF03994, ORF03995, ORF03996, ORF03997,
ORF03998, ORF03999, ORF04000, ORF04031, ORF04032, ORF04033, ORF04034, ORF04035, ORF04036,
ORF04058, ORF04059, ORF04060, ORF04061, ORF04062, ORF04063, ORF04064, ORF04073, ORF04083,
ORF04084, ORF04085, ORF04086, ORF04087, ORF04088, ORF04089, ORF04090, ORF04091, ORF04130,
ORF04162, ORF04163, ORF04164, ORF04171, ORF04183, ORF04184, ORF04203, ORF04204, ORF04205,
ORF04206, ORF04207, ORF04208, ORF04209, ORF04211, ORF04224, ORF04225, ORF04237, ORF04238,
ORF04239, ORF04240, ORF04241, ORF04242, ORF04243, ORF04244, ORF04247, ORF04250, ORF04282,
ORF04302, ORF04390, ORF04391, ORF04398, ORF04402, ORF04403, ORF04404, ORF04416, ORF04417,
ORF04418, ORF04419, ORF04420, ORF04421, ORF04422, ORF04423, ORF04424, ORF04425, ORF04426,
ORF04427, ORF04428, ORF04429, ORF04430, ORF04434, ORF04435, ORF04436, ORF04437, ORF04438,
ORF04439, ORF04451, ORF04476, ORF04477, ORF04478, ORF04479, ORF04480, ORF04481, ORF04482,

TABLE 3-continued low homology with commensal strains

ORF04483, ORF04484, ORF04489, ORF04490, ORF04500, ORF04542, ORF04543, ORF04544, ORF04545,
ORF04546, ORF04547, ORF04552, ORF04569, ORF04572, ORF04573, ORF04608, ORF04612, ORF04623,
ORF04626, ORF04627, ORF04628, ORF04629, ORF04630, ORF04631, ORF04632, ORF04661, ORF04662,
ORF04663, ORF04664, ORF04665, ORF04668, ORF04669, ORF04671, ORF04672, ORF04673, ORF04674,
ORF04675, ORF04676, ORF04677, ORF04678, ORF04679, ORF04691, ORF04692, ORF04693, ORF04694,
ORF04708, ORF04709, ORF04710, ORF04711, ORF04712, ORF04728, ORF04844, ORF04845, ORF04846,
ORF04847, ORF04848, ORF04849, ORF04850, ORF04851, ORF04882, ORF04890, ORF04891, ORF04892,
ORF04893, ORF04894, ORF04895, ORF04898, ORF04900, ORF04915, ORF04916, ORF04917, ORF04918,
ORF04919, ORF04920, ORF04921, ORF04922, ORF04923, ORF04924, ORF04925, ORF04926, ORF04927,
ORF04928, ORF04929, ORF04930, ORF04946, ORF04947, ORF04948, ORF04949, ORF04950, ORF04951,
ORF04952, ORF04953, ORF04954, ORF04955, ORF04956, ORF04957, ORF04958, ORF04959, ORF04960,
ORF04961, ORF04962, ORF04963, ORF04964, ORF04966, ORF04974, ORF04978, ORF04979, ORF04981,
ORF04989, ORF04990, ORF04991, ORF04992, ORF04993, ORF04995

TABLE 4

| Protein | SEQ ID | Annotation | Psort | TMD | CFT073 | % ID |
| --- | --- | --- | --- | --- | --- | --- |
| ORF03526 | 7051 + 7052 | Accessory colonization factor AcfD precursor | I | 0 | upec-2704 | 45.3 |
| ORF01339 | 2677 + 2678 | F1C fimbrial usher | I | 1 | upec-1199 | 99.4 |
| ORF00256 | 511 + 512 | pilin chaperone ecpD2 | I | 1 | upec-0166 | 100 |
| ORF01346 | 2691 + 2692 | IroN protein | O | 0 | upec-1207 | 99.3 |
| ORF04084 | 8167 + 8168 | outer membrane hemin receptor ChuA | O | 0 | upec-4213 | 99.7 |
| ORF02374 | 4747 + 4748 | OMR family pesticin-yersiniabactin receptor protein (IRPC) | O | 0 | upec-2371 | 100 |
| ORF03502 | 7003 + 7004 | polysaccharide biosynthesis protein, putative | O | 0 | upec-3606 | 99.5 |
| ORF02298 | 4595 + 4596 | hypothetical protein | C | 0 | upec-5009 | 30 |
| ORF01228 | 2455 + 2456 | CdtC | O | 0 | upec-1086 | 30.3 |
| ORF01227 | 2453 + 2454 | CdtB | I | 1 | upec-0679 | 31.9 |
| ORF02314 | 4627 + 4628 | gpH | I | 1 | upec-0941 | 48.8 |
| ORF02850 | 5699 + 5700 | DNA transfer protein | C | 0 | upec-4881 | 21.2 |

Columns:
PSORT: predicted location by the PSORT algorithm. I = inner membrane; O = outer membrane; P = periplasm; C = cytoplasm
TMD: number of transmembrane domains
% ID: percentage identitical residues over length of alignment

REFERENCES

The Contents of which are Hereby Incorporated by Reference

[1] Russo & Johnson (2000) *J Infect Dis* 181:1753-1754.
[2] Uehling et al. (1997) *J Urol* 157:2049-2052.
[3] Tammen (1990) *Br J Urol* 65:6-9.
[4] Langermann et al. (1997) *Science* 276:607-611.
[5] WO03/074553.
[6] WO01/66572.
[7] Janke et al. (2001) *FEMS Microbiol Lett* 199:61-66.
[8] WO2004/005535.
[9] Dobrindt et al (2002) *Infect Immun* 70:6365-6372.
[10] US2003/0165870.
[11] Welch et al. (2002) *Proc Natl Acad Sci USA* 99:17020-17024.
[12] American Type Culture Collection: ATCC 700928.
[13] *European Journal of Biochemistry* 2003; 1 Supplement 1 July: abstract P1.3-11.
[14] Geysen et al. (1984) *PNAS USA* 81:3998-4002.
[15] Carter (1994) *Methods Mol Biol* 36:207-223.
[16] Jameson, B A et al. 1988, *CABIOS* 4(1):181-186.
[17] Raddrizzani & Hammer (2000) *Brief Bioinform* 1(2):179-189.
[18] De Lalla et al. (1999) *J. Immunol.* 163:1725-1729.
[19] Brusic et al. (1998) *Bioinformatics* 14(2):121-130
[20] Meister et al. (1995) *Vaccine* 13(6):581-591.
[21] Roberts et al. (1996) *AIDS Res Hum Retroviruses* 12(7): 593-610.
[22] Maksyutov & Zagrebelnaya (1993) *Comput Appl Biosci* 9(3):291-297.
[23] Feller & de la Cruz (1991) *Nature* 349(6311):720-1.
[24] Hopp (1993) *Peptide Research* 6:183-190.
[25] Welling et al. (1985) *FEBS Lett.* 188:215-218.
[26] Davenport et al. (1995) *Immunogenetics* 42:392-297.
[27] Bodanszky (1993) *Principles of Peptide Synthesis* (ISBN: 0387564314).
[28] Fields et al. (1997) *Meth Enzymol* 289: *Solid-Phase Peptide Synthesis.* ISBN: 0121821900.
[29] Chan & White (2000) *Fmoc Solid Phase Peptide Synthesis.* ISBN: 0199637245.
[30] Kullmann (1987) *Enzymatic Peptide Synthesis.* ISBN: 0849368413.
[31] Ibba (1996) *Biotechnol Genet Eng Rev* 13:197-216.
[32] Breedveld (2000) *Lancet* 355(9205):735-740.
[33] Gorman & Clark (1990) *Semin. Immunol.* 2:457-466.
[34] Sambrook et al. (2001) *Molecular Cloning: A Laboratory Manual,* 3rd edition (Cold Spring Harbor Laboratory Press).
[35] Ausubel et al. (eds) (2002) *Short protocols in molecular biology,* 5th edition (Current Protocols).
[36] U.S. Pat. No. 5,707,829
[37] *Current Protocols in Molecular Biology* (F. M. Ausubel et al. eds., 1987) Supplement 30.
[38] EP-B-0509612.
[39] EP-B-0505012.

[40] Johnson & Stell (2001) *J Clin Microbiol* 39:3712-33717.
[41] Tang et al. (1997) *Clin. Chem.* 43:2021-2038.
[42] PCT/IB2005/003494.
[43] Bemadac et al. (1998) *J Bacteriol* 180(18):4872-4878.
[44] EP-1441036.
[45] Sorensen & Mortensen (2005) *Journal of Biotechnology* 115:113-128.
[46] Meynial-Salles et al. (2005) *Applied and Environmental Microbiology* 71:2140-2144.
[47] US2004/0209370.
[48] WO00/68253.
[49] WO97/04110.
[50] Alper et al. (2005) *Proc. Natl. Acad. Sci. USA* 102: 12678-12683.
[51] WO 01/09350.
[52] European patent 0624376.
[53] *Vaccine Design* . . . (1995) eds. Powell & Newman. ISBN: 030644867X. Plenum.
[54] WO00/23105.
[55] WO90/14837.
[56] Podda (2001) *Vaccine* 19:2673-2680.
[57] Frey et al. (2003) *Vaccine* 21:4234-4237.
[58] *Vaccine Adjuvants: Preparation Methods and Research Protocols* (Volume 42 of *Methods in Molecular Medicine* series). ISBN: 1-59259-083-7. Ed. O'Hagan.
[59] U.S. Pat. No. 6,299,884.
[60] U.S. Pat. No. 6,451,325.
[61] Allison & Byars (1992) *Res Immunol* 143:519-525.
[62] Hariharan et al. (1995) *Cancer Res* 55:3486-3489.
[63] U.S. Pat. No. 5,057,540.
[64] WO96/33739.
[65] EP-A-0109942.
[66] WO96/11711.
[67] WO00/07621.
[68] Barr et al. (1998) *Advanced Drug Delivery Reviews* 32:247-271.
[69] Sjolanderet et al. (1998) *Advanced Drug Delivery Reviews* 32:321-338.
[70] Niikura et al. (2002) *Virology* 293:273-280.
[71] Lenz et al. (2001) *J Immunol* 166:5346-5355.
[72] Pinto et al. (2003) *J Infect Dis* 188:327-338.
[73] Gerber et al. (2001) *Virol* 75:4752-4760.
[74] WO03/024480
[75] WO03/024481
[76] Gluck et al. (2002) *Vaccine* 20:B10-B16.
[77] EP-A-0689454.
[78] Johnson et al. (1999) *Bioorg Med Chem Lett* 9:2273-2278.
[79] Evans et al. (2003) *Expert Rev Vaccines* 2:219-229.
[80] Meraldi et al. (2003) *Vaccine* 21:2485-2491.
[81] Pajak et al. (2003) *Vaccine* 21:836-842.
[82] Kandimalla et al. (2003) *Nucleic Acids Research* 31:2393-2400.
[83] WO02/26757.
[84] WO99/62923.
[85] Krieg (2003) *Nature Medicine* 9:831-835.
[86] McCluskie et al. (2002) *FEMS Immunology and Medical Microbiology* 32:179-185.
[87] WO98/40100.
[88] U.S. Pat. No. 6,207,646.
[89] U.S. Pat. No. 6,239,116.
[90] U.S. Pat. No. 6,429,199.
[91] Kandimalla et al. (2003) *Biochemical Society Transactions* 31 (part 3):654-658.
[92] Blackwell et al. (2003) *J Immunol* 170:4061-4068.
[93] Krieg (2002) *Trends Immunol* 23:64-65.
[94] WO01/95935.
[95] Kandimalla et al. (2003) *BBRC* 306:948-953.
[96] Bhagat et al. (2003) *BBRC* 300:853-861.
[97] WO03/035836.
[98] WO95/17211.
[99] WO98/42375.
[100] Beignon et al. (2002) *Infect Immnun* 70:3012-3019.
[101] Pizza et al. (2001) *Vaccine* 19:2534-2541.
[102] Pizza et al. (2000) *Int J Med Microbiol* 290:455-461.
[103] Scharton-Kersten et al. (2000) *Infect Immun* 68:5306-5313.
[104] Ryan et al. (1999) *Infect Immun* 67:6270-6280.
[105] Partidos et al. (1999) *Immunol Lett* 67:209-216.
[106] Peppoloni et al. (2003) *Expert Rev Vaccines* 2:285-293.
[107] Pine et al. (2002) *J Control Release* 85:263-270.
[108] Domenighini et al. (1995) *Mol Microbiol* 15:1165-1167.
[109] WO03/011223.
[110] WO99/40936.
[111] WO99/44636.
[112] Lillard J W et al., (2003) *Blood* 101(3):807-14. Epub Sep. 12, 2002.
[113] Singh et al] (2001) *J Cont Release* 70:267-276.
[114] WO99/27960.
[115] U.S. Pat. No. 6,090,406
[116] U.S. Pat. No. 5,916,588
[117] EP-A-0626169.
[118] WO99/52549.
[119] WO01/21207.
[120] WO01/21152.
[121] Andrianov et al. (1998) *Biomaterials* 19:109-115.
[122] Payne et al. (1998) *Adv Drug Delivery Review* 31:185-196.
[123] U.S. Pat. No. 4,680,338.
[124] U.S. Pat. No. 4,988,815.
[125] WO92/15582.
[126] Stanley (2002) *Clin Exp Dermatol* 27:571-577.
[127] Wu et al. (2004) *Antiviral Res.* 64(2):79-83.
[128] Vasilakos et al. (2000) *Cell Immunol.* 204(1):64-74.
[129] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[130] Jones (2003) *Curr Opin Inivestig Drugs* 4:214-218.
[131] WO04/60308
[132] WO04/64759.
[133] U.S. Pat. No. 6,924,271.
[134] US2005/0070556.
[135] U.S. Pat. No. 5,658,731.
[136] Wong et al. (2003) *J Clin Pharmacol* 43(7):735-742.
[137] US2005/0215517.
[138] WO02/072012.
[139] Signorelli & Hadden (2003) *Int Immunopharmacol* 3(8):1177-1186.
[140] WO2004/064715.
[141] Cooper (1995) *Pharm Biotechnol* 6:559-580.
[142] PCT/US2005/022769.
[143] WO2004/87153.
[144] U.S. Pat. No. 6,605,617.
[145] WO02/18383.
[146] WO2004/018455.
[147] WO03/082272.
[148] U.S. Pat. No. 5,011,828.
[149] U.S. Pat. No. 6,586,409.
[150] WO99/11241.

[151] WO94/00153.
[152] WO98/57659.
[153] European patent applications 0835318, 0735898 and 0761231.
[154] WO03/009869.
[155] Glezen & Alpers (1999) *Clin. Infect. Dis.* 28:219-224.
[156] Johnson et al. (2001) *Infect Immun* 69:1306-1314.
[157] Johnson et al. (2001) *J Infect Dis* 183:897-906 (see also 183:1546).
[158] Almeida & Alpar (1996) *J. Drug Targeting* 3:455-467.
[159] Agarwal & Mishra (1999) *Indian J Exp Biol* 37:6-16.
[160] Costantino et al. (1992) *Vaccine* 10:691-698.
[161] Costantino et al. (1999) *Vaccine* 17:1251-1263.
[162] International patent application WO03/007985.
[163] WO 99/24578.
[164] WO 99/36544.
[165] WO 99/57280.
[166] WO 00/66791.
[167] WO 01/64922.
[168] WO 01/64920.
[169] WO 03/020756.
[170] WO 2004/032958.
[171] WO 2004/048404.
[172] Watson (2000) *Pediatr Infect J* 19:331-332.
[173] Rubin (2000) *Pediatr Clin North Am* 47:269-285, v.
[174] Jedrzejas (2001) *Microbiol Mol Biol Rev* 65:187-207.
[175] Bell (2000) *Pediatr Infect Dis J* 19:1187-1188.
[176] Iwarson (1995) *APMIS* 103:321-326.
[177] Gerlich et al. (1990) *Vaccine* 8 Suppl:S63-S68 & S79-S80.
[178] *Vaccines* (1988) eds. Plotkin & Mortimer. ISBN 0-7216-1946-0.
[179] Del Guidice et al. (1998) *Molecular Aspects of Medicine* 19:1-70.
[180] Hsu et al. (1999) *Clin Liver Dis* 3:901-915.
[181] Stratov et al. (2004) *Curr Drug Tgts* 5(1):71-88.
[182] Gustafsson et al. (1996) *N. Engl. J. Med.* 334:349-355.
[183] Rappuoli et al. (1991) *TIBTECH* 9:232-238.
[184] Sutter et al. (2000) *Pediatr Clin North Am* 47:287-308.
[185] Zimmerman & Spann (1999) *Am Fam Physician* 59:113-118, 125-126.
[186] McMichael (2000) *Vaccine* 19 Suppl 1:S101-S107.
[187] Schuchat (1999) *Lancet* 353(9146):51-56.
[188] International patent application WO02/34771.
[189] WO 99/24578.
[190] WO 99/36544.
[191] WO 99/57280.
[192] WO 02/079243.
[193] WO 02/02606.
[194] Kalman et al. (1999) *Nature Genetics* 21:385-389.
[195] Read et al. (2000) *Nucleic Acids Res* 28:1397-406.
[196] Shirai et al. (2000) *J. Infect. Dis.* 181(Suppl 3):S524-S527.
[197] WO 99/27105.
[198] WO 00/27994.
[199] WO 00/37494.
[200] WO2005/084306.
[201] WO2005/002619.
[202] Ross et al. (2001) *Vaccine* 19:4135-4142.
[203] Dreesen (1997) *Vaccine* 15 Suppl:S2-S6.
[204] *MMWR Morb Mortal Wkly Rep* Jan. 16, 1998; 47(1): 12,19.
[205] Anderson (2000) *Vaccine* 19 Suppl 1:S59-S65.
[206] Kahn (2000) *Curr Opin Pediatr* 12:257-262.
[207] Crowe (1995) *Vaccine* 13:415-421.
[208] Modlin et al. (2001) *J Toxicol Clin Toxicol* 39:85-100.
[209] Demicheli et al. (1998) *Vaccine* 16:880-884.
[210] Stepanov et al. (1996) *J Biotechnol* 44:155-160.
[211] Dale (1999) *Infect Dis Clin North Am* 13:227-243, viii.
[212] Ferretti et al. (2001) *PNAS USA* 98: 4658-4663.
[213] Kuroda et al. (2001) *Lancet* 357(9264):1225-1240; see also pages 1218-1219.
[214] WO 00/09699.
[215] EP-A-0372501
[216] EP-A-0378881
[217] EP-A-0427347
[218] WO93/17712
[219] WO94/03208
[220] WO98/58668
[221] EP-A-0471177
[222] EP-A-0594610.
[223] WO00/56360
[224] WO91/01146
[225] WO00/61761
[226] WO01/72337
[227] Falugi et al. (2001) *Eur J Immunol* 31:3816-3824.
[228] Baraldo et al, (2004) *Infect Immun.* 72:4884-4887
[229] WO02/091998.
[230] Kuo et al. (1995) *Infect Immun* 63:2706-2713.
[231] *Research Disclosure*, 453077 (January 2002)
[232] Donnelly et al. (1997) *Annu Rev Immunol* 15:617-648.
[233] Strugnell et al. (1997) *Immunol Cell Biol* 75(4):364-369.
[234] Cui (2005) *Adv Genet* 54:257-89.
[235] Robinson & Torres (1997) *Seminars in Immunol* 9:271-283.
[236] Brunham et al. (2000) *J Infect Dis* 181 Suppl 3:S538-S543.
[237] Svanholm et al. (2000) *Scand J Immunol* 51(4):345-353.
[238] *DNA Vaccination—Genetic Vaccination* (1998) eds. Koprowski et al. (ISBN 3540633928).
[239] *Gene Vaccination: Theory and Practice* (1998) ed. Raz (ISBN 3540644288).
[240] Findeis et al., *Trends Biotechnol.* (1993) 11:202.
[241] Chiou et al. (1994) *Gene Therapeutics: Methods And Applications Of Direct Gene Transfer.* ed. Wolff.
[242] Wu et al, *J. Biol. Chem.* (1988) 263:621.
[243] Wu et al., *J. Biol. Chem.* (1994) 269:542.
[244] Zenke et al., *Proc. Natl. Acad. Sci. (USA)* (1990) 87:3655.
[245] Wu et al., *J. Biol Chem.* (1991) 266:338.
[246] Jolly, *Cancer Gene Therapy* (1994) 1:51.
[247] Kimura, *Human Gene Therapy* (1994) 5:845.
[248] Connelly, *Human Gene Therapy* (1995) 1:185.
[249] Kaplitt, *Nature Genetics* (1994) 6:148.
[250] WO 90/07936.
[251] WO 94/03622.
[252] WO 93/25698.
[253] WO 93/25234.
[254] U.S. Pat. No. 5,219,740.
[255] WO 93/11230.
[256] WO 93/10218.
[257] U.S. Pat. No. 4,777,127.
[258] GB 2,200,651.
[259] EP-A-0 345 242.
[260] WO 91/02805.
[261] WO 94/12649.
[262] WO 93/03769.
[263] WO 93/19191.
[264] WO 94/28938.
[265] WO 95/11984.
[266] WO 95/00655.
[267] Curiel, *Hum. Gene Ther.* (1992) 3:147.

[268] Wu, *J. Biol. Chem.* (1989) 264:16985.
[269] U.S. Pat. No. 5,814,482.
[270] WO 95/07994.
[271] WO 96/17072.
[272] WO 95/30763.
[273] WO 97/42338.
[274] WO 90/11092.
[275] U.S. Pat. No. 5,580,859.
[276] U.S. Pat. No. 5,422,120.
[277] WO 95/13796.
[278] WO 94/23697.
[279] WO 91/14445.
[280] EP 0524968.
[281] Philip, *Mol. Cell Biol.* (1994) 14:2411.
[282] Woffendin, *Proc. Natl. Acad. Sci.* (1994) 91:11581.
[283] U.S. Pat. No. 5,206,152.
[284] WO 92/11033.
[285] U.S. Pat. No. 5,149,655.
[286] WO 92/11033.
[287] Needleman & Wunsch (1970) *J. Mol. Biol.* 48:443-453.
[288] Rice et al. (2000) *Trends Genet* 16:276-277.
[289] Gennaro (2000) *Remington: The Science and Practice of Pharmacy.* 20th edition, ISBN: 0683306472.
[290] *Method In Enzymology* (S. Colowick and N. Kaplan, eds., Academic Press, Inc.)
[291] *Handbook of Experimental Immunology*, Vols. I-IV (D. M. Weir and C. C. Blackwell, eds., 1986, Blackwell Scientific Publications)
[292] Sambrook et al. (2001) *Molecular Cloning: A Laboratory Manual,* 3rd edition (Cold Spring Harbor Laboratory Press).
[293] *Handbook of Surface and Colloidal Chemistry* (Birdi, K. S. ed., CRC Press, 1997)
[294] Ausubel et al. (eds) (2002) *Short protocols in molecular biology,* 5th edition (Current Protocols).
[295] *Molecular Biology Techniques: An Intensive Laboratory Course,* (Ream et al., eds., 1998, Academic Press)
[296] *PCR (Introduction to Biotechniques Series),* 2nd ed. (Newton & Graham eds., 1997, Springer Verlag)
[297] Dobrindt et al. (2003) *J Bacteriol* 185:1831-1840.
[298] Murphy (1998) *J. Bacteriol* 180:2063-2071.
[299] Huang et al. (2001) *J Infect Dis* 183:1071-1078.
[300] Russo et al. (2002) *Infect Immun* 70:7156-7160.
[301] Russo et al. (2002) *Infect Immun* 71:7164-7169.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08758764B2). An electronic copy of the "Sequence Listing" will also be available from the USPTO upon request and payment of the fee set forth in 37 CFR 1.19(b)(3).

What is claimed:

1. A substantially purified polypeptide comprising an amino acid sequence selected from the group consisting of (a) the sequence which has at least 95% sequence identity to SEQ ID NO: 7052; and (b) a fragment of SEQ ID NO: 7052, wherein the fragment (i) includes at least 100 consecutive amino acids from SEQ ID NO: 7052; or (ii) consists of 40 or more consecutive amino acids from SEQ ID NO: 7052.

2. The polypeptide of claim 1, wherein said at least 100 consecutive amino acids or said 40 or more consecutive amino acids comprise at least one B-cell epitope of (a).

3. The substantially purified polypeptide of claim 1, wherein the at least 100 consecutive amino acids or said 40 or more consecutive amino acids consist of (a) said polypeptide without its N-terminal signal polypeptide, or (b) said polypeptide without 1-10 of its N-terminal amino acid residue(s).

4. The substantially purified polypeptide of claim 1 comprising an amino acid sequence which has at least 98% sequence identity to SEQ ID NO 7052.

5. The substantially purified polypeptide of claim 1 comprising an amino acid sequence which has at least 99% sequence identity to SEQ ID NO 7052.

6. The substantially purified polypeptide of claim 1, wherein the fragment includes at least 120 consecutive amino acids from SEQ ID NO 7052.

7. The substantially purified polypeptide of claim 1, wherein the fragment includes at least 140 consecutive amino acids from SEQ ID NO 7052.

8. The substantially purified polypeptide of claim 1, wherein the fragment includes at least 180 consecutive amino acids from SEQ ID NO 7052.

9. The substantially purified polypeptide of claim 1, wherein the fragment consists of 60 or more consecutive amino acids from SEQ ID NO 7052.

10. The substantially purified polypeptide of claim 1, wherein the fragment consists of 80 or more consecutive amino acids from SEQ ID NO 7052.

11. The substantially purified polypeptide of claim 1, wherein the fragment consists of 100 or more consecutive amino acids from SEQ ID NO 7052.

12. An immunogenic composition comprising the polypeptide of claim 1 in admixture with a pharmaceutically acceptable carrier.

13. An immunogenic composition comprising two or more polypeptides of claim 1 in admixture with a pharmaceutically acceptable carrier.

14. The immunogenic composition of claim 13 or claim 12, further comprising a vaccine adjuvant.

15. The immunogenic composition of claim 12, further comprising an adjuvant.

16. The immunogenic composition of claim 15, wherein the adjuvant is an aluminum salt.

* * * * *